(12) United States Patent
Challita-Eid et al.

(10) Patent No.: US 8,039,603 B2
(45) Date of Patent: *Oct. 18, 2011

(54) NUCLEIC ACID AND CORRESPONDING PROTEIN ENTITLED 121P1F1 USEFUL IN TREATMENT AND DETECTION OF CANCER

(75) Inventors: Pia M. Challita-Eid, Encino, CA (US); Rene S. Hubert, Los Angeles, CA (US); Arthur B. Raitano, Los Angeles, CA (US); Mary Faris, Los Angeles, CA (US); Daniel E. H. Afar, Fremont, CA (US); Wangmao Ge, Tampa, FL (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 12/473,056

(22) Filed: May 27, 2009

(65) Prior Publication Data

US 2009/0306193 A1 Dec. 10, 2009

Related U.S. Application Data

(60) Division of application No. 10/087,190, filed on Feb. 28, 2002, now Pat. No. 7,601,825, which is a continuation-in-part of application No. 09/799,250, filed on Mar. 5, 2001, now Pat. No. 6,924,358.

(51) Int. Cl.
*C07H 21/02* (2006.01)
(52) U.S. Cl. ..................... 536/23.1
(58) Field of Classification Search .................. None
See application file for complete search history.

(56) References Cited

U.S. PATENT DOCUMENTS

| | | | |
|---|---|---|---|
| 6,262,333 B1 | 7/2001 | Endege et al. | |
| 6,342,219 B1 | 1/2002 | Thorpe et al. | |
| 6,569,662 B1 | 5/2003 | Tang et al. | |
| 6,639,063 B1 | 10/2003 | Edwards et al. | |
| 6,924,358 B2 | 8/2005 | Challita-Eid et al. | |
| 7,601,825 B2 * | 10/2009 | Challita-Eid et al. | 536/23.5 |
| 2003/0032087 A1 | 2/2003 | Challita-Eid et al. | |
| 2003/0223997 A1 | 12/2003 | Challita-Eid et al. | |
| 2004/0101874 A1 | 5/2004 | Ghosh et al. | |

FOREIGN PATENT DOCUMENTS

| | | |
|---|---|---|
| WO | WO-99/33982 | 7/1999 |
| WO | WO-99/37771 | 7/1999 |
| WO | WO-99/38972 | 8/1999 |
| WO | WO-99/64576 | 12/1999 |
| WO | WO-00/52044 | 9/2000 |
| WO | WO-01/02568 | 1/2001 |
| WO | WO-01/22920 | 4/2001 |
| WO | WO-01/53312 | 7/2001 |
| WO | WO-01/66753 | 9/2001 |
| WO | WO-01/75067 | 10/2001 |
| WO | WO-01/75171 | 10/2001 |
| WO | WO-02/083876 | 10/2002 |
| WO | WO-02/095009 | 11/2002 |

OTHER PUBLICATIONS

Afar et al., Cancer Research (2001) 61:1686-1692.
Attwood, Science (2000) 290:471-473.
Bendayan, The Journal of Histochemistry and Cytochemistry (1995) 43(9):881-886.
Bost et al., Immunol. Invest. (1988) 17:577-586.
Burgess et al., J. Cell Biol. (1990) 111:2129-2138.
Bussemakers et al., Cancer Research (1991) 51:606-611.
Carninci et al., (1999). "High-Efficiency Full-Length cDNA Cloning" Chapter 2 *In cDNA Preparation and Characterization—Methods in Enzymology*, Weissman, S.M. ed. Academic Press, Inc. 303:19-44.
Carninci et al., (2000). "Normalization and Subtraction of Cap-Trapper-Selected cDNAs to Prepare Full-Length cDNA Libraries for Rapid Discovery of New Genes," Genome Research 10:1617-1630.
DGENE Record Accession No. AAX98924 for WO 99/33982, two pages, 1999.
DGENE Record Accession No. AAX99020 for WO 99/33982, two pages, 1999.
EMBL Accession No. AAM40043, created on Oct. 21, 2001, European Search Report Reference No. XP 002297423, two pages.
EMBL Accession No. AAZ80011, created on Apr. 7, 2000, European Search Report Reference No. XP 002297421, one page.
EMBL Accession No. AYO28916, created on Mar. 30, 2001, European Search Report Reference No. XP 002297424, one page.
EMBL Accession No. BE513408, created on Aug. 8, 2000, European Search Report Reference No. XP 002297422, two pages.
GenBank Accession No. AY028916 created Mar. 29, 2001, located at <http://www.ncbi.nlm.nih.gov/entrez/viewer.fcgi?db=nucleotide&val=13488608> last visited on Nov. 15, 2004.
GenBank Accession No. BAB27765 created on Apr. 3, 2004 located at <http://www.ncbi.nlm.nih.gov/entrez/viewe.fcgi?db=protein&val=12847934> last visited on Nov. 28, 2004, three pages.
GenBank Accession No. BE513408 created Aug. 4, 2000, located at <http://www.ncbi.nlm.nih.gov/entrez/viewer.fcgi?db=nucleotide&val=9720620> last visited on Nov. 15, 2004.
GenBank Accession No. NP_115493 created on Oct. 27, 2004 located at <http://www.ncbi.nlm.nih.gov/entrez/viewer.fcgi?db=protein&val=14149769> last visited on Nov. 28, 2004, two pages.
Harlow et al., (1988). "Immunogenicity" Chapter 5 *In Antibodies, A Laboratory Manual*, Cold Spring Harbor Laboratory Press, pp. 55-137.
Hubert et al., Proc. Natl. Acad. Sci. USA (1999) 96(25):14523-14528.

(Continued)

*Primary Examiner* — Sean Aeder
(74) *Attorney, Agent, or Firm* — Morrison & Foerster LLP

(57) ABSTRACT

A novel gene (designated 121P1F1) and its encoded protein, and variants thereof, are described wherein 121P1F1 exhibits tissue specific expression in normal adult tissue, and is aberrantly expressed in the cancers listed in Table I. Consequently, 121P1F1 provides a diagnostic, prognostic, prophylactic and/or therapeutic target for cancer. The 121P1F1 gene or fragment thereof, or its encoded protein, or variants thereof, or a fragment thereof, can be used to elicit a humoral or cellular immune response; antibodies or T cells reactive with 121P1F1 can be used in active or passive immunization.

20 Claims, 36 Drawing Sheets

OTHER PUBLICATIONS

Klein et al., Nat. Med. (1997) 3:402.
Lazar et al., Mol. Cell. Biol. (1988) 8:1247-1252.
Lerner, Nature (1982) 299:592-596.
Lewin, Genes IV, Oxford University Press (1990) p. 810.
Metzler et al., Nature Structural Biol. (1997) 4:527-531.
Mikayama et al. PNAS USA (1993) 90:10056-10060.
Ngo et al., (1994). *The Protein Folding Problem and Tertiary Structure Prediction* Birkhauser: Boston, MA pp. 433, 492-495.
Non-Final Office Action for U.S. Appl. No. 11/952,930, mailed on Apr. 27, 2009, 9 pages.
Office Action for Canadian Application No. 2,440,147, date mailed on Aug. 2, 2007, 6 pages.
Office Action for European Application No. 02 723 291.7, date mailed on Aug. 17, 2007, 3 pages.
Owens et al., J of Immunol Methods (1994) 168:149-165.
Pinto et al., Clin. Cancer Res. (1996) 2(9):1445-1451.
Reiter et al., Proc. Natl. Acad. Sci. USA (1998) 95:1735.
Shibata et al., (2000). "RIKEN Integrated Sequence Analysis (RISA) System—384-Format Sequencing Pipeline with 384 Multicapillary Sequencer," Genome Research 10:1757-1771.
Skolnick et al., Trends in Biotech. (2000) 18(1):34-39.
Su et al., Proc. Natl. Acad. Sci. USA (1996) 93:7252.
Supplementary Partial European Search Report mailed Oct. 6, 2004, for European Patent Application No. 02723291.7, filed Feb. 28, 2002, 7 pages.
The FANTOM Consortium and the RIKEN Genome Exploration Research Group Phase I & II Team (Dec. 5, 2002). "Analysis of the Mouse Transcriptome Based on Functional Annotation of 60,770 Full-Length cDNAs," Nature 420:563-573.
The RIKEN Genome Exploration Research Group Phase II Team and the FANTOM Consortium (Feb. 8, 2001). "Functional Annotation of a Full-Length Mouse cDNA Collection," Nature 409:685-690.
Tsubouchi et al., (May 2002) "The Mnd1 Protein Forms a Complex with Hop2 to Promote Homologous Chromosome Pairing and Meiotic Double-Strand Break Repair," Molecular and Cellular Biology 22(9):3078-3088.
Database UniProt, EBI accession No. UNIPROT:Q9BWT6 (2001).
Database EPO Proteins, EBI accession No. EPOP:AX974156 (2004).
European Search Report for EP 10011512.0, mailed Feb. 23, 2011, 7 pages.
Huang et al., Genomics (1999) 59(2):178-186.
Schweinfest et al., Gene Analysis Techniques (1990) 7(3):64-70.
Simpson et al., Trends in Biotechnology (2001) 19(10):S40-S48.
Ulrix et al., FEBS Letters (1999) 455(1-2):23-26.

* cited by examiner

Figure 1: 121P1F1 SSH sequence of 254 nucleotides (SEQ ID:1)

```
  1 GATCACAGTC TTTGTATTTT TCTACTTCTG CCTTTAGCTG TTCCCTTTGG TCTCGAAGTG
 61 AAGAAAGCTC TTTTGCTAGC CTGGTTCGCT CTTCCGTTTC ACATCGGCCA ATTTTAGCTT
121 TCTCAATGCT TTTCTGTAGG CTTGCATGCT TTTGACTTCC CTCAGACAAC TGAGATTCCA
181 GAACCTCCAA CTTATGTTTC CTTGCATGAA GAGCTTTACT TGGAAAAGCC CAATAATAAT
241 TAGAAGTTCC GATC
```

Figure 2: The cDNA and Amino Acid Sequence(s)

Figure 2A. The cDNA (SEQ ID. NO:2) and amino acid sequence (SEQ ID. NO:3) of 121P1F1. The start methionine is underlined. The open reading frame extends from nucleic acid 82-699 including the stop codon.

```
  1 ccaaaatcaaacgcgtccgggcctgtccgcccctctccccaagcgcgggccggccagc
  1                     M  S  K  K  G  L  S  A  E  E  K  R
 61 ggaagccctgcgccggcgccATGTCAAAGAAAAAGGACTGAGTGCAGAAGAAAAGAGA
 14  T  R  M  M  E  I  F  S  E  T  K  D  V  F  Q  L  K  D  L  E
121 ACTCGCATGATGGAAATATTTTCTGAAACAAAAGATGTATTTCAATTAAAAGACTTGGAG
 34  K  I  A  P  K  E  K  G  I  T  A  M  S  V  K  E  V  L  Q  S
181 AAGATTGCTCCCAAAGAGAAAGGCATTACTGCTATGTCAGTAAAAGAAGTCCTTCAAAGC
 54  L  V  D  D  G  M  V  D  C  E  R  I  G  T  S  N  Y  Y  W  A
241 TTAGTTGATGATGGTATGGTTGACTGTGAGAGGATCGGAACTTCTAATTATTATTGGGCT
 74  F  P  S  K  A  L  H  A  R  K  H  K  L  E  V  L  E  S  Q  L
301 TTTCCAAGTAAAGCTCTTCATGCAAGGAAACATAAGTTGGAGGTTCTGGAATCTCAGTTG
 94  S  E  G  S  Q  K  H  A  S  L  Q  K  S  I  E  K  A  K  I  G
361 TCTGAGGGAAGTCAAAAGCATGCAAGCCTACAGAAAAGCATTGAGAAAGCTAAAATTGGC
114  R  C  E  T  E  E  R  T  R  L  A  K  E  L  S  S  L  R  D  Q
421 CGATGTGAAACGGAAGAGCGAACCAGGCTAGCAAAAGAGCTTTCTTCACTTCGAGACCAA
134  R  E  Q  L  K  A  E  V  E  K  Y  K  D  C  D  P  Q  V  V  E
481 AGGGAACAGCTAAAGGCAGAAGTAGAAAAATACAAAGACTGTGATCCGCAAGTTGTGGAA
154  E  I  R  Q  A  N  K  V  A  K  E  A  A  N  R  W  T  D  N  I
541 GAAATACGCCAAGCAAATAAAGTAGCCAAAGAAGCTGCTAACAGATGGACTGATAACATA
174  F  A  I  K  S  W  A  K  R  K  F  G  F  E  E  N  K  I  D  R
601 TTCGCAATAAAATCTTGGGCCAAAAGAAAATTTGGGTTTGAAGAAAATAAAATTGATAGA
194  T  F  G  I  P  E  D  F  D  Y  I  D  *
661 ACTTTTGGAATTCCAGAAGACTTTGACTACATAGACTAAAatattccatggtggtgaagg
721 atgtacaagcttgtgaatatgtaaattttaaactattatctaactaagtgtactgaattg
781 tcgtttgcctgtaactgtgtttatcatttattaatgttaaataaagtgtaaaatgcaaa
841 aaaaaaaaaaaaaaaaaaaaaaaaaa
```

Figure 2B. The cDNA (SEQ ID. NO:4) and amino acid sequence (SEQ ID. NO:5) of 121P1F1 splice variant 1A. The start methionine is underlined. The open reading frame extends from nucleic acid 82-462 including the stop codon.

```
   1 ccaaaatcaaacgcgtccgggcctgtccgcccctctcccaagcgcgggccggccagc
   1                     M   S   K   K   G   L   S   A   E   E   K   R
  61 ggaagccctgcgcccgcgccATGTCAAAGAAAAAGGACTGAGTGCAGAAGAAAGAGA
  14 T   R   M   M   E   I   F   S   E   T   K   D   V   F   Q   L   K   D   L   E
 121 ACTCGCATGATGGAAATATTTTCTGAAACAAAAGATGTATTTCAATTAAAAGACTTGGAG
  34 K   I   A   P   K   E   G   I   T   A   M   S   V   K   E   V   L   Q   S
 181 AAGATTGCTCCCAAAGAGAAAGGCATTACTGCTATGTCAGTAAAAGAAGTCCTTCAAAGC
  54 L   V   D   D   G   M   V   D   C   E   R   I   G   T   S   N   Y   Y   W   A
 241 TTAGTTGATGATGGTATGGTTGACTGTGAGAGGATCGGAACTTCTAATTATTATTGGGCT
  74 F   P   S   K   A   L   H   A   R   K   H   K   L   E   V   L   E   S   Q   D
 301 TTTCCAAGTAAAGCTCTTCATGCAAGGAAACATAAGTTGGAGGTTCTGGAATCTCAGGAC
  94 P   G   C   C   F   H   E   I   I   K   V   S   Y   Y   R   K   F   W   L   G
 361 CCTGGCTGCTGCTTCCATGAAATAATTAAAGTCTCCTATTATAGAAAATTCTGGCTGGGC
 114 A   V   A   H   A   C   N   P   S   T   L   G   G   *
 421 GCAGTGGCTCACGCCTGTAATCCCAGCACTTTGGGAGGCTGAggcgggcagatcacgagg
 481 tgactttccccaccccacatgaagtgcaagatggagttgtctgagggaagtcaaagc
 541 atgcaagcctacagaaaagcattgagaaagctaaaattggccgatgtgaaacggaagagc
 601 gaaccaggctagcaaaagagctttcttcacttcgagaccaaagggaacagctaaaggcag
 661 aagtagaaaatacaaagactgtgatccgcaagttgtggaagaaatacgccaagcaaata
 721 aagtagccaaagaagctgctaacagatggactgataacatattcgcaataaaatcttggg
 781 ccaaaagaaatttgggtttgaagaaataaaattgatagaacttttggaattccagaag
 841 actttgactacatagactaaaatattccatggtggtgaaggatgtacaagcttgtgaata
 901 tgtaaattttaaactattatctaactaagtgtactgaattgtcgtttgcctgtaactgtg
 961 tttatcatttattaatgttaaataaagtgtaaatgcaaaaaaaaaaaaaaaaaaaaaaa
1021 aaaaaaaa
```

Figure 2C. The cDNA (SEQ ID. NO:6) and amino acid sequence (SEQ ID.NO:7) of 121P1F1 splice variant 1B. The start methionine is underlined. The open reading frame extends from nucleic acid 501-860 including the stop codon.

```
   1 ccaaaatcaaacgcgtccgggcctgtcccgcccctctcccaagcgcgggcccggccagc
  61 ggaagccctgcgccgcgccatgtcaagaaaaaggactgagtgcagaagaaaagaga
 121 actcgcatgatggaaatatttctgaaacaaaagatgtatttcaattaaaagacttggag
 181 aagattgctcccaagagaaaggcattactgctatgtcagtaaagaagtccttcaaagc
 241 ttagttgatgatggtatggttgactgtgagaggatcggaacttctaattattattgggct
 301 tttccaagtaaagctcttcatgcaaggaaacataagttggaggttctggaatctcaggac
 361 cctggctgctgcttccatgaaataattaaagtctcctattatagaaaattctggctgggc
 421 gcagtggctcacgcctgtaatcccagcactttgggaggctgaggcgggcagatcacgagg
                     1         M  K  C  M  E  L  S  E  G  S  Q  K  H
 481 tgactttccccacccccacATGAAGTGCAAGATGGAGTTGTCTGAGGGAAGTCAAAAGC
     15  A  S  L  Q  K  S  I  E  K  A  K  I  G  R  C  E  T  E  E  R
 541 ATGCAAGCCTACAGAAAAGCATTGAGAAAGCTAAAATTGGCCGATGTGAAACGGAAGAGC
     35  T  R  L  A  K  E  L  S  S  L  R  D  Q  R  E  Q  L  K  A  E
 601 GAACCAGGCTAGCAAAAGAGCTTTCTTCACTTCGAGACCAAAGGGAACAGCTAAAGGCAG
     55  V  E  K  Y  K  D  C  D  P  Q  V  V  E  E  I  R  Q  A  N  K
 661 AAGTAGAAAAATACAAAGACTGTGATCCGCAAGTTGTGGAAGAAATACGCCAAGCAAATA
     75  V  A  K  E  A  A  N  R  W  T  D  N  I  F  A  I  K  S  W  A
 721 AAGTAGCCAAAGAAGCTGCTAACAGATGGACTGATAACATATTCGCAATAAAATCTTGGG
     95  K  R  K  F  G  F  E  E  N  K  I  D  R  T  F  G  I  P  E  D
 781 CCAAAAGAAAATTTGGGTTTGAAGAAAATAAAATTGATAGAACTTTTGGAATTCCAGAAG
    115  F  D  Y  I  D  *
 841 ACTTTGACTACATAGACTAAaatattccatggtggtgaaggatgtacaagcttgtaata
 901 tgtaaattttaaactattatctaactaagtgtactgaattgtcgtttgcctgtaactgtg
 961 tttatcattttattaatgttaaataaagtgtaaatgcaaaaaaaaaaaaaaaaaaaaa
1021 aaaaaaaa
```

Figure 2D. The cDNA (SEQ ID. NO:8) and amino acid sequence (SEQ ID. NO:9) of 121P1F1 splice variant 2. The start methionine is underlined. The open reading frame extends from nucleic acid 82-450 including the stop codon.

```
  1 ccaaaatcaaacgcgtccgggcctgtccgcccctctcccaagcgcgggcccggccagc
  1                    M   S   K   K   K   G   L   S   A   E   E   K   R
 61 ggaagccoctgcgccgcgccATGTCAAAGAAAAAGGACTGAGTGCAGAAGAAAAGAGA
 14  T   R   M   M   E   I   F   S   E   T   K   D   V   F   Q   L   K   D   L   E
121 ACTCGCATGATGGAAATATTTCTGAAACAAAAGATGTATTTCAATTAAAAGACTTGGAG
 34  K   I   A   P   K   E   K   G   I   T   A   M   S   V   K   E   V   L   Q   S
181 AAGATTGCTCCCAAAGAGAAAGGCATTACTGCTATGTCAGTAAAAGAAGTCCTTCAAAGC
 54  L   V   D   D   G   M   V   D   C   E   R   I   G   T   S   N   Y   Y   W   A
241 TTAGTTGATGATGGTATGGTTGACTGTGAGAGGATCGGAACTTCTAATTATTATTGGGCT
 74  F   P   S   K   A   L   R   A   R   K   H   K   L   E   V   L   E   S   Q   L
301 TTTCCAAGTAAAGCTCTTCATGCAAGGAAACATAAGTTGGAGGTTCTGGAATCTCAGTTG
 94  S   E   G   S   Q   K   H   A   S   L   Q   K   S   I   E   K   A   K   I   G
361 TCTGAGGGAAGTCAAAAGCATGCAAGCCTACAGAAAAGCATTGAGAAAGCTAAAATTGGC
114  R   C   E   T   A   K   Q   I   K   *
421 CGATGTGAAACGGCCAAGCAAATAAAGTAGccaaagaagctgctaacagatggactgata
481 acatattcgcaataaaatcttgggccaaaagaaaatttgggtttgaagaaaataaaattg
541 atagaacttttggaattccagaagactttgactacatagactaaaatattccatggtggt
601 gaaggatgtacaagcttgtgaatatgtaaattttaaactattatctaactaagtgtactg
661 aattgtcgtttgcctgtaactgtgtttatcattttattaatgttaaataaagtgtaaaat
721 gcaaaaaaaaaaaaaaaaaaaaaaaaaaa
```

Figure 2E. The cDNA (SEQ ID. NO:10) and amino acid sequence (SEQ ID. NO:11) of 121P1F1 splice variant 3. The start methionine is underlined. The open reading frame extends from nucleic acid 82-654 including the stop codon.

```
  1 ccaaaatcaaacgcgtccgggcctgtccgcccctctcccaagcgcgggcccggccagc
  1                       M  S  K  K  G  L  S  A  E  E  K  R
 61 ggaagccctgcgccgcgccATGTCAAAGAAAAAGGACTGAGTGCAGAAGAAAAGAGA
 14 T  R  M  M  E  I  F  S  E  T  K  D  V  F  Q  L  K  D  L  E
121 ACTCGCATGATGGAAATATTTTCTGAAACAAAAGATGTATTTCAATTAAAAGACTTGGAG
 34 K  I  A  P  K  E  K  G  I  T  A  M  S  V  K  E  V  L  Q  S
181 AAGATTGCTCCCAAAGAGAAAGGCATTACTGCTATGTCAGTAAAAGAAGTCCTTCAAAGC
 54 L  V  D  D  G  M  V  D  C  E  R  I  G  T  S  N  Y  Y  W  A
241 TTAGTTGATGATGGTATGGTTGACTGTGAGAGGATCGGAACTTCTAATTATTATTGGGCT
 74 F  P  S  K  A  L  H  A  R  K  H  K  L  E  V  L  E  S  Q  L
301 TTTCCAAGTAAAGCTCTTCATGCAAGGAAACATAAGTTGGAGGTTCTGGAATCTCAGTTG
 94 S  E  G  S  Q  K  H  A  S  L  Q  K  S  I  E  K  A  K  I  G
361 TCTGAGGGAAGTCAAAAGCATGCAAGCCTACAGAAAAGCATTGAGAAAGCTAAAATTGGC
114 R  C  E  T  E  E  R  T  R  L  A  K  E  L  S  S  L  R  D  Q
421 CGATGTGAAACGGAAGAGCGAACCAGGCTAGCAAAAGAGCTTTCTTCACTTCGAGACCAA
134 R  E  Q  L  K  A  E  V  E  K  Y  K  D  C  D  P  Q  V  V  E
481 AGGGAACAGCTAAAGGCAGAAGTAGAAAAATACAAAGACTGTGATCCGCAAGTTGTGGAA
154 E  I  H  N  I  F  A  I  K  S  W  A  K  R  K  F  G  F  E  E
541 GAAATACATAACATATTCGCAATAAAATCTTGGGCCAAAAGAAAATTTGGGTTTGAAGAA
174 N  K  I  D  R  T  F  G  I  P  E  D  F  D  Y  I  D  *
601 AATAAAATTGATAGAACTTTTGGAATTCCAGAAGACTTTGACTACATAGACTAAaatatt
661 ccatggtggtgaaggatgtacaagcttgtgaatatgtaaattttaaactattatctaact
721 aagtgtactgaattgtcgtttgcctgtaactgtgtttatcattttattaatgttaaataa
781 agtgtaaaatgcaaaaaaaaaaaaaaaaaaaaaaaaaaaaa
```

Figure 2F. The cDNA (SEQ ID. NO:12) and amino acid sequence (SEQ ID. NO:13) of 121P1F1 splice variant 4. The start methionine is underlined. The open reading frame extends from nucleic acid 281-853 including the stop codon.

```
   1 gttttctgtattgtaatatgtagagcacattccagaactgctcagtttcgagttacctaa
  61 tggatcttcactgtgtgccaattagtcgatttctgtgaaaacgccccggtttctgccaaa
 121 gggcaggagtcgctgctcttgtgcgggtgctgctggttgtgtagggcgctgttgctttt
 181 ttaaggacgctctgcactgaattaggcttcctcgtgggtcatgatcagttaagtcctgtc
   1                                                  M  M  E  I  F  S  E
 241 aaagaaaaaggactgagtgcagaagaaaagagaactcgcATGATGGAAATATTTTCTGA
   8  T  K  D  V  F  Q  L  K  D  L  E  K  I  A  P  K  E  K  G  I
 301 AACAAAGATGTATTTCAATTAAAAGACTTGGAGAAGATTGCTCCCAAAGAGAAAGGCAT
  28  T  A  M  S  V  K  E  V  L  Q  S  L  V  D  D  G  M  V  D  C
 361 TACTGCTATGTCAGTAAAAGAAGTCCTTCAAAGCTTAGTTGATGATGGTATGGTTGACTG
  48  E  R  I  G  T  S  N  Y  Y  W  A  F  P  S  K  A  L  H  A  R
 421 TGAGAGGATCGGAACTTCTAATTATTATTGGGCTTTTCCAAGTAAAGCTCTTCATGCAAG
  68  K  H  K  L  E  V  L  E  S  Q  L  S  E  G  S  Q  K  H  A  S
 481 GAAACATAAGTTGGAGGTTCTGGAATCTCAGTTGTCTGAGGGAAGTCAAAAGCATGCAAG
  88  L  Q  K  S  I  E  K  A  K  I  G  R  C  E  T  E  E  R  T  R
 541 CCTACAGAAAAGCATTGAGAAAGCTAAAATTGGCCGATGTGAAACGGAAGAGCGAACCAG
 108  L  A  K  E  L  S  S  L  R  D  Q  R  E  Q  L  K  A  E  V  E
 601 GCTAGCAAAAGAGCTTTCTTCACTTCGAGACCAAAGGGAACAGCTAAAGGCAGAAGTAGA
 128  K  Y  K  D  C  D  P  Q  V  V  E  E  I  R  Q  A  N  K  V  A
 661 AAAATACAAAGACTGTGATCCGCAAGTTGTGGAAGAAATACGCCAAGCAAATAAAGTAGC
 148  K  E  A  A  N  R  W  T  D  N  I  F  A  I  K  S  W  A  K  R
 721 CAAAGAAGCTGCTAACAGATGGACTGATAACATATTCGCAATAAAATCTTGGGCCAAAAG
 168  K  F  G  F  E  E  N  K  I  D  R  T  F  G  I  P  E  D  F  D
 781 AAAATTTGGGTTTGAAGAAAATAAAATTGATAGAACTTTTGGAATTCCAGAAGACTTTGA
 188  Y  I  D  *
 841 CTACATAGACTAAaatattccatggtggtgaaggatgtacaagcttgtgaatatgtaaat
 901 tttaaactattatctaactaagtgtactgaattgtcgtttgcctgtaactgtgtttatca
 961 ttttattaatgttaaataaagtgtaaaatgcagatgttcttcacccttttggtagaaca
1021 aaagcaggatgataaccatatcccccagtgctcatcaaagtaggacactaaaaatccat
1081 ccatctcagtcaaagtcgagcggcgcgaatttagtagtagtagcggccgctctagagga
1141 tccaagcttacgtacgcgtgcatgcgacgtcatagctcttctatagtgtcacctaaattc
1201 aagtt
```

Figure 3:

Figure 3A. Amino acid sequence of 121P1F1 (SEQ ID. NO:14). The 121P1F1 protein has 205 amino acids.

```
  1 MSKKKGLSAE EKRTRMMEIF SETKDVFQLK DLEKIAPKEK GITAMSVKEV LQSLVDDGMV
 61 DCERIGTSNY YWAFPSKALH ARKHKLEVLE SQLSEGSQKH ASLQKSIEKA KIGRCETEER
121 TRLAKELSSL RDQREQLKAE VEKYKDCDPQ VVEEIRQANK VAKEAANRWT DNIFAIKSWA
181 KRKFGFEENK IDRTFGIPED FDYID
```

Figure 3B. Amino acid sequence of 121P1F1 splice variant 1A (SEQ ID. NO:15). The 121P1F1 splice variant 1A protein has 126 amino acids.

```
  1 MSKKKGLSAE EKRTRMMEIF SETKDVFQLK DLEKIAPKEK GITAMSVKEV LQSLVDDGMV
 61 DCERIGTSNY YWAFPSKALH ARKHKLEVLE SQDPGCCFHE IIKVSYYRKF WLGAVAHACN
121 PSTLGG
```

Figure 3C. Amino acid sequence of 121P1F1 splice variant 1B (SEQ ID. NO:16). The 121P1F1 splice variant 1B protein has 119 amino acids.

```
  1 MKCKMELSEG SQKHASLQKS IEKAKIGRCE TEERTRLAKE LSSLRDQREQ LKAEVEKYKD
 61 CDPQVVEEIR QANKVAKEAA NRWTDNIFAI KSWAKRKFGF EENKIDRTFG IPEDFDYID
```

Figure 3D. Amino acid sequence of 121P1F1 splice variant 2 (SEQ ID. NO:17). The 121P1F1 splice variant 2 protein has 122 amino acids.

```
  1 MSKKKGLSAE EKRTRMMEIF SETKDVFQLK DLEKIAPKEK GITAMSVKEV LQSLVDDGMV
 61 DCERIGTSNY YWAFPSKALH ARKHKLEVLE SQLSEGSQKH ASLQKSIEKA KIGRCETAKQ
121 IK
```

Figure 3E. Amino acid sequence of 121P1F1 splice variant 3 (SEQ ID. NO:18).
The 121P1F1 splice variant 3 protein has 190 amino acids.

```
  1 MSKKKGLSAE EKRTRMMEIF SETKDVFQLK DLEKIAPKEK GITAMSVKEV LQSLVDDGMV
 61 DCERIGTSNY YWAFPSKALH ARKHKLEVLE SQLSEGSQKH ASLQKSIEKA KIGRCETEER
121 TRLAKELSSL RDQREQLKAE VEKYKDCDPQ VVEEIHNIFA IKSWAKRKFG FEENKIDRTF
181 GIPEDFDYID
```

Figure 3F. Amino acid sequence of 121P1F1 splice variant 4 (SEQ ID. NO:19).
The 121P1F1 splice variant 4 protein has 190 amino acids.

```
  1 MMEIFSETKD VFQLKDLEKI APKEKGITAM SVKEVLQSLV DDGMVDCERI GTSNYYWAFP
 61 SKALHARKHK LEVLESQLSE GSQKHASLQK SIEKAKIGRC ETEERTRLAK ELSSLRDQRE
121 QLKAEVEKYK DCDPQVVEEI RQANKVAKEA ANRWTDNIFA IKSWAKRKFG FEENKIDRTF
181 GIPEDFDYID
```

Figure 4A

Amino Acid Alignments.

Alignment of 121P1F1 protein and its variants.

A) CLUSTAL W alignment of 121P1F1 and variants 1-3. (SEQ ID NOS: 3, 5, 7, 9 and 11)

```
121P1F01           ------------MSKKKGLSAEEKRTRMMEIFSETKDVFQLKDLEKIAPKEKGITAMSVKE
sv1A               ------------MSKKKGLSAEEKRTRMMEIFSETKDVFQLKDLEKIAPKEKGITAMSVKE
sv1B               ------------MKCKMELSEGSQKHASLQKSIEKAKIGRCETEERTRLAKELSSLRDQRE
sv-2               ------------MSKKKGLSAEEKRTRMMEIFSETKDVFQLKDLEKIAPKEKGITAMSVKE
sv-3               ------------MSKKKGLSAEEKRTRMMEIFSETKDVFQLKDLEKIAPKEKGITAMSVKE

121P1F01           VLQSLVDDGMVDCERIGTSNYYWAFPSKALHARKHKLEVLESQLSEGSQK-HASLQKS-I
sv1A               VLQSLVDDGMVDCERIGTSNYYWAFPSKALHARKHKLEVLESQDP-GCCF-HEIIKVSYY
sv1B               QLKAEVEK-YKDCDPQVVEEIRQANKVAKEAANRWTDNIFAIKSWAKRKFGFEENKID---
sv-2               VLQSLVDDGMVDCERIGTSNYYWAFPSKALHARKHKLEVLESQLSEGSQK-HASLQKS-I
sv-3               VLQSLVDDGMVDCERIGTSNYYWAFPSKALHARKHKLEVLESQLSEGSQK-HASLQKS-I

121P1F01           EKAKIGRCETEERTRLAKELSSLRDQREQLKAEVEKYKDCDPQVVEEIRQANKVAKEAAN
sv1A               PKFWLGAVAHACNPSTLGG-----------------------------------------
sv1B               RTFGIPEDFDYID-----------------------------------------------
sv-2               EKAKIGRCETAKQIK---------------------------------------------
sv-3               EKAKIGRCETEERTRLAKELSSLRDQREQLKAEVEKYKDCDPQVVEEIHNIFAIKSWAKR

121P1F01           RWTDNIFAIKSWAKRKFGFEENKIDRTFGIPEDFDYID
sv1A               --------------------------------------
sv1B               --------------------------------------
sv-2               --------------------------------------
sv-3               KFGFEENKIDRTFGIPEDFDYID---------------
```

Figure 4B

B) Clustal alignment of 121P1F1 and variants 1A and 4 (SEQ ID NOS 3, 13 and 5)

```
                   1            15 16           30 31           45 46           60 61           75 76           90
1. 121P1F01        MSKKKGLSAEEKRTR MMEIFSETKDVFQLK DLEKIAPKEKGITAM SVKEVLQSLVDDGMV DCERIGTSNYYWAFP SKALHARKHKLEVLE
2. sv-4            --------------- MMEIFSETKDVFQLK DLEKIAPKEKGITAM SVKEVLQSLVDDGMV DCERIGTSNYYWAFP SKALHARKHKLEVLE
3. sv-1A           MSKKKGLSAEEKRTR MMEIFSETKDVFQLK DLEKIAPKEKGITAM SVKEVLQSLVDDGMV DCERIGTSNYYWAFP SKALHARKHKLEVLE 91           105 106          120 121          135 136          150 151          165 166          180
1. 121P1F01        SQLSEGSQKHASLQK SIEKAKIGRCETEER TRLAKELSSLRDQRE QLKAEVEKYKDCDPQ VVEEIRQANKVAKEA ANRWTDNIFAIKSWA
2. sv-4            SQLSEGSQKHASLQK SIEKAKIGRCETEER TRLAKELSSLRDQRE QLKAEVEKYKDCDPQ VVEEIRQANKVAKEA ANRWTDNIFAIKSWA
3. sv-1A           SQDPGCCFHEIIKVS YYPKFWLG-------- --------------- ---------AVAHACNPS TLGG----------- ---------------

181          195 196          210 211
1. 121P1F01        KRKFGFEENKIDRTF GIPEDFDYID      205
2. sv-4            KRKFGFEENKIDRTF GIPEDFDYID      190
3. sv-1A           --------------- ----------      126
```

Figure 4C

C) Alignment of 121P1F1 and variant 1 (SEQ ID NO:20) with human GAJ (SEQ ID NO:21)
Identities = 205/205 (100%), Positives = 205/205 (100%)

```
121P1:  1   MSKKKGLSAEEKRTRMMEIFSETKDVFQLKDLEKIAPKEKGITAMSVKEVLQSLVDDGMV  60
            MSKKKGLSAEEKRTRMMEIFSETKDVFQLKDLEKIAPKEKGITAMSVKEVLQSLVDDGMV
Sbjct:  1   MSKKKGLSAEEKRTRMMEIFSETKDVFQLKDLEKIAPKEKGITAMSVKEVLQSLVDDGMV  60

121P1:  61  DCERIGTSNYYWAFPSKALHARKHKLEVLESQLSEGSQKHASLQKSIEKAKIGRCETEER  120
            DCERIGTSNYYWAFPSKALHARKHKLEVLESQLSEGSQKHASLQKSIEKAKIGRCETEER
Sbjct:  61  DCERIGTSNYYWAFPSKALHARKHKLEVLESQLSEGSQKHASLQKSIEKAKIGRCETEER  120

121P1:  121 TRLAKELSSLRDQREQLKAEVEKYKDCDPQVVEEIRQANKVAKEAANRWTDNIFAIKSWA  180
            TRLAKELSSLRDQREQLKAEVEKYKDCDPQVVEEIRQANKVAKEAANRWTDNIFAIKSWA
Sbjct:  121 TRLAKELSSLRDQREQLKAEVEKYKDCDPQVVEEIRQANKVAKEAANRWTDNIFAIKSWA  180

121P1:  181 KRKFGFEENKIDRTFGIPEDFDYID  205
            KRKFGFEENKIDRTFGIPEDFDYID
Sbjct:  181 KRKFGFEENKIDRTFGIPEDFDYID  205
```

Figure 4D

D) Alignment of 121P1F1 and variant 1 (SEQ ID NO:22) with closest mouse homolog, a hypothetical 24.2 KDa protein. (SEQ ID NO:23)
Identities = 183/205 (89%), Positives = 193/205 (93%)

```
121P1: 1    MSKKKGLSAEEKRTRMMEIFSETKDVFQLKDLEKIAPKEKGITAMSVKEVLQSLVDDGMV 60
            MSKK+GLS EEKRTRMMEIF ETKDVFQLKDLEK+APKEKGITAMSVKEVLQSLVDDGMV
Sbjct: 1    MSKKRGLSGEEKRTRMMEIFFETKDVFQLKDLEKLAPKEKGITAMSVKEVLQSLVDDGMV 60

121P1: 61   DCERIGTSNYYWAFPSKALHARKHKLEVLESQLSEGSQKHASLQKSIEKAKIGRCETEER 120
            DCERIGTSNYYWAFPSKALHARK KLE L SQLSEGSQKHA LQKSIEKA++GR ETEER
Sbjct: 61   DCERIGTSNYYWAFPSKALHARKRKLEALNSQLSEGSQKHADLQKSIEKARVGRQETEER 120

121P1: 121  TRLAKELSSLPDQREQLKAEVEKYKDCDPQVVEEIRQANKVAKEAANRWTDNIFAIKSWA 180
               LAKEL S RDQR+QLKAEVEKY++CDPQVVEEIR+ANKVAKEAANRWTDNIFAIKSWA
Sbjct: 121  AMLAKELFSFRDQRQQLKAEVEKYRECDPQVVEEIREANKVAKEAANRWTDNIFAIKSWA 180

121P1: 181  KRKFGFEENKIDRTFGIPEDFDYID 205
            KRKFGFEE+KID+ FGIPEDFDYID
Sbjct: 181  KRKFGFEESKIDKNFGIPEDFDYID 205
```

Figure 4E

E) Alignment of 121P1F1 and variant 1 (SEQ ID NO:24)
  with>gi|1175412|sp|Q09739|YA53_SCHPO HYPOTHETICAL 24.2 KD
  PROTEIN C13A11.03 IN CHROMOSOME I (SEQ ID NO:25)
    gi|7490680|pir||T37610 hypothetical coiled-coil protein -
    fission yeast
    (Schizosaccharomyces pombe)
     gi|984224|emb|CAA90804.1| (Z54096) hypothetical coiled-coil
    protein [Schizosaccharomyces pombe]
         Length = 210

Score =  121 bits (305), Expect = 5e-27
 Identities = 81/202 (40%), Positives = 115/202 (56%), Gaps =
6/202 (2%)

Query: 5
KGLSAEEKRTRMMEIFSETKDVFQLKDLEKIAPKEKGITAMSVKEVLQSLVDDGMVDCER 64
           KGLS EKR R+  IF ++KD FQLK++EK+  K K I
+VK+VLQSLVDD +V E+
Sbjct: 4    KGLSLAEKRRRLEAIFHDSKDFFQLKEVEKLGSK-
KQIVLQTVKDVLQSLVDDNIVKTEK 62

Query: 65  IGTSNYYWAFPSKALHARKHKLEVLESQLSEGSQKHASLQKSIEKAKIGR--
--CETEER 120
           IGTSNYYW+FPS A  +R+  L  L++QL +  QK  +L ++I    K  R
E +
Sbjct: 63
IGTSNYYWSFPSDAKRSRESVLGSLQAQLDDLKQKSKTLDENISFEKSKRDNEGTENDAN
122

Query: 121
TRLAKELSSLRDQREQLKAEVEKYKDCDPQVVEEIRQANKVAKEAANRWTDNIFAIKSWA
180
             + L +   + + LK ++     C+P+  E   + K   EAAN WTD
I  + ++
Sbjct: 123
QYTLELLHAKESELKLLKTQLSNLNHCNPETFELKNENTKKYMEAANLWTDQIHTLIAFC
182

Query: 181 KRKFGFEENKIDRTFGIPEDFD 202
            R  G + N+I    IPED D
Sbjct: 183 -RDMGADTNQIREYCSIPEDLD 203

121P1F1 Hydrophilicity profile
(Hopp T.P., Woods K.R., 1981.
Proc. Natl. Acad. Sci. U.S.A. 78:3824-3828)

121P1F1 variant 1a Hydrophilicity profile
(Hopp T.P., Woods K.R., 1981.
Proc. Natl. Acad. Sci. U.S.A. 78:3824-3828)

121P1F1 Hydropathicity Profile
(Kyte J., Doolittle R.F., 1982. J. Mol. Biol. 157:105-132)

121P1F1 variant 1a Hydropathicity Profile
(Kyte J., Doolittle R.F., 1982. J. Mol. Biol. 157:105-132)

121P1F1 % Accessible Residues Profile
(Janin J., 1979. Nature 277:491-492)

121P1F1 variant 1a % Accessible Residues Profile
(Janin J., 1979. Nature 277:491-492)

121P1F1 Average Flexibility Profile
(Bhaskaran R., Ponnuswamy P.K., 1988.
Int. J. Pept. Protein Res. 32:242-255)

121P1F1 variant 1a Average Flexibility Profile
(Bhaskaran R., Ponnuswamy P.K., 1988.
Int. J. Pept. Protein Res. 32:242-255)

121P1F1 Beta-turn Profile
(Deleage, G., Roux B. 1987. Protein Engineering 1:289-294)

121P1F1 variant 1a Beta-turn Profile
(Deleage, G., Roux B. 1987. Protein Engineering 1:289-294)

Note: Numbers in "()" correspond to those of the original sequence. Black box shows the same sequence as the original one. SNPs are indicated above the box.

Note: Numbers in "()" correspond to those of the original sequence. Black box shows the same sequence as the original one. Single amino acid variations are indicated above the box.

Specific recognition of 121P1F1 antigen by anti-121P1F1 pAb

1. Pre-immune         1:100
2. Pre-immune         1:1,600
3. Anti-121P1F1 serum 1:100
4. Anti-121P1F1 serum 1:400
5. Anti-121P1F1 serum 1:1,600

Expression of 121P1F1 in various cancer cells

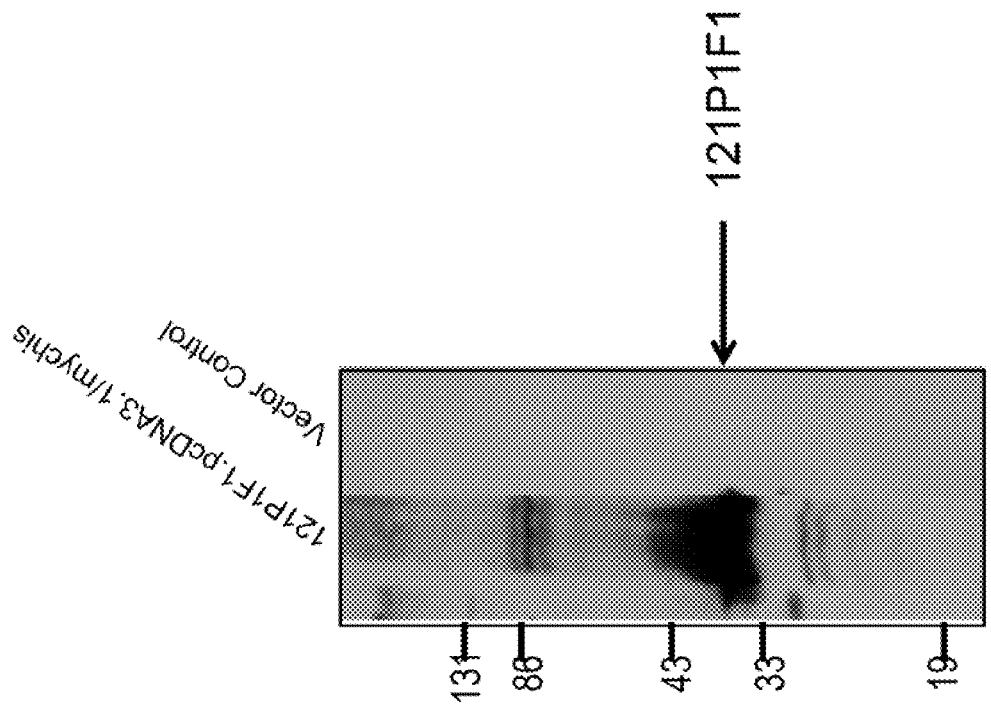
Figure 14 Expression of epitope tagged 121P1F1 in 293T cells

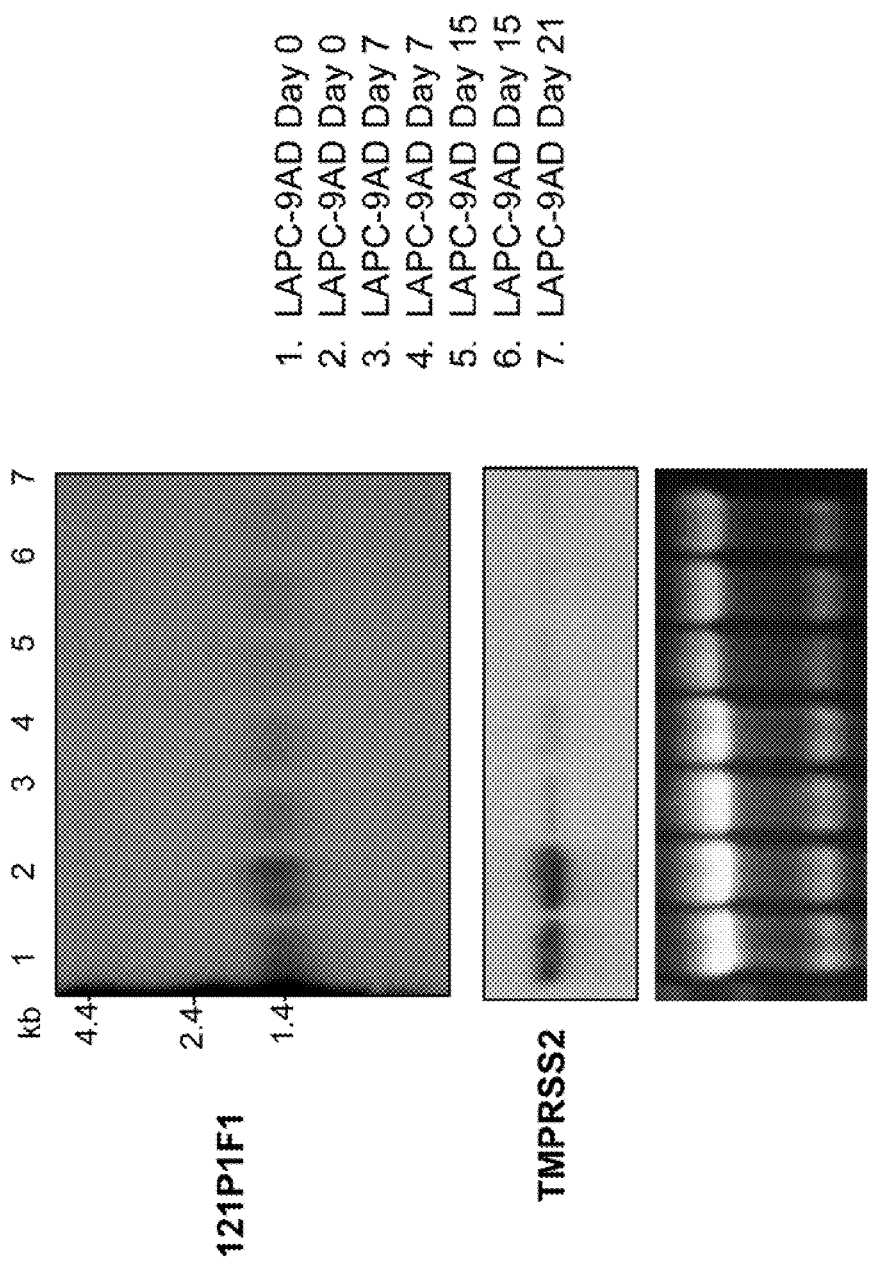
Figure 15  121P1F1 Androgen Regulation *In Vivo*

Figure 16A

Secondary structure prediction of 121P1F1

```
         10        20        30        40        50        60        70
          |         |         |         |         |         |         |
MSKKKGLSAEEKRTRMMEIFSETKDVFQLKDLEKIAPKEKGITAMSVKEVLQSLVDDGMVDCERIGTSNY
ccccccchhhhhhhhhhhhhhchhhhhhhhhhcccccchhhhhhhhhhhhhhcccccchhcccccccc
YWAFPSKALHARKHKLEVLESQLSEGSQKHASLQKSIEKAKIGRCETEERTRLAKELSSLRDQREQLKAE
eeeccchhhhhhhhhhhccccchhhhhhhhhhhccccchhhhhhhhhhhhhhccccchhhhhhhhh
VEKYKDCDPQVVEEIRQANKVAKEAANRWTDNIFAIKSWAKRKFGFEENKIDRTFGIPEDEFDYID
hhhhccccccchhhhhhhhhhhhhhhhhhhhhhhhhhhhhhhhhccchccccccccccccccccc
```

Alpha helix (h) : 61.95%   Extended strand (e) : 1.95%   Random coil (c) : 36.10%

Figure 16B

Secondary structure prediction of variant 1a

```
         10        20        30        40        50        60        70
          |         |         |         |         |         |         |
MSKKKGLSAEEKRTRMMEIFSETKDVFQLKDLEKIAPKEKGITAMSVKEVLQSLVDDGMVDCERIGTSNY
ccccccchhhhhhhhhhhhhhhhhhhhchhhhhhhhhccccchhhhhhhhhhhhhcccchhccccccc
YWAFPSKALHARKHKLEVLESQDPGCCFHEIIKVSYYRKFWLGAVAHACNPSTLGG
eeecccchhhhccccceeecccccccchhhhhhhhhhhhhhhcceeccccccccc
```

Alpha helix (h) : 50.79%    Extended strand (e) : 7.94%    Random coil (c) : 41.27%

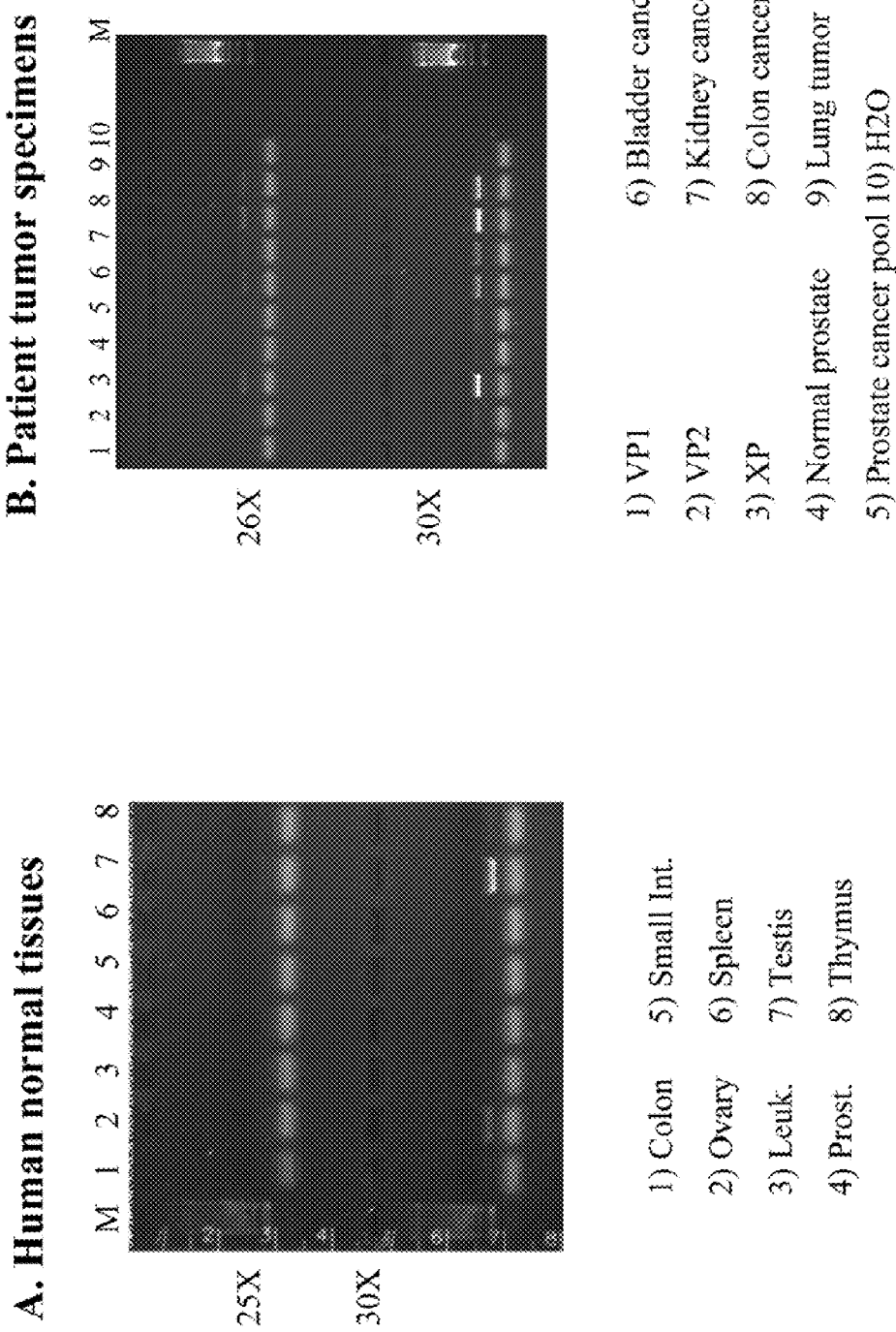
Figure 17 Expression of 121P1F1 by RT-PCR

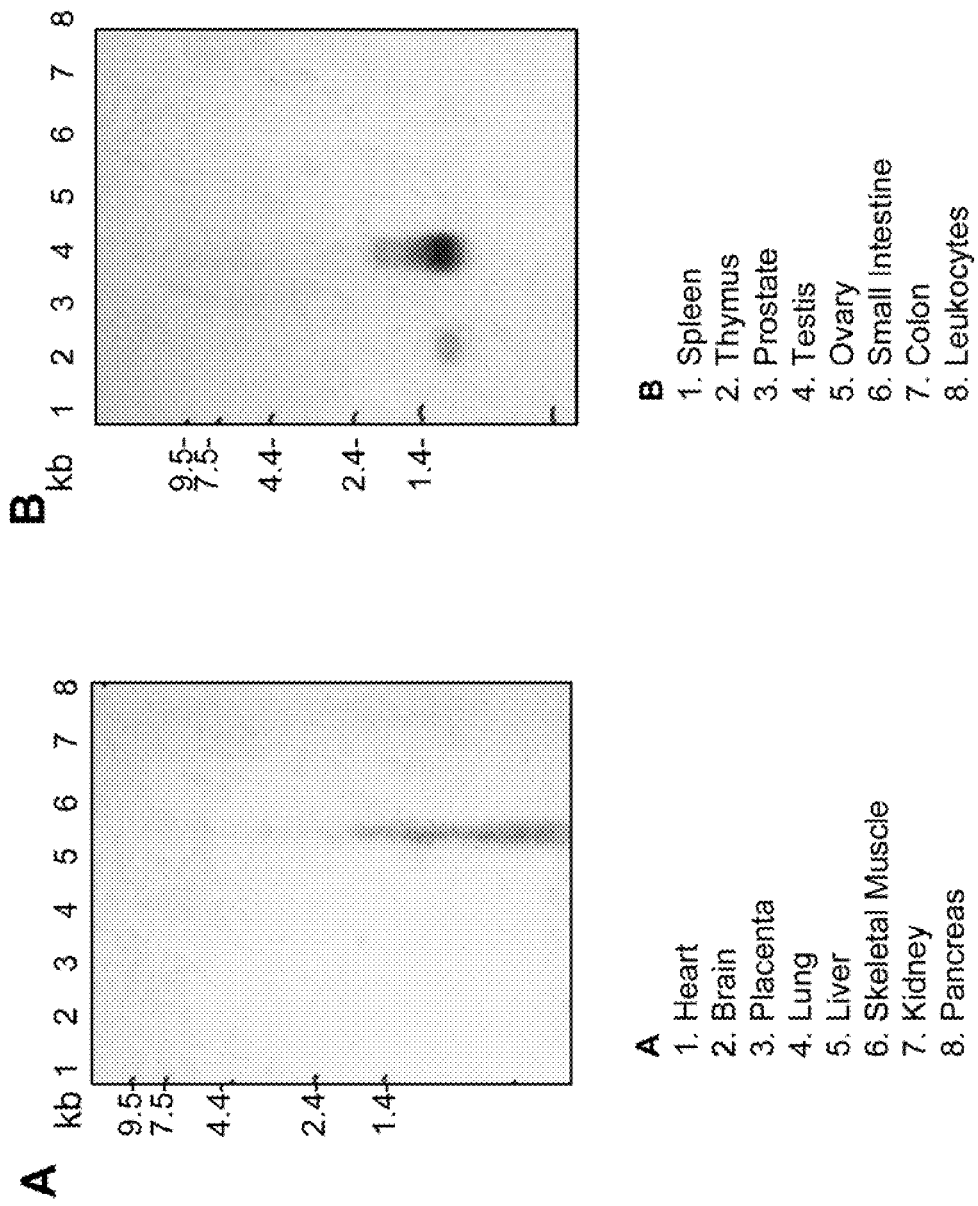
Figure 18 Expression of 121P1F1 in normal human tissues

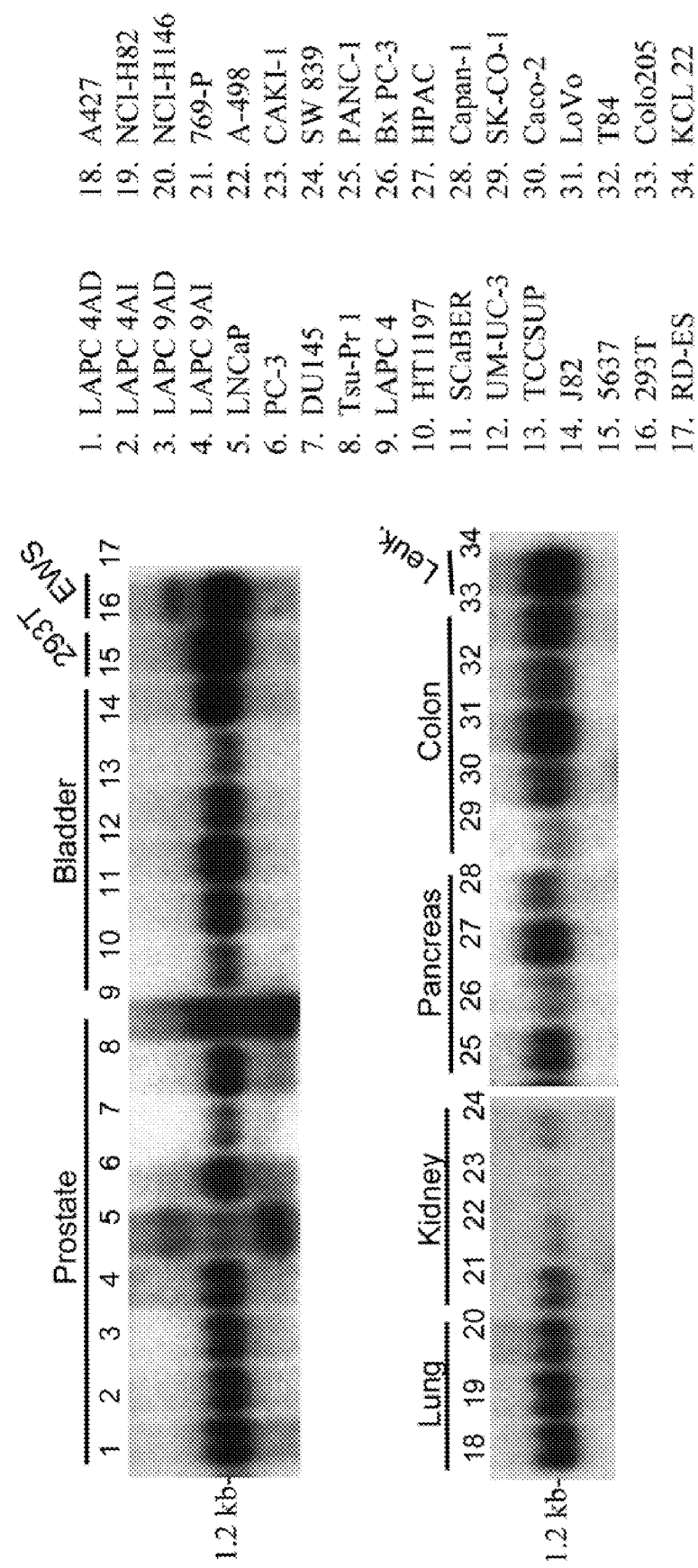
Figure 19 Expression of 121P1F1 in Multiple Cancer Cell lines

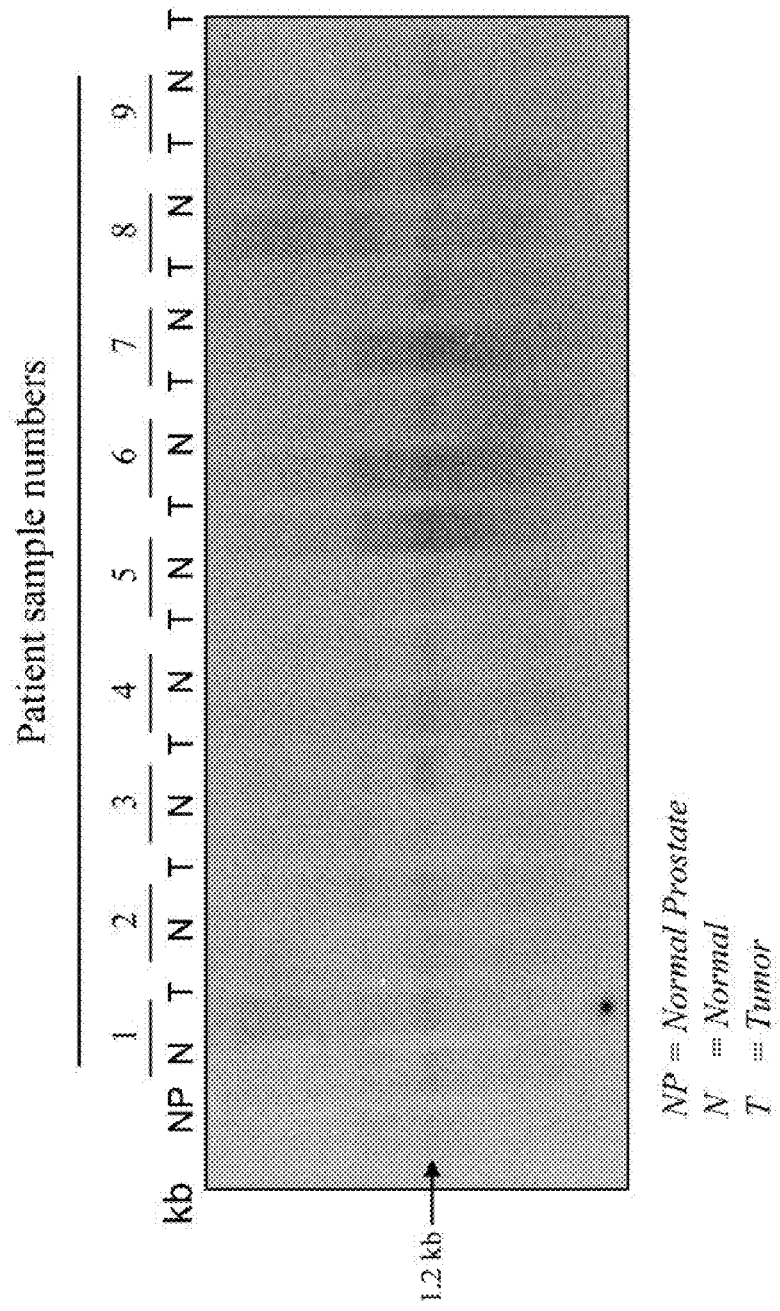
Figure 20 Expression of 121P1F1 in Patient Prostate Cancer Samples
NP = Normal Prostate
N = Normal
T = Tumor

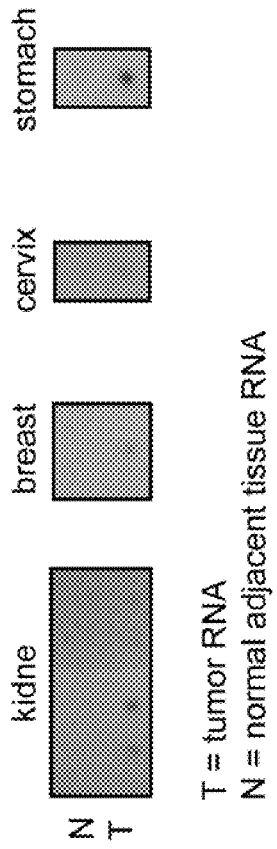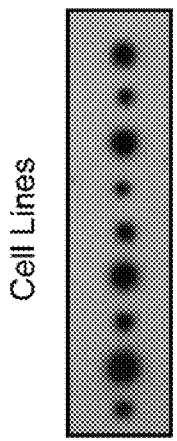
Figure 21 Expression of 121P1F1 in Kidney, Breast, Cervical and Stomach Patients Samples as well as Cancer Cell lines

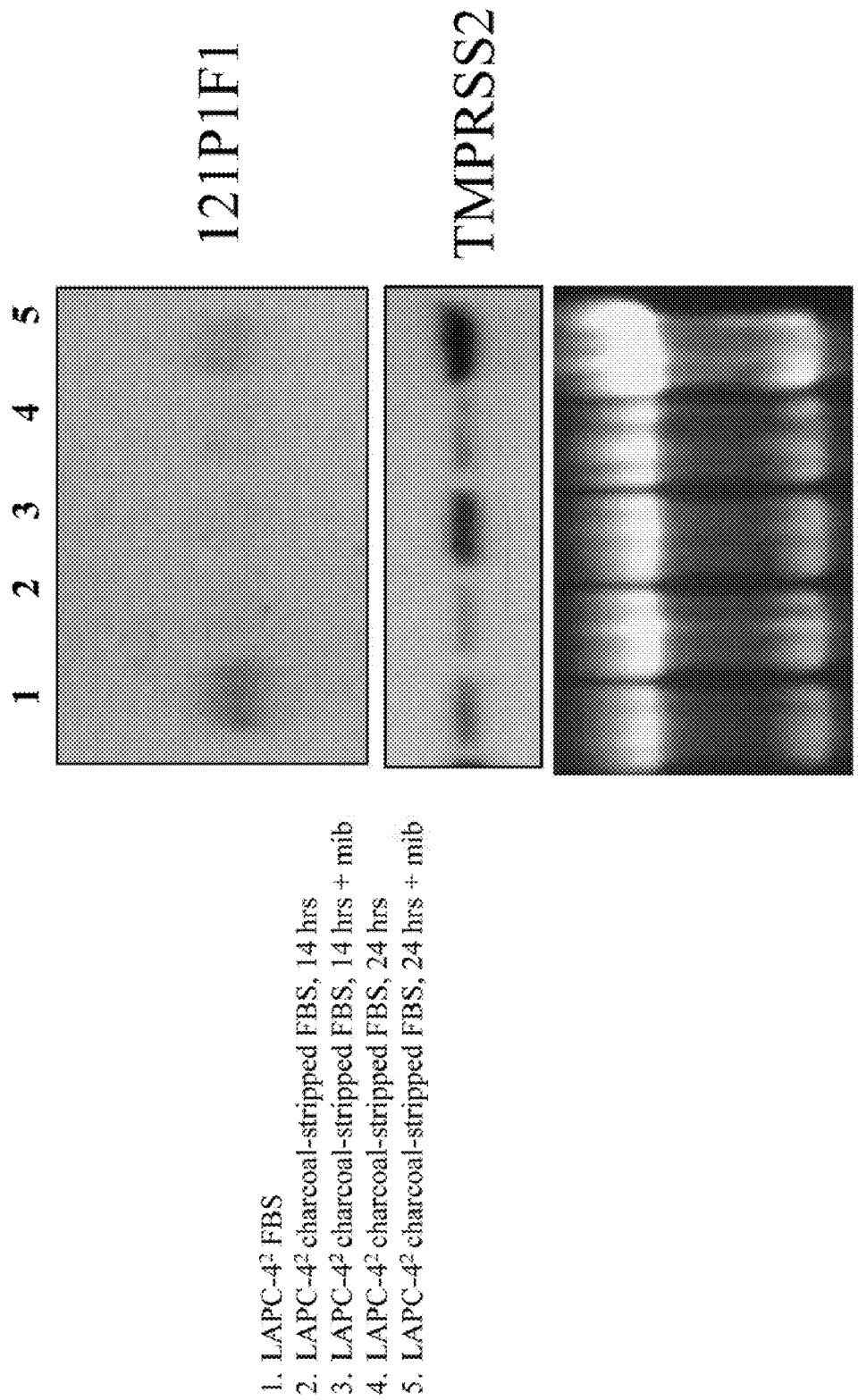

NUCLEIC ACID AND CORRESPONDING PROTEIN ENTITLED 121P1F1 USEFUL IN TREATMENT AND DETECTION OF CANCER

CROSS-REFERENCE TO RELATED APPLICATIONS

This application is a divisional of U.S. Ser. No. 10/087,190 filed Feb. 28, 2002, now U.S. Pat. No. 7,601,825, which is a continuation-in-part of U.S. Ser. No. 09/799,250 filed Mar. 5, 2001, now U.S. Pat. No. 6,924,358. The entire contents of these applications are hereby incorporated by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 511582003412Seqlist.txt | Jun. 25, 2009 | 79,292 bytes |

TECHNICAL FIELD

The invention described herein relates to a gene and its encoded protein, termed 121P1F1, expressed in certain cancers, and to diagnostic and therapeutic methods and compositions useful in the management of cancers that express 121P1F1.

BACKGROUND ART

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein, et al., 1997, Nat. Med. 3:402). More recently identified prostate cancer markers include PCTA-1 (Su, et al., 1996, Proc. Natl. Acad. Sci. USA 93: 7252), prostate-specific membrane (PSM) antigen (Pinto, et al., Clin Cancer Res 1996 Sep. 2 (9): 1445-51), STEAP (Hubert, et al., Proc Natl Acad Sci USA. (1999) 96(25): 14523-8) and prostate stem cell antigen (PSCA) (Reiter, et al., Proc. Natl. Acad. Sci. USA (1998) 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

DISCLOSURE OF THE INVENTION

The present invention relates to a gene, designated 121P1F1, that has now been found to be over-expressed in the cancer(s) listed in Table I. Northern blot expression analysis of 121P1F gene expression in normal tissues shows a restricted expression pattern in adult tissues. The nucleotide (FIG. 2) and amino acid (FIG. 2, and FIG. 3) sequences of 121P1F1 are provided. The tissue-related profile of 121P1F1 in normal adult tissues, combined with the over-expression observed in the tumors listed in Table I, shows that 121P1F1 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 121P1F1 genes, mRNAs, and/or coding sequences, preferably in isolated form, including polynucleotides encoding 121P1F1-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 121P1F1-related protein, as well as the peptides/proteins themselves; DNA, RNA, DNA/RNA hybrids, and related molecules, polynucleotides or oligonucleotides complementary or having at least a 90% homology to the 121P1F1 genes or mRNA sequences or parts thereof, and polynucleotides or oligonucleotides that hybridize to the 121P1F1 genes, mRNAs, or to 121P1F1-encoding polynucleotides. Also provided are means for isolating cDNAs and the genes encoding 121P1F1. Recombinant DNA molecules containing 121P1F1 polynucleotides, cells transformed or transduced with such molecules, and host-vector systems for the expression of 121P1F1 gene products are also provided. The invention further provides antibodies that bind to 121P1F1 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 121P1F1 polynucleotides and proteins in various biological samples, as well as methods for identifying cells that express 121P1F1. A typical embodiment of this invention provides methods for monitoring 121P1F1 gene products in a tissue or hematology sample having or suspected of having some form of growth dysregulation such as cancer.

The invention further provides various immunogenic or therapeutic compositions and strategies for treating cancers that express 121P1F1 such as cancers of tissues listed in Table I, including therapies aimed at inhibiting the transcription, translation, processing or function of 121P1F1 as well as cancer vaccines. In one aspect, the invention provides compositions, and methods comprising them, for treating a cancer that expresses 121P1F1 in a human subject wherein the composition comprises a carrier suitable for human use and a human unit dose of one or more than one agent that inhibits the production or function of 121P1F1. Preferably, the carrier is a uniquely human carrier. In another aspect of the invention, the agent is a moiety that is immunoreactive with 121P1F1 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 121P1F1 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 121P1F1 as described above. The one or more than one nucleic acid molecule may also be, or encodes, a molecule that inhibits production of 121P1F1. Non-limiting examples of such molecules include, but are not limited to, those complementary to a nucleotide sequence essential for production of 121P1F1 (e.g. antisense sequences or molecules that form a triple helix with a nucleotide double helix essential for 121P1F1 production) or a ribozyme effective to lyse 121P1F1 mRNA.

BRIEF DESCRIPTION OF THE DRAWINGS

FIG. 1. The 121P1F1 SSH sequence of 254 nucleotides.

FIG. 2. The cDNA and amino acid sequence of 121P1F1 is shown in FIG. 2A. The start methionine is underlined. The open reading frame extends from nucleic acid 82-699 including the stop codon. The nucleic acid and amino acid sequence of 121P1F1 variant 1A is shown in FIG. 2B, the codon for the start methionine is underlined. The open reading frame for variant 1A extends from nucleic acid 82 to 462 including the stop codon. The nucleic acid and amino acid sequence of 121P1F1 variant 1B is shown in FIG. 2C, the codon for the start methionine is underlined. The open reading frame for variant 1B extends from nucleic acid 501-860 including the stop codon. The nucleic acid and amino acid sequence of 121P1F1 variant 2 is shown in FIG. 2D, the codon for the start methionine is underlined. The open reading frame for variant 2 extends from nucleic acid 82-450 including the stop codon. The nucleic acid and amino acid sequence of 121P1F1 variant 3 is shown in FIG. 2E, the codon for the start methionine is underlined. The open reading frame for variant 3 extends from nucleic acid 82-654 including the stop codon. The nucleic acid and amino acid sequence of 121P1F1 variant 4 is shown in FIG. 2F, the codon for the start methionine is underlined. The open reading frame for variant 4 extends from nucleic acid 281-853 including the stop codon.

FIG. 3. Amino acid sequence of 121P1F1 is shown in FIG. 3A; it has 205 amino acids. The amino acid sequence of 121P1F1 variant 1A is shown in FIG. 3B; it has 126 amino acids. The amino acid sequence of 121P1F1 variant 1B is shown in FIG. 3C, the 121P1F1 variant 1B protein has 119 amino acids. The amino acid sequence of 121P1F1 variant 2 is shown in FIG. 3D, the 121P1F1 variant 2 protein has 122 amino acids. The amino acid sequence of 121P1F1 variant 3 is shown in FIG. 3E, the 121P1F1 variant 3 protein has 190 amino acids. The amino acid sequence of 121P1F1 variant 4 is shown in FIG. 3F, the 121P1F1 variant 4 protein has 190 amino acids.

FIG. 4. A. The amino acid alignments of 121P1F1 protein and variants 1A, 1B, 2, and 3. B. The amino acid alignments of 121P1F1 protein and variants 4 and 1A. C. Alignment with human protein GAJ. D. Alignment with closest mouse homolog. E. Alignment with hypothetical yeast protein.

FIG. 14: Expression of 121P1F1 in 293T cells. Cell lysates of vector or pcDNA 3.1-Myc His 121P1F1 transfected 293T cells were subjected to Western analysis with anti-His polyclonal antibody (Santa Cruz Biotechnology). Seen is a 35 kD band representing expression of 121P1F1 Myc His-tagged protein.

FIG. 15. Androgen regulation of 121P1F1 in vivo. Male mice were injected with LAPC-9AD tumor cells. When tumor reached a palpable size (0.3-0.5 cm in diameter), mice were castrated and tumors harvested at different time points following castration. RNA was isolated from the xenograft tissues. Northern blots with 10 µg of total RNA/lane were probed with the 121P1F1 SSH fragment. Size standards in kilobases (kb) are indicated on the side. Results show expression of 121P1F1 is slightly downregulated 7 days after castration. The protein TMPRSS2 was used as a positive control. A picture of the ethidium-bromide staining of the RNA gel is also presented (lowest panel).

FIG. 16: Secondary structure prediction for 121P1F1 (FIG. 16A) (SEQ ID NO:3) and variant 1a (FIG. 16B) (SEQ ID NO: 5). The secondary structure of 121P1F1 and variant 1a proteins were predicted using the HNN—Hierarchical Neural Network method (Guermeur, 1997), accessed from the ExPasy molecular biology server located on the World Wide Web. This method predicts the presence and location of alpha helices, extended strands, and random coils from the primary protein sequence. The percent of the protein in a given secondary structure is also given.

FIG. 17. RT-PCR analysis of 121P1F1 expression. First strand cDNA was prepared (A) from 8 human normal tissues, and (B) from vital pool 1 (VP1: liver, lung and kidney), vital pool 2 (VP2, pancreas, spleen and stomach), LAPC xenograft pool (XP; LAPC-4AD, LAPC-4AI, LAPC-9AD and LAPC-9AI), normal prostate (NP), prostate cancer pool, bladder cancer pool, kidney cancer pool, colon cancer pool and lung cancer pool. Normalization was performed by PCR using primers to actin and GAPDH. Semi-quantitative PCR, using primers to 121P1F1, was performed at 25 and 30 cycles of amplification.

FIG. 18. Expression of 121P1F1 in normal human tissues by Northern blot analysis. Two multiple tissue northern blots (Clontech) with 2 µg of mRNA/lane, were probed with the 121P1F1 SSH fragment. Size standards in kilobases (kb) are indicated on the side. The results show exclusive expression of an approximately 1.2 kb 121P1F1 transcript in testis and to a lower level in thymus.

FIG. 19. Expression of 121P1F1 in cancer cell lines. RNA was extracted from a number of cancer cell lines. Northern blots with 10 µg of total RNA/lane were probed with the 121P1F1 SSH fragment. Size standards in kilobases (kb) are indicated on the side.

FIG. 20. Expression of 121P1F1 in prostate cancer patient samples. RNA was extracted from the prostate tumors (T) and their normal adjacent tissue (N) derived from prostate cancer patients. Tumors of patients 1, 2 and 3 have a Gleason score of 6. Tumors of patients 4, 5 and 6 have a Gleason score of 7. Tumors of patients 7, 8 and 9 have a Gleason score of 9. Northern blots with 10 µg of total RNA/lane were probed with the 121p1F1 SSH fragment. Size standards in kilobases (kb) are indicated on the side.

FIG. 21. Expression of 121P1F1 in human patient cancer specimens and cancer cell lines. Expression of 121P1F1 was assayed in a panel of human cancers (T) and their respective matched normal tissues (N) on RNA dot blots. 121P1F1 expression was seen in kidney, breast, cervix, and stomach cancers. 121P1F1 was also found to be highly expressed in a panel of cancer cell lines in the following cancer cell lines; HeLa, Daudi, K562, HL-60, G361, A549, MOLT-4, SW480, and Raji.

FIG. 22. Androgen regulation of 121P1F1 in vitro. LAPC-42 cells were grown in charcoal-stripped medium and stimulated with the synthetic androgen mibolerone, for either 14 or 24 hours. Northern blot was performed with 10 µg of total RNA for each sample, and probed with the 121P1F1 SSH fragment. A picture of the ethidium-bromide staining of the RNA gel is also presented (lowest panel). Hybridization of the same northern blot with the androgen-dependent gene TMPRSS2 confirms the quality of the androgen deprivation. The results show that the expression of 121P1F1 goes down in absence of normal serum, and is modulated in presence of mibolerone, 24 hours after stimulation.

DETAILED DESCRIPTION OF THE INVENTION

I.) Definitions

Figure 5A:
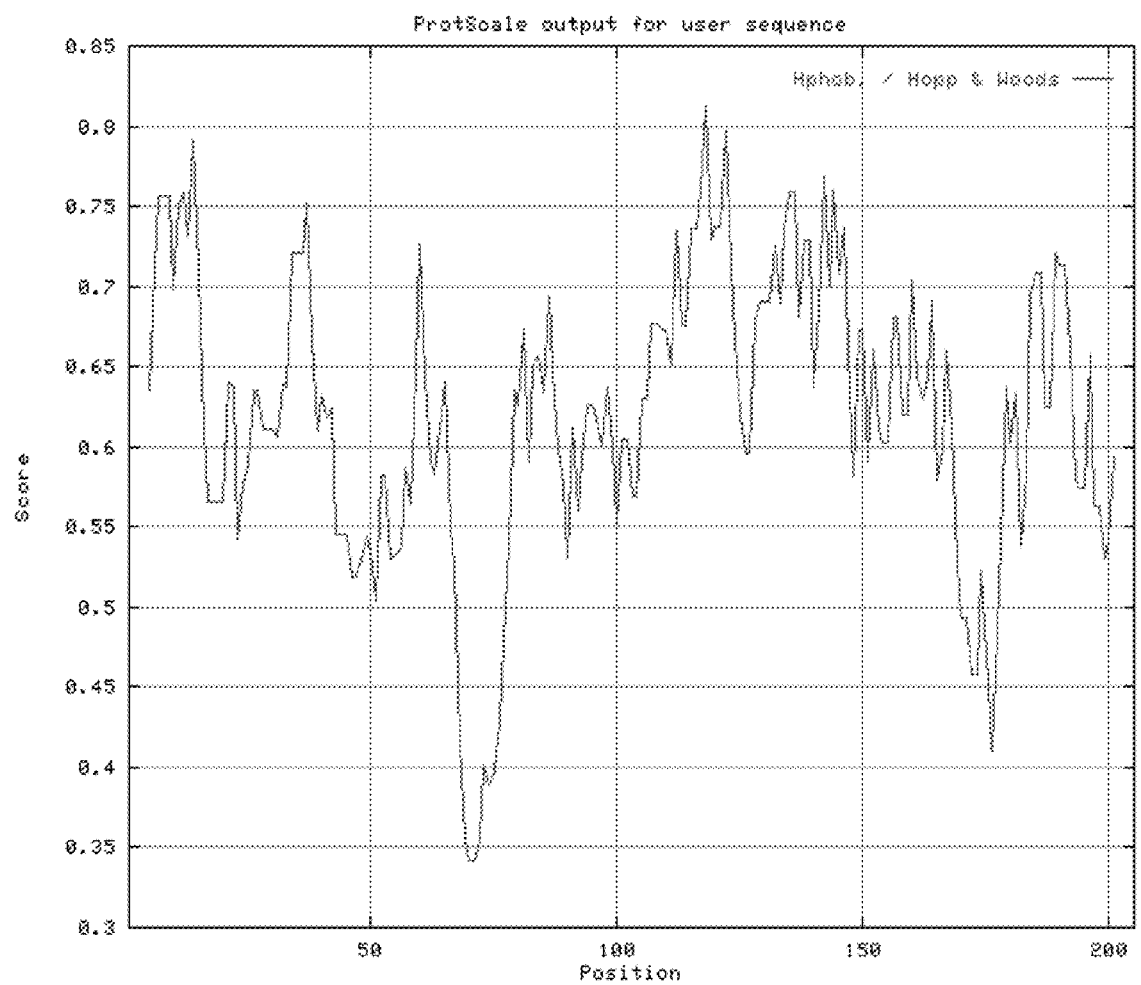
FIG. 5. Hydrophilicity amino acid profile of A) 121P1F1 and B) 121P1F1 var1A determined by computer algorithm sequence analysis using the method of Hopp and Woods (Hopp T. P., Woods K. R., 1981. Proc. Natl. Acad. Sci. U.S.A. 78:3824-3828) accessed on the Protscale website located on the World Wide Web through the ExPasy molecular biology server.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., *Molecular Cloning: A Laboratory Manual* 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 121P1F1 (either by removing the underlying glycosylation site or by deleting the glycosylation by chemical and/or enzymatic means), and/or adding one or more glycosylation sites that are not present in the native sequence 121P1F1. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 121P1F1-related protein). For example an analog of a 121P1F1 protein can be specifically bound by an antibody or T cell that specifically binds to 121P1F1.

The term "antibody" is used in the broadest sense. Therefore an "antibody" can be naturally occurring or man-made such as monoclonal antibodies produced by conventional hybridoma technology. Anti-121P1F1 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-121P1F1 antibodies and clones thereof (including agonist, antagonist and neutralizing antibodies) and anti-121P1F1 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as At211, I131, I125, Y90, Re186, Re188, Sm153, Bi212, P32 and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., *Immunology*, 8th Ed., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 121P1F1 genes or that encode polypeptides other than 121P1F1 gene product or fragments thereof. A skilled artisan can readily employ nucleic acid isolation procedures to obtain an isolated 121P1F1 polynucleotide. A protein is said to be "isolated," for example, when physical, mechanical or chemical methods are employed to remove the 121P1F1 proteins from cellular constituents that are normally associated with the protein. A skilled artisan can readily employ standard purification methods to obtain an isolated 121P1F1 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of an 121P1F1-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

Non-limiting examples of small molecules include compounds that bind or interact with 121P1F1, ligands including hormones, neuropeptides, chemokines, odorants, phospholipids, and functional equivalents thereof that bind and preferably inhibit 121P1F1 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 121P1F1 protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel, et al., *Current Protocols in Molecular Biology*, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 121P1F1 protein shown in FIG. 2 or FIG. 3. An analog is an example of a variant protein. Splice isoforms and single nucleotides polymorphisms (SNPs) are further examples of variants.

The "121P1F1-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 121P1F1 proteins or fragments thereof, as well as fusion proteins of a 121P1F1 protein and a heterologous polypeptide are also included. Such 121P1F1 proteins are collectively referred to as the 121P1F1-related proteins, the proteins of the invention, or 121P1F1. The term "121P1F1-related protein" refers to a polypeptide fragment or an 121P1F1 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100 or more than 100 amino acids.

II.) 121P1F1 Polynucleotides

One aspect of the invention provides polynucleotides corresponding or complementary to all or part of an 121P1F1 gene, mRNA, and/or coding sequence, preferably in isolated form, including polynucleotides encoding an 121P1F1-related protein and fragments thereof, DNA, RNA, DNA/RNA hybrid, and related molecules, polynucleotides or oligonucleotides complementary to an 121P1F1 gene or mRNA sequence or a part thereof, and polynucleotides or oligonucleotides that hybridize to an 121P1F1 gene, mRNA, or to an 121P1F1 encoding polynucleotide (collectively, "121P1F1 polynucleotides"). In all instances when referred to in this section, T can also be U in FIG. 2.

Figure 5B:
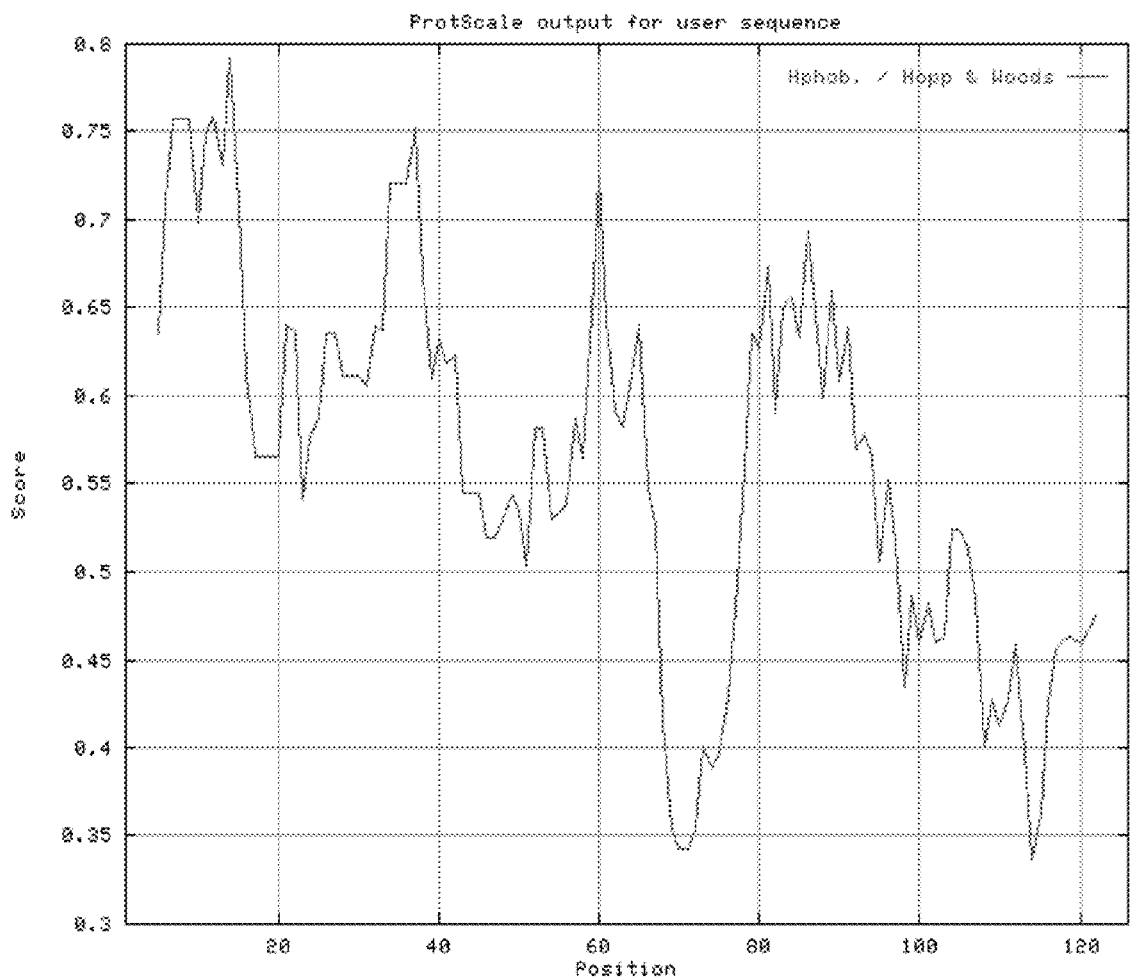
Figure 6A:
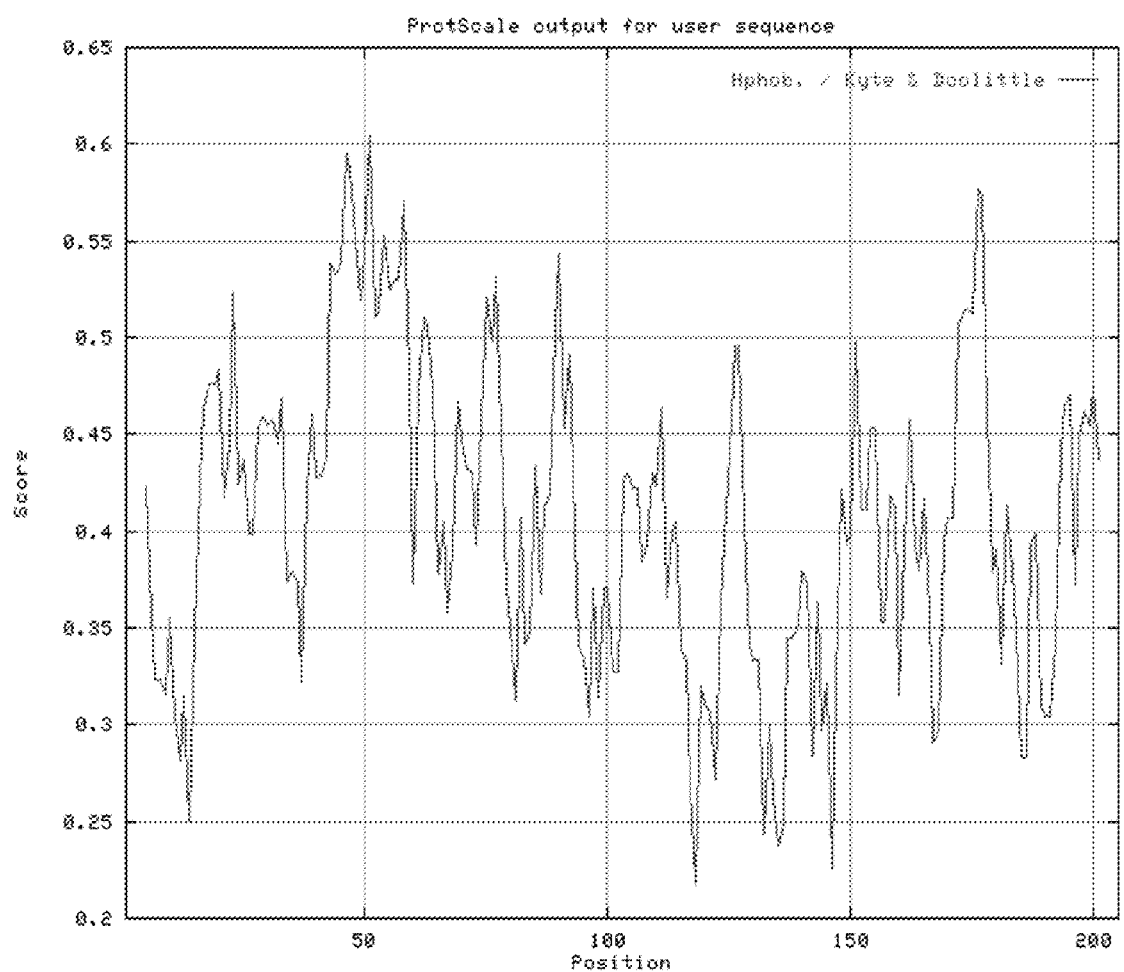
FIG. 6. Hydropathicity amino acid profile of A) 121P1F1 and B) 121P1F1 var1A determined by computer algorithm sequence analysis using the method of Kyte and Doolittle (Kyte J., Doolittle R. F., 1982. J. Mol. Biol. 157:105-132) accessed on the ProtScale website located on the World Wide Web through the ExPasy molecular biology server.
Figure 6B:
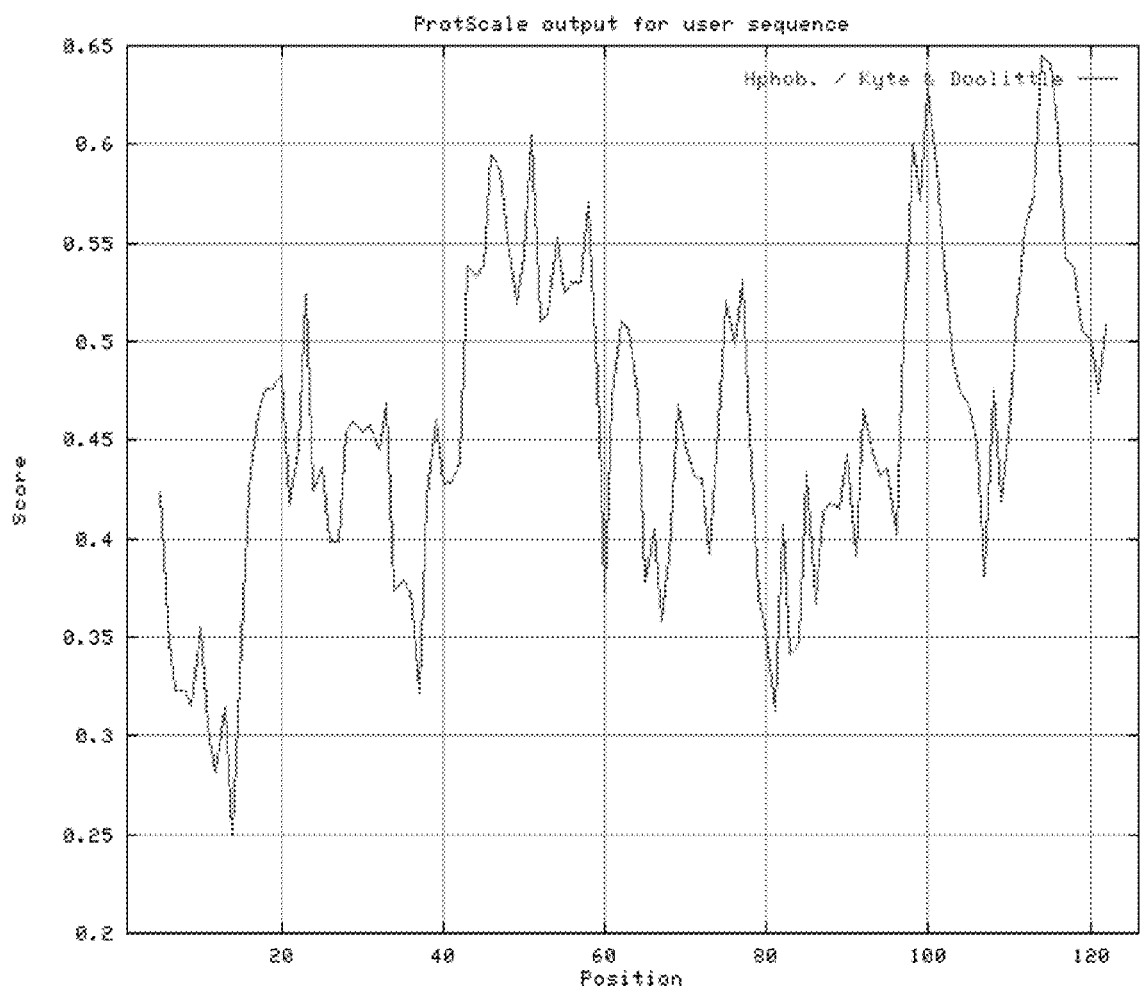
Figure 7A:
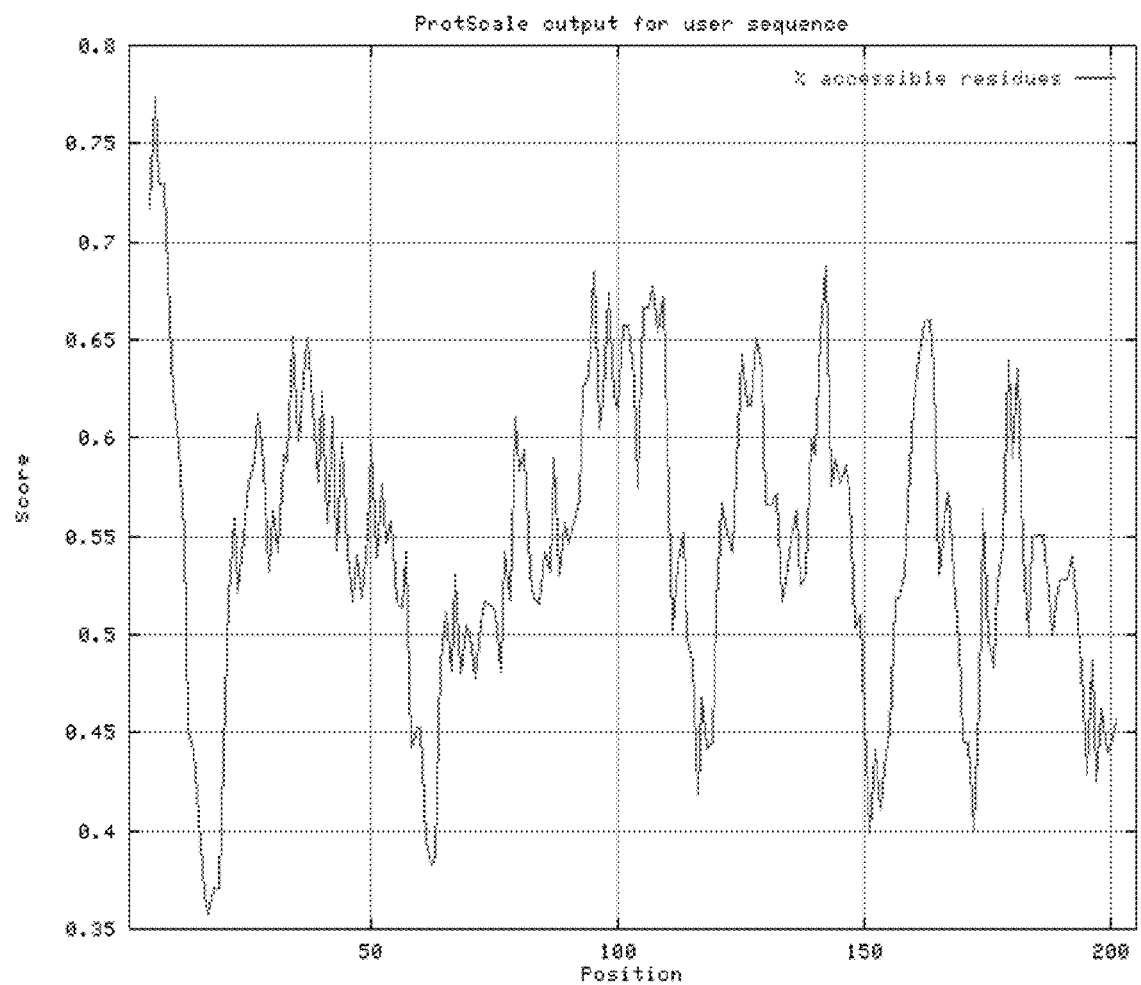
FIG. 7. Percent accessible residues amino acid profile of A) 121P1F1 and B) 121P1F1 var1A determined by computer algorithm sequence analysis using the method of Janin (Janin J., 1979 Nature 277:491-492) accessed on the ProtScale website located on the World Wide Web through the ExPasy molecular biology server.
Figure 7B:
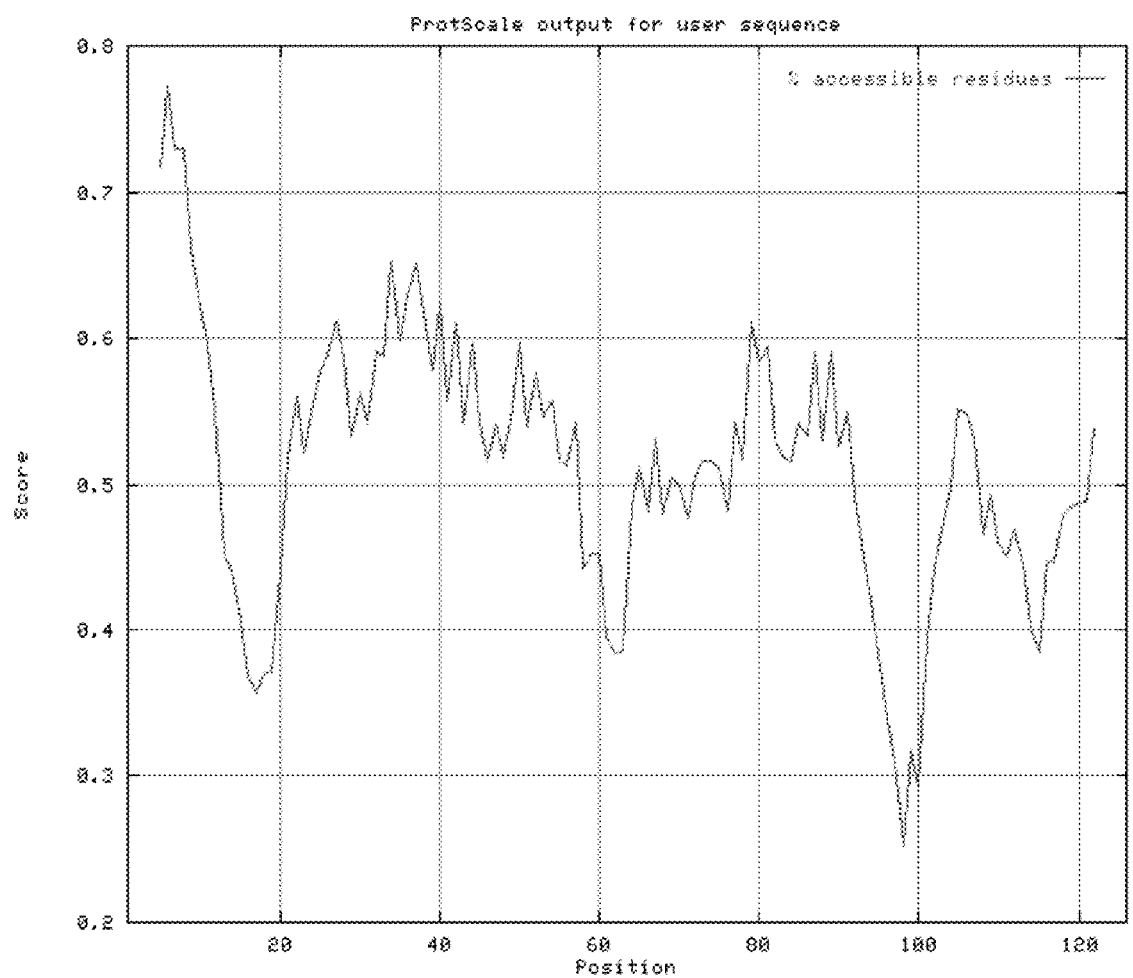
Figure 8A:
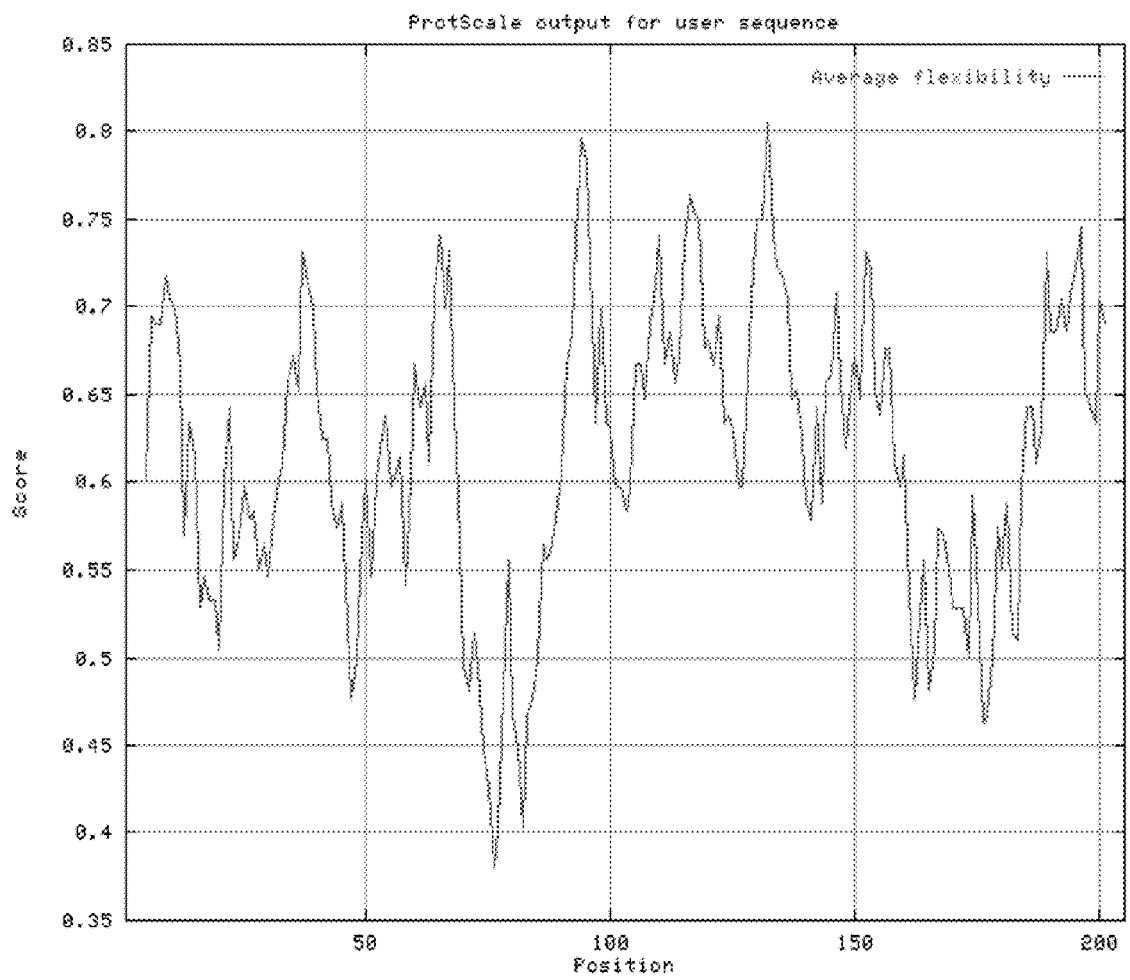
FIG. 8. Average flexibility amino acid profile of A) 121P1F1 and B) 121P1F1 var1A determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web through the ExPasy molecular biology server.
Figure 8B:
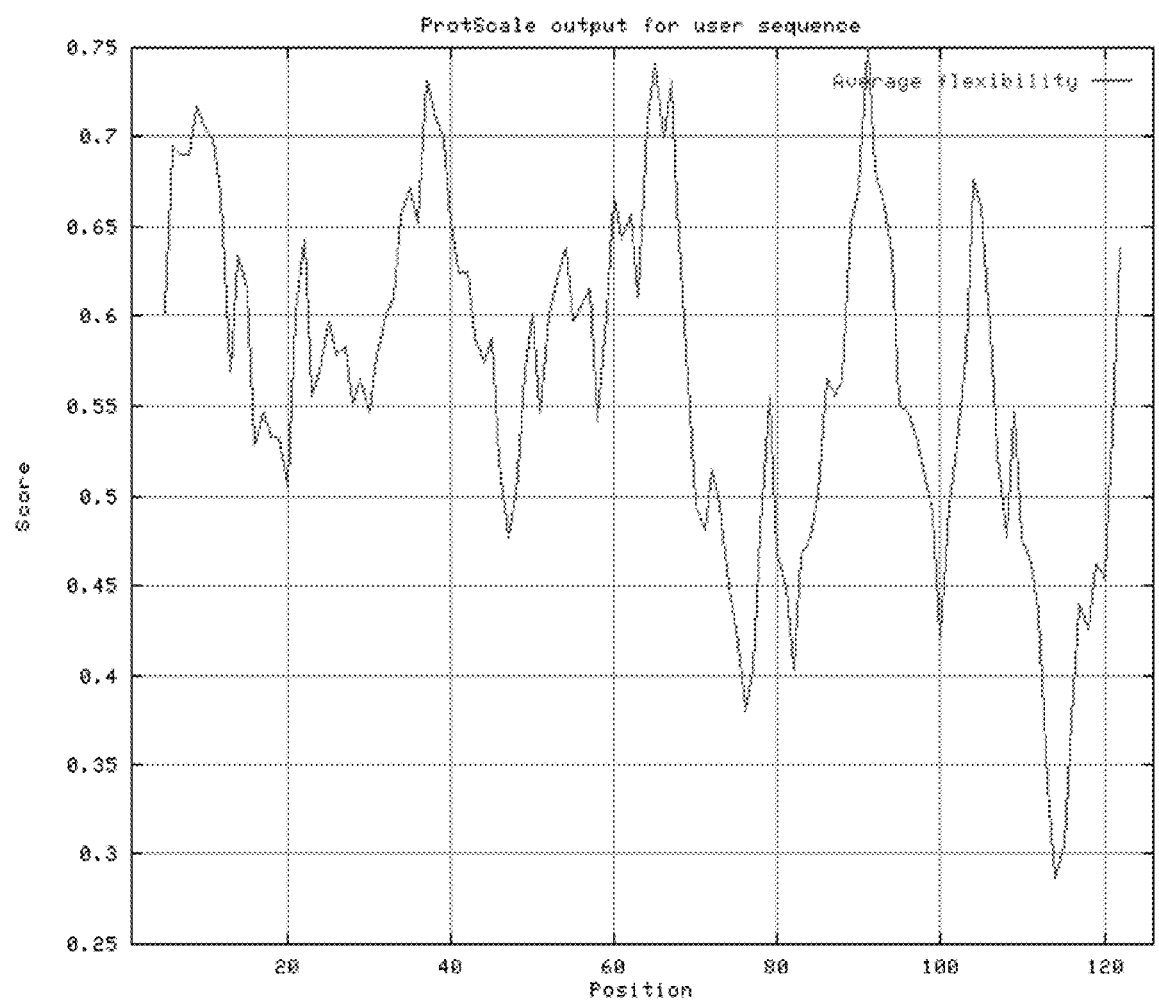
Figure 9A:
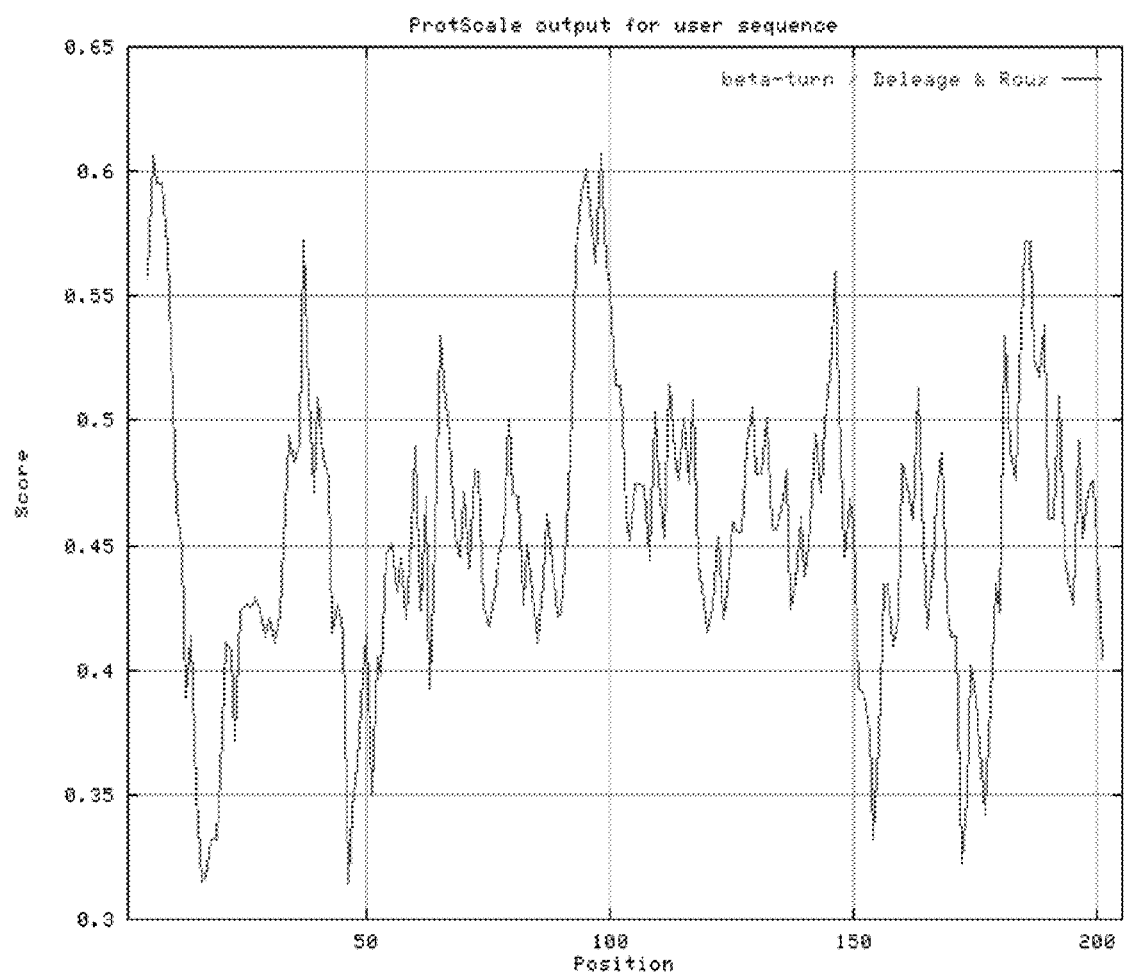
FIG. 9. Beta-turn amino acid profile of A) 121P1F1 and B) 121P1F1 var1A determined by computer algorithm sequence analysis using the method of Deleage and Roux (Deleage, G., Roux B. 1987 Protein Engineering 1:289-294) accessed on the ProtScale website located on the World Wide Web through the ExPasy molecular biology server.
Figure 9B:
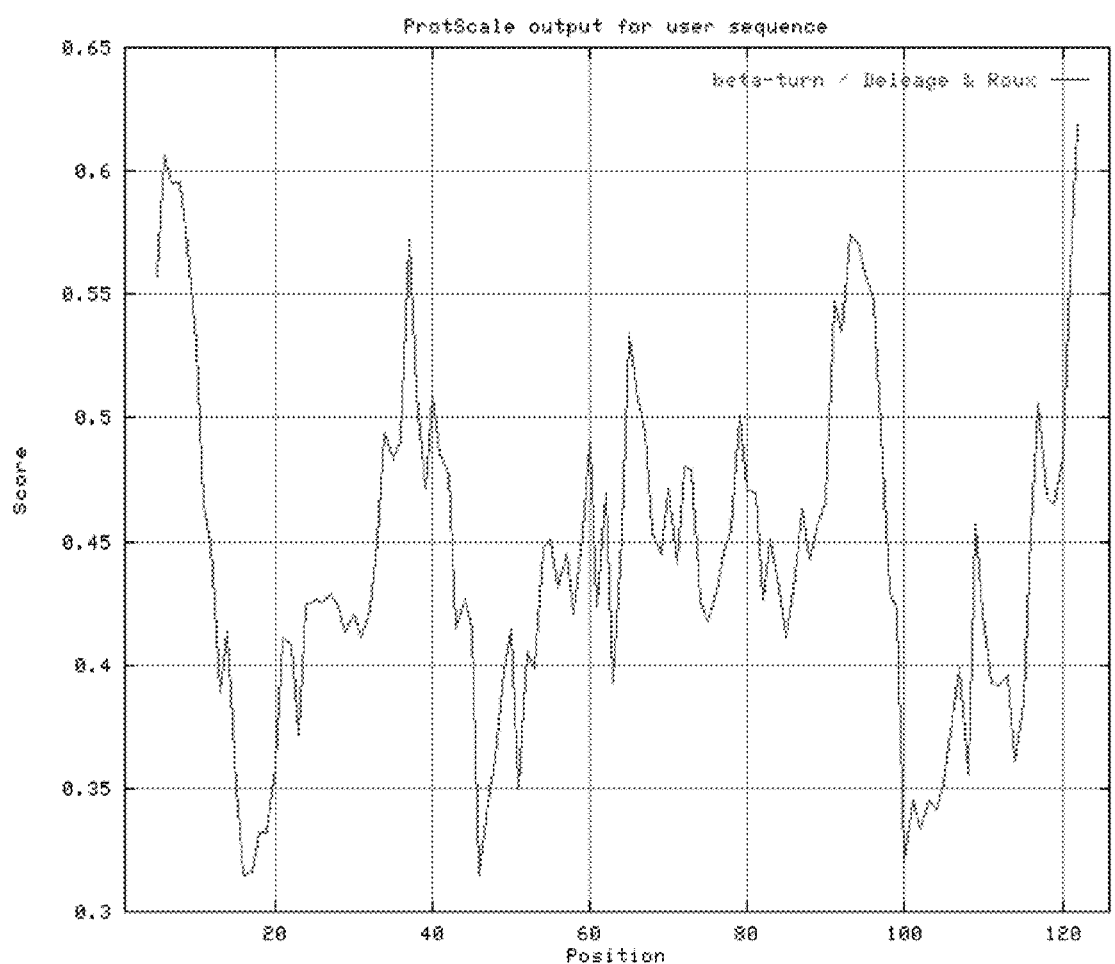

Embodiments of a 121P1F1 polynucleotide include: a 121P1F1 polynucleotide having the sequence shown in FIG. 2, the nucleotide sequence of 121P1F1 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 121P1F1 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 82 through nucleotide residue number 696, followed by a stop codon, wherein T can also be U;

(III) a polynucleotide comprising, consisting essentially of, or consisting of the sequence as shown in FIG. 2B, from nucleotide residue number 82 through nucleotide residue number 459, followed by a stop codon, wherein T can also be U;

(IV) a polynucleotide comprising, consisting essentially of, or consisting of the sequence as shown in FIG. 2C, from nucleotide residue number 501 through nucleotide residue number 857, followed by a stop codon, wherein T can also be U;

(V) a polynucleotide comprising, consisting essentially of, or consisting of the sequence as shown in FIG. 2D, from nucleotide residue number 82 through nucleotide residue number 447, followed by a stop codon, wherein T can also be U;

(VI) a polynucleotide comprising, consisting essentially of, or consisting of the sequence as shown in FIG. 2E, from nucleotide residue number 82 through nucleotide residue number 651, followed by a stop codon, wherein T can also be U;

(VII) a polynucleotide comprising, consisting essentially of, or consisting of the sequence as shown in FIG. 2F, from nucleotide residue number 281 through nucleotide residue number 850, followed by a stop codon, wherein T can also be U;

(VIII) a polynucleotide that encodes an 121P1F1-related protein that is at least 90% homologous to an entire amino acid sequence shown in FIGS. 2A-F;

(IX) a polynucleotide that encodes an 121P1F1-related protein that is at least 90% identical to an entire amino acid sequence shown in FIGS. 2A-F;

(X) a polynucleotide that encodes at least one peptide set forth in Tables V-XVIII, XXVI, and XXVII;

(XI) a polynucleotide that encodes a peptide region of at least 5 amino acids of a peptide of FIG. 3A in any whole number increment up to 205 that includes an amino acid position having a value greater than 0.5 in the Hydrophilicity profile of FIG. 5A, or of FIG. 3B in any whole number increment up to 126 that includes an amino acid position having a value greater than 0.5 in the Hydrophilicity profile of FIG. 5B;

(XII) a polynucleotide that encodes a peptide region of at least 5 amino acids of a peptide of FIG. 3A in any whole number increment up to 205 that includes an amino acid position having a value less than 0.5 in the Hydropathicity profile of FIG. 6A, or of FIG. 3B in any whole number increment up to 126, that includes an amino acid position having a value less than 0.5 in the Hydropathicity profile of FIG. 6B;

(XIII) a polynucleotide that encodes a peptide region of at least 5 amino acids of a peptide of FIG. 3A in any whole number increment up to 205 that includes an amino acid position having a value greater than 0.5 in the Percent Accessible Residues profile of FIG. 7A, or of FIG. 3B in any whole number increment up to 126, that includes an amino acid position having a value greater than 0.5 in the Percent Accessible Residues profile of FIG. 7B;

(XIV) a polynucleotide that encodes a peptide region of at least 5 amino acids of a peptide of FIG. 3A in any whole number increment up to 205 that includes an amino acid position having a value greater than 0.5 in the Average Flexibility profile on FIG. 8A, or of FIG. 3B in any whole number increment up to 126, that includes an amino acid position having a value greater than 0.5 in the Average Flexibility profile on FIG. 8B;

(XV) a polynucleotide that encodes a peptide region of at least 5 amino acids of a peptide of FIG. 3A in any whole number increment up to 205 that includes an amino acid position having a value greater than 0.5 in the Beta-turn profile of FIG. 9A, or of FIG. 3B in any whole number increment up to 126, that includes an amino acid position having a value greater than 0.5 in the Beta-turn profile of FIG. 9B;

(XVI) a polynucleotide that encodes a 121P1F1-related protein whose sequence is encoded by the cDNAs contained in the plasmid deposited with American Type Culture Collection as Accession No. PTA-3139 on Mar. 1, 2001;

(XVII) a polynucleotide that is fully complementary to a polynucleotide of any one of (I)-(XVI);

(XVIII) a polynucleotide that selectively hybridizes under stringent conditions to a polynucleotide of (I)-(XVII);

(XIX) a peptide that is encoded by any of (I)-(XVIII); and, (XX) a polynucleotide of any of (I)-(XVIII) or peptide of (XIX) together with a pharmaceutical excipient and/or in a human unit dose form.

As used herein, a range is understood to specifically disclose all whole unit positions thereof.

Typical embodiments of the invention disclosed herein include 121P1F1 polynucleotides that encode specific portions of 121P1F1 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or 205 contiguous amino acids of 121P1F1;

(b) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, or 126 contiguous amino acids of variant 1A;

(c) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, or 119 contiguous amino acids of variant 1B;

(d) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, or 122 contiguous amino acids of variant 2; or, (e) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 contiguous amino acids of variant 3; or, (f) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 contiguous amino acids of variant 4.

For example, representative embodiments of the invention disclosed herein include: polynucleotides and their encoded peptides themselves encoding about amino acid 1 to about amino acid 10 of the 121P1F1 protein or variants shown in FIG. 2 or FIG. 3, polynucleotides encoding about amino acid 10 to about amino acid 20 of the 121P1F1 protein or variants shown in FIG. 2 or FIG. 3, polynucleotides encoding about amino acid 20 to about amino acid 30 of the 121P1F1 protein or variants shown in FIG. 2 or FIG. 3, polynucleotides encoding about amino acid 30 to about amino acid 40 of the 121P1F1 protein or variants shown in FIG. 2 or FIG. 3, polynucleotides encoding about amino acid 40 to about amino acid 50 of the 121P1F1 protein or variants shown in FIG. 2 or FIG. 3, polynucleotides encoding about amino acid 50 to about amino acid 60 of the 121P1F1 protein or variants shown in FIG. 2 or FIG. 3, polynucleotides encoding about amino acid 60 to about amino acid 70 of the 121P1F1 protein or variants shown in FIG. 2 or FIG. 3, polynucleotides encoding about amino acid 70 to about amino acid 80 of the 121P1F1 protein or variants shown in FIG. 2 or FIG. 3, polynucleotides encoding about amino acid 80 to about amino acid 90 of the 121P1F1 protein or variants shown in FIG. 2 or FIG. 3, polynucleotides encoding about amino acid 90 to about amino acid 100 of the 121P1F1 protein or variants shown in FIG. 2 or FIG. 3, in increments of about 10 amino acids, ending at the carboxyl terminal amino acid set forth in FIG. 2 or FIG. 3. Accordingly polynucleotides encoding portions of the amino acid sequence (of about 10 amino acids), of amino acids 100 through the carboxyl terminal amino acid of the 121P1F1 protein are embodiments of the invention. Wherein it is understood that each particular amino acid position discloses that position plus or minus five amino acid residues.

Polynucleotides encoding relatively long portions of a 121P1F1 protein are also within the scope of the invention. For example, polynucleotides encoding from about amino acid 1 (or 20 or 30 or 40 etc.) to about amino acid 20, (or 30, or 40 or 50 etc.) of the 121P1F1 protein or variants shown in FIG. 2 or FIG. 3 can be generated by a variety of techniques well known in the art. These polynucleotide fragments can include any portion of the 121P1F1 sequence or variants as shown in FIG. 2.

Additional illustrative embodiments of the invention disclosed herein include 121P1F1 polynucleotide fragments encoding one or more of the biological motifs contained within a 121P1F1 protein sequence or variant sequence, including one or more of the motif-bearing subsequences of a 121P1F1 protein or variant set forth in Tables V-XVIII, XXVI, and XXVII. In another embodiment, typical polynucleotide fragments of the invention encode one or more of the regions of 121P1F1 protein or variant that exhibit homology to a known molecule. In another embodiment of the invention, typical polynucleotide fragments can encode one or more of the 121P1F1 protein or variant N-glycosylation sites, cAMP and cGMP-dependent protein kinase phosphorylation sites, casein kinase II phosphorylation sites or N-myristoylation site and amidation sites.

II.A.) Uses of 121P1F1 Polynucleotides

II.A.1.) Monitoring of Genetic Abnormalities

The polynucleotides of the preceding paragraphs have a number of different specific uses. The human 121P1F1 gene maps to the chromosomal location set forth in Example 3. For example, because the 121P1F1 gene maps to this chromosome, polynucleotides that encode different regions of the 121P1F1 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic, et al., *Mutat. Res.* 382(3-4): 81-83 (1998); Johansson, et al., *Blood* 86(10): 3905-3914 (1995) and Finger, et al., *P.N.A.S.* 85(23): 9158-9162 (1988)). Thus, polynucleotides encoding specific regions of the 121P1F1 proteins provide new tools that can be used to delineate, with greater precision than previously possible, cytogenetic abnormalities in the chromosomal region that encodes 121P1F1 that may contribute to the malignant phenotype. In this context, these polynucleotides satisfy a need in the art for expanding the sensitivity of chromosomal screening in order to identify more subtle and less common chromosomal abnormalities (see e.g. Evans, et al., *Am. J. Obstet. Gynecol* 171(4): 1055-1057 (1994)).

Furthermore, as 121P1F1 was shown to be highly expressed in bladder and other cancers, 121P1F1 polynucleotides are used in methods assessing the status of 121P1F1 gene products in normal versus cancerous tissues. Typically, polynucleotides that encode specific regions of the 121P1F1 proteins are used to assess the presence of perturbations (such as deletions, insertions, point mutations, or alterations resulting in a loss of an antigen etc.) in specific regions of the 121P1F1 gene, such as regions containing one or more motifs. Exemplary assays include both RT-PCR assays as well as single-strand conformation polymorphism (SSCP) analysis (see, e.g., Marrogi, et al., *J. Cutan. Pathol.* 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 121P1F1. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 121P1F1 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 121P1F1. See for example, Jack Cohen, Oligodeoxynucleotides, Antisense Inhibitors of Gene Expression, CRC Press, 1989; and Synthesis 1:1-5 (1988). The 121P1F1 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P., et al., *J. Org. Chem.* 55:4693-4698 (1990); and Iyer, R. P., et al., *J. Am. Chem. Soc.* 112:1253-1254 (1990). Additional 121P1F1 antisense oligonucleotides of the present invention include morpholino antisense oligonucleotides known in the art (see, e.g., Partridge, et al., 1996, *Antisense & Nucleic Acid Drug Development* 6: 169-175).

The 121P1F1 antisense oligonucleotides of the present invention typically can be RNA or DNA that is complementary to and stably hybridizes with the first 100 5' codons or last 100 3' codons of a 121P1F1 genomic sequence or the corresponding mRNA. Absolute complementarity is not required, although high degrees of complementarity are preferred. Use of an oligonucleotide complementary to this region allows for the selective hybridization to 121P1F1 mRNA and not to mRNA specifying other regulatory subunits of protein kinase. In one embodiment, 121P1F1 antisense oligonucleotides of the present invention are 15 to 30-mer fragments of the antisense DNA molecule that have a sequence that hybridizes to 121P1F1 mRNA. Optionally, 121P1F1 antisense oligonucleotide is a 30-mer oligonucleotide that is complementary to a region in the first 10 5' codons or last 10 3' codons of 121P1F1. Alternatively, the antisense molecules are modified to employ ribozymes in the inhibition of 121P1F1 expression, see, e.g., L. A. Couture & D. T. Stinchcomb; *Trends Genet* 12: 510-515 (1996).

II.A.3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 121P1F1 polynucleotide in a sample and as a means for detecting a cell expressing a 121P1F1 protein.

Examples of such probes include polypeptides comprising all or part of the human 121P1F1 cDNA sequence shown in FIG. 2. Examples of primer pairs capable of specifically amplifying 121P1F1 mRNAs are also described in the Examples. As will be understood by the skilled artisan, a great many different primers and probes can be prepared based on the sequences provided herein and used effectively to amplify and/or detect a 121P1F1 mRNA.

The 121P1F1 polynucleotides of the invention are useful for a variety of purposes, including but not limited to their use as probes and primers for the amplification and/or detection of the 121P1F1 gene(s), mRNA(s), or fragments thereof; as reagents for the diagnosis and/or prognosis of prostate cancer and other cancers; as coding sequences capable of directing the expression of 121P1F1 polypeptides; as tools for modulating or inhibiting the expression of the 121P1F1 gene(s) and/or translation of the 121P1F1 transcript(s); and as therapeutic agents.

The present invention includes the use of any probe as described herein to identify and isolate a 121P1F1 or 121P1F1 related nucleic acid sequence from a naturally occurring source, such as humans or other mammals, as well as the isolated nucleic acid sequence per se, which would comprise all or most of the sequences found in the probe used.

II.A.4.) Isolation of 121P1F1-Encoding Nucleic Acid Molecules

The 121P1F1 cDNA sequences described herein enable the isolation of other polynucleotides encoding 121P1F1 gene product(s), as well as the isolation of polynucleotides encoding 121P1F1 gene product homologs, alternatively spliced isoforms, allelic variants, and mutant forms of a 121P1F1 gene product as well as polynucleotides that encode analogs of 121P1F1-related proteins. Various molecular cloning methods that can be employed to isolate full length cDNAs encoding an 121P1F1 gene are well known (see, for example, Sambrook, J. et al., *Molecular Cloning: A Laboratory Manual*, 2d edition, Cold Spring Harbor Press, New York, 1989; *Current Protocols in Molecular Biology*, Ausubel et al., Eds., Wiley and Sons, 1995). For example, lambda phage cloning methodologies can be conveniently employed, using commercially available cloning systems (e.g., Lambda ZAP Express, Stratagene). Phage clones containing 121P1F1 gene cDNAs can be identified by probing with a labeled 121P1F1 cDNA or a fragment thereof. For example, in one embodiment, a 121P1F1 cDNA (e.g., FIG. 2) or a portion thereof can be synthesized and used as a probe to retrieve overlapping and full-length cDNAs corresponding to a 121P1F1 gene. A 121P1F1 gene itself can be isolated by screening genomic DNA libraries, bacterial artificial chromosome libraries (BACs), yeast artificial chromosome libraries (YACs), and the like, with 121P1F1 DNA probes or primers.

II.A.5.) Recombinant Nucleic Acid Molecules and Host-Vector Systems

The invention also provides recombinant DNA or RNA molecules containing an 121P1F1 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 121P1F1 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 121P1F1 or a fragment, analog or homolog thereof can be used to generate 121P1F1 proteins or fragments thereof using any number of host-vector systems routinely used and widely known in the art.

A wide range of host-vector systems suitable for the expression of 121P1F1 proteins or fragments thereof are available, see for example, Sambrook, et al., 1989, supra; *Current Protocols in Molecular Biology*, 1995, supra). Preferred vectors for mammalian expression include but are not limited to pcDNA 3.1 myc-His-tag (Invitrogen) and the retroviral vector pSRαtkneo (Muller, et al., 1991, *MCB* 11:1785). Using these expression vectors, 121P1F1 can be expressed in several prostate cancer and non-prostate cell lines, including for example 293, 293T, rat-1, NIH 3T3 and TsuPr1. The host-vector systems of the invention are useful for the production of a 121P1F1 protein or fragment thereof. Such host-vector systems can be employed to study the functional properties of 121P1F1 and 121P1F1 mutations or analogs.

Recombinant human 121P1F1 protein or an analog or homolog or fragment thereof can be produced by mammalian cells transfected with a construct encoding a 121P1F1-related nucleotide. For example, 293T cells can be transfected with an expression plasmid encoding 121P1F1 or fragment, analog or homolog thereof, a 121P1F1-related protein is expressed in the 293T cells, and the recombinant 121P1F1 protein is isolated using standard purification methods (e.g., affinity purification using anti-121P1F1 antibodies). In another embodiment, a 121P1F1 coding sequence is subcloned into the retroviral vector pSRαMSVtkneo and used to infect various mammalian cell lines, such as NIH 3T3, TsuPr1, 293 and rat-1 in order to establish 121P1F1 expressing cell lines. Various other expression systems well known in the art can also be employed. Expression constructs encoding a leader peptide joined in frame to a 121P1F1 coding sequence can be used for the generation of a secreted form of recombinant 121P1F1 protein.

As discussed herein, redundancy in the genetic code permits variation in 121P1F1 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL that is located on the World Wide Web at (.dna.affrc.go.jp/~nakamura/codon.html).

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 121P1F1-Related Proteins

Another aspect of the present invention provides 121P1F1-related proteins. Specific embodiments of 121P1F1 proteins comprise a polypeptide having all or part of the amino acid sequence of human 121P1F1 as shown in FIG. 2 or FIG. 3. Alternatively, embodiments of 121P1F1 proteins comprise variant, homolog or analog polypeptides that have alterations in the amino acid sequence of 121P1F1 shown in FIG. 2 or FIG. 3.

In general, naturally occurring allelic variants of human 121P1F1 share a high degree of structural identity and homology (e.g., 90% or more homology). Typically, allelic variants of a 121P1F1 protein contain conservative amino acid substitutions within the 121P1F1 sequences described herein or contain a substitution of an amino acid from a corresponding position in a homologue of 121P1F1. One class of 121P1F1 allelic variants are proteins that share a high degree of homology with at least a small region of a particular 121P1F1 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff, et al., *PNAS* 1992 Vol 89 10915-10919; Lei, et al., *J Biol Chem* 1995 May 19; 270(20): 11882-6).

Embodiments of the invention disclosed herein include a wide variety of art-accepted variants or analogs of 121P1F1 proteins such as polypeptides having amino acid insertions, deletions and substitutions. 121P1F1 variants can be made using methods known in the art such as site-directed mutagenesis, alanine scanning, and PCR mutagenesis. Site-directed mutagenesis (Carter, et al., *Nucl. Acids Res.*, 13:4331 (1986); Zoller, et al., *Nucl. Acids Res.*, 10:6487 (1987)), cassette mutagenesis (Wells, et al., *Gene*, 34:315 (1985)), restriction selection mutagenesis (Wells, et al., *Philos. Trans. R. Soc. London SerA*, 317:415 (1986)) or other known techniques can be performed on the cloned DNA to produce the 121P1F1 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 121P1F1 variants, analogs or homologs, have the distinguishing attribute of having at least one epitope that is "cross reactive" with a 121P1F1 protein having an amino acid sequence of FIG. 3. As used in this sentence, "cross reactive" means that an antibody or T cell that specifically binds to an 121P1F1 variant also specifically binds to a 121P1F1 protein having an amino acid sequence set forth in FIG. 3. A polypeptide ceases to be a variant of a protein shown in FIG. 3, when it no longer contains any epitope capable of being recognized by an antibody or T cell that specifically binds to the starting 121P1F1 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair, et al., *J. Immunol* 2000 165(12): 6949-6955; Hebbes, et al., *Mol Immunol* (1989) 26(9):865-73; Schwartz, et al., *J Immunol* (1985) 135(4):2598-608.

Other classes of 121P1F1-related protein variants share 70%, 75%, 80%, 85% or 90% or more similarity with an amino acid sequence of FIG. 3, or a fragment thereof. Another specific class of 121P1F1 protein variants or analogs comprise one or more of the 121P1F1 biological motifs described herein or presently known in the art. Thus, encompassed by the present invention are analogs of 121P1F1 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 121P1F1 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 121P1F1 protein shown in FIG. 2 or FIG. 3.

Moreover, representative embodiments of the invention disclosed herein include polypeptides consisting of about amino acid 1 to about amino acid 10 of a 121P1F1 protein shown in FIG. 2 or FIG. 3, polypeptides consisting of about amino acid 10 to about amino acid 20 of a 121P1F1 protein shown in FIG. 2 or FIG. 3, polypeptides consisting of about amino acid 20 to about amino acid 30 of a 121P1F1 protein shown in FIG. 2 or FIG. 3, polypeptides consisting of about amino acid 30 to about amino acid 40 of a 121P1F1 protein shown in FIG. 2 or FIG. 3, polypeptides consisting of about amino acid 40 to about amino acid 50 of a 121P1F1 protein shown in FIG. 2 or FIG. 3, polypeptides consisting of about amino acid 50 to about amino acid 60 of a 121P1F1 protein shown in FIG. 2 or FIG. 3, polypeptides consisting of about amino acid 60 to about amino acid 70 of a 121P1F1 protein shown in FIG. 2 or FIG. 3, polypeptides consisting of about amino acid 70 to about amino acid 80 of a 121P1F1 protein shown in FIG. 2 or FIG. 3, polypeptides consisting of about amino acid 80 to about amino acid 90 of a 121P1F1 protein shown in FIG. 2 or FIG. 3, polypeptides consisting of about amino acid 90 to about amino acid 100 of a 121P1F1 protein shown in FIG. 2 or FIG. 3, etc. throughout the entirety of a 121P1F1 amino acid sequence. Moreover, polypeptides consisting of about amino acid 1 (or 20 or 30 or 40 etc.) to about amino acid 20, (or 130, or 140 or 150 etc.) of a 121P1F1 protein shown in FIG. 2 or FIG. 3 are embodiments of the invention. It is to be appreciated that the starting and stopping positions in this paragraph refer to the specified position as well as that position plus or minus 5 residues.

121P1F1-related proteins are generated using standard peptide synthesis technology or using chemical cleavage methods well known in the art. Alternatively, recombinant methods can be used to generate nucleic acid molecules that encode a 121P1F1-related protein. In one embodiment, nucleic acid molecules provide a means to generate defined fragments of a 121P1F1 protein (or variants, homologs or analogs thereof).

III.A.) Motif-Bearing Protein Embodiments

Additional illustrative embodiments of the invention disclosed herein include 121P1F1 polypeptides comprising the amino acid residues of one or more of the biological motifs contained within a 121P1F1 polypeptide sequence set forth in FIG. 2 or FIG. 3. Various motifs are known in the art, and a protein can be evaluated for the presence of such motifs by a number of publicly available Internet sites located on the World Wide Web (see, e.g., EPIMATRIX and EPIMER, Brown University, and BIMAS).

Motif bearing subsequences of all 121P1F1 variant proteins are set forth and identified in Table XIX.

Table XX sets forth several frequently occurring motifs based on pfam searches (see URL address pfam.wustl.edu/). The columns of Table XX list (1) motif name abbreviation, (2) percent identity found amongst the different member of the motif family, (3) motif name or description and (4) most common function; location information is included if the motif is relevant for location.

Polypeptides comprising one or more of the 121P1F1 motifs discussed above are useful in elucidating the specific characteristics of a malignant phenotype in view of the observation that the 121P1F1 motifs discussed above are associated with growth dysregulation and because 121P1F1 is overexpressed in certain cancers (See, e.g., Table I). Casein kinase II, cAMP and camp-dependent protein kinase, and Protein Kinase C, for example, are enzymes known to be associated with the development of the malignant phenotype (see, e.g., Chen, et al., *Lab Invest.*, 78(2): 165-174 (1998); Gaiddon, et al., *Endocrinology* 136(10): 4331-4338 (1995); Hall, et al., *Nucleic Acids Research* 24(6): 1119-1126 (1996); Peterziel, et al., *Oncogene* 18(46): 6322-6329 (1999) and O'Brian, *Oncol. Rep.* 5(2): 305-309 (1998)). Moreover, both glycosylation and myristoylation are protein modifications also associated with cancer and cancer progression (see, e.g., Dennis, et al., *Biochem. Biophys. Acta* 1473(1):21-34 (1999); Raju, et al., *Exp. Cell Res.* 235(1): 145-154 (1997)). Amidation is another protein modification also associated with cancer and cancer progression (see, e.g., Treston, et al., *J. Natl. Cancer Inst. Monogr.* (13): 169-175 (1992)).

In another embodiment, proteins of the invention comprise one or more of the immunoreactive epitopes identified in accordance with art-accepted methods, such as the peptides set forth in Tables V-XVIII, XXVI, and XXVII. CTL epitopes can be determined using specific algorithms to identify peptides within an 121P1F1 protein that are capable of optimally binding to specified HLA alleles (e.g., Table IV; Epimatrix™ and Epimer™, Brown University, URL located on the World Wide Web at .brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chesnut, et al.; Sette, *Immunogenetics* 1999 50(3-4): 201-212; Sette, et al., *J. Immunol.* 2001 166(2): 1389-1397; Sidney, et al., *Hum. Immunol.* 1997 58(1): 12-20; Kondo, et al., *Immunogenetics* 1997 45(4): 249-258; Sidney, et al., *J. Immunol.* 1996 157(8): 3480-90; and Falk, et al., *Nature* 351: 290-6 (1991); Hunt, et al., *Science* 255:1261-3 (1992); Parker, et al., *J. Immunol.* 149:3580-7 (1992); Parker, et al., *J. Immunol.* 152:163-75 (1994)); Kast, et al., 1994 152(8): 3904-12; Borras-Cuesta, et al., *Hum. Immunol.* 2000 61(3): 266-278; Alexander, et al., *J. Immunol.* 2000 164(3); 164(3): 1625-1633; Alexander, et al., PMID: 7895164, UI: 95202582; O'Sullivan, et al., *J. Immunol.* 1991 147(8): 2663-2669; Alexander, et al., *Immunity* 1994 1(9): 751-761 and Alexander, et al., *Immunol. Res.* 1998 18(2): 79-92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

121P1F1-related proteins are embodied in many forms, preferably in isolated form. A purified 121P1F1 protein molecule will be substantially free of other proteins or molecules that impair the binding of 121P1F1 to antibody, T cell or other ligand. The nature and degree of isolation and purification will depend on the intended use. Embodiments of a 121P1F1-related proteins include purified 121P1F1-related proteins and functional, soluble 121P1F1-related proteins. In one embodiment, a functional, soluble 121P1F1 protein or fragment thereof retains the ability to be bound by antibody, T cell or other ligand.

The invention also provides 121P1F1 proteins comprising biologically active fragments of a 121P1F1 amino acid sequence shown in FIG. 2 or FIG. 3. Such proteins exhibit properties of the starting 121P1F1 protein, such as the ability to elicit the generation of antibodies that specifically bind an epitope associated with the starting 121P1F1 protein; to be bound by such antibodies; to elicit the activation of HTL or CTL; and/or, to be recognized by HTL or CTL that also specifically bind to the starting protein.

121P1F1-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-121P1F1 antibodies, or T cells or in identifying cellular factors that bind to 121P1F1. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within an 121P1F1 protein that are capable of optimally binding to specified HLA alleles (e.g., by using the SYFPEITHI site at World Wide Web URL syfpeithi.bmi-heidelberg.com/; the listings in Table IV(A)-(E); Epimatrix™ and Epimer™, Brown University, URL located on the World Wide Web at (.brown.edu/Research/TB-HIV-_Lab/epimatrix/epimatrix.html); and BIMAS, URL bimas.d-crt.nih.gov/). Illustrating this, peptide epitopes from 121P1F1 that are presented in the context of human MHC class I molecules HLA-A1, A2, A3, A11, A24, B7 and B35 were predicted (Tables V-XVIII, XXVI, and XXVII). Specifically, the complete amino acid sequence of the 121P1F1 protein and relevant portions of other variants, i.e., for HLA Class I predictions 9 flanking residues on either side of a point mutation, and for HLA Class II predictions 14 flanking residues on either side of a point mutation, were entered into the HLA Peptide Motif Search algorithm found in the Bioinformatics and Molecular Analysis Section (BIMAS) web site listed above; for HLA Class II the site SYFPEITHI at URL syfpeithi.bmi-heidelberg.com/ was used.

The HLA peptide motif search algorithm was developed by Dr. Ken Parker based on binding of specific peptide sequences in the groove of HLA Class I molecules, in particular HLA-A2 (see, e.g., Falk, et al., *Nature* 351: 290-6 (1991); Hunt, et al., *Science* 255:1261-3 (1992); Parker, et al., *J. Immunol.* 149:3580-7 (1992); Parker, et al., *J. Immunol.* 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker, et al., *J. Immunol.* 149: 3580-7 (1992)). Selected results of 121P1F1 predicted binding peptides are shown in Tables V-XVIII, XXVI, and XXVII herein. In Tables V-XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue, et al., *Prostate* 30:73-8 (1997) and Peshwa, et al., *Prostate* 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, EPIMER and EPIMATRIX sites, or specified by the HLA class I or class II motifs available in the art or which become part of the art such as set forth in Table IV (or determined using the syfpeithi or BIMAS web sites) are to be "applied" to a 121P1F1 protein in accordance with the invention. As used in this context "applied" means that a 121P1F1 protein is evaluated, e.g., visually or by computer-based patterns finding methods, as appreciated by those of skill in the relevant art. Every subsequence of a 121P1F1 protein of 8, 9, 10, or 11 amino acid residues that bears an HLA Class I motif, or a subsequence of 9 or more amino acid residues that bear an HLA Class II motif are within the scope of the invention.

III.B.) Expression of 121P1F1-Related Proteins

In an embodiment described in the examples that follow, 121P1F1 can be conveniently expressed in cells (such as 293T cells) transfected with a commercially available expression vector such as a CMV-driven expression vector encoding 121P1F1 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 121P1F1 protein in transfected cells. The secreted HIS-tagged 121P1F1 in the culture media can be purified, e.g., using a nickel column using standard techniques.

III.C.) Modifications of 121P1F1-Related Proteins

Modifications of 121P1F1-related proteins such as covalent modifications are included within the scope of this invention. One type of covalent modification includes reacting targeted amino acid residues of a 121P1F1 polypeptide with an organic derivatizing agent that is capable of reacting with selected side chains or the N- or C-terminal residues of a 121P1F1 protein. Another type of covalent modification of a 121P1F1 polypeptide included within the scope of this invention comprises altering the native glycosylation pattern of a protein of the invention. Another type of covalent modification of 121P1F1 comprises linking a 121P1F1 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 121P1F1-related proteins of the present invention can also be modified to form a chimeric molecule comprising 121P1F1 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 121P1F1 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 121P1F1. A chimeric molecule can comprise a fusion of a 121P1F1-related protein with a polyhistidine epitope tag, which provides an epitope to which immobilized nickel can selectively bind, with cytokines or with growth factors. The epitope tag is generally placed at the amino- or carboxyl-terminus of a 121P1F1 protein. In an alternative embodiment, the chimeric molecule can comprise a fusion of a 121P1F1-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 121P1F1 polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions see, e.g., U.S. Pat. No. 5,428,130 issued Jun. 27, 1995.

III.D.) Uses of 121P1F1-Related Proteins

The proteins of the invention have a number of different specific uses. As 121P1F1 is highly expressed in prostate and other cancers, 121P1F1-related proteins are used in methods that assess the status of 121P1F1 gene products in normal versus cancerous tissues, thereby elucidating the malignant phenotype. Typically, polypeptides from specific regions of a 121P1F1 protein are used to assess the presence of perturbations (such as deletions, insertions, point mutations etc.) in those regions (such as regions containing one or more motifs). Exemplary assays utilize antibodies or T cells targeting 121P1F1-related proteins comprising the amino acid residues of one or more of the biological motifs contained within a 121P1F1 polypeptide sequence in order to evaluate the characteristics of this region in normal versus cancerous tissues or to elicit an immune response to the epitope. Alternatively, 121P1F1-related proteins that contain the amino acid residues of one or more of the biological motifs in a 121P1F1 protein are used to screen for factors that interact with that region of 121P1F1.

121P1F1 protein fragments/subsequences are particularly useful in generating and characterizing domain-specific antibodies (e.g., antibodies recognizing an extracellular or intracellular epitope of an 121P1F1 protein), for identifying agents or cellular factors that bind to 121P1F1 or a particular structural domain thereof, and in various therapeutic and diagnostic contexts, including but not limited to diagnostic assays, cancer vaccines and methods of preparing such vaccines.

Proteins encoded by the 121P1F1 genes, or by analogs, homologs or fragments thereof, have a variety of uses, including but not limited to generating antibodies and in methods for identifying ligands and other agents and cellular constituents that bind to an 121P1F1 gene product. Antibodies raised against an 121P1F1 protein or fragment thereof are useful in diagnostic and prognostic assays, and imaging methodologies in the management of human cancers characterized by expression of 121P1F1 protein, such as those listed in Table I. Such antibodies can be expressed intracellularly and used in methods of treating patients with such cancers. 121P1F1-related nucleic acids or proteins are also used in generating HTL or CTL responses.

Various immunological assays useful for the detection of 121P1F1 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 121P1F1-expressing cells (e.g., in radioscintigraphic imaging methods). 121P1F1 proteins are also particularly useful in generating cancer vaccines, as further described herein.

IV.) 121P1F1 Antibodies

Another aspect of the invention provides antibodies that bind to 121P1F1-related proteins. Preferred antibodies specifically bind to a 121P1F1-related protein and do not bind (or bind weakly) to peptides or proteins that are not 121P1F1-related proteins. For example, antibodies that bind 121P1F1 can bind 121P1F1-related proteins such as the homologs or analogs thereof.

121P1F1 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 121P1F1 is also expressed or overexpressed in these other cancers. Moreover, intracellularly expressed antibodies (e.g., single chain antibodies) are therapeutically useful in treating cancers in which the expression of 121P1F1 is involved, such as advanced or metastatic prostate cancers.

The invention also provides various immunological assays useful for the detection and quantification of 121P1F1 and mutant 121P1F1-related proteins. Such assays can comprise one or more 121P1F1 antibodies capable of recognizing and binding a 121P1F1-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 121P1F1 are also provided by the invention, including but not limited to radioscintigraphic imaging methods using labeled 121P1F1 antibodies. Such assays are clinically useful in the detection, monitoring, and prognosis of 121P1F1 expressing cancers such as prostate cancer.

121P1F1 antibodies are also used in methods for purifying a 121P1F1-related protein and for isolating 121P1F1 homologues and related molecules. For example, a method of purifying a 121P1F1-related protein comprises incubating an 121P1F1 antibody, which has been coupled to a solid matrix, with a lysate or other solution containing a 121P1F1-related protein under conditions that permit the 121P1F1 antibody to bind to the 121P1F1-related protein; washing the solid matrix to eliminate impurities; and eluting the 121P1F1-related protein from the coupled antibody. Other uses of 121P1F1 antibodies in accordance with the invention include generating anti-idiotypic antibodies that mimic a 121P1F1 protein.

Various methods for the preparation of antibodies are well known in the art. For example, antibodies can be prepared by immunizing a suitable mammalian host using a 121P1F1-related protein, peptide, or fragment, in isolated or immuno-conjugated form (Antibodies: A Laboratory Manual, CSH Press, Eds., Harlow, and Lane (1988); Harlow, Antibodies, Cold Spring Harbor Press, NY (1989)). In addition, fusion proteins of 121P1F1 can also be used, such as a 121P1F1 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 121P1F1-related protein is synthesized and used as an immunogen.

In addition, naked DNA immunization techniques known in the art are used (with or without purified 121P1F1-related protein or 121P1F1 expressing cells) to generate an immune response to the encoded immunogen (for review, see Donnelly, et al., 1997, *Ann. Rev. Immunol.* 15: 617-648).

The amino acid sequence of a 121P1F1 protein as shown in FIG. 2 or FIG. 3 can be analyzed to select specific regions of the 121P1F1 protein for generating antibodies. For example, hydrophobicity and hydrophilicity analyses of a 121P1F1 amino acid sequence are used to identify hydrophilic regions in the 121P1F1 structure. Regions of a 121P1F1 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 121P1F1 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 121P1F1 immunogen is often conducted by injection over a suitable time period and with use of a suitable adjuvant, as is understood in the art. During the immunization schedule, titers of antibodies can be taken to determine adequacy of antibody formation.

121P1F1 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 121P1F1-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 121P1F1 protein can also be produced in the context of chimeric or complementarity determining region (CDR) grafted antibodies of multiple species origin. Humanized or human 121P1F1 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones, et al., 1986, *Nature* 321: 522-525; Riechmann, et al., 1988, *Nature* 332: 323-327; Verhoeyen, et al., 1988, *Science* 239: 1534-1536). See also, Carter, et al., 1993, *Proc. Natl. Acad. Sci. USA* 89: 4285 and Sims, et al., 1993, *J. Immunol.* 151: 2296.

Methods for producing fully human monoclonal antibodies include phage display and transgenic methods (for review, see Vaughan et al., 1998, *Nature Biotechnology* 16: 535-539). Fully human 121P1F1 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 121P1F1 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, *Exp. Opin. Invest. Drugs* 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of 121P1F1 antibodies with an 121P1F1-related protein can be established by a number of well known means, including Western blot, immunoprecipitation, ELISA, and FACS analyses using, as appropriate, 121P1F1-related proteins, 121P1F1-expressing cells or extracts thereof. A 121P1F1 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 121P1F1 epitopes are generated using methods generally known in the art. Homodimeric antibodies can also be generated by cross-linking techniques known in the art (e.g., Wolff, et al., *Cancer Res.* 53: 2560-2565).

V.) 121P1F1 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S., et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL syfpeithi.bmi-heidelberg.com/; Sette, A. and Sidney, J. *Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert, et al., *Cell* 74:929-937, 1993; Kondo, et al., *J. Immunol.* 155:4307-4312, 1995; Sidney, et al., *J. Immunol.* 157:3480-3490, 1996; Sidney, et al., *Human Immunol.* 45:79-93, 1996; Sette, A. and Sidney, *J. Immunogenetics* 1999 November; 50(3-4):201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont, et al., *Immunity* 8:305, 1998; Stern, et al., *Structure* 2:245, 1994; Jones, E. Y. *Curr. Opin. Immunol.* 9:75, 1997; Brown, J. H., et al., *Nature* 364:33, 1993; Guo, H. C., et al., *Proc. Natl. Acad. Sci. USA* 90:8053, 1993; Guo, H. C., et al., *Nature* 360:364, 1992; Silver, M. L., et al., *Nature* 360:367, 1992; Matsumura, M., et al., *Science* 257:927, 1992; Madden, et al., *Cell* 70:1035, 1992; Fremont, D. H., et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A., et al., *Mol. Immunol.* 32:603, 1995; Celis, E., et al., *Proc. Natl. Acad. Sci. USA* 91:2105, 1994; Tsai, V., et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A., et al., *J. Immunol.* 26:97, 1996; Wentworth, P. A. et al., *Int. Immunol.* 8:651, 1996; Alexander, J., et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B., et al., *J. Exp. Med.* 181:1047, 1995; Doolan, D. L., et al., *Immunity* 7:97, 1997; Bertoni, R. et al., *J. Clin. Invest.* 100:503, 1997; Threlkeld, S. C., et al., *J. Immunol.* 159:1648, 1997; Diepolder, H. M., et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 121P1F1 Transgenic Animals

Nucleic acids that encode a 121P1F1-related protein can also be used to generate either transgenic animals or "knock out" animals that, in turn, are useful in the development and screening of therapeutically useful reagents. In accordance with established techniques, cDNA encoding 121P1F1 can be used to clone genomic DNA that encodes 121P1F1. The cloned genomic sequences can then be used to generate transgenic animals containing cells that express DNA that encode 121P1F1. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 121P1F1 transgene incorporation with tissue-specific enhancers.

Transgenic animals that include a copy of a transgene encoding 121P1F1 can be used to examine the effect of increased expression of DNA that encodes 121P1F1. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 121P1F1 can be used to construct a 121P1F1 "knock out" animal that has a defective or altered gene encoding 121P1F1 as a result of homologous recombination between the endogenous gene encoding 121P1F1 and altered genomic DNA encoding 121P1F1 introduced into an embryonic cell of the animal. For example, cDNA that encodes 121P1F1 can be used to clone genomic DNA encoding 121P1F1 in accordance with established techniques. A portion of the genomic DNA encoding 121P1F1 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell, 69:915 (1992)). The selected cells are then injected into a blastocyst of an animal (e.g., a mouse or rat) to form aggregation chimeras (see, e.g., Bradley, in Teratocarcinomas and Embryonic Stem Cells. A Practical Approach, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 121P1F1 polypeptide.

VII.) Methods for the Detection of 121P1F1

Another aspect of the present invention relates to methods for detecting 121P1F1 polynucleotides and 121P1F1-related proteins, as well as methods for identifying a cell that expresses 121P1F1. The expression profile of 121P1F1 makes it a diagnostic marker for metastasized disease. Accordingly, the status of 121P1F1 gene products provides information useful for predicting a variety of factors including susceptibility to advanced stage disease, rate of progression, and/or tumor aggressiveness. As discussed in detail herein, the status of 121P1F1 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 121P1F1 polynucleotides in a biological sample, such as serum, bone, prostate, and other tissues, urine, semen, cell preparations, and the like. Detectable 121P1F1 polynucleotides include, for example, a 121P1F1 gene or fragment thereof, 121P1F1 mRNA, alternative splice variant 121P1F1 mRNAs, and recombinant DNA or RNA molecules that contain a 121P1F1 polynucleotide. A number of methods for amplifying and/or detecting the presence of 121P1F1 polynucleotides are well known in the art and can be employed in the practice of this aspect of the invention.

In one embodiment, a method for detecting an 121P1F1 mRNA in a biological sample comprises producing cDNA from the sample by reverse transcription using at least one primer; amplifying the cDNA so produced using an 121P1F1 polynucleotides as sense and antisense primers to amplify 121P1F1 cDNAs therein; and detecting the presence of the amplified 121P1F1 cDNA. Optionally, the sequence of the amplified 121P1F1 cDNA can be determined.

In another embodiment, a method of detecting a 121P1F1 gene in a biological sample comprises first isolating genomic DNA from the sample; amplifying the isolated genomic DNA using 121P1F1 polynucleotides as sense and antisense primers; and detecting the presence of the amplified 121P1F1 gene. Any number of appropriate sense and antisense probe combinations can be designed from a 121P1F1 nucleotide sequence (see, e.g., FIG. 2) and used for this purpose.

The invention also provides assays for detecting the presence of an 121P1F1 protein in a tissue or other biological sample such as serum, semen, bone, prostate, urine, cell preparations, and the like. Methods for detecting a 121P1F1-related protein are also well known and include, for example, immunoprecipitation, immunohistochemical analysis, Western blot analysis, molecular binding assays, ELISA, ELIFA and the like. For example, a method of detecting the presence of a 121P1F1-related protein in a biological sample comprises first contacting the sample with a 121P1F1 antibody, a 121P1F1-reactive fragment thereof, or a recombinant protein containing an antigen binding region of a 121P1F1 antibody; and then detecting the binding of 121P1F1-related protein in the sample.

Methods for identifying a cell that expresses 121P1F1 are also within the scope of the invention. In one embodiment, an assay for identifying a cell that expresses a 121P1F1 gene comprises detecting the presence of 121P1F1 mRNA in the cell. Methods for the detection of particular mRNAs in cells are well known and include, for example, hybridization assays using complementary DNA probes (such as in situ hybridization using labeled 121P1F1 riboprobes, Northern blot and related techniques) and various nucleic acid amplification assays (such as RT-PCR using complementary primers specific for 121P1F1, and other amplification type detection methods, such as, for example, branched DNA, SISBA, TMA and the like). Alternatively, an assay for identifying a cell that expresses a 121P1F1 gene comprises detecting the presence of 121P1F1-related protein in the cell or secreted by the cell. Various methods for the detection of proteins are well known in the art and are employed for the detection of 121P1F1-related proteins and cells that express 121P1F1-related proteins.

121P1F1 expression analysis is also useful as a tool for identifying and evaluating agents that modulate 121P1F1 gene expression. For example, 121P1F1 expression is significantly upregulated in prostate cancer, and is expressed in cancers of the tissues listed in Table I. Identification of a molecule or biological agent that inhibits 121P1F1 expression or over-expression in cancer cells is of therapeutic value. For example, such an agent can be identified by using a screen that quantifies 121P1F1 expression by RT-PCR, nucleic acid hybridization or antibody binding.

VIII.) Methods for Monitoring the Status of 121P1F1-Related Genes and Their Products Oncogenesis is known to be a multistep process where cellular growth becomes progressively dysregulated and cells progress from a normal physiological state to precancerous and then cancerous states (see, e.g., Alers et al., *Lab Invest.* 77(5): 437-438 (1997) and Isaacs et al., *Cancer Surv.* 23: 19-32 (1995)). In this context, examining a biological sample for evidence of dysregulated cell growth (such as aberrant 121P1F1 expression in cancers) allows for early detection of such aberrant physiology, before a pathologic state such as cancer has progressed to a stage that therapeutic options are more limited and or the prognosis is worse. In such examinations, the status of 121P1F1 in a biological sample of interest can be compared, for example, to the status of 121P1F1 in a corresponding normal sample (e.g. a sample from that individual or alternatively another individual that is not affected by a pathology). An alteration in the status of 121P1F1 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., *J. Comp. Neurol.* 1996 Dec. 9; 376(2): 306-14 and U.S. Pat. No. 5,837,501) to compare 121P1F1 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 121P1F1 expressing cells) as well as the level, and biological activity of expressed gene products (such as 121P1F1 mRNA, polynucleotides and polypeptides). Typically, an alteration in the status of 121P1F1 comprises a change in the location of 121P1F1 and/or 121P1F1 expressing cells and/or an increase in 121P1F1 mRNA and/or protein expression.

121P1F1 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 121P1F1 gene and gene products are found, for example in Ausubel, et al. eds., 1995, *Current Protocols In Molecular Biology*, Units 2 (Northern Blotting), 4 (Southern Blotting), 15 (Immunoblotting) and 18 (PCR Analysis). Thus, the status of 121P1F1 in a biological sample is evaluated by various methods utilized by skilled artisans including, but not limited to genomic Southern analysis (to examine, for example perturbations in a 121P1F1 gene), Northern analysis and/or PCR analysis of 121P1F1 mRNA (to examine, for example alterations in the polynucleotide sequences or expression levels of 121P1F1 mRNAs), and, Western and/or immunohistochemical analysis (to examine, for example alterations in polypeptide sequences, alterations in polypeptide localization within a sample, alterations in expression levels of 121P1F1 proteins and/or associations of 121P1F1 proteins with polypeptide binding partners). Detectable 121P1F1 polynucleotides include, for example, a 121P1F1 gene or fragment thereof, 121P1F1 mRNA, alternative splice variants, 121P1F1 mRNAs, and recombinant DNA or RNA molecules containing a 121P1F1 polynucleotide.

The expression profile of 121P1F1 makes it a diagnostic marker for local and/or metastasized disease, and provides information on the growth or oncogenic potential of a biological sample. In particular, the status of 121P1F1 provides information useful for predicting susceptibility to particular disease stages, progression, and/or tumor aggressiveness. The invention provides methods and assays for determining 121P1F1 status and diagnosing cancers that express 121P1F1, such as cancers of the tissues listed in Table I. For example, because 121P1F1 mRNA is so highly expressed in prostate and other cancers relative to normal prostate tissue, assays that evaluate the levels of 121P1F1 mRNA transcripts or proteins in a biological sample can be used to diagnose a disease associated with 121P1F1 dysregulation, and can provide prognostic information useful in defining appropriate therapeutic options.

The expression status of 121P1F1 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 121P1F1 in biological samples such as those from individuals suffering from, or suspected of suffering from a pathology characterized by dysregulated cellular growth, such as cancer.

As described above, the status of 121P1F1 in a biological sample can be examined by a number of well-known procedures in the art. For example, the status of 121P1F1 in a biological sample taken from a specific location in the body can be examined by evaluating the sample for the presence or absence of 121P1F1 expressing cells (e.g. those that express 121P1F1 mRNAs or proteins). This examination can provide evidence of dysregulated cellular growth, for example, when 121P1F1-expressing cells are found in a biological sample that does not normally contain such cells (such as a lymph node), because such alterations in the status of 121P1F1 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy, et al., *Prostate* 42(4): 315-317 (2000); Su, et al., *Semin. Surg. Oncol.* 18(1): 17-28 (2000) and Freeman, et al., *J Urol* 1995 August 154(2 Pt 1):474-8).

In one aspect, the invention provides methods for monitoring 121P1F1 gene products by determining the status of 121P1F1 gene products expressed by cells from an individual suspected of having a disease associated with dysregulated cell growth (such as hyperplasia or cancer) and then comparing the status so determined to the status of 121P1F1 gene products in a corresponding normal sample. The presence of aberrant 121P1F1 gene products in the test sample relative to the normal sample provides an indication of the presence of dysregulated cell growth within the cells of the individual.

In another aspect, the invention provides assays useful in determining the presence of cancer in an individual, comprising detecting a significant increase in 121P1F1 mRNA or protein expression in a test cell or tissue sample relative to expression levels in the corresponding normal cell or tissue. The presence of 121P1F1 mRNA can, for example, be evaluated in tissue samples including but not limited to those listed in Table I. The presence of significant 121P1F1 expression in any of these tissues is useful to indicate the emergence, presence and/or severity of a cancer, since the corresponding normal tissues do not express 121P1F1 mRNA or express it at lower levels.

In a related embodiment, 121P1F1 status is determined at the protein level rather than at the nucleic acid level. For example, such a method comprises determining the level of 121P1F1 protein expressed by cells in a test tissue sample and comparing the level so determined to the level of 121P1F1 expressed in a corresponding normal sample. In one embodiment, the presence of 121P1F1 protein is evaluated, for example, using immunohistochemical methods. 121P1F1 antibodies or binding partners capable of detecting 121P1F1 protein expression are used in a variety of assay formats well known in the art for this purpose.

In a further embodiment, one can evaluate the status of 121P1F1 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi, et al., 1999, *J. Cutan. Pathol.* 26(8):369-378). For example, a mutation in the sequence of 121P1F1 may be indicative of the presence or promotion of a tumor. Such assays therefore have diagnostic and predictive value where a mutation in 121P1F1 indicates a potential loss of function or increase in tumor growth.

A wide variety of assays for observing perturbations in nucleotide and amino acid sequences are well known in the art. For example, the size and structure of nucleic acid or amino acid sequences of 121P1F1 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 121P1F1 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo, et al., *Am. J. Pathol.* 155(6): 1985-1992 (1999)). In addition, this alteration is present in at least 70% of cases of high-grade prostatic intraepithelial neoplasia (PIN) (Brooks, et al., *Cancer Epidemiol. Biomarkers Prev.*, 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe, et al., *Int. J. Cancer* 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Unit 12, Frederick M. Ausubel, et al. eds., 1995.

Gene amplification is an additional method for assessing the status of 121P1F1. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 121P1F1 expression. The presence of RT-PCR amplifiable 121P1F1 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik, et al., 1997, *Urol. Res.* 25:373-384; Ghossein, et al., 1995, *J. Clin. Oncol.* 13:1195-2000; Heston, et al., 1995, *Clin. Chem.* 41:1687-1688).

A further aspect of the invention is an assessment of the susceptibility that an individual has for developing cancer. In one embodiment, a method for predicting susceptibility to cancer comprises detecting 121P1F1 mRNA or 121P1F1 protein in a tissue sample, its presence indicating susceptibility to cancer, wherein the degree of 121P1F1 mRNA expression correlates to the degree of susceptibility. In a specific embodiment, the presence of 121P1F1 in prostate or other tissue is examined, with the presence of 121P1F1 in the sample providing an indication of prostate cancer susceptibility (or the emergence or existence of a prostate tumor). Similarly, one can evaluate the integrity 121P1F1 nucleotide and amino acid sequences in a biological sample, in order to identify perturbations in the structure of these molecules such as insertions, deletions, substitutions and the like. The presence of one or more perturbations in 121P1F1 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 121P1F1 mRNA or 121P1F1 protein expressed by tumor cells, comparing the level so determined to the level of 121P1F1 mRNA or 121P1F1 protein expressed in a corresponding normal tissue taken from the same individual or a normal tissue reference sample, wherein the degree of 121P1F1 mRNA or 121P1F1 protein expression in the tumor sample relative to the normal sample indicates the degree of aggressiveness. In a specific embodiment, aggressiveness of a tumor is evaluated by determining the extent to which 121P1F1 is expressed in the tumor cells, with higher expression levels indicating more aggressive tumors. Another embodiment is the evaluation of the integrity of 121P1F1 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 121P1F1 mRNA or 121P1F1 protein expressed by cells in a sample of the tumor, comparing the level so determined to the level of 121P1F1 mRNA or 121P1F1 protein expressed in an equivalent tissue sample taken from the same individual at a different time, wherein the degree of 121P1F1 mRNA or 121P1F1 protein expression in the tumor sample over time provides information on the progression of the cancer. In a specific embodiment, the progression of a cancer is evaluated by determining 121P1F1 expression in the tumor cells over time, where increased expression over time indicates a progression of the cancer. Also, one can evaluate the integrity 121P1F1 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 121P1F1 gene and 121P1F1 gene products (or perturbations in 121P1F1 gene and 121P1F1 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking, et al., 1984, Anal. Quant. Cytol. 6(2):74-88; Epstein, 1995, Hum. Pathol. 26(2):223-9; Thorson, et al., 1998, Mod. Pathol. 11(6):543-51; Baisden, et al., 1999, Am. J. Surg. Pathol. 23(8):918-24). Methods for observing a coincidence between the expression of 121P1F1 gene and 121P1F1 gene products (or perturbations in 121P1F1 gene and 121P1F1 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 121P1F1 gene and 121P1F1 gene products (or perturbations in 121P1F1 gene and 121P1F1 gene products) and another factor associated with malignancy entails detecting the overexpression of 121P1F1 mRNA or protein in a tissue sample, detecting the overexpression of PSA mRNA or protein in a tissue sample (or PSCA or PSM expression), and observing a coincidence of 121P1F1 mRNA or protein and PSA mRNA or protein overexpression (or PSCA or PSM expression). In a specific embodiment, the expression of 121P1F1 and PSA mRNA in prostate tissue is examined, where the coincidence of 121P1F1 and PSA mRNA overexpression in the sample indicates the existence of prostate cancer, prostate cancer susceptibility or the emergence or status of a prostate tumor.

Methods for detecting and quantifying the expression of 121P1F1 mRNA or protein are described herein, and standard nucleic acid and protein detection and quantification technologies are well known in the art. Standard methods for the detection and quantification of 121P1F1 mRNA include in situ hybridization using labeled 121P1F1 riboprobes, Northern blot and related techniques using 121P1F1 polynucleotide probes, RT-PCR analysis using primers specific for 121P1F1, and other amplification type detection methods, such as, for example, branched DNA, SISBA, TMA and the like. In a specific embodiment, semi-quantitative RT-PCR is used to detect and quantify 121P1F1 mRNA expression. Any number of primers capable of amplifying 121P1F1 can be used for this purpose, including but not limited to the various primer sets specifically described herein. In a specific embodiment, polyclonal or monoclonal antibodies specifically reactive with the wild-type 121P1F1 protein can be used in an immunohistochemical assay of biopsied tissue.

IX.) Identification of Molecules that Interact with 121P1F1

The 121P1F1 protein and nucleic acid sequences disclosed herein allow a skilled artisan to identify proteins, small molecules and other agents that interact with 121P1F1, as well as pathways activated by 121P1F1 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 121P1F1 protein sequences. In such methods, peptides that bind to 121P1F1 are identified by screening libraries that encode a random or controlled collection of amino acids. Peptides encoded by the libraries are expressed as fusion proteins of bacteriophage coat proteins, the bacteriophage particles are then screened against the 121P1F1 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 121P1F1 protein sequences are disclosed for example in U.S. Pat. Nos. 5,723,286 issued 3 Mar. 1998 and 5,733,731 issued 31 Mar. 1998.

Alternatively, cell lines that express 121P1F1 are used to identify protein-protein interactions mediated by 121P1F1. Such interactions can be examined using immunoprecipitation techniques (see, e.g., Hamilton B. J., et al. *Biochem. Biophys. Res. Commun.* 1999, 261:646-51). 121P1F1 protein can be immunoprecipitated from 121P1F1-expressing cell lines using anti-121P1F1 antibodies. Alternatively, antibodies against His-tag can be used in a cell line engineered to express fusions of 121P1F1 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 121P1F1 can be identified through related embodiments of such screening assays. For example, small molecules can be identified that interfere with protein function, including molecules that interfere with 121P1F1's ability to mediate phosphorylation and de-phosphorylation, interaction with DNA or RNA molecules as an indication of regulation of cell cycles, second messenger signaling or tumorigenesis. Similarly, small molecules that modulate 121P1F1-related ion channel, protein pump, or cell communication functions are identified and used to treat patients that have a cancer that expresses 121P1F1 (see, e.g., Hille, B., Ionic Channels of Excitable Membranes $2^{nd}$ Ed., Sinauer Assoc., Sunderland, Mass., 1992). Moreover, ligands that regulate 121P1F1 function can be identified based on their ability to bind 121P1F1 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 121P1F1 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 121P1F1.

An embodiment of this invention comprises a method of screening for a molecule that interacts with an 121P1F1 amino acid sequence shown in FIG. 2 or FIG. 3, comprising the steps of contacting a population of molecules with a 121P1F1 amino acid sequence, allowing the population of molecules and the 121P1F1 amino acid sequence to interact under conditions that facilitate an interaction, determining the presence of a molecule that interacts with the 121P1F1 amino acid sequence, and then separating molecules that do not interact with the 121P1F1 amino acid sequence from molecules that do. In a specific embodiment, the method further comprises purifying, characterizing and identifying a molecule that interacts with the 121P1F1 amino acid sequence. The identified molecule can be used to modulate a function performed by 121P1F1. In a preferred embodiment, the 121P1F1 amino acid sequence is contacted with a library of peptides.

X.) Therapeutic Methods and Compositions

The identification of 121P1F1 as a protein that is normally expressed in a restricted set of tissues, but which is also expressed in prostate and other cancers, opens a number of therapeutic approaches to the treatment of such cancers. As contemplated herein, 121P1F1 functions as a transcription factor involved in activating tumor-promoting genes or repressing genes that block tumorigenesis.

Accordingly, therapeutic approaches that inhibit the activity of a 121P1F1 protein are useful for patients suffering from a cancer that expresses 121P1F1. These therapeutic approaches generally fall into two classes. One class comprises various methods for inhibiting the binding or association of a 121P1F1 protein with its binding partner or with other proteins. Another class comprises a variety of methods for inhibiting the transcription of a 121P1F1 gene or translation of 121P1F1 mRNA.

X.A.) Anti-Cancer Vaccines

The invention provides cancer vaccines comprising a 121P1F1-related protein or 121P1F1-related nucleic acid. In view of the expression of 121P1F1, cancer vaccines prevent and/or treat 121P1F1-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge, et al., 1995, *Int. J. Cancer* 63:231-237; Fong, et al., 1997, *J. Immunol.* 159: 3113-3117).

Such methods can be readily practiced by employing a 121P1F1-related protein, or an 121P1F1-encoding nucleic acid molecule and recombinant vectors capable of expressing and presenting the 121P1F1 immunogen (which typically comprises a number of antibody or T cell epitopes). Skilled artisans understand that a wide variety of vaccine systems for delivery of immunoreactive epitopes are known in the art (see, e.g., Heryln, et al., *Ann Med* 1999 February 31(1):66-78; Maruyama, et al., *Cancer Immunol Immunother* 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 121P1F1 protein shown in FIG. 3 or analog or homolog thereof) so that the mammal generates an immune response that is specific for that epitope (e.g. generates antibodies that specifically recognize that epitope). In a preferred method, a 121P1F1 immunogen contains a biological motif, see e.g., Tables V-XVIII, XXVI, and XXVII, or a peptide of a size range from 121P1F1 indicated in FIG. 5, FIG. 6, FIG. 7, FIG. 8, and FIG. 9.

The entire 121P1F1 protein, immunogenic regions or epitopes thereof can be combined and delivered by various means. Such vaccine compositions can include, for example, lipopeptides (e.g., Vitiello, A., et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones, et al., *Vaccine* 13:675-681, 1995), peptide compositions contained in immune stimulating complexes (ISCOMS) (see, e.g., Takahashi, et al., *Nature* 344:873-875, 1990; Hu, et al., *Clin Exp Immunol.* 113:235-243, 1998), multiple antigen peptide systems (MAPs) (see e.g., Tam, J. P., *Proc. Natl. Acad. Sci. USA.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L., et al., *Nature* 320:537, 1986; Kieny, M.-P. et al., *AIDS Bio/Technol-* ogy 4:790, 1986; Top, F. H., et al., *J. Infect. Dis.* 124:148, 1971; Chanda, P. K., et al., *Virology* 175:535, 1990), particles of viral or synthetic origin (e.g., Kofler, N., et al., *J. Immunol. Methods.* 192:25, 1996; Eldridge, J. H., et al., *Sem. Hematol.* 30:16, 1993; Falo, L. D., Jr. et al., *Nature Med.* 7:649, 1995), adjuvants (Warren, H. S., Vogel, F. R., and Chedid, L. A., *Annu. Rev. Immunol.* 4:369, 1986; Gupta, R. K., et al., *Vaccine* 11:293, 1993), liposomes (Reddy, R., et al., *J. Immunol.* 148:1585, 1992; Rock, K. L., *Immunol. Today* 17:131, 1996), or, naked or particle absorbed cDNA (Ulmer, J. B., et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 121P1F1-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 121P1F1 protein that bind corresponding HLA alleles (see e.g., Table IV; Epimer™ and Epimatrix™, Brown University (URL located on the World Wide Web at .brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a 121P1F1 immunogen contains one or more amino acid sequences identified using techniques well known in the art, such as the sequences shown in Tables V-XVIII, XXVI, and XXVII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 121P1F1 protein) so that an immune response is generated. A typical embodiment consists of a method for generating an immune response to 121P1F1 in a host, by contacting the host with a sufficient amount of at least one 121P1F1 B cell or cytotoxic T-cell epitope or analog thereof; and at least one periodic interval thereafter re-contacting the host with the 121P1F1 B cell or cytotoxic T-cell epitope or analog thereof. A specific embodiment consists of a method of generating an immune response against a 121P1F1-related protein or a man-made multiepitopic peptide comprising: administering 121P1F1 immunogen (e.g. a 121P1F1 protein or a peptide fragment thereof, an 121P1F1 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander, et al., *J. Immunol.* 2000 164(3); 164(3): 1625-1633; Alexander, et al., *Immunity* 1994 1(9): 751-761 and Alexander, et al., *Immunol. Res.* 1998 18(2): 79-92). An alternative method comprises generating an immune response in an individual against a 121P1F1 immunogen by: administering in vivo to muscle or skin of the individual's body a DNA molecule that comprises a DNA sequence that encodes an 121P1F1 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 121P1F1, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 121P1F1. Constructs comprising DNA encoding a 121P1F1-related protein/immunogen and appropriate regulatory sequences can be injected directly into muscle or skin of an individual, such that the cells of the muscle or skin take-up the construct and express the encoded 121P1F1 protein/immunogen. Alternatively, a vaccine comprises a 121P1F1-related protein. Expression of the 121P1F1-related protein immunogen results in the generation of prophylactic or therapeutic humoral and cellular immunity against cells that bear a 121P1F1 protein. Various prophylactic and therapeutic genetic immunization techniques known in the art can be used (for review, see information and references published at Internet address located on the World Wide Web at .genweb.com). Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol.

8:658-663; Tsang et al. *J. Natl. Cancer Inst.* 87:982-990 (1995)). Non-viral delivery systems can also be employed by introducing naked DNA encoding a 121P1F1-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 121P1F1-related nucleic acid molecule. In one embodiment, the full-length human 121P1F1 cDNA is employed. In another embodiment, 121P1F1 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 121P1F1 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa, et al., 1996, *Prostate* 28:65-69; Murphy, et al., 1996, *Prostate* 29:371-380). Thus, dendritic cells can be used to present 121P1F1 peptides to T cells in the context of MHC class I or II molecules. In one embodiment, autologous dendritic cells are pulsed with 121P1F1 peptides capable of binding to MHC class I and/or class II molecules. In another embodiment, dendritic cells are pulsed with the complete 121P1F1 protein. Yet another embodiment involves engineering the overexpression of a 121P1F1 gene in dendritic cells using various implementing vectors known in the art, such as adenovirus (Arthur, et al., 1997, *Cancer Gene Ther.* 4:17-25), retrovirus (Henderson, et al., 1996, *Cancer Res.* 56:3763-3770), lentivirus, adeno-associated virus, DNA transfection (Ribas, et al., 1997, *Cancer Res.* 57:2865-2869), or tumor-derived RNA transfection (Ashley, et al., 1997, *J. Exp. Med.* 186:1177-1182). Cells that express 121P1F1 can also be engineered to express immune modulators, such as GM-CSF, and used as immunizing agents.

X.B.) 121P1F1 as a Target for Antibody-Based Therapy

121P1F1 is an attractive target for antibody-based therapeutic strategies. A number of antibody strategies are known in the art for targeting both extracellular and intracellular molecules (see, e.g., complement and ADCC mediated killing as well as the use of intrabodies). Because 121P1F1 is expressed by cancer cells of various lineages relative to corresponding normal cells, systemic administration of 121P1F1-immunoreactive compositions are prepared that exhibit excellent sensitivity without toxic, non-specific and/or non-target effects caused by binding of the immunoreactive composition to non-target organs and tissues. Antibodies specifically reactive with domains of 121P1F1 are useful to treat 121P1F1-expressing cancers systemically, either as conjugates with a toxin or therapeutic agent, or as naked antibodies capable of inhibiting cell proliferation or function.

121P1F1 antibodies can be introduced into a patient such that the antibody binds to 121P1F1 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 121P1F1, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 121P1F1 sequence shown in FIG. 2 or FIG. 3. In addition, skilled artisans understand that it is routine to conjugate antibodies to cytotoxic agents (see, e.g., Slevers, et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 121P1F1), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-121P1F1 antibody) that binds to a marker (e.g. 121P1F1) expressed, accessible to binding or localized on the cell surfaces. A typical embodiment is a method of delivering a cytotoxic and/or therapeutic agent to a cell expressing 121P1F1, comprising conjugating the cytotoxic agent to an antibody that immunospecifically binds to a 121P1F1 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-121P1F1 antibodies can be done in accordance with various approaches that have been successfully employed in the treatment of other types of cancer, including but not limited to colon cancer (Arlen, et al., 1998, *Crit. Rev. Immunol.* 18:133-138), multiple myeloma (Ozaki, et al., 1997, *Blood* 90:3179-3186, Tsunenari, et al., 1997, *Blood* 90:2437-2444), gastric cancer (Kasprzyk, et al., 1992, *Cancer Res.* 52:2771-2776), B-cell lymphoma (Funakoshi, et al., 1996, *J. Immunother. Emphasis Tumor Immunol.* 19:93-101), leukemia (Zhong, et al., 1996, *Leuk. Res.* 20:581-589), colorectal cancer (Moun, et al., 1994, *Cancer Res.* 54:6160-6166; Velders, et al., 1995, *Cancer Res.* 55:4398-4403), and breast cancer (Shepard, et al., 1991, *J. Clin. Immunol.* 11: 117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as HERCEPTIN (trastuzumab) with PACLITAXEL (Genentech, Inc.). The antibodies can be conjugated to a therapeutic agent. To treat prostate cancer, for example, 121P1F1 antibodies can be administered in conjunction with radiation, chemotherapy or hormone ablation. Also, antibodies can be conjugated to a toxin such as calicheamicin (e.g., MYLO-TARG, Wyeth-Ayerst, Madison, N.J., a recombinant humanized IgG$_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 121P1F1 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan, et al. (*Cancer Res.* 53:4637-4642, 1993), Prewett, et al. (*International J. of Onco.* 9:217-224, 1996), and Hancock, et al. (*Cancer Res.* 51:4575-4580, 1991) describe the use of various antibodies together with chemotherapeutic agents.

Although 121P1F1 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 121P1F1 expression, preferably using immunohistochemical assessments of tumor tissue, quantitative 121P1F1 imaging, or other techniques that reliably indicate the presence and degree of 121P1F1 expression. Immunohistochemical analysis of tumor biopsies or surgical specimens is preferred for this purpose. Methods for immunohistochemical analysis of tumor tissues are well known in the art.

Anti-121P1F1 monoclonal antibodies that treat prostate and other cancers include those that initiate a potent immune response against the tumor or those that are directly cytotoxic. In this regard, anti-121P1F1 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-121P1F1 mAbs that exert a direct biological effect on tumor growth are useful to treat cancers that express 121P1F1. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-121P1F1 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 121P1F1 antigen with high affinity but exhibit low or no antigenicity in the patient.

Therapeutic methods of the invention contemplate the administration of single anti-121P1F1 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-121P1F1 mAbs can be administered concomitantly with other therapeutic modalities, including but not limited to various chemotherapeutic agents, androgen-blockers, immune modulators (e.g., IL-2, GM-CSF), surgery or radiation. The anti-121P1F1 mAbs are administered in their "naked" or unconjugated form, or can have a therapeutic agent(s) conjugated to them.

Anti-121P1F1 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-121P1F1 antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-121P1F1 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 121P1F1 expression in the patient, the extent of circulating shed 121P1F1 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 121P1F1 in a given sample (e.g. the levels of circulating 121P1F1 antigen and/or 121P1F1 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-121P1F1 antibodies can also be used in anti-cancer therapy as a vaccine for inducing an immune response to cells expressing a 121P1F1-related protein. In particular, the generation of anti-idiotypic antibodies is well known in the art; this methodology can readily be adapted to generate anti-idiotypic anti-121P1F1 antibodies that mimic an epitope on a 121P1F1-related protein (see, for example, Wagner, et al., 1997, *Hybridoma* 16: 33-40; Foon, et al., 1995, *J. Clin. Invest.* 96:334-342; Herlyn, et al., 1996, *Cancer Immunol. Immunother.* 43:65-76). Such an anti-idiotypic antibody can be used in cancer vaccine strategies.

X.C.) 121P1F1 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 121P1F1 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation.

Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka, et al., *J. Immunol.* 162:3915-3925, 1999; An, L. and Whitton, J. L., *J. Virol.* 71:2292, 1997; Thomson, S. A., et al., *J. Immunol.* 157:822, 1996; Whitton, J. L., et al., *J. Virol.* 67:348, 1993; Hanke, R., et al., *Vaccine* 16:426, 1998. For example, a multi-epitope DNA plasmid encoding supermotif- and/or motif-bearing epitopes derived 121P1F1, the PADRE® universal helper T cell epitope (or multiple HTL epitopes from 121P1F1), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 (51Cr) labeled and used as target cells for epitope-specific CTL lines; cytolysis, detected by 51Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 26), *Plasmodium falciparum* circumsporozoite (CS) protein at positions 378-398 (DIEKKIAKMEKASS-VFNVVNS; SEQ ID NO: 27), and *Streptococcus* 18 kD protein at positions 116-131 (GAVDSILGGVATYGAA; SEQ ID NO: 28). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 29), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 121P1F1. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 121P1F1.

X.D. Adoptive Immunotherapy

Antigenic 121P1F1-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 121P1F1. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 121P1F1. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 121P1F1-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 121P1F1, a vaccine comprising 121P1F1-specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., *Remington's Pharmaceutical Sciences*, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5 \times 10^7$ to $5 \times 10^9$ pfu.

For antibodies, a treatment generally involves repeated administration of the anti-121P1F1 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-121P1F1 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 121P1F1 expression in the patient, the extent of circulating shed 121P1F1 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 121P1F1

As disclosed herein, 121P1F1 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

121P1F1 can be analogized to a prostate associated antigen PSA, the archetypal marker that has been used by medical practitioners for years to identify and monitor the presence of prostate cancer (see, e.g., Merrill, et al., *J. Urol.* 163(2): 503-5120 (2000); Polascik, et al., *J. Urol.* August; 162(2): 293-306 (1999) and Fortier, et al., *J. Nat. Cancer Inst.* 91(19): 1635-1640 (1999)). A variety of other diagnostic markers are also used in similar contexts including p53 and K-ras (see, e.g., Tulchinsky, et al., *Int J Mol Med* 1999 July 4(1):99-102 and Minimoto, et al., *Cancer Detect Prev* 2000; 24(1):1-12). Therefore, this disclosure of 121P1F1 polynucleotides and polypeptides (as well as 121P1F1 polynucleotide probes and anti-121P1F1 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 121P1F1 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief, et al., *Biochem. Mol. Biol. Int.* 33(3):567-74 (1994)) and primers (for example in PCR analysis, see, e.g., Okegawa et al., *J. Urol.* 163(4): 1189-1190 (2000)) to observe the presence and/or the level of PSA mRNAs in methods of monitoring PSA overexpression or the metastasis of prostate cancers, the 121P1F1 polynucleotides described herein can be utilized in the same way to detect 121P1F1 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan, et al., *Urology* 55(4):560-3 (2000)) or the metastasis of prostate cells (see, e.g., Alanen, et al., *Pathol. Res. Pract.* 192(3):233-7 (1996)), the 121P1F1 polypeptides described herein can be utilized to generate antibodies for use in detecting 121P1F1 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 121P1F1 polynucleotides and/or polypeptides can be used to provide evidence of metastasis. For example, when a biological sample from tissue that does not normally contain 121P1F1-expressing cells (lymph node) is found to contain 121P1F1-expressing cells such as the 121P1F1 expression seen in LAPC4 and LAPC9, xenografts isolated from lymph node and bone metastasis, respectively, this finding is indicative of metastasis.

Alternatively 121P1F1 polynucleotides and/or polypeptides can be used to provide evidence of cancer, for example, when cells in a biological sample that do not normally express 121P1F1 or express 121P1F1 at a different level are found to express 121P1F1 or have an increased expression of 121P1F1 (see, e.g., the 121P1F1 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 121P1F1) such as PSA, PSCA etc. (see, e.g., Alanen, et al., *Pathol. Res. Pract.* 192(3): 233-237 (1996)).

Just as PSA polynucleotide fragments and polynucleotide variants are employed by skilled artisans for use in methods of monitoring PSA, 121P1F1 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G., *Biotechniques* 25(3): 472-476, 478-480 (1998); Robertson, et al., *Methods Mol. Biol.* 98:121-154 (1998)). An additional illustration of the use of such fragments is provided in Example 4, where a 121P1F1 polynucleotide fragment is used as a probe to show the expression of 121P1F1 RNAs in cancer cells. In addition, variant polynucleotide sequences are typically used as primers and probes for the corresponding mRNAs in PCR and Northern analyses (see, e.g., Sawai, et al., Fetal Diagn. Ther. 1996 November-December 11(6): 407-13 and *Current Protocols In Molecular Biology*, Volume 2, Unit 2, Frederick M. Ausubel, et al., eds., 1995)). Polynucleotide fragments and variants are useful in this context where they are capable of binding to a target polynucleotide sequence (e.g., a 121P1F1 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 121P1F1 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., *Current Protocols In Molecular Biology*, Volume 2, Unit 16, Frederick M. Ausubel, et al., eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 121P1F1 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g., a 121P1F1 polypeptide shown in FIG. 3).

As shown herein, the 121P1F1 polynucleotides and polypeptides (as well as the 121P1F1 polynucleotide probes and anti-121P1F1 antibodies or T cells used to identify the presence of these molecules) exhibit specific properties that make them useful in diagnosing cancers such as those listed in Table I. Diagnostic assays that measure the presence of 121P1F1 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., *Pathol. Res. Pract.* 192(3): 233-237 (1996)), and consequently, materials such as 121P1F1 polynucleotides and polypeptides (as well as the 121P1F1 polynucleotide probes and anti-121P1F1 antibodies used to identify the presence of these molecules) need to be employed to confirm a metastases of prostatic origin.

Finally, in addition to their use in diagnostic assays, the 121P1F1 polynucleotides disclosed herein have a number of other utilities such as their use in the identification of oncogenetic associated chromosomal abnormalities in the chromosomal region to which the 121P1F1 gene maps (see Example 3 below). Moreover, in addition to their use in diagnostic assays, the 121P1F1-related proteins and polynucleotides disclosed herein have other utilities such as their use in the forensic analysis of tissues of unknown origin (see, e.g., Takahama, K., *Forensic Sci Int* 1996 Jun. 28; 80(1-2): 63-9).

Additionally, 121P1F1-related proteins or polynucleotides of the invention can be used to treat a pathologic condition characterized by the over-expression of 121P1F1. For example, the amino acid or nucleic acid sequence of FIG. 2 or FIG. 3, or fragments of either, can be used to generate an immune response to a 121P1F1 antigen. Antibodies or other molecules that react with 121P1F1 can be used to modulate the function of this molecule, and thereby provide a therapeutic benefit.

XII.) Inhibition of 121P1F1 Protein Function

The invention includes various methods and compositions for inhibiting the binding of 121P1F1 to its binding partner or its association with other protein(s) as well as methods for inhibiting 121P1F1 function.

XII.A.) Inhibition of 121P1F1 with Intracellular Antibodies

In one approach, a recombinant vector that encodes single chain antibodies that specifically bind to 121P1F1 are introduced into 121P1F1 expressing cells via gene transfer technologies. Accordingly, the encoded single chain anti-121P1F1 antibody is expressed intracellularly, binds to 121P1F1 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson, et al., 1995, *Proc. Natl. Acad. Sci. USA* 92: 3137-3141; Beerli, et al., 1994, *J. Biol. Chem.* 289: 23931-23936; Deshane, et al., 1994, *Gene Ther.* 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 121P1F1 in the nucleus, thereby preventing its activity within the nucleus. Nuclear targeting signals are engineered into such 121P1F1 intrabodies in order to achieve the desired targeting. Such 121P1F1 intrabodies are designed to bind specifically to a particular 121P1F1 domain. In another embodiment, cytosolic intrabodies that specifically bind to a 121P1F1 protein are used to prevent 121P1F1 from gaining access to the nucleus, thereby preventing it from exerting any biological activity within the nucleus (e.g., preventing 121P1F1 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 121P1F1 with Recombinant Proteins

In another approach, recombinant molecules bind to 121P1F1 and thereby inhibit 121P1F1 function. For example, these recombinant molecules prevent or inhibit 121P1F1 from accessing/binding to its binding partner(s) or associating with other protein(s). Such recombinant molecules can, for example, contain the reactive part(s) of a 121P1F1 specific antibody molecule. In a particular embodiment, the 121P1F1 binding domain of a 121P1F1 binding partner is engineered into a dimeric fusion protein, whereby the fusion protein comprises two 121P1F1 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 121P1F1, whereby the dimeric fusion protein specifically binds to 121P1F1 and blocks 121P1F1 interaction with a binding partner. Such dimeric fusion proteins are further combined into multimeric proteins using known antibody linking technologies.

XII.C.) Inhibition of 121P1F1 Transcription or Translation

The present invention also comprises various methods and compositions for inhibiting the transcription of the 121P1F1 gene. Similarly, the invention also provides methods and compositions for inhibiting the translation of 121P1F1 mRNA into protein.

In one approach, a method of inhibiting the transcription of the 121P1F1 gene comprises contacting the 121P1F1 gene with a 121P1F1 antisense polynucleotide. In another approach, a method of inhibiting 121P1F1 mRNA translation comprises contacting a 121P1F1 mRNA with an antisense polynucleotide. In another approach, a 121P1F1 specific ribozyme is used to cleave a 121P1F1 message, thereby inhibiting translation. Such antisense and ribozyme based methods can also be directed to the regulatory regions of the 121P1F1 gene, such as 121P1F1 promoter and/or enhancer elements. Similarly, proteins capable of inhibiting a 121P1F1 gene transcription factor are used to inhibit 121P1F1 mRNA transcription. The various polynucleotides and compositions useful in the aforementioned methods have been described above. The use of antisense and ribozyme molecules to inhibit transcription and translation is well known in the art.

Other factors that inhibit the transcription of 121P1F1 by interfering with 121P1F1 transcriptional activation are also useful to treat cancers expressing 121P1F1. Similarly, factors that interfere with 121P1F1 processing are useful to treat cancers that express 121P1F1. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 121P1F1 (i.e., antisense, ribozyme, polynucleotides encoding intrabodies and other 121P1F1 inhibitory molecules). A number of gene therapy approaches are known in the art. Recombinant vectors encoding 121P1F1 antisense polynucleotides, ribozymes, factors capable of interfering with 121P1F1 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 121P1F1 to a binding partner, etc.

In vivo, the effect of a 121P1F1 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein, et al., 1997, *Nature Medicine* 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 121P1F1-related protein or a 121P1F1 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the 121P1F1 Gene

Suppression Subtractive Hybridization (SSH) was used to identify cDNAs corresponding to genes that are differentially expressed in prostate cancer. The SSH reaction utilized cDNA from two LAPC-9 AD xenografts. Specifically, to isolate genes that are involved in the progression of androgen dependent (AD) prostate cancer to androgen independent (AI) cancer, the LAPC-9 AD xenograft in male SCID mice was used. Mice that harbored LAPC-9 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that were turned on or off during the transition to androgen independence.

The gene 121P1F1 was derived from an LAPC-9 AD minus LAPC-9 AD (28 days post-castration) subtraction. The SSH DNA sequence of 254 bp (FIG. 1) is novel and did not exhibit significant homology to any known human genes in public databases.

The 121P1F1 SSH cDNA of 254 bp is listed in FIG. 1. The full length 121P1F1 cDNAs and ORFs are described in FIG. 2 with the protein sequences listed in FIG. 3.

Materials and Methods

LAPC Xenografts and Human Tissues:

LAPC xenografts were obtained from Dr. Charles Sawyers (UCLA) and generated as described (Klein, et al, 1997, *Nature Med.* 3: 402-408; Craft, et al., 1999, *Cancer Res.* 59: 5030-5036). Androgen dependent and independent LAPC-4 xenografts LAPC-4 AD and AI, respectively) and LAPC-9 AD and AI xenografts were grown in male SCID mice and were passaged as small tissue chunks in recipient males. LAPC-4 and -9 AI xenografts were derived from LAPC-4 or -9 AD tumors, respectively. To generate the AI xenografts, male mice bearing AD tumors were castrated and maintained for 2-3 months. After the tumors re-grew, the tumors were harvested and passaged in castrated males or in female SCID mice.

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
                                    (SEQ ID NO: 30)
5'TTTTGATCAAGCTT30 3'

Adaptor 1:
                                    (SEQ ID NO: 31)
5'CTAATACGACTCACTATAGGGCTCGAGCGGCCGCCCGGGCAG3'

(SEQ ID NO: 32)
3'GGCCCGTCCTAG5'

Adaptor 2:
                                    (SEQ ID NO: 33)
5'GTAATACGACTCACTATAGGGCAGCGTGGTCGCGGCCGAG3'

(SEQ ID NO: 34)
3'CGGCTCCTAG5'

PCR primer 1:
                                    (SEQ ID NO: 35)
5'CTAATACGACTCACTATAGGGC3'
```

```
Nested primer (NP)1:
                                            (SEQ ID NO: 36)
5'TCGAGCGGCCGCCCGGGCAGGA3'

Nested primer (NP)2:
                                            (SEQ ID NO: 37)
5'AGCGTGGTCGCGGCCGAGGA3'
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer xenograft LAPC-9AD. The gene 121P1F1 was derived from an LAPC-9 AD minus LAPC-9 AD (28 days post-castration) subtraction. The SSH DNA sequence (FIG. 1) was identified.

The cDNA derived from prostate cancer xenograft LAPC-9AD tissue was used as the source of the "driver" cDNA, while the cDNA from prostate cancer xenograft LAPC-9AD (28 days post-castration) was used as the source of the "tester" cDNA. Double stranded cDNAs corresponding to tester and driver cDNAs were synthesized from 2 μg of poly (A)+ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 μl of Dpn II digested cDNA from the relevant tissue source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 U of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 μg of mRNA with oligo (dT) 12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 μl with water prior to normalization.

Normalization of the first strand cDNAs from multiple tissues was performed by using the primers 5'atatcgc-cgcgctcgtcgtcgacaa 3' (SEQ ID NO: 38) and 5'agccacacg-cagctcattgtagaagg 3' (SEQ ID NO: 39) to amplify β-actin. First strand cDNA (5 μl) were amplified in a total volume of 50 μl containing 0.4 μM primers, 0.2 μM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five μl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 121P1F1 gene, 5 μl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 17. RT-PCR expression analysis was performed on first strand cDNAs generated using pools of tissues from multiple samples. The cDNAs were shown to be normalized using beta-actin primers. PCR Expression was observed in human testis, prostate cancer xenografts, colon cancer tissue pools, lung cancer tissue pools, kidney cancer tissue pools, bladder cancer tissue pools, and prostate cancer tissue pools.

Example 2

Full Length Cloning of 121P1F1 and Homolog Comparison to Known Sequences

To isolate genes that are involved in the progression of androgen dependent (AD) prostate cancer to androgen independent (AI) cancer, an experiment was conducted with the LAPC-9AD xenograft in male SCID mice. Mice that harbored LAPC-9AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 121P1F1 was derived from an LAPC-9AD minus LAPC-9AD (28 days post-castration) subtraction. The SSH DNA sequence of 254 bp (FIG. 1) is novel and did not exhibit significant homology to any known human genes in public databases.

A cDNA (clone A) of 863 bp was isolated from a Human Testis cDNA library, revealing an ORF of 205 amino acids (FIG. 2 and FIG. 3). It is probable that 121P1F1 is a cytoplasmic protein based on two topology algorithms (J. Mol. Biol. 2000, 300:1005 and Bioinformatics, 1998, 14:378) and based on its homology to Dynactin. However, it is also possible that 121P1F1 is localized in the nucleus based on PSORT analysis.

Sequence analysis of 121P1F1 reveals highest homology to human GAJ protein (FIG. 4C); the two proteins are 100% homologous over a 205 amino acid region. 121P1F1 also displays homology to a mouse putative protein (FIG. 4D). The two proteins are 89% identical over a 202 amino acid region. Also, 121P1F1 shows 40% identity over a 202 amino acid region with the 24.2 kDa hypothetical coiled-coil protein of fission yeast. (FIG. 4E)

The 121P1F1 cDNA was deposited on Mar. 1, 2001 with the American Type Culture Collection (ATCC; Manassas, Va.), and has been assigned Accession No. PTA-3139.

Example 3

Chromosomal Localization

Chromosomal localization can implicate genes in disease pathogenesis. Several chromosome mapping approaches are available, including fluorescent in situ hybridization (FISH), human/hamster radiation hybrid (RH) panels (Walter, et al., 1994; *Nature Genetics* 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

121P1F1 maps to chromosome 4q, using 121P1F1 sequence and the NCBI BLAST tool located on the World Wide Web.

Example 4

Expression Analysis of 121P1F1 in Normal Tissues and Patient Specimens

Expression analysis by RT-PCR demonstrated that 121P1F1 expression is reminiscent of a cancer-testis gene (FIG. 17A). Normal tissue expression is restricted to testis and, to a lower extent, it is detected in the thymus and ovary. Analysis of human patient cancer RNA pools shows expression in prostate, kidney, and bladder cancers, as well as lung cancers (FIG. 17B).

Extensive Northern blot analysis of 121P1F1 in 16 human normal tissues confirmed the expression observed by RT-PCR (FIG. 18). A 1.2 kb transcript was detected in testis and at lower levels in thymus. 121P1F1 expression was also shown in prostate cancer xenografts and in all cancer cell lines tested, such as in prostate (LAPC 4AD, LAPC 4AI, LAPC 9AD, LAPC 9AI, LNCaP, PC-3, DU145 Tsu-Pr1, and LAPC4); bladder (HT1197, SCaBER, UM-UC-3, TCCSUP, J82, 5637), lung (A427, NCI-H82, NCI-H146), kidney (769-P, A-498, CAKI-1, SW 839), pancreas (PANC-1, Bx PC-3, HPAC, Capan-1); colon (SK-CO-1, Caco-2, LoVo, T84, Colo205) and in the cancer cell lines 293T, RD-ES and KCL22. (FIG. 19). These results indicated that 121P1F1 is a testis specific gene that is upregulated in cancers.

Northern blot analysis showed that 121P1F1 is expressed in prostate tumor tissues derived from prostate cancer patients (FIG. 20). It was also expressed in kidney, cervix, breast and stomach patient cancer samples (FIG. 21). The expression detected in normal adjacent tissues (isolated from diseased tissues) but not in normal tissues, isolated from healthy donors, indicate that these tissues are not fully normal and that 121P1F1 is expressed in early stage tumors, and thus can be used as a diagnostic target.

Since 121P1F1 was derived from a LAPC-9 AD minus LAPC-9 AD (28 days post-castration) subtraction, an assay was performed for androgen regulation of 121P1F1 (FIG. 22). LAPC-4 cells were grown in charcoal-stripped medium and stimulated with the synthetic androgen mibolerone, for either 14 or 24 hours. It was shown that the expression of 121P1F1 went down in absence of normal serum, and is modulated in presence of mibolerone, 24 hours after stimulation. The experimental samples were confirmed by testing for the expression of the androgen-regulated prostate cancer gene TMPRSS2. This experiment showed that, as expected, TMPRSS2 levels go down in presence of charcoal-stripped serum, and expression is induced at 14 and 24 hours in presence of mibolerone.

FIG. 15 shows androgen regulation of 121P1F1 in vivo. Male mice were injected with LAPC-9AD tumor cells. When tumor reached a palpable size (0.3-0.5 cm in diameter), mice were castrated and tumors harvested at different time points following castration. RNA was isolated from the xenograft tissues. Northern blots with 10 µg of total RNA/lane were probed with the 121P1F1 SSH fragment; size standards in kilobases (kb) are indicated on the side. Results show that expression of 121P1F1 is slightly downregulated 7 days after castration. The protein TMPRSS2 was used as a positive control. A picture of the ethidium-bromide staining of the RNA gel is also presented (lowest panel).

121P1F1 expression is reminiscent of a cancer-testis gene. Its restricted normal tissue expression and the upregulation detected in prostate cancer, bladder cancer, kidney cancer, colon cancer, and lung cancer, indicate that 121P1F1 is therapeutic and prophylactic target and a diagnostic and prognostic marker for human cancers.

Example 5

Splice Variants of 121P1F1 and Single Nucleotide Polymorphisms Splice Variants

Splice variants are alternatively spliced transcripts. When a gene is transcribed from genomic DNA, the initial RNA is generally spliced to produce functional mRNA, which has only exons and is used for translation into an amino acid sequence. Accordingly, a given gene can have zero to many alternatively spliced mRNA products. Alternative transcripts each have a unique exon makeup, and can have different coding and/or non-coding (5' or 3' end) portions, from the original transcript. Alternative transcripts can code for similar proteins with the same or a similar function or may encode proteins with different functions, and may be expressed in the same tissue at the same time, or at different tissue at different times. Proteins encoded by alternative transcripts can have similar or different cellular or extracellular localizations, e.g., be secreted.

Splice variants are identified by a variety of art-accepted methods. For example, splice variants are identified by use of EST data. First, all human ESTs were grouped into clusters which show direct or indirect identity with each other. Second, ESTs in the same cluster were further grouped into sub-clusters and assembled into a consensus sequence. The starting gene is compared to the consensus sequence(s). Each consensus sequence is a potential splice variant for that gene (see, e.g., Web URL located on the World Wide Web at .doubletwist.com/products/c11_agentsOverview.jhtml). Even when a variant is identified that is not a full-length clone, that portion of the variant is very useful for antigen generation and for further cloning of the full-length splice variant, using techniques known in the art.

Moreover, computer programs are available in the art that identify splice variants based on genomic sequences. Genomic-based variant identification programs include FgenesH (A. Salamov and V. Solovyev, "Ab initio gene finding in *Drosophila* genomic DNA," Genome Research. 2000 April; 10(4):516-22); Grail (Web URL compbio.ornl.gov/Grail-bin/ EmptyGrailForm) and GenScan (Web URL genes.mit.edu/ GENSCAN.html). For a general discussion of splice variant identification protocols see., e.g., Southan C., "A genomic perspective on human proteases," *FEBS Lett.* (2001 Jun. 8) 498(2-3):214-8; and de Souza, S. J., et al., "Identification of human chromosome 22 transcribed sequences with ORF expressed sequence tags," *Proc. Natl. Acad. Sci. USA.* (2000 Nov. 7) 97(23):12690-3.

For variants identified by the EST-based method, Table XXII shows the nucleotide sequences of the splice variants. Table XXIII shows the alignment of the splice variant with the 121P1F1 nucleic acid sequence. Table XXIV displays alignments of an amino acid sequence encoded by a splice variant with 121P1F1 v.1. Table XXV lays out the amino acid translation of the splice variant for the identified reading frame orientation. Tables XXII through XXV are set forth herein on a variant-by-variant basis.

For variants identified by any one of the genomic sequence-based methods, Table XXII shows the nucleotide sequences of the splice variant. Table XXIII shows the alignment of the splice variant with the 121P1F1 nucleic acid sequence. Table XXIV displays the alignment of amino acid sequence of the predicted transcripts with 121P1F1. The genomic-based computer programs predict a transcript from genomic sequence, and not only predict exons but also set open reading frame as the first forward open reading frame. The predicted transcript does not contain 5' or 3' untranslated region (UTR). It starts with ATG and ends with a stop codon, TAG, TGA or TAA. In case the transcript is predicted on the reverse strand of the genomic sequence, the sequence of the transcript is reverse-complemented to the genomic sequence of the exons. Thus, the genomic-based programs provide the correct transcript sequence, with 5' to 3' orientation and +1 as the open reading frame. However, due to the possibility of inaccurate prediction of exons or the possibility of sequencing errors in genomic data, other peptides in other forward open reading frames can also be encoded by the variant.

To further confirm the parameters of a splice variant, a variety of techniques are available in the art, such as full-length cloning, proteomic validation, PCR-based validation, and 5' RACE validation, etc. (see e.g., Proteomic Validation: Brennan S O, Fellowes A P, George P M.; "Albumin banks peninsula: a new termination variant characterised by electrospray mass spectrometry." Biochim Biophys Acta. 1999 Aug. 17; 1433(1-2):321-6; Ferranti P, et al., "Differential splicing of pre-messenger RNA produces multiple forms of mature caprine alpha(s1)-casein." *Eur J Biochem.* 1997 Oct. 1; 249(1): 1-7; PCR-based Validation: Wellmann, S, et al., "Specific reverse transcription-PCR quantification of vascular endothelial growth factor (VEGF) splice variants by LightCycler technology." *Clin Chem.* 2001 April; 47(4):654-60; Jia, H. P., et al., Discovery of new human beta-defensins using a genomics-based approach," *Gene.* 2001 Jan. 24; 263 (1-2):211-8; PCR-based and 5' RACE Validation: Brigle, K. E., et al., "Organization of the murine reduced folate carrier gene and identification of variant splice forms," *Biochim Biophys Acta.* 1997 Aug. 7; 1353(2): 191-8.

It is known in the art that genomic regions are modulated in cancers. When the genomic region to which 121P1F1 maps is modulated in a particular cancer, the splice variants of 121P1F1 are modulated as well. Disclosed herein is that 121P1F1 has a particular expression profile. Splice variants of 121P1F1 that are structurally and/or functionally similar to 121P1F1 share this expression pattern, thus serving as tumor-associated markers/antigens.

Using the EST assembly approach, we identified four splice variants. They were designated as splice variant 1 to 4. Splice variant 1 has two potential open reading frames and thus two potential translated peptide sequences, designated as 1A and 1B.

Single Nucleotide Polymorphisms (SNPs)

A Single Nucleotide Polymorphism (SNP) is a single base pair variation in a nucleotide sequence. As appreciated by those in the art, in a single nucleotide change in a codon can cause the codon to encode a different amino acid. Thus a SNP can change amino acids of the protein encoded by the gene and thus change the functions of the protein. Some SNPs cause inherited diseases and some others contribute to quantitative variations in phenotype and reactions to environmental factors including diet and drugs among individuals. Therefore, the occurrence of one or more SNPs is relevant in many contexts, including but not limited to diagnosis of inherited or acquired disease, determination of drug reactions and dosage, identification of genes responsible for disease and discovery of the genetic relationship between individuals (P. Nowotny, J. M. Kwon and A. M. Goate, "SNP analysis to dissect human traits," *Curr. Opin. Neurobiol.* 2001 October; 11(5):637-641; M. Pirmohamed and B. K. Park, "Genetic susceptibility to adverse drug reactions," *Trends Pharmacol. Sci.* 2001 June; 22(6):298-305; J. H. Riley, C. J. Allan, E. Lai and A. Roses, "The use of single nucleotide polymorphisms in the isolation of common disease genes," *Pharmacogenomics* 2000 February; 1(1):39-47; R. Judson, J. C. Stephens and A. Windemuth, "The predictive power of haplotypes in clinical response," *Pharmacogenomics* 2000 February; 1(1): 15-26).

SNPs are identified by a variety of art-accepted methods (P. Bean, "The promising voyage of SNP target discovery," *Am. Clin. Lab.* 2001 October-November; 20(9):18-20; K. M. Weiss, "In search of human variation," *Genome Res.* 1998 July; 8(7):691-697; M. M. She, "Enabling large-scale pharmacogenetic studies by high-throughput mutation detection and genotyping technologies," *Clin. Chem.* 2001 February; 47(2):164-172).

For example, SNPs are identified by sequencing DNA fragments that show polymorphism by gel-based methods such as restriction fragment length polymorphism (RFLP) and denaturing gradient gel electrophoresis (DGGE). SNPs can also be discovered by direct sequencing of DNA samples pooled from different individuals or by comparing sequences from different DNA samples. With the accumulation of sequence data in public and private databases, one can also discover SNPs by comparing sequences using computer programs (Z. Gu, L. Hillier and P. Y. Kwok, "Single nucleotide polymorphism hunting in cyberspace," *Hum. Mutat.* 1998; 12(4):221-225). SNPs can be verified by a variety of methods including direct sequencing and high throughput microarrays (P. Y. Kwok, "Methods for genotyping single nucleotide polymorphisms," *Annu. Rev. Genomics Hum. Genet.* 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," *Mol. Diagn.* 2000 December; 5(4):329-340).

As disclosed herein SNPs are identified by directly sequencing cDNA clones and by comparing our sequences with public and proprietary sequences. By sequencing cDNA clones, SNPs are identified. By comparing these sequences with high quality proprietary or public sequences (e.g., NCBI/GenBank, accessible at the World Wide Web (.ncbi.nlm.nih.gov), SNPs are identified. SNPs are identified by aligning variant sequences with NCBI genes and ESTs. Typically, only ESTs with over 97% identity are considered; differences within 50 base pairs of the ends are not considered. Only SNPs that occur twice from two independent sequences are included.

Example 6

Production of Recombinant 121P1F1 in Prokaryotic Systems

To express recombinant 121P1F1 in prokaryotic cells, the full or partial length 121P1F1 cDNA sequences can be cloned into any one of a variety of expression vectors known in the art. One or more of the following regions of 121P1F1 are expressed in these constructs: amino acids 1 to 205 of 121P1F1; amino acids 1-126 of splice variant 1a; amino acids 1-119 of splice variant 1b; amino acids 1-122 of splice variant 2; amino acids 1-190 of splice variant 3; amino acids 1-190 of splice variant 4, or any 8, 9, 10, 11, 12, 13, 14, 15, 16, 17, 18, 19, 20, 21, 22, 23, 24, 25, 26, 27, 28, 29, 30 or more contiguous amino acids from 121P1F1, splice variants, or analogs thereof.

A. In Vitro Transcription and Translation Constructs:

pCRII: To generate 121P1F1 sense and anti-sense RNA probes for RNA in situ investigations, pCRII constructs (Invitrogen, Carlsbad Calif.) are generated encoding either all or fragments of the 121P1F1 cDNA. The pCRII vector has Sp6 and T7 promoters flanking the insert to drive the transcription of 121P1F1 RNA for use as probes in RNA in situ hybridization experiments. These probes are used to analyze the cell and tissue expression of 121P1F1 at the RNA level. Transcribed 121P1F1 RNA representing the cDNA amino acid coding region of the 121P1F1 gene is used in in vitro translation systems such as the TNT Coupled Reticulolysate System (Promega, Corp., Madison, Wis.) to synthesize 121P1F1 protein.

B. Bacterial Constructs:

pGEX Constructs: To generate recombinant 121P1F1 proteins in bacteria that are fused to the Glutathione S-transferase (GST) protein, all or parts of the 121P1F1 cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 121P1F1 protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as PRESCISSION recognition site in pGEX-6P-1, can be employed such that it permits cleavage of the GST tag from 121P1F1-related protein. The ampicillin resistance gene and pBR322 origin permits selection and maintenance of the pGEX plasmids in *E. coli*. In one embodiment, amino acids 1-114 of 121P1F1 is cloned into the pGEX-6P-1 vector, expressed in bacteria, purified, and a 121P1F1 cleavage product generated utilizing PreScission protease.

pMAL Constructs: To generate, in bacteria, recombinant 121P1F1 proteins that are fused to maltose-binding protein (MBP), all or parts of the 121P1F1 cDNA protein coding sequence are fused to the MBP gene by cloning into the pMAL-c2X and pMAL-p2X vectors (New England Biolabs, Beverly, Mass.). These constructs allow controlled expression of recombinant 121P1F1 protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 121P1F1. The pMAL-c2X and pMAL-p2X vectors are optimized to express the recombinant protein in the cytoplasm or periplasm respectively. Periplasm expression enhances folding of proteins with disulfide bonds.

pET Constructs: To express 121P1F1 in bacterial cells, all or parts of the 121P1F1 cDNA protein coding sequence are cloned into the pET family of vectors (Novagen, Madison, Wis.). These vectors allow tightly controlled expression of recombinant 121P1F1 protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the 121P1F1 protein are expressed as amino-terminal fusions to NusA.

C. Yeast Constructs:

pESC Constructs: To express 121P1F1 in the yeast species *Saccharomyces cerevisiae* for generation of recombinant protein and functional studies, all or parts of the 121P1F1 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either FLAG or Myc epitope tags in the same yeast cell. This system is useful to confirm protein-protein interactions of 121P1F1. In addition, expression in yeast yields similar post-translational modifications, such as glycosylations and phosphorylations, that are found when expressed in eukaryotic cells.

pESP Constructs: To express 121P1F1 in the yeast species *Saccharomyces pombe*, all or parts of the 121P1F1 cDNA protein coding sequence are cloned into the pESP family of vectors. These vectors allow controlled high level of expression of a 121P1F1 protein sequence that is fused at either the amino terminus or at the carboxyl terminus to GST which aids purification of the recombinant protein. A FLAG epitope tag allows detection of the recombinant protein with anti-FLAG antibody.

Example 7

Production of Recombinant 121P1F1 in Eukaryotic Systems

A. Mammalian Constructs:

One or more of the following regions of 121P1F1 are expressed in these constructs: amino acids 1 to 205 of 121P1F1; amino acids 1-126 of splice variant 1a; amino acids 1-119 of splice variant 1b; amino acids 1-122 of splice variant 2; amino acids 1-190 of splice variant 3; amino acids 1-190 of splice variant 4, or any 8, 9, 10, 11, 12, 13, 14, 15, 16, 17, 18, 19, 20, 21, 22, 23, 24, 25, 26, 27, 28, 29, 30 or more contiguous amino acids from 121P1F1, splice variants, or analogs thereof. In certain embodiments a region of 121P1F1 is expressed that encodes an amino acid not shared amongst at least two variants.

The constructs can be transfected into any one of a wide variety of mammalian cells such as 293T cells. Transfected 293T cell lysates can be probed with the anti-121P1F1 polyclonal serum, described herein.

pcDNA4/HisMax Constructs: To express 121P1F1 in mammalian cells, a 121P1F1 ORF, or portions thereof, of 121P1F1 are cloned into pcDNA4/HisMax Version A (Invitrogen, Carlsbad, Calif.). Protein expression is driven from the cytomegalovirus (CMV) promoter and the SP16 translational enhancer. The recombinant protein has XPRESS and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs: To express 121P1F1 in mammalian cells, a 121P1F1 ORF, or portions thereof, of 121P1F1 with a consensus Kozak translation initiation site is cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*. FIG. 14 shows expression of 121P1F1 pcDNA3.1/mychis in transiently infected 293T cells.

pcDNA3.1/CT-GFP-TOPO Construct: To express 121P1F1 in mammalian cells and to allow detection of the recombinant proteins using fluorescence, a 121P1F1 ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of a 121P1F1 protein.

PAPtag: A 121P1F1 ORF, or portions thereof, is cloned into pAPtag-5 (GenHunter Corp. Nashville, Tenn.). This construct generates an alkaline phosphatase fusion at the carboxyl-terminus of a 121P1F1 protein while fusing the IgGκ signal sequence to the amino-terminus. Constructs are also generated in which alkaline phosphatase with an amino-terminal IgGκ signal sequence is fused to the amino-terminus of a 121P1F1 protein. The resulting recombinant 121P1F1 proteins are optimized for secretion into the media of transfected mammalian cells and can be used to identify proteins such as ligands or receptors that interact with 121P1F1 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli*.

ptag5: A 121P1F1 ORF, or portions thereof, is cloned into pTag-5. This vector is similar to pAPtag but without the alkaline phosphatase fusion. This construct generates 121P1F1 protein with an amino-terminal IgGκ signal sequence and myc and 6×His epitope tags at the carboxyl-terminus that facilitate detection and affinity purification. The resulting recombinant 121P1F1 protein is optimized for secretion into the media of transfected mammalian cells, and is used as immunogen or ligand to identify proteins such as ligands or receptors that interact with the 121P1F1 proteins. Protein expression is driven from the CMV promoter. The Zeocin resistance gene present in the vector allows for selection of mammalian cells expressing the protein, and the ampicillin resistance gene permits selection of the plasmid in *E. coli*.

PsecFc: A 121P1F1 ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 121P1F1 proteins, while fusing the IgGK signal sequence to N-terminus. 121P1F1 fusions utilizing the murine IgG1 Fc region are also used. The resulting recombinant 121P1F1 proteins are optimized for secretion into the media of transfected mammalian cells, and can be used as immunogens or to identify proteins such as ligands or receptors that interact with 121P1F1 protein. Protein expression is driven from the CMV promoter. The hygromycin resistance gene present in the vector allows for selection of mammalian cells that express the recombinant protein, and the ampicillin resistance gene permits selection of the plasmid in *E. coli*.

pSRα Constructs: To generate mammalian cell lines that express 121P1F1 constitutively, 121P1F1 ORF, or portions thereof, of 121P1F1 are cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 121P1F1, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG tag to the carboxyl-terminus of 121P1F1 sequences to allow detection using anti-Flag antibodies. For example, the FLAG sequence 5' gat tac aag gat gac gac gat aag 3' (SEQ ID NO: 40) is added to cloning primer at the 3' end of the ORF. Additional pSRα constructs are made to produce both amino-terminal and carboxyl-terminal GFP and myc/6×His fusion proteins of the full-length 121P1F1 proteins.

Additional Viral Vectors: Additional constructs are made for viral-mediated delivery and expression of 121P1F1. High virus titer leading to high level expression of 121P1F1 is achieved in viral delivery systems such as adenoviral vectors and herpes amplicon vectors. A 121P1F1 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 121P1F1 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 121P1F1 in mammalian cells, coding sequences of 121P1F1, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 121P1F1. These vectors are thereafter used to control expression of 121P1F1 in various cell lines such as PC3, NIH 3T3, 293 or rat-1 cells.

B. Baculovirus Expression Systems

To generate recombinant 121P1F1 proteins in a baculovirus expression system, 121P1F1 ORF, or portions thereof, are cloned into the baculovirus transfer vector pBlueBac 4.5 (Invitrogen), which provides a His-tag at the N-terminus. Specifically, pBlueBac-121P1F1 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 121P1F1 protein is then generated by infection of HighFive insect cells (Invitrogen) with purified baculovirus. Recombinant 121P1F1 protein can be detected using anti-121P1F1 or anti-His-tag antibody. 121P1F1 protein can be purified and used in various cell-based assays or as immunogen to generate polyclonal and monoclonal antibodies specific for 121P1F1.

Example 8

Antigenicity Profiles and Secondary Structure

FIG. 5A, FIG. 6A, FIG. 7A, FIG. 8A, and FIG. 9A depict graphically five amino acid profiles of the 121P1F1 amino acid sequence; FIG. 5B, FIG. 6B, FIG. 7B, FIG. 8B, and FIG. 9B depict graphically five amino acid profiles of the 121P1F1 variant 1A amino acid sequence. Each assessment is available by accessing the ProtScale website located on the World Wide Web at (.expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the 121P1F1 protein and variant 1A. Each of the above amino acid profiles of 121P1F1 were generated using the following ProtScale parameters for analysis: 1) A window size of 9; 2) 100% weight of the window edges compared to the window center; and 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the full length 121P1F1 protein indicated, e.g., by the profiles set forth in FIG. 5A, FIG. 6A, FIG. 7A, FIG. 8A, and/or FIG. 9A are used to prepare immunogens, either peptides or nucleic acids that encode them, to generate therapeutic and diagnostic anti-121P1F1 antibodies. Antigenic sequences of the 121P1F1 variant 1A protein indicated, e.g., by the profiles set forth in FIG. 5B, FIG. 6B, FIG. 7B, FIG. 8B, and/or FIG. 9B are used to prepare immunogens, either peptides or nucleic acids that encode them, to generate therapeutic and diagnostic anti-121P1F1-variant 1A antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 121P1F1 protein or from variants 1a, 1b, 2, 3, or 4 (see FIGS. 2 and 3). In particular, peptide immunogens of the invention can comprise, a peptide region of at least 5 amino acids of FIG. 2 in any whole number increment up to 205 that includes an amino acid position having a value greater than 0.5 in the Hydrophilicity profile of FIG. 5; a peptide region of at least 5 amino acids of FIG. 2 in any whole number increment up to 205 that includes an amino acid position having a value less than 0.5 in the Hydropathicity profile of FIG. 6; a peptide region of at least 5 amino acids of FIG. 2 in any whole number increment up to 205 that includes an amino acid position having a value greater than 0.5 in the Percent Accessible Residues profile of FIG. 7; a peptide region of at least 5 amino acids of FIG. 2 in any whole number increment up to 205 that includes an amino acid position having a value greater than 0.5 in the Average Flexibility profile on FIG. 8; and, a peptide region of at least 5 amino acids of FIG. 2 in any whole number increment up to 205 that includes an amino acid position having a value greater than 0.5 in the Beta-turn profile of FIG. 9. Peptide immunogens of the invention can also comprise nucleic acids that encode any of the forgoing. In addition, peptide immunogens can comprise amino acids of variant 1a, that contain characteristics of the above mentioned parameters set forth in FIG. 5B, FIG. 6B, FIG. 7B, FIG. 8B, or FIG. 9B.

All immunogens of the invention, peptide or nucleic acid, can be embodied in human unit dose form, or comprised by a composition that includes a pharmaceutical excipient compatible with human physiology.

The secondary structure of 121P1F1, namely the predicted presence and location of alpha helices, extended strands, and random coils, is predicted from the primary amino acid sequence using the HNN—Hierarchical Neural Network method (Guermeur, 1997, Web URL pbil.ibcp.fr/cgi-bin/npsa_automat.pl?page=npsa_nn.html), accessed from the ExPasy molecular biology server located on the World Wide Web at (.expasy.ch/tools/). The analysis indicates that 121P1F1 is composed 61.95% alpha helix, 1.95% extended strand, and 36.10% random coil (FIG. 16A). The secondary structure of variant 1a is presented in FIG. 16B.

Analysis of 121P1F1 using a variety of transmembrane prediction algorithms accessed from the ExPasy molecular biology server located on the World Wide Web at (.expasy.ch/tools/) did not predict the presence of such domains, suggesting that 121P1F1 and the variants are soluble proteins.

Example 9

Generation of 121P1F1 Polyclonal Antibodies

Polyclonal antibodies can be raised in a mammal, for example, by one or more injections of an immunizing agent and, if desired, an adjuvant. Typically, the immunizing agent and The anti-serum from the GST-fusion cleavage immunogen is affinity purified by passage over a column composed of the GST-cleavage antigen covalently coupled to Affigel matrix (BioRad, Hercules, Calif.). The serum is then further purified by protein G affinity chromatography to isolate the IgG fraction. Serum from rabbits immunized with whole fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Figure 13:
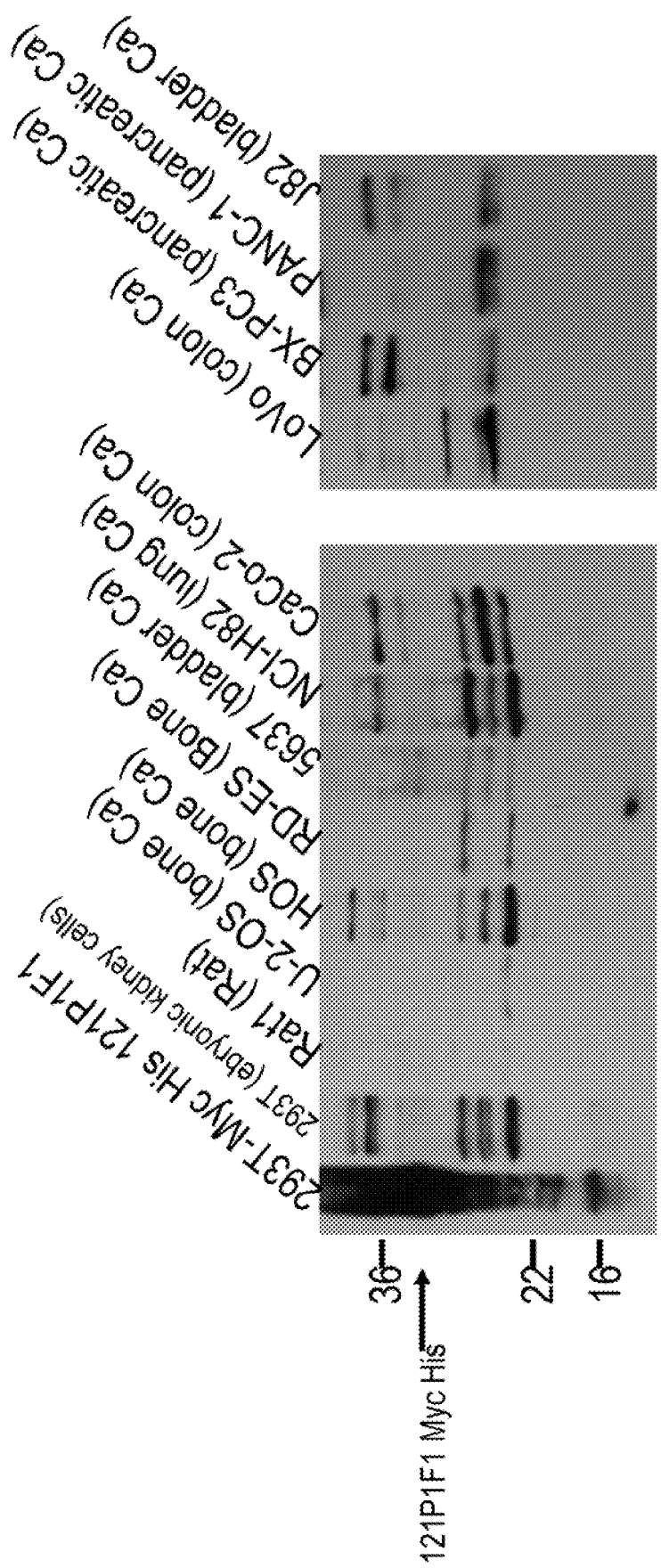
FIG. 13: Expression of 121P1F1 in various cancer cells. Anti-121P1F1 polyclonal antibody was used to carry out Western blot analysis of 121P1F1 expression in cell lysates from the indicated cancer cell lines and Myc His tagged 121P1F1 expressed in 293T cells. Seen is specific anti-121P1F1 reactive bands in each of the cancer cell lines indicative of endogenous 121P1F1 expression and possibly recognition of 121P1F1 splice variants of different molecular weights.

Both crude and affinity purified polyclonal antibodies are further tested by various immunoassays against both recombinant cells and cells and tissues that endogenously express 121P1F1. To generate recombinant 121P1F1 cells, the full-length 121P1F1 cDNA is cloned into pcDNA 3.1 Myc-His expression vector (Invitrogen, see the Example entitled "Production of Recombinant 121P1F1 in Eukaryotic Systems"). After transfection of the construct into 293T cells, cell lysates were probed with the anti-121P1F1 polyclonal antibody (FIG. 13) and with anti-His antibody (Santa Cruz Biotechnologies, Santa Cruz, Calif.) (FIG. 14) demonstrating specific reactivity to denatured 121P1F1 protein using the Western blot technique. The polyclonal antibody was also used to test a panel of tumor cell lines by Western analysis, for which the results are also shown in FIG. 13. The polyclonal antibody shows strong reactivity to MYC-HIS tagged 121P1F1 in transfected 293T cells and also to several proteins in the tumor cell lines, indicating reactivity to endogenous 121P1F1 and to variant molecules of different molecular weights. In addition, immunoprecipitation, fluorescent microscopy, immunohistochemistry, and flow cytometric techniques on recombinant cells and patient tissues samples are used to characterize 121P1F1 protein expression using the polyclonal antibody.

Example 10

Generation of 121P1F1 Monoclonal Antibodies (mAbs)

In one embodiment, therapeutic mAbs to 121P1F1 comprise those that react with epitopes of the protein that would disrupt or modulate the biological function of 121P1F1, for example those that would disrupt its interaction with ligands, proteins, or substrates that mediate its biological activity. Immunogens for generation of such mAbs include those designed to encode or contain the entire 121P1F1 protein or its variants or regions of the 121P1F1 protein or its variants predicted to be antigenic from computer analysis of the amino acid sequence (see, e.g., FIG. 5, FIG. 6, FIG. 7, FIG. 8, or FIG. 9, and the Example entitled "Antigenicity Profiles"). Immunogens include peptides, recombinant bacterial proteins, and mammalian expressed Tag 5 proteins and human and murine IgG FC fusion proteins. In addition, cells expressing high levels of 121P1F1, such as 293T-121P1F1 or 300.19-121P1F1 murine Pre-B cells, are used to immunize mice.

To generate mAbs to 121P1F1, mice are first immunized intraperitoneally (IP) with, typically, 10-50 μg of protein immunogen or 10⁷ 121P1F1-expressing cells mixed in complete Freund's adjuvant. Mice are then subsequently immunized IP every 2-4 weeks with, typically, 10-50 μg of protein immunogen or 10⁷ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding 121P1F1 sequence is used to immunize mice by direct injection of the plasmid DNA. For example, the entire coding sequence of 121P1F1, amino acids 1-205, is cloned into the Tag5 mammalian secretion vector and the recombinant vector is used as immunogen. In another example the same amino acids are cloned into an Fc-fusion secretion vector in which the 121P1F1 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing 121P1F1. In another embodiment the GST-fusion cleavage protein described in Example 8 is used as immunogen.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Antibodies: A Laboratory Manual, CSH Press, Eds., Harlow, and Lane (1988)).

In one embodiment, monoclonal antibodies are derived that distinguish variant 1a from 121P1F1 and the other variants. For example, a Tag5 protein encoding amino acids 93-126 of variant 1a is produced and purified from the supernatants of 293T cells transfected with the cognate Tag5 cDNA vector. Balb C mice are initially immunized intraperitoneally with 25 μg of the Tag5-variant 1a protein mixed in complete Freund's adjuvant. Mice are subsequently immunized every two weeks with 25 μg of the antigen mixed in incomplete Freund's adjuvant for a total of three immunizations. ELISA using the Tag5 antigen determines the titer of serum from immunized mice. Reactivity and specificity of serum to the full length variant 1a protein is monitored by Western blotting, immunoprecipitation and flow cytometry using 293T cells transfected with an expression vector encoding the variant 1a cDNA (see e.g., the Example entitled "Production of Recombinant 121P1F1 in Eukaryotic Systems"). Other recombinant variant 1a-expressing cells or cells endogenously expressing variant 1a are also used. Specificity is also determined by lack of reactivity to cells expressing 121P1F1 and the other variants. Mice showing the strongest reactivity to variant 1a are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 121P1F1 specific antibody-producing clones. Monoclonal antibodies are also raised that distinguish variant 1b and variant 2 from each other, from variants 3 and 4 and from 121P1F1. This is accomplished through immunization with antigens, such as KLH-coupled peptides, that encode amino acids specific to variant 1b (amino acids 1-6) and variant 2 (amino acids 118-122).

The binding affinity of a 121P1F1 monoclonal antibody is determined using standard technologies. Affinity measurements quantify the strength of antibody to epitope binding and are used to help define which 121P1F1 monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 11

HLA Class I and Class II Binding Assays

HLA class I and class II binding assays using purified HLA molecules are performed in accordance with disclosed protocols (e.g., PCT publications WO 94/20127 and WO 94/03205; Sidney et al., Current Protocols in Immunology 18.3.1 (1998); Sidney, et al., J. Immunol. 154:247 (1995); Sette, et al., Mol. Immunol. 31:813 (1994)). Briefly, purified MHC molecules (5 to 500 nM) are incubated with various unlabeled peptide inhibitors and 1-10 nM 125I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and IC50≧[HLA], the measured IC50 values are reasonable approximations of the true KD values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the IC50 of a positive control for inhibition by the IC50 for each tested peptide (typically unlabeled versions of the radiolabeled probe peptide). For database purposes, and inter-experiment comparisons, relative binding values are compiled. These values can subsequently be converted back into IC50 nM values by dividing the IC50 nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 12

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables V-XVIII, XXVI, and XXVII employ the protein sequence data from the gene product of 121P1F1 set forth in FIGS. 2 and 3.

Computer searches for epitopes bearing HLA Class I or Class II supermotifs or motifs are performed as follows. All translated 121P1F1 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or ΔG) of peptide-HLA molecule interactions can be approximated as a linear polynomial function of the type:

"$\Delta G\text{''}=a_{1i} \times a_{2i} \times a_{3i} \ldots \times a_{ni}$"

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota, et al., J. Mol. Biol. 267:1258-126, 1997; (see also Sidney et al., Human Immunol. 45:79-93, 1996; and Southwood, et al., J. Immunol. 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from 121P1F1 are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 121P1F1 protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 121P1F1 protein(s) scanned above is also analyzed for the presence of 8-, 9-10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 121P1F1 protein can also be performed to identify HLA-A1- and A24-motif-containing sequences.

High affinity and/or cross-reactive binding epitopes that bear other motif and/or supermotifs are identified using analogous methodology.

Example 13

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the Detacha-Bead® reagent. Typically about $200\text{-}250 \times 10^6$ PBMC are processed to obtain $24 \times 10^6$ CD8+ T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 µl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 µl/ml Detacha-Bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 µg/ml of peptide at a cell concentration of $1\text{-}2 \times 10^6$/ml in the presence of 3 µg/ml $\beta_2$-microglobulin for 4 hours at 20° C. The DC are then irradiated (4,200 rads), washed 1 time with medium and counted again.

Setting up induction cultures. 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells. Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 µg/ml of peptide in the presence of 3 µg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai, et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 µg/ml peptide overnight at 37° C.

Adherent target cells are removed from culture flasks with trypsin-EDTA. Target cells are labeled with 200 µCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 µl) and effectors (100 µl) are plated in 96 well round-bottom plates and incubated for 5 hours at 37° C. At that time, 100 µl of supernatant are collected from each well and percent lysis is determined according to the formula:

[(cpm of the test sample−cpm of the spontaneous $^{51}$Cr release sample)/(cpm of the maximal $^{51}$Cr release sample−cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 µg/ml 0.1M NaHCO$_3$, pH8.2) overnight at 4° C. The plates are washed with $Ca^{2+}$, $Mg^{2+}$-free PBS/0.05% Tween 20 and blocked with PBS/10% FCS for two hours, after which the CTLs (100 µl/well) and targets (100 µl/well) are added to each well, leaving empty wells for the standards and blanks (which received media only). The target cells, either peptide-pulsed or endogenous targets, are used at a concentration of $1\times10^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 µl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4,200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 µM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5\times10^4$ CD8$^+$ cells are added to a T25 flask containing the following: $1\times10^6$ autologous PBMC per ml which have been peptide-pulsed with 10 µg/ml peptide for two hours at 37° C. and irradiated (4,200 rad); $2\times10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 121P1F1. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 14

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst, et al., *J. Immunol.* 157:2539, 1996; and Pogue, et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 121P1F1-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette, et al., In: *Persistent Viral Infections*, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 15

Identification and Confirmation of 121P1F1-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 121P1F1-derived, HLA class II HTL epitopes, a 121P1F1 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood, et al., *J. Immunol.* 160:3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood, et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 121P1F1-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 121P1F1-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 121P1F1 antigens are analyzed for sequences carrying one of the two DR3-specific binding motifs reported by Geluk, et al. (*J. Immunol.* 152:5742-5748, 1994). The corresponding peptides are then synthesized and confirmed as having the ability to bind DR3 with an affinity of 1 µM or better, i.e., less than 1 µM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 16

Immunogenicity of 121P1F1-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 121P1F1-expressing tumors.

Example 17

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney, et al., *Human Immunol.* 45:79-93, 1996). To obtain overall phenotypic frequencies, cumulative gene frequencies are calculated, and the cumulative antigen frequencies derived by the use of the inverse formula [af=1−(1−Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni, et al., *J. Clin. Invest.* 100:503, 1997; Doolan, et al., *Immunity* 7:97, 1997; and Threlkeld, et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 18

CTL Recognition of Endogenously Processed Antigens after Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 121P1F1 expression vectors.

The results demonstrate that CTL lines obtained from animals primed with peptide epitope recognize endogenously synthesized 121P1F1 antigen. The choice of transgenic mouse model to be used for such an analysis depends upon the epitope(s) that are being evaluated. In addition to HLA-A*0201/$K^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 19

Activity of CTL-HTL Conjugated Epitopes in Transgenic Mice

This example illustrates the induction of CTLs and HTLs in transgenic mice, by use of a 121P1F1-derived CTL and HTL peptide vaccine compositions. The vaccine composition used herein comprise peptides to be administered to a patient with a 121P1F1-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures. Immunization of transgenic mice is performed as described (Alexander et al., *J. Immunol.* 159:4753-4761, 1997). For example, A2/$K^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines. Target cells for peptide-specific cytotoxicity assays are Jurkat cells transfected with the HLA-A2.1/$K^b$ chimeric gene (e.g., Vitiello, et al., *J. Exp. Med.* 173:1007, 1991)

In vitro CTL activation. One week after priming, spleen cells ($30 \times 10^6$ cells/flask) are co-cultured at 37° C. with syngeneic, irradiated (3000 rads), peptide coated lymphoblasts ($10 \times 10^6$ cells/flask) in 10 ml of culture medium/T25 flask. After six days, effector cells are harvested and assayed for cytotoxic activity.

Assay for cytotoxic activity: Target cells (1.0 to $1.5 \times 10^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^{4}$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/ (maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E):target (T) ratio of 50:1 (i.e., $5 \times 10^5$ effector cells for 10,000 targets) in the absence of peptide and 5:1 (i.e., $5 \times 10^4$ effector cells for 10,000 targets) in the presence of peptide, the specific lytic units would be: $[(1/50,000)-(1/500,000)] \times 10^6 = 18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analyses similar to this may be performed to confirm the immunogenicity of peptide conjugates containing multiple CTL epitopes and/ or multiple HTL epitopes. In accordance with these procedures, it is found that a CTL response is induced, and concomitantly that an HTL response is induced upon administration of such compositions.

Example 20

Selection of CTL and HTL Epitopes for Inclusion in an 121P1F1-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 121P1F1 clearance. The number of epitopes used depends on observations of patients who spontaneously clear 121P1F1. For example, if it has been observed that patients who spontaneously clear 121P1F1 generate an immune response to at least three (3) from 121P1F1 antigen, then three or four (3-4) epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 121P1F1, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 121P1F1.

Example 21

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 121P1F1, are selected such that multiple supermotifs/motifs are represented to ensure broad population coverage. Similarly, HLA class II epitopes are selected from 121P1F1 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 22

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts, et al., *J. Immunol.* 156:683-692, 1996; Demotz, et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama, et al, *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander, et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander, et al. *Immunity* 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett, et al., *Aids Res. and Human Retroviruses* 14, Supplement 3:S299-S309, 1998) or recombinant vaccinia, for example, expressing a minigene or DNA encoding the complete protein of interest (see, e.g., Hanke, et al., *Vaccine* 16:439-445, 1998; Sedegah et al., *Proc. Natl. Acad. Sci. USA* 95:7648-53, 1998; Hanke and McMichael, *Immunol. Letters* 66:177-181, 1999; and Robinson, et al., *Nature Med.* 5:526-34, 1999).

For example, the efficacy of the DNA minigene used in a prime boost protocol is initially evaluated in transgenic mice. In this example, A2.1/$K^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 µg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 23

Peptide Compositions for Prophylactic Uses

Vaccine compositions of the present invention can be used to prevent 121P1F1 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 121P1F1-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 121P1F1-associated disease.

Alternatively, a composition typically comprising transfecting agents is used for the administration of a nucleic acid-based vaccine in accordance with methodologies known in the art and disclosed herein.

Example 24

Polyepitopic Vaccine Compositions Derived from Native 121P1F1 Sequences

A native 121P1F1 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes is selected; it can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 121P1F1 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native 121P1F1, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 25

Polyepitopic Vaccine Compositions from Multiple Antigens

The 121P1F1 peptide epitopes of the present invention are used in conjunction with epitopes from other target tumor-associated antigens, to create a vaccine composition that is useful for the prevention or treatment of cancer that expresses 121P1F1 and such other antigens. For example, a vaccine composition can be provided as a single polypeptide that incorporates multiple epitopes from 121P1F1 as well as tumor-associated antigens that are often expressed with a target cancer associated with 121P1F1 expression, or can be administered as a composition comprising a cocktail of one or more discrete epitopes. Alternatively, the vaccine can be administered as a minigene construct or as dendritic cells which have been loaded with the peptide epitopes in vitro.

Example 26

Use of Peptides to Evaluate an Immune Response

Peptides of the invention may be used to analyze an immune response for the presence of specific antibodies, CTL or HTL directed to 121P1F1. Such an analysis can be performed in a manner described by Ogg, et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 121P1F1 HLA-A*0201-specific CTL frequencies from HLA A*0201-positive individuals at different stages of disease or following immunization comprising an 121P1F1 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 121P1F1 epitope, and thus the status of exposure to 121P1F1, or exposure to a vaccine that elicits a protective or therapeutic response.

Example 27

Use of Peptide Epitopes to Evaluate Recall Responses

The peptide epitopes of the invention are used as reagents to evaluate T cell responses, such as acute or recall responses, in patients. Such an analysis may be performed on patients who have recovered from 121P1F1-associated disease or who have been vaccinated with an 121P1F1 vaccine.

For example, the class I restricted CTL response of persons who have been vaccinated may be analyzed. The vaccine may be any 121P1F1 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI)

and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture format, $4 \times 10^5$ PBMC are stimulated with peptide in 8 replicate cultures in 96-well round bottom plate in 100 μl/well of complete RPMI. On days 3 and 10, 100 μl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104, 1108, 1996; Rehermann, et al., *J. Clin. Invest.* 97:1655-1665, 1996; and Rehermann, et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release-spontaneous release)/maximum release–spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 121P1F1 or an 121P1F1 vaccine.

Similarly, Class II restricted HTL responses may also be analyzed. Purified PBMC are cultured in a 96-well flat bottom plate at a density of $1.5 \times 10^5$ cells/well and are stimulated with 10 μg/ml synthetic peptide of the invention, whole 121P1F1 antigen, or PHA. Cells are routinely plated in replicates of 4-6 wells for each condition. After seven days of culture, the medium is removed and replaced with fresh medium containing 10 U/ml IL-2. Two days later, 1 μCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 28

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 μg of peptide composition;

Group II: 3 subjects are injected with placebo and 6 subjects are injected with 50 μg peptide composition;

Group III: 3 subjects are injected with placebo and 6 subjects are injected with 500 μg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 29

Phase II Trials in Patients Expressing 121P1F1

Phase II trials are performed to study the effect of administering the CTL-HTL peptide compositions to patients having cancer that expresses 121P1F1. The main objectives of the trial are to determine an effective dose and regimen for inducing CTLs in cancer patients that express 121P1F1, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 121P1F1.

Clinical manifestations or antigen-specific T-cell responses are monitored to assess the effects of administering the peptide compositions. The vaccine composition is found to be both safe and efficacious in the treatment of 121P1F1-associated disease.

Example 30

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 121P1F1 is generated.

Example 31

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 121P1F1 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as PROGENIPOIETIN (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g. *Nature Med.* 4:328, 1998; *Nature Med.* 2:52, 1996 and *Prostate* 32:272, 1997). Although $2\text{-}50\times10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 121P1F1 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 32

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 121P1F1. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo, et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 121P1F1 to isolate peptides corresponding to 121P1F1 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 33

Complementary Polynucleotides

Sequences complementary to the 121P1F1-encoding sequences, or any parts thereof, are used to detect, decrease, or inhibit expression of naturally occurring 121P1F1. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 121P1F1. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 121P1F1-encoding transcript.

Example 34

Purification of Naturally-Occurring or Recombinant 121P1F1 Using 121P1F1 Specific Antibodies Naturally occurring or recombinant 121P1F1 is substantially purified by immunoaffinity chromatography using antibodies specific for 121P1F1. An immunoaffinity column is constructed by covalently coupling anti-121P1F1 antibody to an activated chromatographic resin, such as CNBr-activated SEPHAROSE (Amersham Pharmacia Biotech). After the coupling, the resin is blocked and washed according to the manufacturer's instructions.

Media containing 121P1F1 are passed over the immunoaffinity column, and the column is washed under conditions that allow the preferential absorbance of 121P1F1 (e.g., high ionic strength buffers in the presence of detergent). The column is eluted under conditions that disrupt antibody/121P1F1 binding (e.g., a buffer of pH 2 to pH 3, or a high concentration of a chaotrope, such as urea or thiocyanate ion), and GCR.P is collected.

Example 35

Identification of Molecules which Interact with 121P1F1

121P1F1, or biologically active fragments thereof, are labeled with 121 1 Bolton-Hunter reagent. (See, e.g., Bolton et al. (1973) *Biochem. J.* 133:529.) Candidate molecules previously arrayed in the wells of a multi-well plate are incubated with the labeled 121P1F1, washed, and any wells with labeled 121P1F1 complex are assayed. Data obtained using different concentrations of 121P1F1 are used to calculate values for the number, affinity, and association of 121P1F1 with the candidate molecules.

Example 36

In Vivo Assay for 121P1F1 Tumor Growth Promotion

The effect of the 121P1F1 protein on tumor cell growth is evaluated in vivo by evaluating tumor development and growth of cells expressing or lacking 121P1F1. For example, SCID mice are injected subcutaneously on each flank with 1×106 of either 3T3, prostate, kidney or breast cancer cell lines (e.g. PC3, DU145, CaKi, SW 839, MCF7 cells) containing tkNeo empty vector or 121P1F1. At least two strategies can be used: (1) Constitutive 121P1F1 expression under regulation of a promoter, such as a constitutive promoter obtained from the genomes of viruses such as polyoma virus, fowlpox virus (see UK 2,211,504, published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if 121P1F1-expressing cells grow at a faster rate and whether tumors produced by 121P1F1-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 121P1F1 has an effect on local growth in the prostate, kidney or mammary gland, and whether 121P1F1 affects the ability of the cells to metastasize, specifically to lungs, lymph nodes, and bone marrow.

The assay is also useful to determine the 121P1F1 inhibitory effect of candidate therapeutic compositions, such as for example, 121P1F1 intrabodies, 121P1F1 antisense molecules and ribozymes.

Example 37

121P1F1 Monoclonal Antibody-Mediated Inhibition of Prostate and Kidney Tumors In Vivo The significant expression of 121P1F1 in cancer tissues, together with its restrictive expression in normal tissues, makes 121P1F1 a good target for antibody therapy. Similarly, 121P1F1 is a target for T cell-based immunotherapy. Thus, the therapeutic efficacy of anti-121P1F1 mAbs in human prostate cancer xenograft mouse models is evaluated by using androgen-independent LAPC-4 and LAPC-9 xenografts (Craft, N., et al., *Cancer Res*, 1999. 59(19): p. 5030-6) the androgen independent recombinant cell line PC3-121P1F1 and 3T3-121P1F1 (see, e.g., Kaighn, M. E., et al., *Invest Urol*, 1979. 17(1): p. 16-23). Similarly, anti-121P1F1 mAbs are evaluated in human kidney cancer xenograft models such as AGS-K3 and AGS-K6 and in recombinant kidney cell lines such as CaKi-121P1F1.

Antibody efficacy on tumor growth and metastasis formation is studied, e.g., in a mouse orthotopic prostate cancer xenograft models and mouse kidney xenograft models. The antibodies can be unconjugated, as discussed in this Example, or can be conjugated to a therapeutic modality, as appreciated in the art. Anti-121P1F1 mAbs inhibit formation of both the androgen-dependent LAPC-9 and androgen-independent PC3-121P1F1 tumor xenografts. Anti-121P1F1 mAbs also retard the growth of established orthotopic tumors and prolonged survival of tumor-bearing mice. These results indicate the utility of anti-121P1F1 mAbs in the treatment of local and advanced stages of prostate cancer. (See, e.g., Saffran, D., et al., *PNAS* 10:1073-1078 or on the World Wide Web at .pnas.org/cgi/doi/10.1073/pnas.051624698). Similarly, anti-121P1F1 mAbs can inhibit formation of AGS-K3 and AGS-K6 tumors in SCID mice, and prevent or retard the growth of CaKi-121P1F1 tumor xenografts. These results indicate utility of anti-121P1F1 mAbs for treatment of kidney cancer.

Administration of the anti-121P1F1 mAbs leads to retardation of established orthotopic tumor growth and inhibition of metastasis to distant sites, resulting in a significant prolongation in the survival of tumor-bearing mice. These studies indicate that 121P1F1 as an attractive target for immunotherapy and demonstrate the therapeutic potential of anti-121P1F1 mAbs for the treatment of local and metastatic prostate cancer. This example demonstrates that unconjugated 121P1F1 monoclonal antibodies are effective to inhibit the growth of human prostate tumor xenografts and human kidney xenografts grown in SCID mice; accordingly a combination of such efficacious monoclonal antibodies is also effective.

Tumor Inhibition Using Multiple Unconjugated 121P1F1 Mabs

Materials and Methods

121P1F1 Monoclonal Antibodies:

Monoclonal antibodies are raised against 121P1F1 as described in the Example entitled "Generation of 121P1F1 Monoclonal Antibodies (mAbs)." The antibodies are characterized by ELISA, Western blot, FACS, and immunoprecipitation for their capacity to bind 121P1F1. Epitope mapping data for the anti-121P1F1 mAbs, as determined by ELISA and Western analysis, recognize epitopes on the 121P1F1 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). The AGS-K3 and AGS-K6 kidney xenografts are also passaged by subcutaneous implants in 6- to 8-week old SCID mice. Single-cell suspensions of tumor cells are prepared as described in Craft, et al. The prostate carcinoma cell line PC3 (American Type Culture Collection) is maintained in RPMI supplemented with L-glutamine and 10% FBS, and the kidney carcinoma line CaKi as well as NIH-3T3 cells (American Type Culture Collection) are maintained in DMEM supplemented with L-glutamine and 10% FBS.

A PC3-121P1F1, CaKi-121P1F1 and 3T3-121P1F1 cell populations are generated by retroviral gene transfer as described in Hubert, R. S., et al., STEAP: a prostate-specific cell-surface antigen highly expressed in human prostate tumors. *Proc Natl Acad Sci USA*, 1999. 96(25): p. 14523-8.

Xenograft Mouse Models.

Subcutaneous (s.c.) tumors are generated by injection of $1\times10^6$ LAPC-9, AGS-K3, AGS-K6, PC3, PC3-121P1F1, CaKi or CaKi-121P1F1 cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-121P1F1 mAbs are determined by a capture ELISA kit (Bethyl Laboratories, Montgomery, Tex.). (See, e.g., (Saffran, D., et al., *PNAS* 10:1073-1078 or on the World Wide Web at .pnas.org/cgi/doi/10.1073/pnas.051624698)

Orthotopic injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells ($5\times10^5$) mixed with Matrigel are injected into each dorsal lobe in a 10-μl volume. To monitor tumor growth, mice are bled on a weekly basis for determination of PSA levels. For kidney orthotopic models, an incision is made through the abdominal muscles to expose the kidney. AGS-K3 or AGS-K6 cells mixed with Matrigel are injected under the kidney capsule. The mice are segregated into groups for the appropriate treatments, with anti-121P1F1 or control mAbs being injected i.p.

Anti-121P1F1 mAbs Inhibit Growth of 121P1F1-Expressing Xenograft-Cancer Tumors

The effect of anti-121P1F1 mAbs on tumor formation is tested by using LAPC-9 and AGS-K3 orthotopic models. As compared with the s.c. tumor model, the orthotopic model, which requires injection of tumor cells directly in the mouse prostate or kidney, respectively, results in local tumor growth, development of metastasis in distal sites, deterioration of mouse health, and subsequent death (Saffran, D., et al., *PNAS* supra; Fu, X., et al., *Int J Cancer*, 1992. 52(6): p. 987-90; Kubota, T., *J Cell Biochem*, 1994. 56(1): p. 4-8). The features make the orthotopic model more representative of human disease progression and allow the therapeutic effect of mAbs on clinically relevant end points to be followed.

Accordingly, tumor cells are injected into the mouse prostate or kidney, and 2 days later, the mice are segregated into two groups and treated with either: a) 200-500 μg of anti-121P1F1 Ab, or b) PBS three times per week for two to five weeks.

A major advantage of the orthotopic prostate-cancer model is the ability to study the development of metastases. Formation of metastasis in mice bearing established orthotopic tumors is studied by IHC analysis on lung sections using an antibody against a prostate-specific cell-surface protein STEAP expressed at high levels in LAPC-9 xenografts (Hubert, R. S., et al., *Proc Natl Acad Sci USA*, 1999. 96(25): p. 14523-8) or anti-G250 antibody for kidney cancer models.

Mice bearing established orthotopic LAPC-9 tumors are administered 1000 μg injections of either anti-121P1F1 mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate/kidney and lungs are analyzed for the presence of tumor cells by IHC analysis.

These studies demonstrate a broad anti-tumor efficacy of anti-121P1F1 antibodies on initiation and progression of prostate and kidney cancer in xenograft mouse models. Anti-121P1F1 antibodies inhibit tumor formation of both androgen-dependent and androgen-independent tumors, retard the growth of already established tumors, and prolong the survival of treated mice. Moreover, anti-121P1F1 mAbs demonstrate a dramatic inhibitory effect on the spread of local prostate tumor to distal sites, even in the presence of a large tumor burden. Thus, anti-121P1F1 mAbs are efficacious on major clinically relevant end points (tumor growth), prolongation of survival, and health.

Example 38

Therapeutic and Diagnostic Use of Anti-121P1F1 Antibodies in Humans

Anti-121P1F1 monoclonal antibodies are safely and effectively used for diagnostic, prophylactic, prognostic and/or therapeutic purposes in humans. Western blot and immunohistochemical analysis of cancer tissues and cancer xenografts with anti-121P1F1 mAb show strong extensive staining in carcinoma but significantly lower or undetectable levels in normal tissues. Detection of 121P1F1 in carcinoma and in metastatic disease demonstrates the usefulness of the mAb as a diagnostic and/or prognostic indicator. Anti-121P1F1 antibodies are therefore used in diagnostic applications such as immunohistochemistry of kidney biopsy specimens to detect cancer from suspect patients.

As determined by flow cytometry, anti-121P1F1 mAb specifically binds to carcinoma cells. Thus, anti-121P1F1 antibodies are used in diagnostic whole body imaging applications, such as radioimmunoscintigraphy and radioimmunotherapy, (see, e.g., Potamianos S., et. al. Anti-cancer Res 20(2A):925-948 (2000)) for the detection of localized and metastatic cancers that exhibit expression of 121P1F1. Shedding or release of an extracellular domain of 121P1F1 into the extracellular milieu, such as that seen for alkaline phosphodiesterase B10 (Meerson, N. R., Hepatology 27:563-568 (1998)), allows diagnostic detection of 121P1F1 by anti-121P1F1 antibodies in serum and/or urine samples from suspect patients.

Anti-121P1F1 antibodies that specifically bind 121P1F1 are used in therapeutic applications for the treatment of cancers that express 121P1F1. Anti-121P1F1 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-121P1F1 antibodies are tested for efficacy of tumor prevention and growth inhibition in the SCID mouse cancer xenograft models, e.g., kidney cancer models AGS-K3 and AGS-K6, (see, e.g., the Example entitled "Monoclonal Antibody-mediated Inhibition of Prostate and Kidney Tumors In vivo." Conjugated and unconjugated anti-121P1F1 antibodies are used as a therapeutic modality in human clinical trials either alone or in combination with other treatments as described in following Examples.

Example 39

Human Clinical Trials for the Treatment and Diagnosis of Human Carcinomas Through Use of Human Anti-121P1F1 Antibodies In Vivo Antibodies are used in accordance with the present invention which recognize an epitope on 121P1F1, and are used in the treatment of certain tumors such as those listed in Table I. Based upon a number of factors, including 121P1F1 expression levels, tumors such as those listed in Table I are presently preferred indications. In connection with each of these indications, three clinical approaches are successfully pursued.

I.) Adjunctive therapy: In adjunctive therapy, patients are treated with anti-121P1F1 antibodies in combination with a chemotherapeutic or antineoplastic agent and/or radiation therapy. Primary cancer targets, such as those listed in Table I, are treated under standard protocols by the addition anti-121P1F1 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-121P1F1 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-121P1F1 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-121P1F1 antibodies, the radiolabeled antibodies are utilized as a diagnostic and/or imaging agent. In such a role, the labeled antibodies localize to both solid tumors, as well as, metastatic lesions of cells expressing 121P1F1. In connection with the use of the anti-121P1F1 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-121P1F1 antibody is used as an imaging agent in a Phase I human clinical trial in patients having a carcinoma that expresses 121P1F1 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-121P1F1 antibodies can be administered with doses in the range of 5 to 400 mg/m$^2$, with the lower doses used, e.g., in connection with safety studies. The affinity of anti-121P1F1 antibodies relative to the affinity of a known antibody for its target is one parameter used by those of skill in the art for determining analogous dose regimens. Further, anti-121P1F1 antibodies that are fully human antibodies, as compared to the chimeric antibody, have slower clearance; accordingly, dosing in patients with such fully human anti-121P1F1 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-121P1F1 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-121P1F1 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-121P1F1 antibodies. As will be appreciated, one criteria that can be utilized in connection with enrollment of patients is 121P1F1 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 121P1F1. Standard tests and follow-up are utilized to monitor each of these safety concerns. Anti-121P1F1 antibodies are found to be safe upon human administration.

Example 40

Human Clinical Trial Adjunctive Therapy with Human Anti-121P1F1 Antibody and Chemotherapeutic Agent A phase I human clinical trial is initiated to assess the safety of six intravenous doses of a human anti-121P1F1 antibody in connection with the treatment of a solid tumor, e.g., a cancer of a tissue listed in Table I. In the study, the safety of single doses of anti-121P1F1 antibodies when utilized as an adjunctive therapy to an antineoplastic or chemotherapeutic agent, such as cisplatin, topotecan, doxorubicin, adriamycin, taxol, or the like, is assessed. The trial design includes delivery of six single doses of an anti-121P1F1 antibody with dosage of antibody escalating from approximately about 25 mg/m 2 to about 275 mg/m 2 over the course of the treatment in accordance with the following schedule:

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 121P1F1. Standard tests and follow-up are utilized to monitor each of these safety concerns. Patients are also assessed for clinical outcome, and particularly reduction in tumor mass as evidenced by MRI or other imaging.

The anti-121P1F1 antibodies are demonstrated to be safe and efficacious, Phase II trials confirm the efficacy and refine optimum dosing.

Example 41

Human Clinical Trial: Monotherapy with Human Anti-121P1F1 Antibody

Anti-121P1F1 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-121P1F1 antibodies.

Example 42

Human Clinical Trial: Diagnostic Imaging with Anti-121P1F1 Antibody

Once again, as the adjunctive therapy discussed above is safe within the safety criteria discussed above, a human clinical trial is conducted concerning the use of anti-121P1F1 antibodies as a diagnostic imaging agent. The protocol is designed in a substantially similar manner to those described in the art, such as in Divgi, et al., *J. Natl. Cancer Inst.* 83:97-104 (1991). The antibodies are found to be both safe and efficacious when used as a diagnostic modality.

Example 43

Homology Comparison of 121P1F1 to Known Sequences

The 121P1F1 gene is identical to a previously cloned and sequenced gene, namely human GAJ protein (gi|14149769) showing 100% identity to that protein. The closest homolog to the 121P1F1 protein is a mouse hypothetical 24.2 kDa protein (gi|12847934) of unknown function. The 121P1F1 protein consists of 205 amino acids, with calculated molecular weight of 23.7 kDa, and pI of 8.2. 121P1F1 is an intracellular protein, with primary localization to the nucleus. 121P1F1 can also localize to the cytosol. Motif analysis revealed the presence of a basic leucine zipper motif (bZIP) (Table XXI) in 121P1F1 at amino acids 117-143, and a steroid hormone receptor signature at aa 168-189. The basic-leucine zipper (bZIP) (Table XXI) motif mediates sequence-specific DNA-binding and dimerization of leucine zipper motifs with other basic helix-loop-helix proteins (Alber, T., *Curr Opin Genet Dev.* 1992, 2:205). This dimerization of the transcription factor is critical in order for DNA binding and transcriptional activation to occur. Members of the leucine zipper family of proteins include the Myc proto-oncogene (Amati B, et al., *EMBO J.* 1993, 12:5083). The Myc-Max dimer is a transactivating complex which regulates the expression of various genes, including genes involved in cell proliferation, growth and apoptosis, as well as differentiation (Luscher B. Gene. 2001, 277:1; Holzel, M, et al., *EMBO Rep.* 2001, 2:1125; Ben-Porath I, Yanuka O, Benvenisty N. *Mol Cell Biol.* 1999, 19:3529). Myc is overexpressed in a variety of cancers, including prostate, breast and colon cancer (Jenkins R B, Qian J, Lieber M M, Bostwick D G. *Cancer Res.* 1997, 57:524; Buttyan R, et al., *Prostate.* 1987; 11:327; Chrzan P, et al., *Clin Biochem.* 2001, 34:557; Hashimoto K, et al., *Carcinogenesis* 2001, 22:1965). The steroid hormone receptor signature is a fingerprint with similarity to the zinc finger motif. It is often found in transcription factors, where it regulates DNA-protein and protein-protein interactions by determining the specificity of interacting partners (Green S, et al., *EMBO J.* 1988, 7:3037; Ribeiro R C, Kushner P J, Baxter, J D. *Annu Rev Med.* 1995; 46:443).

The presence of leucine zipper and protein-protein interaction domains along with its localization to the nucleus indicate that 121P1F1 plays a role in regulating gene transcription in mammalian cells, and thereby regulates cellular proliferation, transformation, differentiation and apoptosis. These biological functions have a direct effect on transformation, tumor growth and progression.

Accordingly, when 121P1F1 functions as a regulator of cell transformation, tumor formation, or as a modulator of transcription involved in activating genes associated with inflammation, tumorigenesis or proliferation, 121P1F1 is useful for therapeutic, diagnostic, prognostic and/or preventative purposes. In addition, when a molecule, such as a variant or SNP of 121P1F1, is expressed in cancerous tissues, such as those listed in Table I, it is useful for therapeutic, diagnostic, prognostic and/or preventative purposes.

Figure 10:
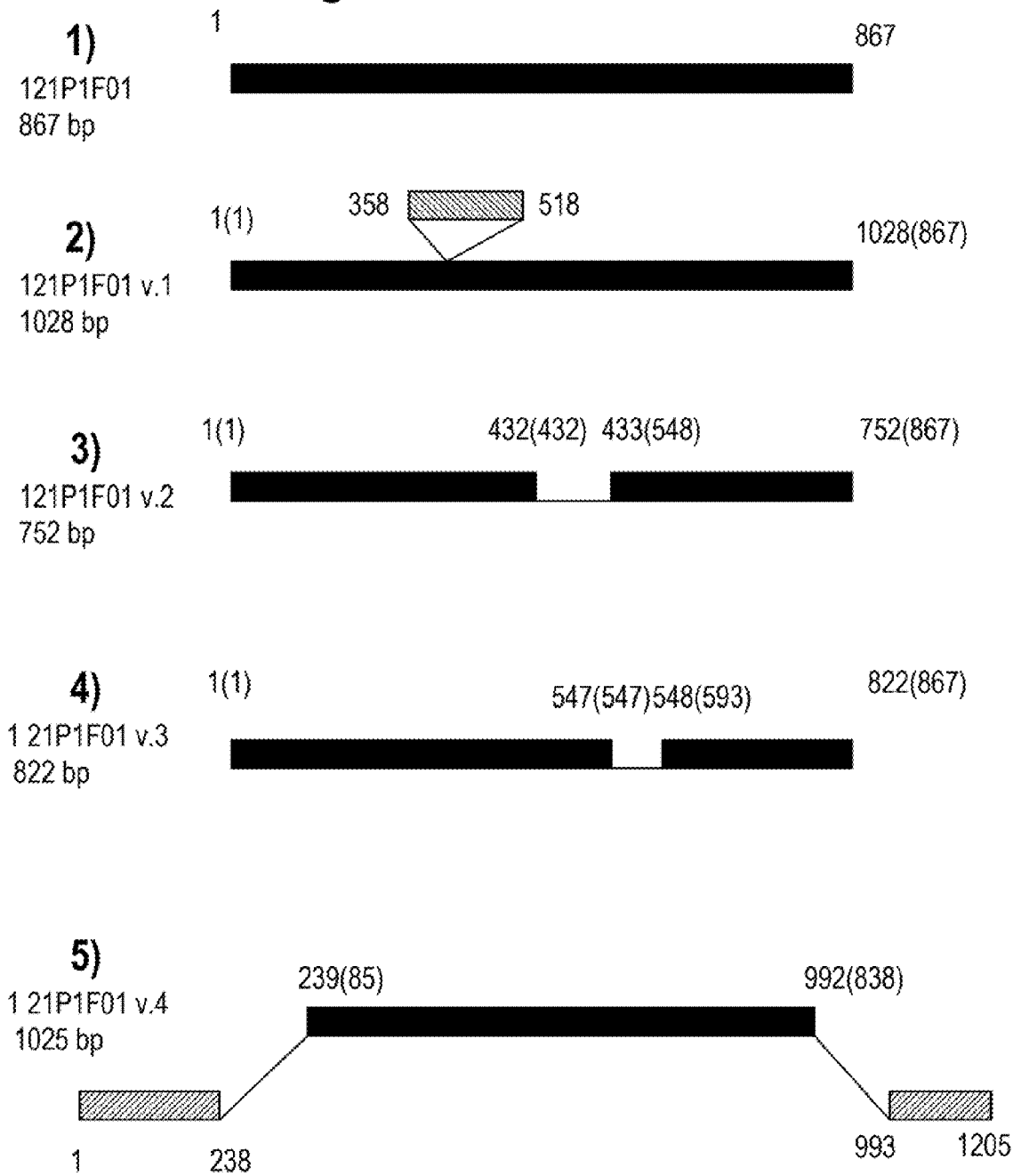
FIG. 10. Nucleotide splice variants of 121P1F1.
Figure 11:
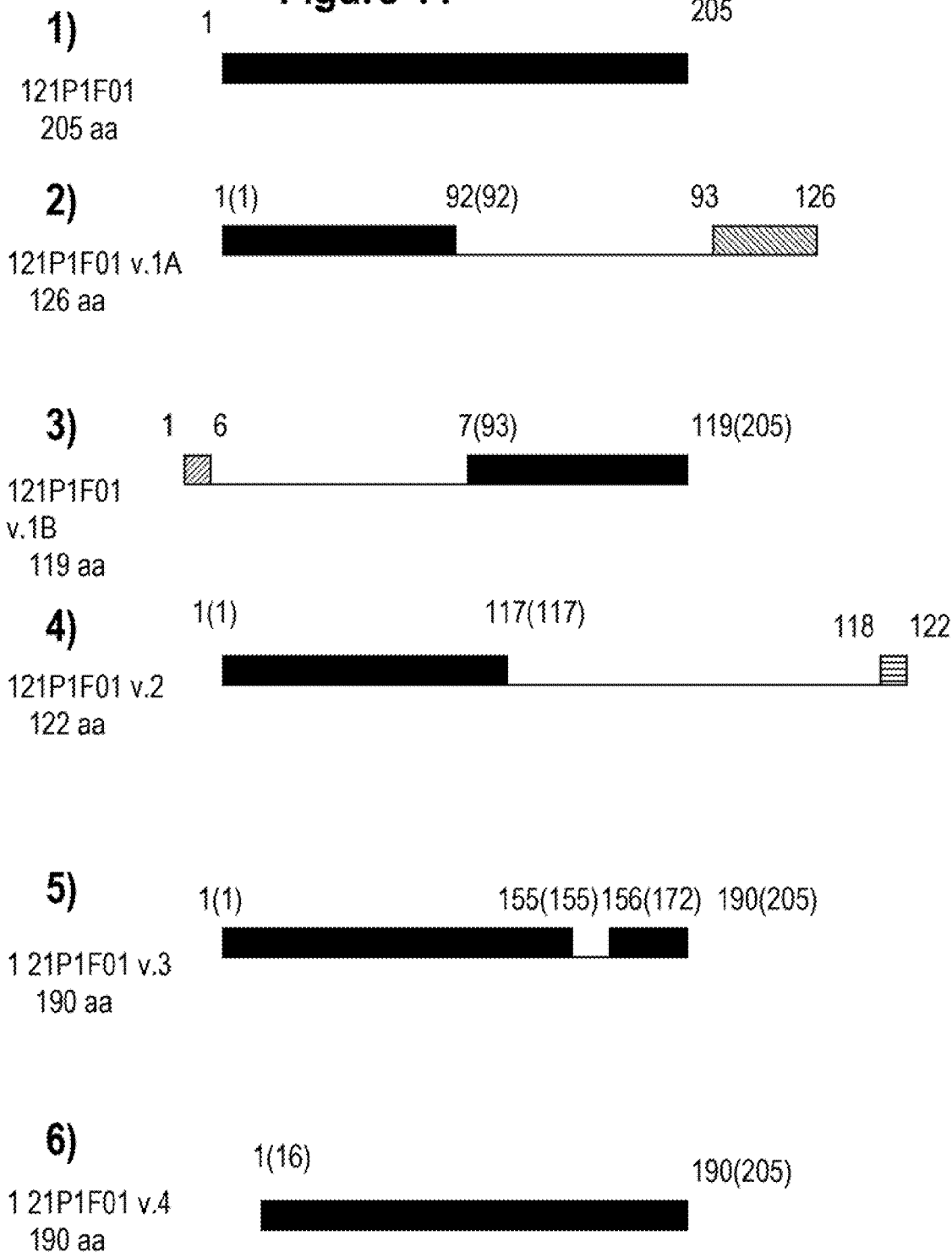
FIG. 11. Protein splice variants of 121P1F1.
Figure 12:
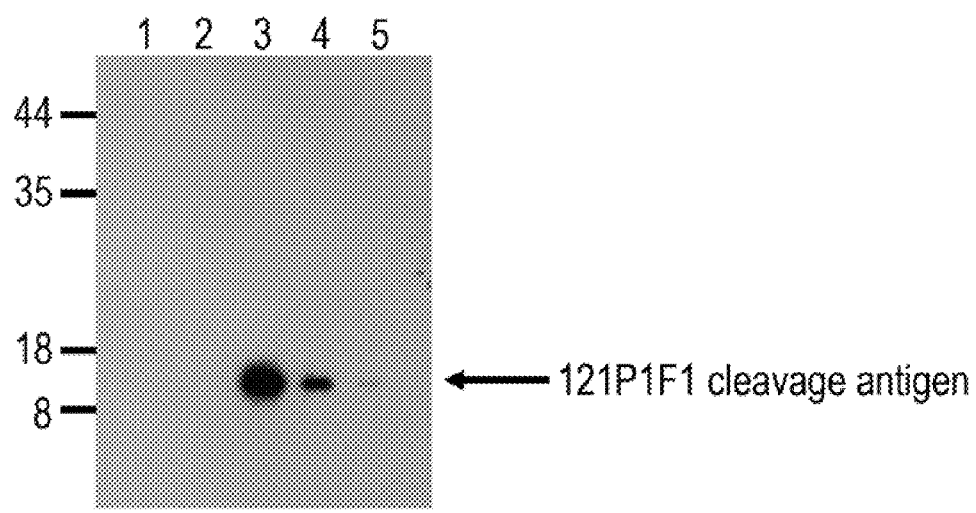
FIG. 12: Specific recognition of 121P1F1 antigen by anti-121P1F1 polyclonal antibody. The indicated dilutions of anti-121P1F1 polyclonal antibody serum or pre-immune serum was used to probe a blot containing GST-121P1F1 cleavage antigen. Reactivity was visualized by incubation with goat anti-rabbit HRP-conjugated secondary antibody and development by enhanced chemiluminescence and exposure to autoradiography film.

Several variants of 121P1F1 have been identified, including the 5 variants shown in FIG. 10 and FIG. 11. Several of the variants (e.g., V1A, V2, V3 and V4) contain portions of 121P1F1 while lacking others. Other variants contain additional sequences not found in 121P1F1 (e.g., V1A, V2 and V3). For example, variant 1A is identical to 121P1F1 in its first 92 aa, while lacking aa 93-205 of 121P1F1 and diverging from 121P1F1 in its C-terminal 34 aa (FIG. 4A and FIG. 4B). Variants 1B, 3 and 4 contain a Myc-like leucine zipper, indicating that they bind DNA and function as transcription factors in a manner similar to full length 121P1F1. Properties of 121P1F1 and splice variants 1A and 4 are shown in Table XXI.

Example 44

Regulation of Transcription

The nuclear localization of 121P1F1 coupled to the presence of bZIP and protein interaction domains within its sequence indicate that 121P1F1 is a transcription factor and modulates the transcriptional regulation of eukaryotic genes. This function is supported by published reports, which show that Myc regulates the expression of multiple genes including Tmp, a gene that promotes transformation (Ben-Porath I, Yanuka O, Benvenisty N. Mol Cell Biol. 1999, 19:3529), and p21WAF1, a gene that controls the cell cycle (Mitchell K O and El-Deiry W S, Cell Growth Differ 1999, 10:223). Regulation of gene expression is confirmed, e.g., by studying gene expression in cells expressing or lacking 121P1F1. For this purpose, two types of experiments are performed.

In the first set of experiments, RNA from parental and 121P1F1-expressing cells are extracted and hybridized to commercially available gene arrays (Clontech) (Smid-Koopman, E., et al., *Br J Cance* 2000. 83:246). Resting cells as well as cells treated with FBS, androgen or growth factors are compared. Differentially expressed genes are identified in accordance with procedures known in the art. The differentially expressed genes are then mapped to biological pathways (Chen K, et al., *Thyroid.* 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. In addition, a Myc/Max specific response element, namely E-box hexamer CACGTG reporter is also evaluated (Ben-Porath I et al, Mol Cell Biol 1999; 19:3529). These transcriptional reporters contain consensus binding sites for known transcription factors that lie downstream of well-characterized signal transduction pathways, and represent a good tool to ascertain pathway activation and screen for positive and negative modulators of pathway activation.

Thus, 121P1F1 plays a role in gene regulation, and it is used as a target for diagnostic, prognostic, preventative and/or therapeutic purposes.

Example 45

Identification and Confirmation of Potential Signal Transduction Pathways

Many mammalian proteins have been reported to interact with signaling molecules and to participate in regulating signaling pathways. (*J Neurochem.* 2001; 76:217-223). Based on their ability to mediate protein interactions, leucine zipper proteins have been reported to regulate signaling pathways important for cell survival and growth (Nagamura-Inoue T, et al., *Int Rev Immunol.* 2001, 20:83). Using immunoprecipitation and Western blotting techniques, proteins are identified that associate with 121P1F1 and mediate signaling events. Several pathways known to play a role in cancer biology can be regulated by 121P1F1, including phospholipid pathways such as PI3K, AKT, etc, adhesion and migration pathways, including FAK, Rho, Rac-1, etc, as well as mitogenic/survival cascades such as ERK, p38, etc (Cell Growth Differ. 2000, 11:279; J Biol Chem. 1999, 274:801; Oncogene. 2000, 19:3003, J. Cell Biol. 1997, 138:913.).

To confirm that 121P1F1 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 121P1F1 are mapped and used for the identification and validation of therapeutic targets. When 121P1F1 is involved in cell signaling, it is used as a target for diagnostic, prognostic, preventative and/or therapeutic purposes.

Example 46

Involvement in Tumor Progression

Based on the documented role of bZip and Steroid hormone receptor motifs in cell growth and proliferation (Holzel M, et al., *EMBO Rep.* 2001, 2:1125), the 121P1F1 gene can contribute to the growth of cancer cells. The role of 121P1F1 in tumor growth is confirmed in a variety of primary and transfected cell lines including prostate, breast and kidney cell lines, as well as NIH 3T3 cells engineered to stably express 121P1F1. Parental cells lacking 121P1F1 and cells expressing 121P1F1 are evaluated for cell growth using a well-documented proliferation assay (Fraser S P, Grimes J A, Djamgoz M B. Prostate. 2000; 44:61, Johnson D E, Ochieng J, Evans S L. Anticancer Drugs. 1996, 7:288).

To confirm the role of 121P1F1 in the transformation process, its effect in colony forming assays is investigated. Parental NIH-3T3 cells lacking 121P1F1 are compared to NIH-3T3 cells expressing 121P1F1, using a soft agar assay under stringent and more permissive conditions (Song Z., et al., *Cancer Res.* 2000; 60:6730).

To confirm the role of 121P1F1 in invasion and metastasis of cancer cells, a well-established assay is used, e.g., a Transwell Insert System assay (Becton Dickinson) (*Cancer Res.* 1999; 59:6010). Control cells, including prostate, breast and kidney cell lines lacking 121P1F1 are compared to cells expressing 121P1F1. Cells are loaded with the fluorescent dye, calcein, and plated in the top well of the Transwell insert coated with a basement membrane analog. Invasion is determined by fluorescence of cells in the lower chamber relative to the fluorescence of the entire cell population.

121P1F1 can also play a role in the regulation of the cell cycle and apoptosis. Parental cells and cells expressing 121P1F1 are compared for differences in cell cycle regulation using a well-established BrdU assay (Abdel-Malek Z A., *J Cell Physiol.* 1988, 136:247). In short, cells are grown under both optimal (full serum) and limiting (low serum) conditions, and are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 121P1F1, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 121P1F1 can play a critical role in regulating tumor progression and tumor load.

When 121P1F1 plays a role in cell growth, transformation, invasion or apoptosis, it is used as a target for diagnostic, prognostic, preventative and/or therapeutic purposes.

Example 47

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). Based on the effect of phsophodieseterase inhibitors on endothelial cells, 121P1F1 plays a role in angiogenesis (De-Fouw L., et al., *Microvasc Res* 2001, 62:263). Several assays have been developed to measure angiogenesis in vitro and in vivo, such as the tissue culture assays based on endothelial cell tube formation and endothelial cell proliferation. Using these assays as well as in vitro neo-vascularization, the role of 121P1F1 in angiogenesis, enhancement or inhibition, is confirmed.

For example, endothelial cells engineered to express 121P1F1 are evaluated using tube formation and proliferation assays. The effect of 121P1F1 is also confirmed in animal models in vivo. For example, cells either expressing or lacking 121P1F1 are implanted subcutaneously in immunocompromised mice. Endothelial cell migration and angiogenesis are evaluated 5-15 days later using immunohistochemistry techniques. Demonstration of an effect of 121P1F1 on angiogenesis confirms its usefulness as a target for diagnostic, prognostic, preventative and/or therapeutic purposes

Example 48

Involvement in Protein-Protein Interactions

Protein containing bZip motifs have been shown to interact with other proteins, specially proteins containing helix-loop-helix structures, thereby regulating gene transcription as well as cell growth (Schneider A, et al., *Curr Top Microbiol Immunol.* 1997; 224: 137; Amati B, Land H. *Curr Opin Genet Dev.* 1994, 4:102). Using immunoprecipitation techniques as well as two yeast hybrid systems, proteins are identified that associate with 121P1F1. Immunoprecipitates from cells expressing 121P1F1 and cells lacking 121P1F1 are compared for specific protein-protein associations.

Studies are performed to confirm the extent of association of 121P1F1 with effector molecules, such as nuclear proteins, transcription factors, kinases, phosphates etc. Studies comparing 121P1F1 positive and 121P1F1 negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (*Curr Opin Chem Biol.* 1999, 3:64). A vector carrying a library of proteins fused to the activation domain of a transcription factor is introduced into yeast expressing a 121P1F1 DNA-binding domain fusion protein and a reporter construct. Protein-protein interaction is detected by calorimetric reporter activity. Specific association with effector molecules and transcription factors directs one of skill to the mode of action of 121P1F1, and thus identifies therapeutic, prognostic, preventative and/or diagnostic targets for cancer. This and similar assays are also used to identify and screen for small molecules that interact with 121P1F1.

Thus it is found that 121P1F1 associates with proteins and small molecules. Accordingly, 121P1F1 and these proteins and small molecules are used for diagnostic, prognostic, preventative and/or therapeutic purposes.

Example 49

Involvement in DNA-Protein Interactions

As previously mentioned, the basic-leucine zipper (bZIP) motif contain a basic region that mediates sequence-specific DNA-protein binding, as well as a leucine zipper region needed for protein dimerization. Electrophoretic mobility shift assays (EMSA) and DNA footprinting are used to identify 121P1F1-binding DNA sequences, and define specific response elements. In short, nuclear lysates are extracted from parental 121P1F1-negative as well as 121P1F1-expressing cells. The lysates are incubated in the presence of 32P-labeled DNA probes. DNA-protein complexes are either separated by electrophoresis or exposed to a restriction nuclease, and analyzed by radiography. This process provides 121P1F1 specific DNA elements that are valuable tools in designing and testing inhibitors of 121P1F1.

When 121P1F1 functions as a transcription factor, it is used as a target for diagnostic, prognostic, preventative and therapeutic purposes.

Throughout this application, various website data content, publications, patent applications and patents are referenced. The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that Express 121P1F1 When Malignant

Prostate
Bladder
Kidney
Colon
Lung
Pancreas
Breast
Cervix
Stomach

TABLE II

AMINO ACID ABBREVIATIONS

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX
Adapted from the GCG Software 9.0 BloSuM62 amino acid substitution matrix (block substitution matrix). The higher the value, the more likely a substitution is found in related, natural proteins. (See URL located on the World Wide Web at .ikp.unibe.ch/manual/blosum62.html.)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|  | 9 | −3 | −4 | −2 | −3 | −3 | −1 | −3 | −1 | −1 | −3 | −3 | −3 | −3 | −1 | −1 | −1 | −2 | −2 | C |
|  |  | 6 | 2 | −3 | −1 | −1 | −3 | −1 | −4 | −3 | 1 | −1 | 0 | −2 | 0 | −1 | −3 | −4 | −3 | D |
|  |  |  | 5 | −3 | −2 | 0 | −3 | 1 | −3 | −2 | 0 | −1 | 2 | 0 | 0 | −1 | −2 | −3 | −2 | E |
|  |  |  |  | 6 | −3 | −1 | 0 | −3 | 0 | 0 | −3 | −4 | −3 | −3 | −2 | −2 | −1 | 1 | 3 | F |
|  |  |  |  |  | 6 | −2 | −4 | −2 | −4 | −3 | 0 | −2 | −2 | −2 | 0 | −2 | −3 | −2 | −3 | G |
|  |  |  |  |  |  | 8 | −3 | −1 | −3 | −2 | 1 | −2 | 0 | 0 | −1 | −2 | −3 | −2 | 2 | H |
|  |  |  |  |  |  |  | 4 | −3 | 2 | 1 | −3 | −3 | −3 | −3 | −2 | −1 | 3 | −3 | −1 | I |
|  |  |  |  |  |  |  |  | 5 | −2 | −1 | 0 | −1 | 1 | 2 | 0 | −1 | −2 | −3 | −2 | K |
|  |  |  |  |  |  |  |  |  | 4 | 2 | −3 | −3 | −2 | −2 | −2 | −1 | 1 | −2 | −1 | L |
|  |  |  |  |  |  |  |  |  |  | 5 | −2 | −2 | 0 | −1 | −1 | −1 | 1 | −1 | −1 | M |
|  |  |  |  |  |  |  |  |  |  |  | 6 | −2 | 0 | 0 | 1 | 0 | −3 | −4 | −2 | N |
|  |  |  |  |  |  |  |  |  |  |  |  | 7 | −1 | −2 | −1 | −1 | −2 | −4 | −3 | P |
|  |  |  |  |  |  |  |  |  |  |  |  |  | 5 | 1 | 0 | −1 | −2 | −2 | −1 | Q |
|  |  |  |  |  |  |  |  |  |  |  |  |  |  | 5 | −1 | −1 | −3 | −3 | −2 | R |
|  |  |  |  |  |  |  |  |  |  |  |  |  |  |  | 4 | 1 | −2 | −3 | −2 | S |
|  |  |  |  |  |  |  |  |  |  |  |  |  |  |  |  | 5 | 0 | −2 | −2 | T |
|  |  |  |  |  |  |  |  |  |  |  |  |  |  |  |  |  | 4 | −3 | −1 | V |
|  |  |  |  |  |  |  |  |  |  |  |  |  |  |  |  |  |  | 11 | 2 | W |
|  |  |  |  |  |  |  |  |  |  |  |  |  |  |  |  |  |  |  | 7 | Y |

TABLE IV (A)

| | POSITION 2 (Primary Anchor) | POSITION 3 (Primary Anchor) | POSITION C Terminus (Primary Anchor) |
|---|---|---|---|
| SUPERMOTIF | | | |
| A1 | T*ILVMS* | | FWY |
| A2 | LIVM*ATQ* | | IVM*ATL* |
| A3 | VSMA*TLI* | | RK |
| A24 | YF*WIVLMT* | | FI*YWLM* |
| B7 | P | | VILF*MWYA* |
| B27 | RHK | | FYL*WMIVA* |
| B44 | ED | | FWYLIMVA |
| B58 | ATS | | FWY*LIVMA* |
| B62 | QL*IVMP* | | FWYMIVLA |
| MOTIFS | | | |
| A1 | TSM | | Y |
| A1 | | DE*AS* | Y |
| A2.1 | LM*VQIAT* | | V*LIMAT* |
| A3 | LMV*ISATFCGD* | | KYR*HFA* |
| A11 | VTML*ISAGNCDF* | | K*RYH* |
| A24 | YF*WM* | | FLIW |
| A*3101 | MVT*ALIS* | | R*K* |
| A*3301 | MVALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

| HLA CLASS II SUPERMOTIF | | |
|---|---|---|
| 1 | 6 | 9 |
| W, F, Y, V, .I, L | A, V, I, L, P, C, S, T | A, V, I, L, C, S, T, M, Y |

TABLE IV (C)

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VSTC*PALIM* | MH | | MH |
| | deleterious | | | | W | | | R | | WDE |
| DR1 | preferred | M*FLIVWY* | | | PAMQ | | VMAT*SPLIC* | M | | AVM |
| | deleterious | | C | CH | FD | CWD | | GDE | D | |
| DR7 | preferred | M*FLIVWY* | M | W | A | | IVMSAC*TPL* | M | | IV |
| | deleterious | | | C | G | | | GRD | N | G |

| | MOTIFS | 1° anchor 1 | 2 | 3 | 1° anchor 4 | 5 | 1° anchor 6 |
|---|---|---|---|---|---|---|---|
| DR3 | | | | | | | |
| motif a preferred | | LIVMFY | | | D | | |
| motif b preferred | | LIVMFAY | | | DNQEST | | KRH |
| DR Supermotif | | MF*LIVWY* | | | | | VMSTAC*PLI* |

Italicized residues indicate less preferred or "tolerated" residues.

TABLE IV (D)

| | | | | | POSITION | | | | | |
|---|---|---|---|---|---|---|---|---|---|---|
| | | | | | Position: | | | | | |
| Super-Motifs | | 1 | 2 | 3 | 4 | 5 | 6 | 7 | 8 | C-terminus |
| A1 | | | 1° Anchor T*ILVMS* | | | | | | | 1° Anchor FWY |
| A2 | | | 1° Anchor LIVM*ATQ* | | | | | | | 1° Anchor LIVMAT |
| A3 | preferred | | 1° Anchor VSMA*TLI* | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* | | | | | | | 1° Anchor FI*YWLM* |
| B7 | preferred | FWY (5/5) LIVM (3/5) | 1° Anchor P | FWY (4/5) | | | | | FWY (3/5) | 1° Anchor VILF*MWYA* |
| | deleterious | DE (3/5); P (5/5); G (4/5); A (3/5); QN (3/5) | | | | | DE (3/5) | G (4/5) | QN (4/5) | DE (4/5) |
| B27 | | | 1° Anchor RHK | | | | | | | 1° Anchor FYL*WMIVA* |

TABLE IV (D)-continued

| | POSITION | | | | | | | | |
|---|---|---|---|---|---|---|---|---|---|
| Super-Motifs | 1 | 2 | 3 | 4 | 5 | 6 | 7 | 8 | C-terminus |
| B44 | | 1° Anchor E$D$ | | | | | | | 1° Anchor FWYLIMVA |
| B58 | | 1° Anchor ATS | | | | | | | 1° Anchor FWY$LIVMA$ |
| B62 | | 1° Anchor Q$LIVMP$ | | | | | | | 1° Anchor FWY$MIVLA$ |

TABLE IV (E)

| | | POSITION: | | | | |
|---|---|---|---|---|---|---|
| | | 1 | 2 | 3 | 4 | 5 |
| A1 9-mer | preferred | GFYW | 1° Anchor STM | DEA | YFW | |
| | deleterious | DE | | RHKLIVMP | A | G |
| A1 9-mer | preferred | GRHK | ASTCLIVM | 1° Anchor DE$AS$ | GSTC | |
| | deleterious | A | RHKDEPYFW | | DE | PQN |
| A1 10-mer | preferred | YFW | 1° Anchor STM | DEAQN | A | YFWQN |
| | deleterious | GP | | RHKGLIVM | DE | RHK |
| A1 10-mer | preferred | YFW | STCLIVM | 1° Anchor DE$AS$ | A | YFW |
| | deleterious | RHK | RHKDEPYFW | | | P |
| A2.1 9-mer | preferred | YFW | 1° Anchor LM$IVQAT$ | YFW | STC | YFW |
| | deleterious | DEP | | DERKH | | |
| A2.1 10-mer | preferred | AYFW | 1° Anchor LM$IVQAT$ | LVIM | G | |
| | deleterious | DEP | | DE | RKHA | P |
| A3 | preferred | RHK | 1° Anchor LMVISATFCGD | YFW | PRHKYFW | A |
| | deleterious | DEP | | DE | | |
| A11 | preferred | A | 1° Anchor VTLMISAGNCDF | YFW | YFW | A |
| | deleterious | DEP | | | | |
| A24 9-mer | preferred | YFWRHK | 1° Anchor YFW$M$ | | STC | |
| | deleterious | DEG | | DE | G | QNP |
| A24 10-mer | preferred | | 1° Anchor YFW$M$ | | P | YFWP |
| | deleterious | | | GDE | QN | RHK |
| A3101 | preferred | RHK | 1° Anchor MVT$ALIS$ | YFW | P | RHK |
| | deleterious | DEP | | DE | | ADE |
| A3301 | preferred | | 1° Anchor MVALF$IST$ | YFW | | |
| | deleterious | GP | | DE | | |
| A6801 | preferred | YFWSTC | 1° Anchor AVT$MSLI$ | | | YFWLIVM |
| | deleterious | GP | | DEG | | RHK |
| B0702 | preferred | RHKFWY | 1° Anchor P | RHK | | RHK |
| | deleterious | DEQNP | | DEP | DE | DE |
| B3501 | preferred | FWYLIVM | 1° Anchor P | FWY | | |
| | deleterious | AGP | | | | G |
| B51 | preferred | LIVMFWY | 1° Anchor P | FWY | STC | FWY |
| | deleterious | AGPDERHKSTC | | | | DE |
| B5301 | preferred | LIVMFWY | 1° Anchor P | FWY | STC | FWY |
| | deleterious | AGPQN | | | | |
| B5401 | preferred | FWY | 1° Anchor P | FWYL IVM | | LIVM |
| | deleterious | GPQNDE | | GDES | | RHKDE |

TABLE IV (E)-continued

| | | \multicolumn{5}{c}{TC POSITION:} | | | | |
|---|---|---|---|---|---|---|
| | | 6 | 7 | 8 | 9 or C-terminus | C-terminus |
| A1 9-mer | preferred | P | DEQN | YFW | 1° Anchor Y | |
| | deleterious | A | | | | |
| A1 9-mer | preferred | ASTC | LIVM | DE | 1° Anchor Y | |
| | deleterious | RHK | PG | GP | | |
| A1 10-mer | preferred | | PASTC | GDE | P | 1° Anchor Y |
| | deleterious | QNA | RHKYFW | RHK | A | |
| A1 10-mer | preferred | | PG | G | YFW | 1° Anchor Y |
| | deleterious | G | | PRHK | QN | |
| A2.1 9-mer | preferred | | A | P | 1° Anchor V*LIMAT* | |
| | deleterious | RKH | DERKH | | | |
| A2.1 10-mer | preferred | G | | FYWL VIM | | 1° Anchor V*LIMAT* |
| | deleterious | | RKH | DERKH | RKH | |
| A3 | preferred | YFW | | P | 1° Anchor KYR*HFA* | |
| | deleterious | | | | | |
| A11 | preferred | YFW | YFW | P | 1° Anchor K*RYH* | |
| | deleterious | | A | G | | |
| A24 9-mer | preferred | | YFW | YFW | 1° Anchor FLIW | |
| | deleterious | DERHK | G | AQN | | |
| A24 10-mer | preferred | | P | | | 1° Anchor FLIW |
| | deleterious | DE | A | QN | DEA | |
| A3101 | preferred | YFW | YFW | AP | 1° Anchor R*K* | |
| | deleterious | DE | DE | DE | | |
| A3301 | preferred | | AYFW | | 1° Anchor RK | |
| | deleterious | | | | | |
| A6801 | preferred | | YFW | P | 1° Anchor RK | |
| | deleterious | | | A | | |
| B0702 | preferred | RHK | RHK | PA | 1° Anchor LMF*WYAIV* | |
| | deleterious | GDE | QN | DE | | |
| B3501 | preferred | | FWY | | 1° Anchor LMFWY*IVA* | |
| | deleterious | G | | | | |
| B51 | preferred | | G | FWY | 1° Anchor LIVF*WYAM* | |
| | deleterious | G | DEQN | GDE | | |
| B5301 | preferred | | LIVMFWY | FWY | 1°Anchor IMFWY*ALV* | |
| | deleterious | G | RHKQN | DE | | |
| B5401 | preferred | | ALIVM | FWYAP | 1° Anchor ATIV*LMFWY* | |
| | deleterious | DE | QNDGE | DE | | |

Italicized residues indicate less preferred or "tolerated" residues. The information in this Table is specific for 9-mers unless otherwise specified.

TABLE V (A)

HLA PEPTIDE SCORING RESULTS - 121P1F1 - A1, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 169 | WTDNIFAIK | 50.000 | Portion of |
| 2 | 114 | RCETEERTR | 9.000 | SEQ ID |
| 3 | 16 | MMEIFSETK | 9.000 | NO: 3; |
| 4 | 195 | FGIPEDFDY | 6.250 | each |
| 5 | 106 | SIEKAKIGR | 4.500 | start |
| 6 | 20 | FSETKDVFQ | 2.700 | posi- |
| 7 | 59 | MVDCERIGT | 2.500 | tion |
| 8 | 185 | GFEENKIDR | 2.250 | is |
| 9 | 116 | ETEERTRLA | 2.250 | specified, |
| 10 | 152 | VEEIRQANK | 1.800 | the |
| 11 | 101 | ASLQKSIEK | 1.500 | length |
| 12 | 93 | LSEGSQKHA | 1.350 | of each |
| 13 | 54 | LVDDGMVDC | 1.000 | peptide |
| 14 | 146 | DCDPQVVEE | 1.000 | is 9 |
| 15 | 85 | KLEVLESQL | 0.900 | amino |
| 16 | 151 | VVEEIRQAN | 0.900 | acids, |
| 17 | 8 | SAEEKRTRM | 0.900 | the end |
| 18 | 88 | VLESQLSEG | 0.900 | position |
| 19 | 130 | LRDQREQLK | 0.500 | for |
| 20 | 117 | TEERTRLAK | 0.450 | each |
| 21 | 193 | RTFGIPEDF | 0.250 | peptide |
| 22 | 66 | GTSNYYWAF | 0.250 | is the |
| 23 | 77 | KALHARKHK | 0.200 | start |
| 24 | 72 | WAFPSKALH | 0.200 | position |
| 25 | 138 | KAEVEKYKD | 0.180 | plus |
| 26 | 7 | LSAEEKRTR | 0.150 | eight |
| 27 | 126 | ELSSLRDQR | 0.100 | |
| 28 | 34 | KIAPKEKGI | 0.100 | |
| 29 | 61 | DCERIGTSN | 0.090 | |
| 30 | 133 | QREQLKAEV | 0.090 | |
| 31 | 40 | KGITAMSVK | 0.050 | |
| 32 | 22 | ETKDVFQLK | 0.050 | |
| 33 | 26 | VFQLKDLEK | 0.050 | |
| 34 | 136 | QLKAEVEKY | 0.050 | |
| 35 | 197 | IPEDFDYID | 0.045 | |
| 36 | 47 | VKEVLQSLV | 0.045 | |
| 37 | 162 | AKEAANRWT | 0.045 | |
| 38 | 186 | FEENKIDRT | 0.045 | |
| 39 | 91 | SQLSEGSQK | 0.030 | |
| 40 | 63 | ERIGTSNYY | 0.025 | |
| 41 | 42 | ITAMSVKEV | 0.025 | |
| 42 | 5 | KGLSAEEKR | 0.025 | |
| 43 | 144 | YKDCDPQVV | 0.025 | |
| 44 | 148 | DPQVVEEIR | 0.025 | |
| 45 | 124 | AKELSSLRD | 0.022 | |
| 46 | 175 | AIKSWAKRK | 0.020 | |
| 47 | 174 | FAIKSWAKR | 0.020 | |
| 48 | 30 | KDLEKIAPK | 0.020 | |
| 49 | 155 | IRQANKVAK | 0.020 | |
| 50 | 160 | KVAKEAANR | 0.020 | |

TABLE VI (A)

HLA PEPTIDE SCORING RESULTS - 121P1F1 - A1, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 116 | ETEERTRLAK | 225.000 | Portion |
| 2 | 151 | VVEEIRQANK | 36.000 | of SEQ |
| 3 | 20 | FSETKDVFQL | 6.750 | ID NO: 3; |
| 4 | 169 | WTDNIFAIKS | 6.250 | each start |
| 5 | 146 | DCDPQVVEEI | 5.000 | position |
| 6 | 61 | DCERIGTSNY | 4.500 | is |
| 7 | 31 | DLEKIAPKEK | 1.800 | specified, |
| 8 | 93 | LSEGSQKHAS | 1.350 | the length |
| 9 | 25 | DVFQLKDLEK | 1.000 | of each |
| 10 | 100 | HASLQKSIEK | 1.000 | peptide |
| 11 | 29 | LKDLEKIAPK | 1.000 | is 10 amino |
| 12 | 8 | SAEEKRTRMM | 0.900 | acids, |
| 13 | 85 | KLEVLESQLS | 0.900 | the end |
| 14 | 88 | VLESQLSEGS | 0.900 | position |
| 15 | 138 | KAEVEKYKDC | 0.900 | for each |
| 16 | 114 | RCETEERTRL | 0.900 | peptide |
| 17 | 105 | KSIEKAKIGR | 0.750 | is the |
| 18 | 72 | WAFPSKALHA | 0.500 | start |
| 19 | 59 | MVDCERIGTS | 0.500 | position |
| 20 | 186 | FEENKIDRTF | 0.450 | plus nine |
| 21 | 90 | ESQLSEGSQK | 0.300 | |
| 22 | 55 | VDDGMVDCER | 0.250 | |
| 23 | 172 | NIFAIKSWAK | 0.200 | |
| 24 | 96 | GSQKHASLQK | 0.150 | |
| 25 | 184 | FGFEENKIDR | 0.125 | |
| 26 | 194 | TFGIPEDFDY | 0.125 | |
| 27 | 130 | LRDQREQLKA | 0.125 | |
| 28 | 18 | EIFSETKDVF | 0.100 | |
| 29 | 6 | GLSAEEKRTR | 0.100 | |
| 30 | 34 | KIAPKEKGIT | 0.100 | |
| 31 | 15 | RMMEIFSETK | 0.100 | |
| 32 | 68 | SNYYWAFPSK | 0.100 | |
| 33 | 106 | SIEKAKIGRC | 0.090 | |
| 34 | 177 | KSWAKRKFGF | 0.075 | |
| 35 | 67 | TSNYYWAFPS | 0.075 | |
| 36 | 54 | LVDDGMVDCE | 0.050 | |
| 37 | 185 | GFEENKIDRT | 0.045 | |
| 38 | 124 | AKELSSLRDQ | 0.045 | |
| 39 | 152 | VEEIRQANKV | 0.045 | |
| 40 | 16 | MMEIFSETKD | 0.045 | |
| 41 | 154 | EIRQANKVAK | 0.040 | |
| 42 | 65 | IGTSNYYWAF | 0.025 | |
| 43 | 42 | ITAMSVKEVL | 0.025 | |
| 44 | 23 | TKDVFQLKDL | 0.025 | |
| 45 | 190 | KIDRTFGIPE | 0.025 | |
| 46 | 58 | GMVDCERIGT | 0.025 | |
| 47 | 195 | FGIPEDFDYI | 0.025 | |
| 48 | 44 | AMSVKEVLQS | 0.025 | |
| 49 | 47 | VKEVLQSLVD | 0.022 | |
| 50 | 174 | FAIKSWAKRK | 0.020 | |

TABLE VII (A)

HLA PEPTIDE SCORING RESULTS - 121P1F1 - A2, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 15 | RMMEIFSET | 155.125 | Portion |
| 2 | 122 | RLAKELSSL | 49.134 | of SEQ |
| 3 | 196 | GIPEDFDYI | 30.116 | ID NO: 3; |
| 4 | 78 | ALHARKHKL | 21.362 | each |
| 5 | 27 | FQLKDLEKI | 20.290 | start |
| 6 | 172 | NIFAIKSWA | 13.901 | position |
| 7 | 6 | GLSAEEKRT | 7.452 | is |
| 8 | 102 | SLQKSIEKA | 5.599 | specified, |
| 9 | 21 | SETKDVFQL | 5.541 | the length |
| 10 | 34 | KIAPKEKGI | 5.021 | of each |
| 11 | 85 | KLEVLESQL | 4.785 | peptide |
| 12 | 42 | ITAMSVKEV | 3.777 | is 9 |
| 13 | 129 | SLRDQREQL | 3.262 | amino |
| 14 | 54 | LVDDGMVDC | 2.787 | acids, |
| 15 | 18 | EIFSETKDV | 2.654 | the end |
| 16 | 115 | CETEERTRL | 1.703 | position |
| 17 | 150 | QVVEEIRQA | 0.820 | for each |
| 18 | 46 | SVKEVLQSL | 0.617 | peptide |
| 19 | 139 | AEVEKYKDC | 0.594 | is the |
| 20 | 65 | IGTSNYYWA | 0.455 | start |
| 21 | 59 | MVDCERIGT | 0.443 | position |
| 22 | 51 | LQSLVDDGM | 0.420 | plus eight |
| 23 | 189 | NKIDRTFGI | 0.345 | |
| 24 | 92 | QLSEGSQKH | 0.306 | |
| 25 | 28 | QLKDLEKIA | 0.292 | |
| 26 | 24 | KDVFQLKDL | 0.239 | |
| 27 | 43 | TAMSVKEVL | 0.221 | |
| 28 | 52 | QSLVDDGMV | 0.218 | |
| 29 | 50 | VLQSLVDDG | 0.143 | |
| 30 | 153 | EEIRQANKV | 0.101 | |
| 31 | 70 | YYWAFPSKA | 0.100 | |
| 32 | 168 | RWTDNIFAI | 0.079 | |
| 33 | 177 | KSWAKRKFG | 0.078 | |
| 34 | 144 | YKDCDPQVV | 0.073 | |
| 35 | 165 | AANRWTDNI | 0.071 | |
| 36 | 157 | QANKVAKEA | 0.069 | |
| 37 | 64 | RIGTSNYYW | 0.056 | |
| 38 | 186 | FEENKIDRT | 0.048 | |
| 39 | 167 | NRWTDNIFA | 0.031 | |
| 40 | 183 | KFGFEENKI | 0.025 | |
| 41 | 99 | KHASLQKSI | 0.025 | |
| 42 | 53 | SLVDDGMVD | 0.025 | |
| 43 | 88 | VLESQLSEG | 0.019 | |
| 44 | 8 | SAEEKRTRM | 0.018 | |
| 45 | 58 | GMVDCERIG | 0.018 | |
| 46 | 72 | WAFPSKALH | 0.018 | |
| 47 | 147 | CDPQVVEEI | 0.016 | |
| 48 | 104 | QKSIEKAKI | 0.014 | |
| 49 | 71 | YWAFPSKAL | 0.014 | |
| 50 | 195 | FGIPEDFDY | 0.013 | |

TABLE VIII (A)

HLA PEPTIDE SCORING RESULTS - 121P1F1 - A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 53 | SLVDDGMVDC | 46.848 | Portion |
| 2 | 58 | GMVDCERIGT | 22.066 | of SEQ |
| 3 | 41 | GITAMSVKEV | 21.996 | ID NO: 3; |
| 4 | 92 | QLSEGSQKHA | 20.369 | each start |
| 5 | 64 | RIGTSNYYWA | 5.636 | position |
| 6 | 50 | VLQSLVDDGM | 4.138 | is |
| 7 | 77 | KALHARKHKL | 3.842 | specified, |
| 8 | 27 | FQLKDLEKIA | 3.515 | the length |
| 9 | 17 | MEIFSETKDV | 2.299 | of each |
| 10 | 195 | FGIPEDFDYI | 1.604 | peptide |
| 11 | 51 | LQSLVDDGMV | 1.558 | is 10 |
| 12 | 72 | WAFPSKALHA | 1.174 | amino |
| 13 | 46 | SVKEVLQSLV | 0.873 | acids, |
| 14 | 5 | KGLSAEEKRT | 0.630 | the end |
| 15 | 20 | FSETKDVFQL | 0.548 | position |
| 16 | 45 | MSVKEVLQSL | 0.545 | for each |
| 17 | 156 | RQANKVAKEA | 0.504 | peptide |
| 18 | 94 | SEGSQKHASL | 0.415 | is the |
| 19 | 15 | RMMEIFSETK | 0.304 | start |
| 20 | 128 | SSLRDQREQL | 0.253 | position |
| 21 | 7 | LSAEEKRTRM | 0.226 | plus nine |
| 22 | 34 | KIAPKEKGIT | 0.191 | |
| 23 | 38 | KEKGITAMSV | 0.166 | |
| 24 | 132 | DQREQLKAEV | 0.165 | |
| 25 | 167 | NRWTDNIFAI | 0.160 | |
| 26 | 152 | VEEIRQANKV | 0.147 | |
| 27 | 101 | ASLQKSIEKA | 0.135 | |
| 28 | 44 | AMSVKEVLQS | 0.124 | |
| 29 | 35 | IAPKEKGITA | 0.117 | |
| 30 | 70 | YYWAFPSKAL | 0.113 | |
| 31 | 42 | ITAMSVKEVL | 0.101 | |
| 32 | 79 | LHARKHKLEV | 0.082 | |
| 33 | 177 | KSWAKRKFGF | 0.082 | |
| 34 | 115 | CETEERTRLA | 0.079 | |
| 35 | 103 | LQKSIEKAKI | 0.063 | |
| 36 | 172 | NIFAIKSWAK | 0.057 | |
| 37 | 182 | RKFGFEENKI | 0.054 | |
| 38 | 157 | QANKVAKEAA | 0.034 | |
| 39 | 91 | SQLSEGSQKH | 0.028 | |
| 40 | 161 | VAKEAANRWT | 0.028 | |
| 41 | 23 | TKDVFQLKDL | 0.027 | |
| 42 | 150 | QVVEEIRQAN | 0.027 | |
| 43 | 121 | TRLAKELSSL | 0.025 | |
| 44 | 142 | EKYKDCDPQV | 0.023 | |
| 45 | 138 | KAEVEKYKDC | 0.023 | |
| 46 | 160 | KVAKEAANRW | 0.023 | |
| 47 | 87 | EVLESQLSEG | 0.017 | |
| 48 | 85 | KLEVLESQLS | 0.017 | |
| 49 | 84 | HKLEVLESQL | 0.015 | |
| 50 | 102 | SLQKSIEKAK | 0.015 | |

TABLE IX (A)

HLA PEPTIDE SCORING RESULTS - 121P1F1 - A3, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 16 | MMEIFSETK | 60.000 | Portion |
| 2 | 136 | QLKAEVEKY | 12.000 | of SEQ |
| 3 | 169 | WTDNIFAIK | 4.500 | ID NO: 3; |
| 4 | 175 | AIKSWAKRK | 3.000 | each |
| 5 | 66 | GTSNYYWAF | 2.700 | start |
| 6 | 85 | KLEVLESQL | 1.800 | position |
| 7 | 22 | ETKDVFQLK | 1.350 | is |
| 8 | 97 | SQKHASLQK | 1.200 | specified, |
| 9 | 160 | KVAKEAANR | 1.200 | the |
| 10 | 126 | ELSSLRDQR | 1.200 | length |
| 11 | 193 | RTFGIPEDF | 1.125 | of each |
| 12 | 15 | RMMEIFSET | 1.012 | peptide |
| 13 | 122 | RLAKELSSL | 0.900 | is 9 |
| 14 | 91 | SQLSEGSQK | 0.900 | amino |
| 15 | 196 | GIPEDFDYI | 0.810 | acids, |
| 16 | 106 | SIEKAKIGR | 0.800 | the end |
| 17 | 78 | ALHARKHKL | 0.600 | position |
| 18 | 129 | SLRDQREQL | 0.600 | for each |
| 19 | 77 | KALHARKHK | 0.450 | peptide |
| 20 | 103 | LQKSIEKAK | 0.450 | is the |
| 21 | 182 | RKFGFEENK | 0.450 | start |
| 22 | 102 | SLQKSIEKA | 0.300 | position |
| 23 | 92 | QLSEGSQKH | 0.300 | plus eight |
| 24 | 101 | ASLQKSIEK | 0.300 | |
| 25 | 69 | NYYWAFPSK | 0.300 | |
| 26 | 135 | EQLKAEVEK | 0.270 | |
| 27 | 30 | KDLEKIAPK | 0.203 | |
| 28 | 46 | SVKEVLQSL | 0.203 | |
| 29 | 172 | NIFAIKSWA | 0.150 | |
| 30 | 6 | GLSAEEKRT | 0.150 | |
| 31 | 40 | KGITAMSVK | 0.135 | |
| 32 | 34 | KIAPKEKGI | 0.135 | |
| 33 | 117 | TEERTRLAK | 0.120 | |
| 34 | 28 | QLKDLEKIA | 0.100 | |
| 35 | 4 | KKGLSAEEK | 0.060 | |
| 36 | 173 | IFAIKSWAK | 0.060 | |
| 37 | 50 | VLQSLVDDG | 0.060 | |
| 38 | 174 | FAIKSWAKR | 0.060 | |
| 39 | 152 | VEEIRQANK | 0.060 | |
| 40 | 64 | RIGTSNYYW | 0.060 | |
| 41 | 123 | LAKELSSLR | 0.060 | |
| 42 | 74 | FPSKALHAR | 0.060 | |
| 43 | 53 | SLVDDGMVD | 0.060 | |
| 44 | 27 | FQLKDLEKI | 0.041 | |
| 45 | 26 | VFQLKDLEK | 0.040 | |
| 46 | 185 | GFEENKIDR | 0.036 | |
| 47 | 54 | LVDDGMVDC | 0.030 | |
| 48 | 32 | LEKIAPKEK | 0.030 | |
| 49 | 88 | VLESQLSEG | 0.030 | |
| 50 | 195 | FGIPEDFDY | 0.027 | |

TABLE X (A)

HLA PEPTIDE SCORING RESULTS - 121P1F1 - A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 15 | RMMEIFSETK | 135.000 | Portion |
| 2 | 172 | NIFAIKSWAK | 30.000 | of SEQ |
| 3 | 129 | SLRDQREQLK | 20.000 | ID NO: 3; |
| 4 | 136 | QLKAEVEKYK | 15.000 | each |
| 5 | 102 | SLQKSIEKAK | 15.000 | start |
| 6 | 25 | DVFQLKDLEK | 6.000 | position |
| 7 | 122 | RLAKELSSLR | 4.000 | is |
| 8 | 31 | DLEKIAPKEK | 3.000 | specified, |
| 9 | 151 | VVEEIRQANK | 3.000 | the |
| 10 | 6 | GLSAEEKRTR | 1.200 | length |
| 11 | 111 | KIGRCETEER | 1.200 | of each |
| 12 | 58 | GMVDCERIGT | 0.900 | peptide |
| 13 | 116 | ETEERTRLAK | 0.900 | is 10 |
| 14 | 154 | EIRQANKVAK | 0.600 | amino |
| 15 | 96 | GSQKHASLQK | 0.600 | acids, |
| 16 | 68 | SNYYWAFPSK | 0.600 | the end |
| 17 | 53 | SLVDDGMVDC | 0.450 | position |
| 18 | 174 | FAIKSWAKRK | 0.450 | for each |
| 19 | 177 | KSWAKRKFGF | 0.450 | peptide |
| 20 | 100 | HASLQKSIEK | 0.400 | is the |
| 21 | 50 | VLQSLVDDGM | 0.300 | start |
| 22 | 18 | EIFSETKDVF | 0.300 | position |
| 23 | 105 | KSIEKAKIGR | 0.270 | plus nine |
| 24 | 21 | SETKDVFQLK | 0.270 | |
| 25 | 44 | AMSVKEVLQS | 0.240 | |
| 26 | 74 | FPSKALHARK | 0.200 | |
| 27 | 181 | KRKFGFEENK | 0.180 | |
| 28 | 135 | EQLKAEVEKY | 0.162 | |
| 29 | 92 | QLSEGSQKHA | 0.150 | |
| 30 | 85 | KLEVLESQLS | 0.120 | |
| 31 | 3 | KKKGLSAEEK | 0.090 | |
| 32 | 168 | RWTDNIFAIK | 0.090 | |
| 33 | 41 | GITAMSVKEV | 0.090 | |
| 34 | 196 | GIPEDFDYID | 0.081 | |
| 35 | 184 | FGFEENKIDR | 0.060 | |
| 36 | 134 | REQLKAEVEK | 0.060 | |
| 37 | 64 | RIGTSNYYWA | 0.060 | |
| 38 | 160 | KVAKEAANRW | 0.060 | |
| 39 | 125 | KELSSLRDQR | 0.054 | |
| 40 | 42 | ITAMSVKEVL | 0.045 | |
| 41 | 28 | QLKDLEKIAP | 0.040 | |
| 42 | 88 | VLESQLSEGS | 0.040 | |
| 43 | 190 | KIDRTFGIPE | 0.036 | |
| 44 | 29 | LKDLEKIAPK | 0.030 | |
| 45 | 46 | SVKEVLQSLV | 0.030 | |
| 46 | 72 | WAFPSKALHA | 0.030 | |
| 47 | 90 | ESQLSEGSQK | 0.030 | |
| 48 | 77 | KALHARKHKL | 0.027 | |
| 49 | 20 | FSETKDVFQL | 0.027 | |
| 50 | 165 | AANRWTDNIF | 0.020 | |

TABLE XI (A)

HLA PEPTIDE SCORING RESULTS - 121P1F1 - A11, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 160 | KVAKEAANR | 1.200 | Portion of SEQ ID NO: 3; each start position is specified, the length of each peptide is 9 amino acids, the end position for each peptide is the start position plus eight |
| 2 | 97 | SQKHASLQK | 1.200 | |
| 3 | 169 | WTDNIFAIK | 1.000 | |
| 4 | 91 | SQLSEGSQK | 0.900 | |
| 5 | 69 | NYYWAFPSK | 0.800 | |
| 6 | 77 | KALHARKHK | 0.450 | |
| 7 | 16 | MMEIFSETK | 0.400 | |
| 8 | 173 | IFAIKSWAK | 0.400 | |
| 9 | 26 | VFQLKDLEK | 0.400 | |
| 10 | 103 | LQKSIEKAK | 0.300 | |
| 11 | 22 | ETKDVFQLK | 0.300 | |
| 12 | 135 | EQLKAEVEK | 0.270 | |
| 13 | 185 | GFEENKIDR | 0.240 | |
| 14 | 175 | AIKSWAKRK | 0.200 | |
| 15 | 106 | SIEKAKIGR | 0.160 | |
| 16 | 182 | RKFGFEENK | 0.120 | |
| 17 | 117 | TEERTRLAK | 0.120 | |
| 18 | 40 | KGITAMSVK | 0.090 | |
| 19 | 30 | KDLEKIAPK | 0.090 | |
| 20 | 101 | ASLQKSIEK | 0.060 | |
| 21 | 4 | KKGLSAEEK | 0.060 | |
| 22 | 152 | VEEIRQANK | 0.060 | |
| 23 | 174 | FAIKSWAKR | 0.060 | |
| 24 | 66 | GTSNYYWAF | 0.060 | |
| 25 | 193 | RTFGIPEDF | 0.060 | |
| 26 | 123 | LAKELSSLR | 0.040 | |
| 27 | 74 | FPSKALHAR | 0.040 | |
| 28 | 32 | LEKIAPKEK | 0.030 | |
| 29 | 126 | ELSSLRDQR | 0.024 | |
| 30 | 64 | RIGTSNYYW | 0.024 | |
| 31 | 46 | SVKEVLQSL | 0.020 | |
| 32 | 155 | IRQANKVAK | 0.020 | |
| 33 | 130 | LRDQREQLK | 0.020 | |
| 34 | 5 | KGLSAEEKR | 0.018 | |
| 35 | 114 | RCETEERTR | 0.012 | |
| 36 | 148 | DPQVVEEIR | 0.012 | |
| 37 | 196 | GIPEDFDYI | 0.012 | |
| 38 | 85 | KLEVLESQL | 0.012 | |
| 39 | 122 | RLAKELSSL | 0.012 | |
| 40 | 143 | KYKDCDPQV | 0.012 | |
| 41 | 137 | LKAEVEKYK | 0.010 | |
| 42 | 27 | FQLKDLEKI | 0.009 | |
| 43 | 172 | NIFAIKSWA | 0.008 | |
| 44 | 70 | YYWAFPSKA | 0.008 | |
| 45 | 34 | KIAPKEKGI | 0.006 | |
| 46 | 51 | LQSLVDDGM | 0.006 | |
| 47 | 13 | RTRMMEIFS | 0.006 | |
| 48 | 183 | KFGFEENKI | 0.006 | |
| 49 | 42 | ITAMSVKEV | 0.005 | |
| 50 | 136 | QLKAEVEKY | 0.004 | |

TABLE XII (A)

HLA PEPTIDE SCORING RESULTS - 121P1F1 - A11, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 15 | RMMEIFSETK | 2.400 | Portion of SEQ ID NO: 3; each start position is specified, the length of each peptide is 10 amino acids, the end position for each peptide is the start position plus nine |
| 2 | 25 | DVFQLKDLEK | 2.400 | |
| 3 | 151 | VVEEIRQANK | 2.000 | |
| 4 | 172 | NIFAIKSWAK | 1.600 | |
| 5 | 116 | ETEERTRLAK | 0.600 | |
| 6 | 100 | HASLQKSIEK | 0.400 | |
| 7 | 129 | SLRDQREQLK | 0.400 | |
| 8 | 111 | KIGRCETEER | 0.240 | |
| 9 | 122 | RLAKELSSLR | 0.240 | |
| 10 | 136 | QLKAEVEKYK | 0.200 | |
| 11 | 102 | SLQKSIEKAK | 0.200 | |
| 12 | 74 | FPSKALHARK | 0.200 | |
| 13 | 134 | REQLKAEVEK | 0.180 | |
| 14 | 174 | FAIKSWAKRK | 0.150 | |
| 15 | 96 | GSQKHASLQK | 0.120 | |
| 16 | 154 | EIRQANKVAK | 0.120 | |
| 17 | 68 | SNYYWAFPSK | 0.080 | |
| 18 | 181 | KRKFGFEENK | 0.060 | |
| 19 | 3 | KKKGLSAEEK | 0.060 | |
| 20 | 168 | RWTDNIFAIK | 0.060 | |
| 21 | 21 | SETKDVFQLK | 0.060 | |
| 22 | 31 | DLEKIAPKEK | 0.060 | |
| 23 | 160 | KVAKEAANRW | 0.060 | |
| 24 | 125 | KELSSLRDQR | 0.054 | |
| 25 | 73 | AFPSKALHAR | 0.040 | |
| 26 | 173 | IFAIKSWAKR | 0.040 | |
| 27 | 105 | KSIEKAKIGR | 0.036 | |
| 28 | 6 | GLSAEEKRTR | 0.024 | |
| 29 | 64 | RIGTSNYYWA | 0.024 | |

TABLE XII (A)-continued

HLA PEPTIDE SCORING RESULTS - 121P1F1 - A11, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) |
|---|---|---|---|
| 30 | 29 | LKDLEKIAPK | 0.020 |
| 31 | 46 | SVKEVLQSLV | 0.020 |
| 32 | 184 | FGFEENKIDR | 0.016 |
| 33 | 4 | KKGLSAEEKR | 0.012 |
| 34 | 143 | KYKDCDPQVV | 0.012 |
| 35 | 42 | ITAMSVKEVL | 0.010 |
| 36 | 76 | SKALHARKHK | 0.010 |
| 37 | 156 | RQANKVAKEA | 0.009 |
| 38 | 77 | KALHARKHKL | 0.009 |
| 39 | 13 | RTRMMEIFSE | 0.009 |
| 40 | 91 | SQLSEGSQKH | 0.009 |
| 41 | 69 | NYYWAFPSKA | 0.008 |
| 42 | 72 | WAFPSKALHA | 0.008 |
| 43 | 159 | NKVAKEAANR | 0.006 |
| 44 | 39 | EKGITAMSVK | 0.006 |
| 45 | 114 | RCETEERTRL | 0.006 |
| 46 | 120 | RTRLAKELSS | 0.006 |
| 47 | 51 | LQSLVDDGMV | 0.006 |
| 48 | 90 | ESQLSEGSQK | 0.006 |
| 49 | 103 | LQKSIEKAKI | 0.006 |
| 50 | 193 | RTFGIPEDFD | 0.006 |

TABLE XIII (A)

HLA PEPTIDE SCORING RESULTS - 121P1F1 - A24, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 85 | KLEVLESQL | 14.400 | Portion of SEQ |
| 2 | 183 | KFGFEENKI | 13.200 | ID NO: 3; each |
| 3 | 143 | KYKDCDPQV | 12.000 | start position is |
| 4 | 19 | IFSETKDVF | 12.000 | specified, the |
| 5 | 43 | TAMSVKEVL | 8.400 | length of each |
| 6 | 46 | SVKEVLQSL | 8.064 | peptide is 9 |
| 7 | 122 | RLAKELSSL | 8.000 | amino acids, |
| 8 | 193 | RTFGIPEDF | 5.600 | the end |
| 9 | 70 | YYWAFPSKA | 5.500 | position for |
| 10 | 129 | SLRDQREQL | 4.800 | each peptide is |
| 11 | 78 | ALHARKHKL | 4.400 | the start |
| 12 | 71 | YWAFPSKAL | 4.000 | position plus |
| 13 | 95 | EGSQKHASL | 4.000 | eight |
| 14 | 166 | ANRWTDNIF | 2.400 | |
| 15 | 34 | KIAPKEKGI | 2.400 | |
| 16 | 168 | RWTDNIFAI | 2.400 | |
| 17 | 196 | GIPEDFDYI | 2.160 | |
| 18 | 178 | SWAKRKFGF | 2.000 | |
| 19 | 66 | GTSNYYWAF | 2.000 | |
| 20 | 27 | FQLKDLEKI | 1.650 | |
| 21 | 165 | AANRWTDNI | 1.500 | |
| 22 | 57 | DGMVDCERI | 1.500 | |
| 23 | 24 | KDVFQLKDL | 1.200 | |
| 24 | 8 | SAEEKRTRM | 0.900 | |
| 25 | 73 | AFPSKALHA | 0.750 | |
| 26 | 51 | LQSLVDDGM | 0.700 | |
| 27 | 15 | RMMEIFSET | 0.665 | |
| 28 | 69 | NYYWAFPSK | 0.600 | |
| 29 | 119 | ERTRLAKEL | 0.528 | |
| 30 | 115 | CETEERTRL | 0.480 | |
| 31 | 187 | EENKIDRTF | 0.420 | |
| 32 | 12 | KRTRMMEIF | 0.400 | |
| 33 | 81 | ARKHKLEVL | 0.400 | |
| 34 | 21 | SETKDVFQL | 0.400 | |
| 35 | 151 | VVEEIRQAN | 0.302 | |
| 36 | 99 | KHASLQKSI | 0.240 | |
| 37 | 147 | CDPQVVEEI | 0.231 | |
| 38 | 157 | QANKVAKEA | 0.231 | |
| 39 | 176 | IKSWAKRKF | 0.220 | |
| 40 | 109 | KAKIGRCET | 0.220 | |
| 41 | 61 | DCERIGTSN | 0.210 | |

TABLE XIII (A)-continued

HLA PEPTIDE SCORING RESULTS - 121P1F1 - A24, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) |
|---|---|---|---|
| 42 | 13 | RTRMMEIFS | 0.200 |
| 43 | 120 | RTRLAKELS | 0.200 |
| 44 | 64 | RIGTSNYYW | 0.200 |
| 45 | 189 | NKIDRTFGI | 0.180 |
| 46 | 150 | QVVEEIRQA | 0.180 |
| 47 | 195 | FGIPEDFDY | 0.180 |
| 48 | 116 | ETEERTRLA | 0.180 |
| 49 | 102 | SLQKSIEKA | 0.165 |
| 50 | 171 | DNIFAIKSW | 0.150 |

TABLE XIV (A)

HLA PEPTIDE SCORING RESULTS - 121P1F1 - A24, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 70 | YYWAFPSKAL | 200.000 | Portion of SEQ |
| 2 | 143 | KYKDCDPQVV | 14.400 | ID NO: 3; each |
| 3 | 77 | KALHARKHKL | 13.200 | start position is |
| 4 | 114 | RCETEERTRL | 12.000 | specified, the |
| 5 | 45 | MSVKEVLQSL | 10.080 | length of each |
| 6 | 26 | VFQLKDLEKI | 8.250 | peptide is 10 |
| 7 | 20 | FSETKDVFQL | 6.000 | amino acids, |
| 8 | 128 | SSLRDQREQL | 6.000 | the end |
| 9 | 42 | ITAMSVKEVL | 5.600 | position for |
| 10 | 69 | NYYWAFPSKA | 5.500 | each peptide is |
| 11 | 80 | HARKHKLEVL | 4.000 | the start |
| 12 | 177 | KSWAKRKFGF | 4.000 | position plus |
| 13 | 165 | AANRWTDNIF | 3.600 | nine |
| 14 | 175 | AIKSWAKRKF | 2.200 | |
| 15 | 195 | FGIPEDFDYI | 2.160 | |
| 16 | 18 | EIFSETKDVF | 2.000 | |
| 17 | 65 | IGTSNYYWAF | 2.000 | |
| 18 | 146 | DCDPQVVEEI | 1.848 | |
| 19 | 103 | LQKSIEKAKI | 1.100 | |
| 20 | 50 | VLQSLVDDGM | 1.050 | |
| 21 | 188 | ENKIDRTFGI | 1.000 | |
| 22 | 164 | EAANRWTDNI | 1.000 | |
| 23 | 8 | SAEEKRTRMM | 0.900 | |
| 24 | 185 | GFEENKIDRT | 0.900 | |
| 25 | 84 | HKLEVLESQL | 0.864 | |
| 26 | 121 | TRLAKELSSL | 0.600 | |
| 27 | 36 | APKEKGITAM | 0.600 | |
| 28 | 7 | LSAEEKRTRM | 0.600 | |
| 29 | 118 | EERTRLAKEL | 0.528 | |
| 30 | 194 | TFGIPEDFDY | 0.500 | |
| 31 | 186 | FEENKIDRTF | 0.420 | |
| 32 | 23 | TKDVFQLKDL | 0.400 | |
| 33 | 94 | SEGSQKHASL | 0.400 | |
| 34 | 85 | KLEVLESQLS | 0.360 | |
| 35 | 156 | RQANKVAKEA | 0.308 | |
| 36 | 150 | QVVEEIRQAN | 0.302 | |
| 37 | 138 | KAEVEKYKDC | 0.300 | |
| 38 | 5 | KGLSAEEKRT | 0.300 | |
| 39 | 192 | DRTFGIPEDF | 0.280 | |
| 40 | 182 | RKFGFEENKI | 0.264 | |
| 41 | 34 | KIAPKEKGIT | 0.240 | |
| 42 | 160 | KVAKEAANRW | 0.240 | |
| 43 | 171 | DNIFAIKSWA | 0.210 | |
| 44 | 64 | RIGTSNYYWA | 0.200 | |
| 45 | 11 | EKRTRMMEIF | 0.200 | |
| 46 | 120 | RTRLAKELSS | 0.200 | |
| 47 | 27 | FQLKDLEKIA | 0.180 | |
| 48 | 88 | VLESQLSEGS | 0.180 | |
| 49 | 58 | GMVDCERIGT | 0.180 | |
| 50 | 53 | SLVDDGMVDC | 0.180 | |

TABLE XV (A)

HLA PEPTIDE SCORING RESULTS - 121P1F1 - B7, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 129 | SLRDQREQL | 60.000 | Portion of SEQ |
| 2 | 43 | TAMSVKEVL | 36.000 | ID NO: 3; each |
| 3 | 46 | SVKEVLQSL | 20.000 | start position is |
| 4 | 78 | ALHARKHKL | 12.000 | specified, the |
| 5 | 36 | APKEKGITA | 6.000 | length of each |
| 6 | 80 | HARKHKLEV | 6.000 | peptide is 9 |
| 7 | 122 | RLAKELSSL | 4.000 | amino acids, |
| 8 | 95 | EGSQKHASL | 4.000 | the end |
| 9 | 165 | AANRWTDNI | 3.600 | position for |
| 10 | 8 | SAEEKRTRM | 1.350 | each peptide is |
| 11 | 85 | KLEVLESQL | 1.200 | the start |
| 12 | 81 | ARKHKLEVL | 1.200 | position plus |
| 13 | 57 | DGMVDCERI | 1.200 | eight |
| 14 | 51 | LQSLVDDGM | 1.000 | |
| 15 | 154 | EIRQANKVA | 1.000 | |
| 16 | 115 | CETEERTRL | 0.600 | |
| 17 | 71 | YWAFPSKAL | 0.600 | |
| 18 | 166 | ANRWTDNIF | 0.600 | |
| 19 | 150 | QVVEEIRQA | 0.500 | |
| 20 | 109 | KAKIGRCET | 0.450 | |
| 21 | 27 | FQLKDLEKI | 0.400 | |
| 22 | 11 | EKRTRMMEI | 0.400 | |
| 23 | 21 | SETKDVFQL | 0.400 | |
| 24 | 196 | GIPEDFDYI | 0.400 | |
| 25 | 34 | KIAPKEKGI | 0.400 | |
| 26 | 119 | ERTRLAKEL | 0.400 | |
| 27 | 24 | KDVFQLKDL | 0.400 | |
| 28 | 35 | IAPKEKGIT | 0.300 | |
| 29 | 15 | RMMEIFSET | 0.300 | |
| 30 | 158 | ANKVAKEAA | 0.300 | |
| 31 | 157 | QANKVAKEA | 0.300 | |
| 32 | 59 | MVDCERIGT | 0.225 | |
| 33 | 148 | DPQVVEEIR | 0.200 | |
| 34 | 18 | EIFSETKDV | 0.200 | |
| 35 | 52 | QSLVDDGMV | 0.200 | |
| 36 | 74 | FPSKALHAR | 0.200 | |
| 37 | 120 | RTRLAKELS | 0.200 | |
| 38 | 13 | RTRMMEIFS | 0.200 | |
| 39 | 42 | ITAMSVKEV | 0.200 | |
| 40 | 54 | LVDDGMVDC | 0.150 | |
| 41 | 65 | IGTSNYYWA | 0.100 | |
| 42 | 102 | SLQKSIEKA | 0.100 | |
| 43 | 132 | DQREQLKAE | 0.100 | |
| 44 | 1 | MSKKKGLSA | 0.100 | |
| 45 | 112 | IGRCETEER | 0.100 | |
| 46 | 6 | GLSAEEKRT | 0.100 | |
| 47 | 28 | QLKDLEKIA | 0.100 | |
| 48 | 172 | NIFAIKSWA | 0.100 | |
| 49 | 9 | AEEKRTRMM | 0.090 | |
| 50 | 164 | EAANRWTDN | 0.060 | |

TABLE XVI (A)

HLA PEPTIDE SCORING RESULTS - 121P1F1 - B7, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 80 | HARKHKLEVL | 120.000 | Portion of SEQ |
| 2 | 36 | APKEKGITAM | 60.000 | ID NO: 3; each |
| 3 | 77 | KALHARKHKL | 12.000 | start position is |
| 4 | 128 | SSLRDQREQL | 6.000 | specified, the |
| 5 | 42 | ITAMSVKEVL | 4.000 | length of each |
| 6 | 45 | MSVKEVLQSL | 4.000 | peptide is 10 |
| 7 | 118 | EERTRLAKEL | 4.000 | amino acids, |
| 8 | 166 | ANRWTDNIFA | 3.000 | the end |
| 9 | 132 | DQREQLKAEV | 2.000 | position for |
| 10 | 114 | RCETEERTRL | 1.800 | each peptide is |
| 11 | 7 | LSAEEKRTRM | 1.500 | the start |
| 12 | 20 | FSETKDVFQL | 1.200 | position plus |

TABLE XVI (A)-continued

HLA PEPTIDE SCORING RESULTS - 121P1F1 - B7, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 13 | 164 | EAANRWTDNI | 1.200 | nine |
| 14 | 46 | SVKEVLQSLV | 1.000 | |
| 15 | 50 | VLQSLVDDGM | 1.000 | |
| 16 | 112 | IGRCETEERT | 1.000 | |
| 17 | 8 | SAEEKRTRMM | 0.900 | |
| 18 | 70 | YYWAFPSKAL | 0.600 | |
| 19 | 94 | SEGSQKHASL | 0.400 | |
| 20 | 188 | ENKIDRTFGI | 0.400 | |
| 21 | 103 | LQKSIEKAKI | 0.400 | |
| 22 | 121 | TRLAKELSSL | 0.400 | |
| 23 | 195 | FGIPEDFDYI | 0.400 | |
| 24 | 84 | HKLEVLESQL | 0.400 | |
| 25 | 72 | WAFPSKALHA | 0.300 | |
| 26 | 35 | IAPKEKGITA | 0.300 | |
| 27 | 101 | ASLQKSIEKA | 0.300 | |
| 28 | 157 | QANKVAKEAA | 0.300 | |
| 29 | 161 | VAKEAANRWT | 0.300 | |
| 30 | 120 | RTRLAKELSS | 0.200 | |
| 31 | 41 | GITAMSVKEV | 0.200 | |
| 32 | 148 | DPQVVEEIRQ | 0.200 | |
| 33 | 51 | LQSLVDDGMV | 0.200 | |
| 34 | 74 | FPSKALHARK | 0.200 | |
| 35 | 165 | AANRWTDNIF | 0.180 | |
| 36 | 58 | GMVDCERIGT | 0.150 | |
| 37 | 150 | QVVEEIRQAN | 0.150 | |
| 38 | 23 | TKDVFQLKDL | 0.120 | |
| 39 | 146 | DCDPQVVEEI | 0.120 | |
| 40 | 34 | KIAPKEKGIT | 0.100 | |
| 41 | 27 | FQLKDLEKIA | 0.100 | |
| 42 | 53 | SLVDDGMVDC | 0.100 | |
| 43 | 13 | RTRMMEIFSE | 0.100 | |
| 44 | 156 | RQANKVAKEA | 0.100 | |
| 45 | 154 | EIRQANKVAK | 0.100 | |
| 46 | 5 | KGLSAEEKRT | 0.100 | |
| 47 | 92 | QLSEGSQKHA | 0.100 | |
| 48 | 160 | KVAKEAANRW | 0.100 | |
| 49 | 64 | RIGTSNYYWA | 0.100 | |
| 50 | 129 | SLRDQREQLK | 0.100 | |

TABLE XVII (A)

HLA PEPTIDE SCORING RESULTS - 121P1F1 - B35, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 36 | APKEKGITA | 12.000 | Portion of SEQ |
| 2 | 136 | QLKAEVEKY | 9.000 | ID NO: 3; each |
| 3 | 161 | VAKEAANRW | 9.000 | start position is |
| 4 | 129 | SLRDQREQL | 6.000 | specified, the |
| 5 | 46 | SVKEVLQSL | 6.000 | length of each |
| 6 | 8 | SAEEKRTRM | 3.600 | peptide is 9 |
| 7 | 166 | ANRWTDNIF | 3.000 | amino acids, |
| 8 | 195 | FGIPEDFDY | 3.000 | the end |
| 9 | 43 | TAMSVKEVL | 3.000 | position for |
| 10 | 122 | RLAKELSSL | 3.000 | each peptide is |
| 11 | 51 | LQSLVDDGM | 2.000 | the start |
| 12 | 193 | RTFGIPEDF | 2.000 | position plus |
| 13 | 80 | HARKHKLEV | 1.800 | eight |
| 14 | 109 | KAKIGRCET | 1.800 | |
| 15 | 52 | QSLVDDGMV | 1.500 | |
| 16 | 1 | MSKKKGLSA | 1.500 | |
| 17 | 196 | GIPEDFDYI | 1.200 | |
| 18 | 165 | AANRWTDNI | 1.200 | |
| 19 | 66 | GTSNYYWAF | 1.000 | |
| 20 | 78 | ALHARKHKL | 1.000 | |
| 21 | 95 | EGSQKHASL | 1.000 | |
| 22 | 64 | RIGTSNYYW | 1.000 | |
| 23 | 34 | KIAPKEKGI | 0.800 | |
| 24 | 45 | MSVKEVLQS | 0.750 | |

TABLE XVII (A)-continued

HLA PEPTIDE SCORING RESULTS - 121P1F1 - B35, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) |
|---|---|---|---|
| 25 | 57 | DGMVDCERI | 0.600 |
| 26 | 120 | RTRLAKELS | 0.600 |
| 27 | 13 | RTRMMEIFS | 0.600 |
| 28 | 28 | QLKDLEKIA | 0.600 |
| 29 | 27 | FQLKDLEKI | 0.600 |
| 30 | 85 | KLEVLESQL | 0.600 |
| 31 | 62 | CERIGTSNY | 0.600 |
| 32 | 171 | DNIFAIKSW | 0.500 |
| 33 | 35 | IAPKEKGIT | 0.450 |
| 34 | 15 | RMMEIFSET | 0.400 |
| 35 | 154 | EIRQANKVA | 0.300 |
| 36 | 157 | QANKVAKEA | 0.300 |
| 37 | 150 | QVVEEIRQA | 0.300 |
| 38 | 115 | CETEERTRL | 0.300 |
| 39 | 158 | ANKVAKEAA | 0.300 |
| 40 | 164 | EAANRWTDN | 0.300 |
| 41 | 81 | ARKHKLEVL | 0.300 |
| 42 | 18 | EIFSETKDV | 0.300 |
| 43 | 143 | KYKDCDPQV | 0.240 |
| 44 | 42 | ITAMSVKEV | 0.200 |
| 45 | 105 | KSIEKAKIG | 0.200 |
| 46 | 74 | FPSKALHAR | 0.200 |
| 47 | 148 | DPQVVEEIR | 0.200 |
| 48 | 12 | KRTRMMEIF | 0.200 |
| 49 | 24 | KDVFQLKDL | 0.200 |
| 50 | 63 | ERIGTSNYY | 0.200 |

TABLE XVIII (A)

HLA PEPTIDE SCORING RESULTS - 121P1F1 - B35, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 36 | APKEKGITAM | 240.000 | Portion of SEQ |
| 2 | 7 | LSAEEKRTRM | 20.000 | ID NO: 3; each |
| 3 | 177 | KSWAKRKFGF | 10.000 | start position is |
| 4 | 80 | HARKHKLEVL | 9.000 | specified, the |
| 5 | 77 | KALHARKHKL | 6.000 | length of each |
| 6 | 45 | MSVKEVLQSL | 5.000 | peptide is 10 |
| 7 | 128 | SSLRDQREQL | 5.000 | amino acids, |
| 8 | 8 | SAEEKRTRMM | 3.600 | the end position |
| 9 | 175 | AIKSWAKRKF | 3.000 | for each |
| 10 | 165 | AANRWTDNIF | 3.000 | peptide is the |
| 11 | 135 | EQLKAEVEKY | 3.000 | start position |
| 12 | 20 | FSETKDVFQL | 2.250 | plus nine |
| 13 | 50 | VLQSLVDDGM | 2.000 | |
| 14 | 161 | VAKEAANRWT | 1.800 | |
| 15 | 103 | LQKSIEKAKI | 1.800 | |
| 16 | 132 | DQREQLKAEV | 1.200 | |
| 17 | 188 | ENKIDRTFGI | 1.200 | |
| 18 | 46 | SVKEVLQSLV | 1.200 | |
| 19 | 164 | EAANRWTDNI | 1.200 | |
| 20 | 65 | IGTSNYYWAF | 1.000 | |
| 21 | 42 | ITAMSVKEVL | 1.000 | |
| 22 | 160 | KVAKEAANRW | 1.000 | |
| 23 | 18 | EIFSETKDVF | 1.000 | |
| 24 | 114 | RCETEERTRL | 0.900 | |
| 25 | 120 | RTRLAKELSS | 0.600 | |
| 26 | 62 | CERIGTSNYY | 0.600 | |
| 27 | 61 | DCERIGTSNY | 0.600 | |
| 28 | 195 | FGIPEDFDYI | 0.600 | |
| 29 | 67 | TSNYYWAFPS | 0.500 | |
| 30 | 101 | ASLQKSIEKA | 0.500 | |
| 31 | 166 | ANRWTDNIFA | 0.450 | |
| 32 | 143 | KYKDCDPQVV | 0.360 | |
| 33 | 97 | SQKHASLQKS | 0.300 | |
| 34 | 58 | GMVDCERIGT | 0.300 | |
| 35 | 5 | KGLSAEEKRT | 0.300 | |
| 36 | 194 | TFGIPEDFDY | 0.300 | |

TABLE XVIII (A)-continued

HLA PEPTIDE SCORING RESULTS - 121P1F1 - B35, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) |
|---|---|---|---|
| 37 | 34 | KIAPKEKGIT | 0.300 |
| 38 | 158 | ANKVAKEAAN | 0.300 |
| 39 | 148 | DPQVVEEIRQ | 0.300 |
| 40 | 11 | EKRTRMMEIF | 0.300 |
| 41 | 112 | IGRCETEERT | 0.300 |
| 42 | 35 | IAPKEKGITA | 0.300 |
| 43 | 118 | EERTRLAKEL | 0.300 |
| 44 | 157 | QANKVAKEAA | 0.300 |
| 45 | 72 | WAFPSKALHA | 0.300 |
| 46 | 51 | LQSLVDDGMV | 0.300 |
| 47 | 105 | KSIEKAKIGR | 0.200 |
| 48 | 64 | RIGTSNYYWA | 0.200 |
| 49 | 74 | FPSKALHARK | 0.200 |
| 50 | 150 | QVVEEIRQAN | 0.200 |

TABLE V (B)

VARIANT 1A KLEVLESQDPGCCFHEIIKVSYYRKFWLGAVAHACNPSTLGG
HLA PEPTIDE SCORING RESULTS - 121P1F1 - A1, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 98 | FHEIIKVSY | 4.500 | Portion of SEQ |
| 2 | 88 | VLESQDPGC | 1.800 | ID NO: 5; each |
| 3 | 95 | GCCFHEIIK | 1.000 | start position is |
| 4 | 91 | SQDPGCCFH | 0.750 | specified, the |
| 5 | 118 | ACNPSTLGG | 0.500 | length of each |
| 6 | 90 | ESQDPGCCF | 0.150 | peptide is 9 |
| 7 | 85 | KLEVLESQD | 0.090 | amino acids, |
| 8 | 104 | VSYYRKFWL | 0.075 | the end position |
| 9 | 96 | CCFHEIIKV | 0.050 | for each |
| 10 | 101 | IIKVSYYRK | 0.040 | peptide is the |
| 11 | 99 | HEIIKVSYY | 0.025 | start position |
| 12 | 115 | VAHACNPST | 0.020 | plus eight |
| 13 | 100 | EIIKVSYYR | 0.020 | |
| 14 | 103 | KVSYYRKFW | 0.010 | |
| 15 | 117 | HACNPSTLG | 0.010 | |
| 16 | 111 | WLGAVAHAC | 0.010 | |
| 17 | 114 | AVAHACNPS | 0.010 | |
| 18 | 87 | EVLESQDPG | 0.010 | |
| 19 | 102 | IKVSYYRKF | 0.005 | |
| 20 | 112 | LGAVAHACN | 0.005 | |
| 21 | 93 | DPGCCFHEI | 0.003 | |
| 22 | 108 | RKFWLGAVA | 0.001 | |
| 23 | 110 | FWLGAVAHA | 0.001 | |
| 24 | 113 | GAVAHACNP | 0.001 | |
| 25 | 97 | CFHEIIKVS | 0.001 | |
| 26 | 116 | AHACNPSTL | 0.001 | |
| 27 | 89 | LESQDPGCC | 0.001 | |
| 28 | 92 | QDPGCCFHE | 0.000 | |
| 29 | 94 | PGCCFHEII | 0.000 | |
| 30 | 110 | KFWLGAVAH | 0.000 | |
| 31 | 105 | SYYRKFWLG | 0.000 | |
| 32 | 86 | LEVLESQDP | 0.000 | |
| 33 | 107 | YRKFWLGAV | 0.000 | |
| 34 | 106 | YYRKFWLGA | 0.000 | |

TABLE VI (B)

VARIANT 1A HKLEVLESQDPGCCFHEIIKVSYYRKFWLGAVAHACNPSTLGG
HLA PEPTIDE SCORING RESULTS - 121P1F1 - A1, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 98 | FHEIIKVSYY | 2.250 | Portion of SEQ |
| 2 | 88 | VLESQDPGCC | 0.900 | ID NO: 5; each |
| 3 | 91 | SQDPGCCFHE | 0.375 | start position is |
| 4 | 85 | KLEVLESQDP | 0.090 | specified, the |
| 5 | 95 | GCCFHEIIKV | 0.050 | length of each |
| 6 | 117 | HACNPSTLGG | 0.050 | peptide is 10 |
| 7 | 97 | CFHEIIKVSY | 0.050 | amino acids, |
| 8 | 103 | KVSYYRKFWL | 0.050 | the end |
| 9 | 100 | EIIKVSYYRK | 0.040 | position for |
| 10 | 94 | PGCCFHEIIK | 0.025 | each peptide is |
| 11 | 111 | WLGAVAHACN | 0.020 | the start |
| 12 | 114 | AVAHACNPST | 0.020 | position plus |
| 13 | 87 | EVLESQDPGC | 0.020 | nine |
| 14 | 90 | ESQDPGCCFH | 0.015 | |
| 15 | 104 | VSYYRKFWLG | 0.015 | |
| 16 | 113 | GAVAHACNPS | 0.010 | |
| 17 | 99 | HEIIKVSYYR | 0.010 | |
| 18 | 115 | VAHACNPSTL | 0.010 | |
| 19 | 101 | IIKVSYYRKF | 0.010 | |
| 20 | 96 | CCFHEIIKVS | 0.010 | |
| 21 | 89 | LESQDPGCCF | 0.005 | |
| 22 | 93 | DPGCCFHEII | 0.003 | |
| 23 | 108 | RKFWLGAVAH | 0.001 | |
| 24 | 92 | QDPGCCFHEI | 0.001 | |
| 25 | 116 | AHACNPSTLG | 0.001 | |
| 26 | 102 | IKVSYYRKFW | 0.001 | |
| 27 | 110 | FWLGAVAHAC | 0.001 | |
| 28 | 86 | LEVLESQDPG | 0.001 | |
| 29 | 105 | SYYRKFWLGA | 0.000 | |
| 30 | 112 | LGAVAHACNP | 0.000 | |
| 31 | 109 | KFWLGAVAHA | 0.000 | |
| 32 | 107 | YRKFWLGAVA | 0.000 | |
| 33 | 84 | HKLEVLESQD | 0.000 | |
| 34 | 106 | YYRKFWLGAV | 0.000 | |

TABLE VII (B)

VARIANT 1A KLEVLESQDPGCCFHEIIKVSYYRKFWLGAVAHACNPSTLGG
HLA PEPTIDE SCORING RESULTS - 121P1F1 - A2, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 104 | VSYYRKFWL | 24.199 | Portion of SEQ |
| 2 | 111 | WLGAVAHAC | 22.853 | ID NO: 5; each |
| 3 | 96 | CCFHEIIKV | 3.864 | start position is |
| 4 | 88 | VLESQDPGC | 0.541 | specified, the |
| 5 | 115 | VAHACNPST | 0.176 | length of each |
| 6 | 103 | KVSYYRKFW | 0.126 | peptide is 9 |
| 7 | 110 | FWLGAVAHA | 0.027 | amino acids, |
| 8 | 89 | LESQDPGCC | 0.021 | the end |
| 9 | 91 | SQDPGCCFH | 0.017 | position for |
| 10 | 116 | AHACNPSTL | 0.015 | each peptide is |
| 11 | 108 | RKFWLGAVA | 0.010 | the start |
| 12 | 93 | DPGCCFHEI | 0.010 | position plus |
| 13 | 114 | AVAHACNPS | 0.007 | eight |
| 14 | 87 | EVLESQDPG | 0.004 | |
| 15 | 85 | KLEVLESQD | 0.003 | |
| 16 | 106 | YYRKFWLGA | 0.002 | |
| 17 | 109 | KFWLGAVAH | 0.002 | |
| 18 | 94 | PGCCFHEII | 0.001 | |
| 19 | 100 | EIIKVSYYR | 0.001 | |
| 20 | 112 | LGAVAHACN | 0.001 | |
| 21 | 99 | HEIIKVSYY | 0.001 | |
| 22 | 86 | LEVLESQDP | 0.000 | |
| 23 | 118 | ACNPSTLGG | 0.000 | |
| 24 | 105 | SYYRKFWLG | 0.000 | |
| 25 | 107 | YRKFWLGAV | 0.000 | |

TABLE VII (B)-continued

VARIANT 1A KLEVLESQDPGCCFHEIIKVSYYRKFWLGAVAHACNPSTLGG
HLA PEPTIDE SCORING RESULTS - 121P1F1 - A2, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) |
|---|---|---|---|
| 26 | 113 | GAVAHACNP | 0.000 |
| 27 | 97  | CFHEIIKVS | 0.000 |
| 28 | 101 | IIKVSYYRK | 0.000 |
| 29 | 90  | ESQDPGCCF | 0.000 |
| 30 | 92  | QDPGCCFHE | 0.000 |
| 31 | 102 | IKVSYYRKF | 0.000 |
| 32 | 95  | GCCFHEIIK | 0.000 |
| 33 | 117 | HACNPSTLG | 0.000 |
| 34 | 98  | FHEIIKVSY | 0.000 |

TABLE VIII (B)

VARIANT 1A: HKLEVLESQDPGCCFHEIIKVSYYRKFWLGAVAHACNPSTLGG
HLA PEPTIDE SCORING RESULTS - 121P1F1 - A2, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1  | 103 | KVSYYRKFWL | 208.697 | Portion of SEQ |
| 2  | 95  | GCCFHEIIKV | 1.044   | ID NO: 5; each |
| 3  | 114 | AVAHACNPST | 0.652   | start position is |
| 4  | 115 | VAHACNPSTL | 0.504   | specified, the |
| 5  | 87  | EVLESQDPGC | 0.495   | length of each |
| 6  | 111 | WLGAVAHACN | 0.343   | peptide is 10 |
| 7  | 109 | KFWLGAVAHA | 0.231   | amino acids, |
| 8  | 88  | VLESQDPGCC | 0.070   | the end |
| 9  | 104 | VSYYRKFWLG | 0.038   | position for |
| 10 | 92  | QDPGCCFHEI | 0.028   | each peptide is |
| 11 | 105 | SYYRKFWLGA | 0.014   | the start |
| 12 | 110 | FWLGAVAHAC | 0.012   | position plus |
| 13 | 93  | DPGCCFHEII | 0.004   | nine |
| 14 | 91  | SQDPGCCFHE | 0.004   | |
| 15 | 85  | KLEVLESQDP | 0.003   | |
| 16 | 89  | LESQDPGCCF | 0.002   | |
| 17 | 96  | CCFHEIIKVS | 0.002   | |
| 18 | 86  | LEVLESQDPG | 0.001   | |
| 19 | 113 | GAVAHACNPS | 0.001   | |
| 20 | 106 | YYRKFWLGAV | 0.001   | |
| 21 | 102 | IKVSYYRKFW | 0.001   | |
| 22 | 90  | ESQDPGCCFH | 0.001   | |
| 23 | 108 | RKFWLGAVAH | 0.000   | |
| 24 | 100 | EIIKVSYYRK | 0.000   | |
| 25 | 97  | CFHEIIKVSY | 0.000   | |
| 26 | 98  | FHEIIKVSYY | 0.000   | |
| 27 | 101 | IIKVSYYRKF | 0.000   | |
| 28 | 112 | LGAVAHACNP | 0.000   | |
| 29 | 99  | HEIIKVSYYR | 0.000   | |
| 30 | 116 | AHACNPSTLG | 0.000   | |
| 31 | 107 | YRKFWLGAVA | 0.000   | |
| 32 | 117 | HACNPSTLGG | 0.000   | |
| 33 | 84  | HKLEVLESQD | 0.000   | |
| 34 | 94  | PGCCFHEIIK | 0.000   | |

TABLE IX (B)

VARIANT 1A KLEVLESQDPGCCFHEIIKVSYYRKFWLGAVAHACNPSTLGG
HLA PEPTIDE SCORING RESULTS - 121P1F1 - A3, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 101 | IIKVSYYRK | 6.000 | Portion of |
| 2 | 95  | GCCFHEIIK | 1.200 | SEQ ID |
| 3 | 100 | EIIKVSYYR | 0.810 | NO: 5; |
| 4 | 111 | WLGAVAHAC | 0.300 | each start |
| 5 | 88  | VLESQDPGC | 0.200 | position is |

TABLE IX (B)-continued

VARIANT 1A KLEVLESQDPGCCFHEIIKVSYYRKFWLGAVAHACNPSTLGG
HLA PEPTIDE SCORING RESULTS - 121P1F1 - A3, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 6 | 103 | KVSYYRKFW | 0.090 | specified, |
| 7 | 85 | KLEVLESQD | 0.060 | the length |
| 8 | 99 | HEIIKVSYY | 0.054 | of each |
| 9 | 104 | VSYYRKFWL | 0.045 | peptide is |
| 10 | 96 | CCFHEIIKV | 0.030 | 9 amino |
| 11 | 91 | SQDPGCCFH | 0.009 | acids, the |
| 12 | 98 | FHEIIKVSY | 0.006 | end |
| 13 | 93 | DPGCCFHEI | 0.005 | position |
| 14 | 90 | ESQDPGCCF | 0.005 | for each |
| 15 | 114 | AVAHACNPS | 0.004 | peptide is |
| 16 | 109 | KFWLGAVAH | 0.003 | the start |
| 17 | 87 | EVLESQDPG | 0.001 | position |
| 18 | 110 | FWLGAVAHA | 0.001 | plus eight |
| 19 | 106 | YYRKFWLGA | 0.001 | |
| 20 | 115 | VAHACNPST | 0.001 | |
| 21 | 108 | RKFWLGAVA | 0.001 | |
| 22 | 102 | IKVSYYRKF | 0.001 | |
| 23 | 105 | SYYRKFWLG | 0.001 | |
| 24 | 113 | GAVAHACNP | 0.001 | |
| 25 | 118 | ACNPSTLGG | 0.001 | |
| 26 | 116 | AHACNPSTL | 0.001 | |
| 27 | 117 | HACNPSTLG | 0.000 | |
| 28 | 107 | YRKFWLGAV | 0.000 | |
| 29 | 94 | PGCCFHEII | 0.000 | |
| 30 | 89 | LESQDPGCC | 0.000 | |
| 31 | 92 | QDPGCCFHE | 0.000 | |
| 32 | 86 | LEVLESQDP | 0.000 | |
| 33 | 97 | CFHEIIKVS | 0.000 | |
| 34 | 112 | LGAVAHACN | 0.000 | |

TABLE X (B)

VARIANT 1A HKLEVLESQDPGCCFHEIIKVSYYRKFWLGAVAHACNPSTLGG
HLA PEPTIDE SCORING RESULTS - 121P1F1 - A3, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 100 | EIIKVSYYRK | 2.700 | Portion of |
| 2 | 103 | KVSYYRKFWL | 0.540 | SEQ ID |
| 3 | 99 | HEIIKVSYYR | 0.081 | NO: 5; each |
| 4 | 88 | VLESQDPGCC | 0.060 | start |
| 5 | 85 | KLEVLESQDP | 0.060 | position is |
| 6 | 101 | IIKVSYYRKF | 0.060 | specified, |
| 7 | 111 | WLGAVAHACN | 0.020 | the length |
| 8 | 95 | GCCFHEIIKV | 0.018 | of each |
| 9 | 88 | EVLESQDPGC | 0.013 | peptide is |
| 10 | 98 | FHEIIKVSYY | 0.012 | 10 amino |
| 11 | 114 | AVAHACNPST | 0.010 | acids, the |
| 12 | 97 | CFHEIIKVSY | 0.009 | end |
| 13 | 109 | KFWLGAVAHA | 0.009 | position for |
| 14 | 89 | LESQDPGCCF | 0.009 | each |
| 15 | 105 | SYYRKFWLGA | 0.006 | peptide is |
| 16 | 115 | VAHACNPSTL | 0.006 | the start |
| 17 | 93 | DPGCCFHEII | 0.005 | position |
| 18 | 104 | VSYYRKFWLG | 0.005 | plus nine |
| 19 | 94 | PGCCFHEIIK | 0.004 | |
| 20 | 91 | SQDPGCCFHE | 0.003 | |
| 21 | 92 | QDPGCCFHEI | 0.003 | |
| 22 | 96 | CCFHEIIKVS | 0.002 | |
| 23 | 113 | GAVAHACNPS | 0.002 | |
| 24 | 108 | RKFWLGAVAH | 0.001 | |
| 25 | 110 | FWLGAVAHAC | 0.001 | |
| 26 | 102 | IKVSYYRKFW | 0.000 | |
| 27 | 117 | HACNPSTLGG | 0.000 | |
| 28 | 90 | ESQDPGCCFH | 0.000 | |
| 29 | 106 | YYRKFWLGAV | 0.000 | |
| 30 | 107 | YRKFWLGAVA | 0.000 | |
| 31 | 86 | LEVLESQDPG | 0.000 | |

TABLE X (B)-continued

VARIANT 1A HKLEVLESQDPGCCFHEIIKVSYYRKFWLGAVAHACNPSTLGG
HLA PEPTIDE SCORING RESULTS - 121P1F1 - A3, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 32 | 84 | HKLEVLESQD | 0.000 | |
| 33 | 33 | AHACNPSTLG | 0.000 | |
| 34 | 29 | LGAVAHACNP | 0.000 | |

TABLE XI (B)

VARIANT 1A KLEVLESQDPGCCFHEIIKVSYYRKFWLGAVAHACNPSTLGG
HLA PEPTIDE SCORING RESULTS - 121P1F1 - A11, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 95 | GCCFHEIIK | 1.200 | Portion of |
| 2 | 101 | IIKVSYYRK | 0.800 | SEQ ID |
| 3 | 100 | EIIKVSYYR | 0.072 | NO: 5; |
| 4 | 103 | KVSYYRKFW | 0.030 | each start |
| 5 | 109 | KFWLGAVAH | 0.012 | position is |
| 6 | 96 | CCFHEIIKV | 0.008 | specified, |
| 7 | 106 | YYRKFWLGA | 0.008 | the length |
| 8 | 91 | SQDPGCCFH | 0.006 | of each |
| 9 | 114 | AVAHACNPS | 0.002 | peptide is |
| 10 | 105 | SYYRKFWLG | 0.002 | 9 amino |
| 11 | 85 | KLEVLESQD | 0.001 | acids, the |
| 12 | 104 | VSYYRKFWL | 0.001 | end |
| 13 | 108 | RKFWLGAVA | 0.001 | position |
| 14 | 87 | EVLESQDPG | 0.001 | for each |
| 15 | 113 | GAVAHACNP | 0.001 | peptide is |
| 16 | 99 | HEIIKVSYY | 0.001 | the start |
| 17 | 93 | DPGCCFHEI | 0.001 | position |
| 18 | 88 | VLESQDPGC | 0.000 | plus eight |
| 19 | 118 | ACNPSTLGG | 0.000 | |
| 20 | 111 | WLGAVAHAC | 0.000 | |
| 21 | 110 | FWLGAVAHA | 0.000 | |
| 22 | 116 | AHACNPSTL | 0.000 | |
| 23 | 98 | FHEIIKVSY | 0.000 | |
| 24 | 115 | VAHACNPST | 0.000 | |
| 25 | 117 | HACNPSTLG | 0.000 | |
| 26 | 107 | YRKFWLGAV | 0.000 | |
| 27 | 97 | CFHEIIKVS | 0.000 | |
| 28 | 86 | LEVLESQDP | 0.000 | |
| 29 | 92 | QDPGCCFHE | 0.000 | |
| 30 | 89 | LESQDPGCC | 0.000 | |
| 31 | 90 | ESQDPGCCF | 0.000 | |
| 32 | 102 | IKVSYYRKF | 0.000 | |
| 33 | 112 | LGAVAHACN | 0.000 | |
| 34 | 94 | PGCCFHEII | 0.000 | |

TABLE XII (B)

VARIANT 1A HKLEVLESQDPGCCFHEIIKVSYYRKFWLGAVAHACNPSTLGG
HLA PEPTIDE SCORING RESULTS - 121P1F1 - A11, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 100 | EIIKVSYYRK | 0.360 | Portion of |
| 2 | 103 | KVSYYRKFWL | 0.180 | SEQ ID |
| 3 | 99 | HEIIKVSYYR | 0.036 | NO: 5; |
| 4 | 105 | SYYRKFWLGA | 0.016 | each start |
| 5 | 95 | GCCFHEIIKV | 0.012 | position is |
| 6 | 109 | KFWLGAVAHA | 0.012 | specified, |
| 7 | 94 | PGCCFHEIIK | 0.004 | the length |
| 8 | 106 | YYRKFWLGAV | 0.004 | of each |
| 9 | 97 | CFHEIIKVSY | 0.002 | peptide is |
| 10 | 114 | AVAHACNPST | 0.002 | 10 amino |
| 11 | 115 | VAHACNPSTL | 0.002 | acids, the |

TABLE XII (B)-continued

VARIANT 1A HKLEVLESQDPGCCFHEIIKVSYYRKFWLGAVAHACNPSTLGG HLA PEPTIDE SCORING RESULTS - 121P1F1 - A11, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 12 | 91 | SQDPGCCFHE | 0.002 | end |
| 13 | 85 | KLEVLESQDP | 0.001 | position |
| 14 | 108 | RKFWLGAVAH | 0.001 | for each |
| 15 | 113 | GAVAHACNPS | 0.001 | peptide is |
| 16 | 87 | EVLESQDPGC | 0.001 | the start |
| 17 | 93 | DPGCCFHEII | 0.001 | position |
| 18 | 89 | LESQDPGCCF | 0.001 | plus nine |
| 19 | 101 | IIKVSYYRKF | 0.000 | |
| 20 | 111 | WLGAVAHACN | 0.000 | |
| 21 | 117 | HACNPSTLGG | 0.000 | |
| 22 | 88 | VLESQDPGCC | 0.000 | |
| 23 | 98 | FHEIIKVSYY | 0.000 | |
| 24 | 92 | QDPGCCFHEI | 0.000 | |
| 25 | 96 | CCFHEIIKVS | 0.000 | |
| 26 | 107 | YRKFWLGAVA | 0.000 | |
| 27 | 102 | IKVSYYRKFW | 0.000 | |
| 28 | 86 | LEVLESQDPG | 0.000 | |
| 29 | 104 | VSYYRKFWLG | 0.000 | |
| 30 | 90 | ESQDPGCCFH | 0.000 | |
| 31 | 84 | HKLEVLESQD | 0.000 | |
| 32 | 110 | FWLGAVAHAC | 0.000 | |
| 33 | 112 | LGAVAHACNP | 0.000 | |
| 34 | 116 | AHACNPSTLG | 0.000 | |

TABLE XIII (B)

VARIANT 1A KLEVLESQDPGCCFHEIIKVSYYRKFWLGAVAHACNPSTLGG HLA PEPTIDE SCORING RESULTS - 121P1F1 - A24, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 106 | YYRKFWLGA | 5.000 | Portion of |
| 2 | 104 | VSYYRKFWL | 4.000 | SEQ ID |
| 3 | 90 | ESQDPGCCF | 3.600 | NO: 5; each |
| 4 | 93 | DPGCCFHEI | 1.320 | start |
| 5 | 97 | CFHEIIKVS | 0.840 | position is |
| 6 | 105 | SYYRKFWLG | 0.600 | specified, |
| 7 | 116 | AHACNPSTL | 0.400 | the length |
| 8 | 102 | IKVSYYRKF | 0.330 | of each |
| 9 | 103 | KVSYYRKFW | 0.200 | peptide is |
| 10 | 88 | VLESQDPGC | 0.150 | 9 amino |
| 11 | 110 | FWLGAVAHA | 0.150 | acids, the |
| 12 | 111 | WLGAVAHAC | 0.140 | end |
| 13 | 114 | AVAHACNPS | 0.120 | position |
| 14 | 96 | CCFHEIIKV | 0.110 | for each |
| 15 | 112 | LGAVAHACN | 0.100 | peptide is |
| 16 | 115 | VAHACNPST | 0.100 | the start |
| 17 | 94 | PGCCFHEII | 0.100 | position |
| 18 | 109 | KFWLGAVAH | 0.100 | plus eight |
| 19 | 85 | KLEVLESQD | 0.036 | |
| 20 | 108 | RKFWLGAVA | 0.024 | |
| 21 | 98 | FHEIIKVSY | 0.021 | |
| 22 | 100 | EIIKVSYYR | 0.021 | |
| 23 | 87 | EVLESQDPG | 0.018 | |
| 24 | 118 | ACNPSTLGG | 0.018 | |
| 25 | 113 | GAVAHACNP | 0.015 | |
| 26 | 99 | HEIIKVSYY | 0.015 | |
| 27 | 91 | SQDPGCCFH | 0.012 | |
| 28 | 101 | IIKVSYYRK | 0.010 | |
| 29 | 89 | LESQDPGCC | 0.010 | |
| 30 | 95 | GCCFHEIIK | 0.010 | |
| 31 | 117 | HACNPSTLG | 0.010 | |
| 32 | 107 | YRKFWLGAV | 0.010 | |
| 33 | 86 | LEVLESQDP | 0.002 | |
| 34 | 92 | QDPGCCFHE | 0.002 | |

TABLE XIV (B)

VARIANT 1A HKLEVLESQDPGCCFHEIIKVSYYRKFWLGAVAHACNPSTLGG HLA PEPTIDE SCORING RESULTS - 121P1F1 - A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 103 | KVSYYRKFWL | 8.000 | Portion of |
| 2 | 105 | SYYRKFWLGA | 5.000 | SEQ ID |
| 3 | 106 | YYRKFWLGAV | 5.000 | NO: 5; each |
| 4 | 115 | VAHACNPSTL | 4.000 | start |
| 5 | 101 | IIKVSYYRKF | 2.200 | position is |
| 6 | 93 | DPGCCFHEII | 1.000 | specified, |
| 7 | 109 | KFWLGAVAHA | 1.000 | the length |
| 8 | 97 | CFHEIIKVSY | 0.840 | of each |
| 9 | 110 | FWLGAVAHAC | 0.210 | peptide is |

TABLE XIV (B)-continued

VARIANT 1A
HKLEVLESQDPGCCFHEIIKVSYYRKFWLGAVAHACNPSTLGG
HLA PEPTIDE SCORING RESULTS - 121P1F1 - A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 10 | 89 | LESQDPGCCF | 0.200 | 10 amino |
| 11 | 92 | QDPGCCFHEI | 0.198 | acids, the |
| 12 | 87 | EVLESQDPGC | 0.180 | end |
| 13 | 113 | GAVAHACNPS | 0.180 | position |
| 14 | 88 | VLESQDPGCC | 0.150 | for each |
| 15 | 96 | CCFHEIIKVS | 0.140 | peptide is |
| 16 | 95 | GCCFHEIIKV | 0.110 | the start |
| 17 | 114 | AVAHACNPST | 0.100 | position |
| 18 | 111 | WLGAVAHACN | 0.100 | plus nine |
| 19 | 85 | KLEVLESQDP | 0.036 | |
| 20 | 90 | ESQDPGCCFH | 0.018 | |
| 21 | 100 | EIIKVSYYRK | 0.015 | |
| 22 | 102 | IKVSYYRKFW | 0.015 | |
| 23 | 98 | FHEIIKVSYY | 0.015 | |
| 24 | 91 | SQDPGCCFHE | 0.012 | |
| 25 | 104 | VSYYRKFWLG | 0.012 | |
| 26 | 107 | YRKFWLGAVA | 0.012 | |
| 27 | 112 | LGAVAHACNP | 0.010 | |
| 28 | 117 | HACNPSTLGG | 0.010 | |
| 29 | 84 | HKLEVLESQD | 0.002 | |
| 30 | 99 | HEIIKVSYYR | 0.002 | |
| 31 | 108 | RKFWLGAVAH | 0.002 | |
| 32 | 86 | LEVLESQDPG | 0.002 | |
| 33 | 94 | PGCCFHEIIK | 0.001 | |
| 34 | 116 | AHACNPSTLG | 0.001 | |

TABLE XV (B)

VARIANT 1A
KLEVLESQDPGCCFHEIIKVSYYRKFWLGAVAHACNPSTLGG HLA
PEPTIDE SCORING RESULTS - 121P1F1 - B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 93 | DPGCCFHEI | 8.000 | Portion of |
| 2 | 104 | VSYYRKFWL | 4.000 | SEQ ID |
| 3 | 116 | AHACNPSTL | 1.200 | NO: 5; |
| 4 | 115 | VAHACNPST | 0.300 | each start |
| 5 | 114 | AVAHACNPS | 0.300 | position is |
| 6 | 96 | CCFHEIIKV | 0.200 | specified, |
| 7 | 103 | KVSYYRKFW | 0.150 | the length |
| 8 | 111 | WLGAVAHAC | 0.100 | of each |
| 9 | 106 | YYRKFWLGA | 0.100 | peptide is |
| 10 | 87 | EVLESQDPG | 0.050 | 9 amino |
| 11 | 117 | HACNPSTLG | 0.045 | acids, the |
| 12 | 94 | PGCCFHEII | 0.040 | end |
| 13 | 113 | GAVAHACNP | 0.030 | position |
| 14 | 90 | ESQDPGCCF | 0.030 | for each |
| 15 | 118 | ACNPSTLGG | 0.030 | peptide is |
| 16 | 88 | VLESQDPGC | 0.030 | the start |
| 17 | 107 | YRKFWLGAV | 0.020 | position |
| 18 | 112 | LGAVAHACN | 0.020 | plus eight |
| 19 | 89 | LESQDPGCC | 0.010 | |
| 20 | 110 | FWLGAVAHA | 0.010 | |
| 21 | 108 | RKFWLGAVA | 0.010 | |
| 22 | 95 | GCCFHEIIK | 0.010 | |

TABLE XV (B)-continued

VARIANT 1A
KLEVLESQDPGCCFHEIIKVSYYRKFWLGAVAHACNPSTLGG HLA
PEPTIDE SCORING RESULTS - 121P1F1 - B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) |
|---|---|---|---|
| 23 | 101 | IIKVSYYRK | 0.010 |
| 24 | 100 | EIIKVSYYR | 0.010 |
| 25 | 85 | KLEVLESQD | 0.003 |
| 26 | 91 | SQDPGCCFH | 0.003 |
| 27 | 97 | CFHEIIKVS | 0.002 |
| 28 | 102 | IKVSYYRKF | 0.002 |
| 29 | 100 | HEIIKVSYY | 0.002 |
| 30 | 109 | KFWLGAVAH | 0.001 |
| 31 | 86 | LEVLESQDP | 0.001 |
| 32 | 92 | QDPGCCFHE | 0.001 |
| 33 | 105 | SYYRKFWLG | 0.001 |
| 34 | 98 | FHEIIKVSY | 0.001 |

TABLE XVI (B)

VARIANT 1A
HKLEVLESQDPGCCFHEIIKVSYYRKFWLGAVAHACNPSTLGG HLA
PEPTIDE SCORING RESULTS - 121P1F1 - B7, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 103 | KVSYYRKFWL | 20.000 | Portion of |
| 2 | 115 | VAHACNPSTL | 12.000 | SEQ ID |
| 3 | 93 | DPGCCFHEII | 8.000 | NO: 5; |
| 4 | 114 | AVAHACNPST | 1.500 | each start |
| 5 | 87 | EVLESQDPGC | 0.500 | position is |
| 6 | 106 | YYRKFWLGAV | 0.200 | specified, |
| 7 | 95 | GCCFHEIIKV | 0.200 | the length |
| 8 | 114 | GAVAHACNPS | 0.060 | of each |
| 9 | 92 | QDPGCCFHEI | 0.040 | peptide is |
| 10 | 117 | HACNPSTLGG | 0.030 | 10 amino |
| 11 | 88 | VLESQDPGCC | 0.030 | acids, the |
| 12 | 96 | CCFHEIIKVS | 0.020 | end |
| 13 | 101 | IIKVSYYRKF | 0.020 | position |
| 14 | 111 | WLGAVAHACN | 0.020 | for each |
| 15 | 110 | FWLGAVAHAC | 0.010 | peptide is |
| 16 | 107 | YRKFWLGAVA | 0.010 | the start |
| 17 | 105 | SYYRKFWLGA | 0.010 | position |
| 18 | 104 | VSYYRKFWLG | 0.010 | plus nine |
| 19 | 109 | KFWLGAVAHA | 0.010 | |
| 20 | 100 | EIIKVSYYRK | 0.010 | |
| 21 | 90 | ESQDPGCCFH | 0.010 | |
| 22 | 112 | LGAVAHACNP | 0.010 | |
| 23 | 116 | AHACNPSTLG | 0.005 | |
| 24 | 102 | IKVSYYRKFW | 0.003 | |
| 25 | 89 | LESQDPGCCF | 0.003 | |
| 26 | 91 | SQDPGCCFHE | 0.003 | |
| 27 | 85 | KLEVLESQDP | 0.003 | |
| 28 | 97 | CFHEIIKVSY | 0.002 | |
| 29 | 108 | RKFWLGAVAH | 0.001 | |
| 30 | 94 | PGCCFHEIIK | 0.001 | |
| 31 | 86 | LEVLESQDPG | 0.001 | |
| 32 | 99 | HEIIKVSYYR | 0.001 | |
| 33 | 84 | HKLEVLESQD | 0.001 | |
| 34 | 98 | FHEIIKVSYY | 0.001 | |

TABLE XVII (B)

VARIANT 1A
KLEVLESQDPGCCFHEIIKVSYYRKFWLGAVAHACNPSTLGG HLA
PEPTIDE SCORING RESULTS - 121P1F1 - B35, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 90 | ESQDPGCCF | 10.000 | Portion of |
| 2 | 93 | DPGCCFHEI | 8.000 | SEQ ID |
| 3 | 104 | VSYYRKFWL | 5.000 | NO: 5; each |
| 4 | 103 | KVSYYRKFW | 1.000 | start |
| 5 | 115 | VAHACNPST | 0.300 | position is |
| 6 | 96 | CCFHEIIKV | 0.300 | specified, |
| 7 | 99 | HEIIKVSYY | 0.200 | the length |
| 8 | 112 | LGAVAHACN | 0.100 | of each |
| 9 | 111 | WLGAVAHAC | 0.100 | peptide is |
| 10 | 114 | AVAHACNPS | 0.100 | 9 amino |
| 11 | 116 | AHACNPSTL | 0.100 | acids, the |
| 12 | 102 | IKVSYYRKF | 0.100 | end |
| 13 | 107 | YRKFWLGAV | 0.060 | position |
| 14 | 98 | FHEIIKVSY | 0.060 | for each |
| 15 | 94 | PGCCFHEII | 0.040 | peptide is |
| 16 | 117 | HACNPSTLG | 0.030 | the start |
| 17 | 106 | YYRKFWLGA | 0.030 | position |
| 18 | 101 | IIKVSYYRK | 0.030 | plus eight |
| 19 | 113 | GAVAHACNP | 0.030 | |
| 20 | 88 | VLESQDPGC | 0.030 | |
| 21 | 87 | EVLESQDPG | 0.020 | |
| 22 | 97 | CFHEIIKVS | 0.020 | |
| 23 | 108 | RKFWLGAVA | 0.020 | |
| 24 | 89 | LESQDPGCC | 0.015 | |
| 25 | 95 | GCCFHEIIK | 0.010 | |
| 26 | 118 | ACNPSTLGG | 0.010 | |
| 27 | 110 | FWLGAVAHA | 0.010 | |
| 28 | 100 | EIIKVSYYR | 0.010 | |
| 29 | 85 | KLEVLESQD | 0.006 | |
| 30 | 91 | SQDPGCCFH | 0.003 | |
| 31 | 109 | KFWLGAVAH | 0.002 | |
| 32 | 86 | LEVLESQDP | 0.002 | |
| 33 | 92 | QDPGCCFHE | 0.001 | |
| 34 | 105 | SYYRKFWLG | 0.001 | |

TABLE XVIII (B)

VARIANT 1A
HKLEVLESQDPGCCFHEIIKVSYYRKFWLGAVAHACNPSTLGG HLA
PEPTIDE SCORING RESULTS - 121P1F1 - B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 93 | DPGCCFHEII | 8.000 | Portion of |
| 2 | 115 | VAHACNPSTL | 3.000 | SEQ ID |
| 3 | 101 | IIKVSYYRKF | 3.000 | NO: 5; each |
| 4 | 103 | KVSYYRKFWL | 2.000 | start |
| 5 | 97 | CFHEIIKVSY | 0.400 | position is |
| 6 | 113 | GAVAHACNPS | 0.300 | specified, |
| 7 | 95 | GCCFHEIIKV | 0.300 | the length |
| 8 | 87 | EVLESQDPGC | 0.200 | of each |
| 9 | 114 | AVAHACNPST | 0.100 | peptide is |
| 10 | 89 | LESQDPGCCF | 0.100 | 10 amino |
| 11 | 90 | ESQDPGCCFH | 0.100 | acids, the |
| 12 | 111 | WLGAVAHACN | 0.100 | end |
| 13 | 96 | CCFHEIIKVS | 0.100 | position |
| 14 | 106 | YYRKFWLGAV | 0.060 | for each |

TABLE XVIII (B)-continued

VARIANT 1A
HKLEVLESQDPGCCFHEIIKVSYYRKFWLGAVAHACNPSTLGG HLA
PEPTIDE SCORING RESULTS - 121P1F1 - B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 15 | 98 | FHEIIKVSYY | 0.060 | peptide is |
| 16 | 102 | IKVSYYRKFW | 0.050 | the start |
| 17 | 104 | VSYYRKFWLG | 0.050 | position |
| 18 | 88 | VLESQDPGCC | 0.045 | plus nine |
| 19 | 92 | QDPGCCFHEI | 0.040 | |
| 20 | 107 | YRKFWLGAVA | 0.030 | |
| 21 | 117 | HACNPSTLGG | 0.030 | |
| 22 | 109 | KFWLGAVAHA | 0.020 | |
| 23 | 105 | SYYRKFWLGA | 0.010 | |
| 24 | 110 | FWLGAVAHAC | 0.010 | |
| 25 | 112 | LGAVAHACNP | 0.010 | |
| 26 | 100 | EIIKVSYYRK | 0.010 | |
| 27 | 85 | KLEVLESQDP | 0.009 | |
| 28 | 91 | SQDPGCCFHE | 0.003 | |
| 29 | 108 | RKFWLGAVAH | 0.002 | |
| 30 | 84 | HKLEVLESQD | 0.002 | |
| 31 | 86 | LEVLESQDPG | 0.001 | |
| 32 | 116 | AHACNPSTLG | 0.001 | |
| 33 | 94 | PGCCFHEIIK | 0.001 | |
| 34 | 99 | HEIIKVSYYR | 0.001 | |

TABLE V (C)

VARIANT 1B MKCKMELSEGSQKH
HLA PEPTIDE SCORING RESULTS - 121P1F1 - A1, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 4 | KMELSEGSQ | 0.450 | Portion of |
| 2 | 5 | MELSEGSQK | 0.010 | SEQ ID |
| 3 | 6 | ELSEGSQKH | 0.010 | NO: 7; each |
| 4 | 2 | KCKMELSEG | 0.001 | start |
| 5 | 3 | CKMELSEGS | 0.001 | position |
| 6 | 1 | MKCKMELSE | 0.000 | is specified, the length of each peptide is 9 amino acids, the end position for each peptide is the start position plus eight |

TABLE VI (C)

VARIANT 1B MKCKMELSEGSQKHA HLA PEPTIDE SCORING RESULTS - 121P1F1 - A1, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 4 | KMELSEGSQK | 9.000 | Portion of SEQ ID NO: 7; each start position is specified, the length of each peptide is 10 amino acids, the end position for each peptide is the start position plus nine |
| 2 | 6 | ELSEGSQKHA | 0.010 | |
| 3 | 2 | KCKMELSEGS | 0.001 | |
| 4 | 5 | MELSEGSQKH | 0.001 | |
| 5 | 3 | CKMELSEGSQ | 0.001 | |
| 6 | 1 | MKCKMELSEG | 0.000 | |

TABLE VII (C)

VARIANT 1B MKCKMELSEGSQKH HLA PEPTIDE SCORING RESULTS - 121P1F1 - A2, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 6 | ELSEGSQKH | 0.023 | Portion of SEQ ID NO: 7; each start position is specified, the length of each peptide is 9 amino acids, the end position for each peptide is the start position plus eight |
| 2 | 5 | MELSEGSQK | 0.002 | |
| 3 | 3 | CKMELSEGS | 0.001 | |
| 4 | 4 | KMELSEGSQ | 0.000 | |
| 5 | 2 | KCKMELSEG | 0.000 | |
| 6 | 1 | MKCKMELSE | 0.000 | |

TABLE VIII (C)

VARIANT 1B MKCKMELSEGSQKHA HLA PEPTIDE SCORING RESULTS - 121P1F1 - A2, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 6 | ELSEGSQKHA | 1.528 | Portion of SEQ ID NO: 7; each start position is specified, the length of each peptide is 10 amino acids, the end position for each peptide is the start position plus nine |
| 2 | 5 | MELSEGSQKH | 0.009 | |
| 3 | 4 | KMELSEGSQK | 0.002 | |
| 4 | 1 | MKCKMELSEG | 0.000 | |
| 5 | 3 | CKMELSEGSQ | 0.000 | |
| 6 | 2 | KCKMELSEGS | 0.000 | |

TABLE IX (C)

VARIANT 1B MKCKMELSEGSQKHA HLA PEPTIDE SCORING RESULTS - 121P1F1 - A3, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 6 | ELSEGSQKH | 0.090 | Portion of SEQ ID NO: 7; each start position is specified, the length of each peptide is 9 amino acids, the end position for each peptide is the start position plus eight |
| 2 | 5 | MELSEGSQK | 0.090 | |
| 3 | 4 | KMELSEGSQ | 0.018 | |
| 4 | 2 | KCKMELSEG | 0.001 | |
| 5 | 3 | CKMELSEGS | 0.000 | |
| 6 | 1 | MKCKMELSE | 0.000 | |

TABLE X (C)

VARIANT 1B MKCKMELSEGSQKHA HLA PEPTIDE SCORING RESULTS - 121P1F1 - A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 4 | KMELSEGSQK | 60.000 | Portion of SEQ ID NO: 7; each start position is specified, the length |
| 2 | 6 | ELSEGSQKHA | 0.045 | |
| 3 | 2 | KCKMELSEGS | 0.001 | |
| 4 | 5 | MELSEGSQKH | 0.001 | |
| 5 | 1 | MKCKMELSEG | 0.000 | |
| 6 | 3 | CKMELSEGSQ | 0.000 | |

TABLE X (C)-continued

VARIANT 1B MKCKMELSEGSQKHA HLA
PEPTIDE SCORING RESULTS - 121P1F1 - A3, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) |
|---|---|---|---|
| | | | of each peptide is 10 amino acids, the end position for each peptide is the start position plus nine |

TABLE XI (C)

VARIANT 1B MKCKMELSEGSQKH HLA
PEPTIDE SCORING RESULTS - 121P1F1 - A11, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 5 | MELSEGSQK | 0.090 | Portion of SEQ ID NO: 7; each start position is specified, the length of each peptide is 9 amino acids, the end position for each peptide is the start position plus eight |
| 2 | 4 | KMELSEGSQ | 0.001 | |
| 3 | 6 | ELSEGSQKH | 0.001 | |
| 4 | 2 | KCKMELSEG | 0.001 | |
| 5 | 3 | CKMELSEGS | 0.000 | |
| 6 | 1 | MKCKMELSE | 0.000 | |

TABLE XII (C)

VARIANT 1B MKCKMELSEGSQKHA HLA
PEPTIDE SCORING RESULTS - 121P1F1 - A11, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 4 | KMELSEGSQK | 1.200 | Portion of SEQ ID NO: 7; each start position is specified, the length of each peptide is 10 amino acids, the end position for each peptide is the start position plus nine |
| 2 | 5 | MELSEGSQKH | 0.001 | |
| 3 | 2 | KCKMELSEGS | 0.001 | |
| 4 | 6 | ELSEGSQKHA | 0.001 | |
| 5 | 3 | CKMELSEGSQ | 0.000 | |
| 6 | 1 | MKCKMELSEG | 0.000 | |

TABLE XIII (C)

VARIANT 1B MKCKMELSEGSQKH HLA
PEPTIDE SCORING RESULTS - 121P1F1 - A24, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 4 | KMELSEGSQ | 0.030 | Portion of SEQ ID NO: 7; each start position is specified, the length of each peptide is 9 amino acids, the end position for each peptide is the start position plus eight |
| 2 | 2 | KCKMELSEG | 0.022 | |
| 3 | 3 | CKMELSEGS | 0.022 | |
| 4 | 6 | ELSEGSQKH | 0.016 | |
| 5 | 5 | MELSEGSQK | 0.002 | |
| 6 | 1 | MKCKMELSE | 0.001 | |

TABLE XIV (C)

VARIANT 1B MKCKMELSEGSQKHA HLA PEPTIDE SCORING RESULTS - 121P1F1 - A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 2 | KCKMELSEGS | 0.240 | Portion of SEQ ID NO: 7; each start position is specified, the length of each peptide is 10 amino acids, the |
| 2 | 6 | ELSEGSQKHA | 0.120 | |
| 3 | 4 | KMELSEGSQK | 0.030 | |
| 4 | 5 | MELSEGSQKH | 0.002 | |
| 5 | 3 | CKMELSEGSQ | 0.002 | |
| 6 | 1 | MKCKMELSEG | 0.001 | |

TABLE XIV (C)-continued

VARIANT 1B MKCKMELSEGSQKHA
HLA PEPTIDE SCORING RESULTS - 121P1F1 - A24, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| | | | | end position for each peptide is the start position plus nine |

TABLE XV (C)

VARIANT 1B MKCKMELSEGSQKH
HLA PEPTIDE SCORING RESULTS - 121P1F1 - B7, 9-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 6 | ELSEGSQKH | 0.010 | Portion of SEQ ID NO: 7; each start position is specified, the length of each peptide is 9 amino acids, the end position for each peptide is the start position plus eight |
| 2 | 2 | KCKMELSEG | 0.010 | |
| 3 | 3 | CKMELSEGS | 0.006 | |
| 4 | 4 | KMELSEGSQ | 0.003 | |
| 5 | 5 | MELSEGSQK | 0.001 | |
| 6 | 1 | MKCKMELSE | 0.001 | |

TABLE XVI (C)

VARIANT 1B MKCKMELSEGSQKHA
HLA PEPTIDE SCORING RESULTS - 121P1F1 - B7, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 6 | ELSEGSQKHA | 0.100 | Portion of SEQ ID NO: 7; each start position is specified, the length of each peptide is 10 amino acids, the end position for each peptide is the start position plus nine |
| 2 | 2 | KCKMELSEGS | 0.020 | |
| 3 | 3 | CKMELSEGSQ | 0.003 | |
| 4 | 4 | KMELSEGSQK | 0.003 | |
| 5 | 5 | MELSEGSQKH | 0.001 | |
| 6 | 1 | MKCKMELSEG | 0.001 | |

TABLE XVII (C)

VARIANT 1B MKCKMELSEGSQKH
HLA PEPTIDE SCORING RESULTS - 121P1F1 - B35, 9-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 2 | KCKMELSEG | 0.090 | Portion of SEQ ID NO: 7; each start position is specified, the length of each peptide is 9 amino acids, the end position for each peptide is the start position plus eight |
| 2 | 6 | ELSEGSQKH | 0.020 | |
| 3 | 3 | CKMELSEGS | 0.020 | |
| 4 | 4 | KMELSEGSQ | 0.006 | |
| 5 | 5 | MELSEGSQK | 0.002 | |
| 6 | 1 | MKCKMELSE | 0.001 | |

TABLE XVIII (C)

VARIANT 1B MKCKMELSEGSQKHA
HLA PEPTIDE SCORING RESULTS - 121P1F1 - B35, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 2 | KCKMELSEGS | 0.600 | Portion of SEQ ID NO: |
| 2 | 6 | ELSEGSQKHA | 0.200 | |

TABLE XVIII (C)-continued

VARIANT 1B MKCKMELSEGSQKHA
HLA PEPTIDE SCORING RESULTS - 121P1F1 - B35, 10-MERS

| RANK | START POSITION | RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 3 | 4 | KMELSEGSQK | 0.009 | 7; each start position is specified, the length of each peptide is 10 amino acids, the end position for each peptide is the start position plus nine |
| 4 | 3 | CKMELSEGSQ | 0.002 | |
| 5 | 1 | MKCKMELSEG | 0.002 | |
| 6 | 5 | MELSEGSQKH | 0.001 | |

TABLE V (D)

VARIANT 2 AKIGRCETAKQIK
HLA PEPTIDE SCORING RESULTS - 121P1F1 - A1, 9-MERS

| RANK | START POSITION | RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 114 | RCETAKQIK | 18.000 | Portion of SEQ ID NO: 9; each start position is specified, the length of each peptide is 9 amino acids, the end position for each peptide is the start position plus eight |
| 2 | 111 | KIGRCETAK | 0.020 | |
| 3 | 113 | GRCETAKQI | 0.001 | |
| 4 | 112 | IGRCETAKQ | 0.001 | |
| 5 | 110 | AKIGRCETA | 0.001 | |

TABLE VI (D)

VARIANT 2 KAKIGRCETAKQIK
HLA PEPTIDE SCORING RESULTS - 121P1F1 - A1, 10-MERS

| RANK | START POSITION | RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 113 | GRCETAKQIK | 0.010 | Portion of SEQ ID NO: 9; each start position is specified, the length of each peptide is 10 amino acids, the end position for each peptide is the start position plus nine |
| 2 | 110 | AKIGRCETAK | 0.010 | |
| 3 | 111 | KIGRCETAKQ | 0.002 | |
| 4 | 109 | KAKIGRCETA | 0.001 | |
| 5 | 112 | IGRCETAKQI | 0.000 | |

TABLE VII (D)

VARIANT 2 AKIGRCETAKQIK
HLA PEPTIDE SCORING RESULTS - 121P1F1 - A2, 9-MERS

| RANK | START POSITION | RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 111 | KIGRCETAK | 0.007 | Portion of SEQ ID NO: 9; each start position is specified, the length of each peptide is 9 amino acids, the end position for each peptide is the start position plus eight |
| 2 | 113 | GRCETAKQI | 0.006 | |
| 3 | 110 | AKIGRCETA | 0.003 | |
| 4 | 112 | IGRCETAKQ | 0.000 | |
| 5 | 114 | RCETAKQIK | 0.000 | |

TABLE VIII (D)

VARIANT 2 KAKIGRCETAKQIK
HLA PEPTIDE SCORING RESULTS - 121P1F1 - A2, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 112 | IGRCETAKQI | 0.009 | Portion of SEQ ID NO: 9; each start position is specified, the length of each peptide is 10 amino acids, the end position for each peptide is the start position plus nine |
| 2 | 111 | KIGRCETAKQ | 0.007 | |
| 3 | 109 | KAKIGRCETA | 0.004 | |
| 4 | 110 | AKIGRCETAK | 0.000 | |
| 5 | 113 | GRCETAKQIK | 0.000 | |

TABLE IX (D)

VARIANT 2 AKIGRCETAKQIK
HLA PEPTIDE SCORING RESULTS - 121P1F1 - A3, 9-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 111 | KIGRCETAK | 6.000 | Portion of SEQ ID NO: 9; each start position is specified, the length of each peptide is 9 amino acids, the end position for each peptide is the start position plus eight |
| 2 | 114 | RCETAKQIK | 0.200 | |
| 3 | 113 | GRCETAKQI | 0.001 | |
| 4 | 110 | AKIGRCETA | 0.000 | |
| 5 | 112 | IGRCETAKQ | 0.000 | |

TABLE X (D)

VARIANT 2 KAKIGRCETAKQIK
HLA PEPTIDE SCORING RESULTS - 121P1F1 - A3, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 113 | GRCETAKQIK | 0.090 | Portion of SEQ ID NO: 9; each start position is specified, the length of each peptide is 10 amino acids, the end position for each peptide is the start position plus nine |
| 2 | 110 | AKIGRCETAK | 0.045 | |
| 3 | 111 | KIGRCETAKQ | 0.006 | |
| 4 | 109 | KAKIGRCETA | 0.006 | |
| 5 | 112 | IGRCETAKQI | 0.000 | |

TABLE XI (D)

VARIANT 2 AKIGRCETAKQIK
HLA PEPTIDE SCORING RESULTS - 121P1F1 - A11, 9-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 111 | KIGRCETAK | 1.200 | Portion of SEQ ID NO: 9; each start position is specified, the length of each peptide is 9 amino acids, the end position for each peptide is the start position plus eight |
| 2 | 114 | RCETAKQIK | 0.600 | |
| 3 | 110 | AKIGRCETA | 0.000 | |
| 4 | 113 | GRCETAKQI | 0.000 | |
| 5 | 112 | IGRCETAKQ | 0.000 | |

TABLE XII (D)

VARIANT 2 KAKIGRCETAKQIK
HLA PEPTIDE SCORING RESULTS - 121P1F1 - A11, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 113 | GRCETAKQIK | 0.060 | Portion of SEQ ID NO: 9; each start position is specified, the length of each peptide is 10 amino acids, the end position for each peptide is the start position plus nine |
| 2 | 110 | AKIGRCETAK | 0.030 | |
| 3 | 109 | KAKIGRCETA | 0.006 | |
| 4 | 111 | KIGRCETAKQ | 0.001 | |
| 5 | 112 | IGRCETAKQI | 0.000 | |

TABLE XIII (D)

VARIANT 2 AKIGRCETAKQIK
HLA PEPTIDE SCORING RESULTS - 121P1F1 - A24, 9-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 113 | GRCETAKQI | 0.120 | Portion of SEQ ID NO: 9; each start position is specified, the length of each peptide is 9 amino acids, the end position for each peptide is the start position plus eight |
| 2 | 114 | RCETAKQIK | 0.036 | |
| 3 | 111 | KIGRCETAK | 0.020 | |
| 4 | 110 | AKIGRCETA | 0.015 | |
| 5 | 112 | IGRCETAKQ | 0.011 | |

TABLE XIV (D)

VARIANT 2 KAKIGRCETAKQIK
HLA PEPTIDE SCORING RESULTS - 121P1F1 - A24, 10-MERS

| RANK | START POSITION | SUBSEQUENCE RESIDUE LISTING | SCORE (ESTIMATE OF HALF TIME OF DIS-ASSOCIATION OF A MOLECULE CONTAINING THIS SUBSEQUENCE) | |
|---|---|---|---|---|
| 1 | 112 | IGRCETAKQI | 1.000 | Portion of SEQ ID NO: 9; each start position is specified, the length of each peptide is 10 amino acids, the end position for each peptide is the start position plus nine |
| 2 | 109 | KAKIGRCETA | 0.200 | |
| 3 | 111 | KIGRCETAKQ | 0.022 | |
| 4 | 110 | AKIGRCETAK | 0.002 | |
| 5 | 113 | GRCETAKQIK | 0.001 | |

TABLE XV (D)

VARIANT 2 AKIGRCETAKQIK
HLA PEPTIDE SCORING RESULTS-121P1F1-B7, 9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 112 | IGRCETAKQ | 0.100 | Portion of SEQ ID NO: 9; each start position is specified, the length of each peptide is 9 amino acids, the |
| 2 | 113 | GRCETAKQI | 0.040 | |
| 3 | 110 | AKIGRCETA | 0.030 | |
| 4 | 111 | KIGRCETAK | 0.010 | |
| 5 | 114 | RCETAKQIK | 0.003 | |

TABLE XV (D)-continued

VARIANT 2 AKIGRCETAKQIK
HLA PEPTIDE SCORING RESULTS-121P1F1-B7, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| | | | | end position for each peptide is the start position plus eight |

TABLE XVI (D)

VARIANT 2 KAKIGRCETAKQIK
HLA PEPTIDE SCORING RESULTS-121P1F1-B7, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 112 | IGRCETAKQI | 4.000 | Portion of SEQ ID NO: 9; each start position is specified, the length of each peptide is 10 amino acids, the end position for each peptide is the start position plus nine |
| 2 | 109 | KAKIGRCETA | 0.300 | |
| 3 | 111 | KIGRCETAKQ | 0.010 | |
| 4 | 110 | AKIGRCETAK | 0.003 | |
| 5 | 113 | GRCETAKQIK | 0.001 | |

TABLE XVII (D)

VARIANT 2 AKIGRCETAKQIK
HLA PEPTIDE SCORING RESULTS-121P1F1-B35, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 113 | GRCETAKQI | 0.080 | Portion of SEQ ID NO: 9; each start position is specified, the length of each peptide is 9 amino acids, the end position for each peptide is the start position plus eight |
| 2 | 112 | IGRCETAKQ | 0.045 | |
| 3 | 111 | KIGRCETAK | 0.020 | |
| 4 | 110 | AKIGRCETA | 0.010 | |
| 5 | 114 | RCETAKQIK | 0.006 | |

TABLE XVIII (D)

VARIANT 2 KAKIGRCETAKQIK
HLA PEPTIDE SCORING RESULTS-121P1F1-B35, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 109 | KAKIGRCETA | 1.800 | Portion of SEQ ID NO: 9; each start position is specified, the length of each peptide is 10 amino acids, the |
| 2 | 112 | IGRCETAKQI | 1.200 | |
| 3 | 111 | KIGRCETAKQ | 0.030 | |
| 4 | 113 | GRCETAKQIK | 0.002 | |
| 5 | 110 | AKIGRCETAK | 0.001 | |

TABLE XVIII (D)-continued

VARIANT 2 KAKIGRCETAKQIK
HLA PEPTIDE SCORING RESULTS-121P1F1-B35, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| | | | | end position for each peptide is the start position plus nine |

TABLE V (E)

VARIANT 3 DPQVVEEIHNIFAIKSW
HLA PEPTIDE SCORING RESULTS-121P1F1-A1, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 151 | VVEEIHNIF | 9.000 | Portion of SEQ ID NO: 11; each start position is specified, the length of each peptide is 9 amino acids, the end position for each peptide is the start position plus eight |
| 2 | 154 | EIHNIFAIK | 0.400 | |
| 3 | 152 | VEEIHNIFA | 0.225 | |
| 4 | 151 | QVVEEIHNI | 0.010 | |
| 5 | 155 | IHNIFAIKS | 0.003 | |
| 6 | 156 | HNIFAIKSW | 0.003 | |
| 7 | 153 | EEIHNIFAI | 0.003 | |
| 8 | 148 | DPQVVEEIH | 0.003 | |
| 9 | 149 | PQVVEEIHN | 0.001 | |

TABLE VI (E)

VARIANT 3 CDPQVVEEIHNIFAIKSWA
HLA PEPTIDE SCORING RESULTS-121P1F1-A1, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 151 | VVEEIHNIFA | 4.500 | Portion of SEQ ID NO: 11; each start position is specified, the length of each peptide is 10 amino acids, the end position for each peptide is the start position plus nine |
| 2 | 152 | VEEIHNIFAI | 0.225 | |
| 3 | 150 | QVVEEIHNIF | 0.100 | |
| 4 | 154 | EIHNIFAIKS | 0.050 | |
| 5 | 153 | EEIHNIFAIK | 0.020 | |
| 6 | 148 | DPQVVEEIHN | 0.013 | |
| 7 | 156 | HNIFAIKSWA | 0.003 | |
| 8 | 155 | IHNIFAIKSW | 0.001 | |
| 9 | 147 | CDPQVVEEIH | 0.001 | |
| 10 | 149 | PQVVEEIHNI | 0.000 | |

TABLE VII (E)

VARIANT 3 DPQVVEEIHNIFAIKSW
HLA PEPTIDE SCORING RESULTS-121P1F1-A2, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 150 | QVVEEIHNI | 8.608 | Portion of SEQ ID NO: 11; each start position is specified, the length of each peptide is 9 amino acids, the end position for |
| 2 | 153 | EEIHNIFAI | 0.203 | |
| 3 | 152 | VEEIHNIFA | 0.058 | |
| 4 | 151 | VVEEIHNIF | 0.001 | |
| 5 | 155 | IHNIFAIKS | 0.000 | |
| 6 | 149 | PQVVEEIHN | 0.000 | |
| 7 | 154 | EIHNIFAIK | 0.000 | |
| 8 | 156 | HNIFAIKSW | 0.000 | |

TABLE VII (E)-continued

VARIANT 3 DPQVVEEIHNIFAIKSW
HLA PEPTIDE SCORING RESULTS-121P1F1-A2, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 9 | 148 | DPQVVEEIH | 0.000 | each peptide is the start position plus eight |

TABLE VIII (E)

VARIANT 3 CDPQVVEEIHNIFAIKSWA
HLA PEPTIDE SCORING RESULTS-121P1F1-A2, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 151 | VVEEIHNIFA | 1.067 | Portion of SEQ |
| 2 | 152 | VEEIHNIFAI | 0.294 | ID NO: 11; each |
| 3 | 149 | PQVVEEIHNI | 0.054 | start position is |
| 4 | 150 | QVVEEIHNIF | 0.011 | specified, the |
| 5 | 156 | HNIFAIKSWA | 0.006 | length of each |
| 6 | 154 | EIHNIFAIKS | 0.003 | peptide is 10 |
| 7 | 155 | IHNIFAIKSW | 0.000 | amino acids, the |
| 8 | 148 | DPQVVEEIHN | 0.000 | end position for |
| 9 | 147 | CDPQVVEEIH | 0.000 | each peptide is |
| 10 | 153 | EEIHNIFAIK | 0.000 | the start position plus nine |

TABLE IX (E)

VARIANT 3 DPQVVEEIHNIFAIKSW
HLA PEPTTDE SCORING RESULTS-121P1F1-A3, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 154 | EIHNIFAIK | 2.700 | Portion of SEQ |
| 2 | 151 | VVEEIHNIF | 0.450 | ID NO: 11; each |
| 3 | 150 | QVVEEIHNI | 0.203 | start position is |
| 4 | 153 | EEIHNIFAI | 0.004 | specified, the |
| 5 | 152 | VEEIHNIFA | 0.001 | length of each |
| 6 | 148 | DPQVVEEIH | 0.001 | peptide is 9 |
| 7 | 156 | HNIFAIKSW | 0.000 | amino acids, the |
| 8 | 155 | IHNIFAIKS | 0.000 | end position for |
| 9 | 149 | PQVVEEIHN | 0.000 | each peptide is the start position plus eight |

TABLE X (E)

VARIANT 3 CDPQVVEEIHNIFAIKSWA
HLA PEPTIDE SCORING RESULTS-121P1F1-A3, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 150 | QVVEEIHNIF | 0.675 | Portion of SEQ |
| 2 | 153 | EEIHNIFAIK | 0.122 | ID NO: 11; each |
| 3 | 151 | VVEEIHNIFA | 0.060 | start position is |
| 4 | 152 | VEEIHNIFAI | 0.008 | specified, the |
| 5 | 154 | EIHNIFAIKS | 0.007 | length of each |
| 6 | 149 | PQVVEEIHNI | 0.004 | peptide is 10 |
| 7 | 156 | HNIFAIKSWA | 0.001 | amino acids, the |
| 8 | 147 | CDPQVVEEIH | 0.000 | end position for |

TABLE X (E)-continued

VARIANT 3 CDPQVVEEIHNIFAIKSWA
HLA PEPTIDE SCORING RESULTS-121P1F1-A3, 10-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 9 | 155 | IHNIFAIKSW | 0.000 | each peptide is |
| 10 | 148 | DPQVVEEIHN | 0.000 | the start position plus nine |

TABLE XI (E)

VARIANT 3 DPQVVEEIHNIFAIKSW
HLA PEPTIDE SCORING RESULTS-121P1F1-A11, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 154 | EIHNIFAIK | 0.120 | Portion of SEQ |
| 2 | 150 | QVVEEIHNI | 0.030 | ID NO: 11; each |
| 3 | 151 | VVEEIHNIF | 0.020 | start position is |
| 4 | 152 | VEEIHNIFA | 0.001 | specified, the |
| 5 | 153 | EEIHNIFAI | 0.001 | length of each |
| 6 | 148 | DPQVVEEIH | 0.001 | peptide is 9 |
| 7 | 156 | HNIFAIKSW | 0.000 | amino acids, the |
| 8 | 149 | PQVVEEIHN | 0.000 | end position for |
| 9 | 155 | IHNIFAIKS | 0.000 | each peptide is the start position plus eight |

TABLE XII (E)

VARIANT 3 CDPQVVEEIHNIFAIKSWA
HLA PEPTIDE SCORING RESULTS - 121P1F1 - A11, 10-MERS

| RANK | START POSITION | RESIDUE LISTING | SUBSEQUENCE Score (estimate of half time of disassociation of a molecule containing this subsequence) | |
|---|---|---|---|---|
| 1 | 151 | VVEEIHNIFA | 0.040 | Portion of SEQ ID NO: 11; each |
| 2 | 150 | QVVEEIHNIF | 0.030 | start position is specified, the |
| 3 | 153 | EEIHNIFAIK | 0.027 | length of each peptide is 10 |
| 4 | 152 | VEEIHNIFAI | 0.002 | amino acids, the end position for |
| 5 | 149 | PQVVEEIHNI | 0.001 | each peptide is the start position |
| 6 | 156 | HNIFAIKSWA | 0.001 | plus nine |
| 7 | 154 | EIHNIFAIKS | 0.000 | |
| 8 | 147 | CDPQVVEEIH | 0.000 | |
| 9 | 148 | DPQVVEEIHN | 0.000 | |
| 10 | 155 | IHNIFAIKSW | 0.000 | |

TABLE XIII (E)

VARIANT 3 DPQVVEEIHNIFAIKSW
HLA PEPTIDE SCORING RESULTS-121P1F1-A24, 9-MERS

| RANK | START POSITION | RESIDUE LISTING | SUBSEQUENCE SCORE (ESTIMATE OF HALF TIME OF DISASSOCIATION OF A MOLECULE CONTAINING THIS SUBSEQUENCE) | |
|---|---|---|---|---|
| 1 | 151 | VVEEIHNIF | 6.048 | Portion of SEQ |
| 2 | 150 | QVVEEIHNI | 1.800 | ID NO: 11; each |
| 3 | 156 | HNIFAIKSW | 0.150 | start position is |
| 4 | 153 | EEIHNIFAI | 0.150 | specified, the |
| 5 | 148 | DPQVVEEIH | 0.021 | length of each |
| 6 | 154 | EIHNIFAIK | 0.017 | peptide is 9 |
| 7 | 155 | IHNIFAIKS | 0.017 | amino acids, the |
| 8 | 149 | PQVVEEIHN | 0.015 | end position for |
| 9 | 152 | VEEIHNIFA | 0.015 | each peptide is the start position plus eight |

TABLE XIV (E)

VARIANT 3 CDPQVVEEIHNIFAIKSWA
HLA PEPTIDE SCORING RESULTS-121P1F1-A24, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | |
|---|---|---|---|---|
| 1 | 150 | QVVEEIHNIF | 6.048 | Portion of SEQ ID |
| 2 | 156 | HNIFAIKSWA | 0.210 | NO: 11; each |
| 3 | 151 | VVEEIHNIFA | 0.180 | start position is |
| 4 | 148 | DPQVVEEIHN | 0.150 | specified, the |
| 5 | 149 | PQVVEEIHNI | 0.150 | length of each |
| 6 | 152 | VEEIHNIFAI | 0.150 | peptide is 10 |
| 7 | 154 | EIHNIFAIKS | 0.110 | amino acids, the |
| 8 | 155 | IHNIFAIKSW | 0.015 | end position for |
| 9 | 153 | EEIHNIFAIK | 0.003 | each peptide is |
| 10 | 147 | CDPQVVEEIH | 0.002 | the start position plus nine |

TABLE XV (E)

VARIANT 3 DPQVVEEIHNIFAIKSW
HLA PEPTIDE SCORING RESULTS - 121P1F1 - B7, 9-MERS

| RANK | START POSITION | SUBSEQUENCE RESIDUE LISTING | Score (estimate of half time of disassociation of a molecule containing this subsequence) | |
|---|---|---|---|---|
| 1 | 150 | QVVEEIHNI | 2.000 | Portion of SEQ ID NO: 11; each |
| 2 | 148 | DPQVVEEIH | 0.200 | start position is specified, the |
| 3 | 153 | EEIHNIFAI | 0.040 | length of each peptide is 9 amino |
| 4 | 151 | VVEEIHNIF | 0.030 | acids, the end position for each |
| 5 | 156 | HNIFAIKSW | 0.020 | peptide is the start position plus |
| 6 | 154 | EIHNIFAIK | 0.010 | eight |
| 7 | 152 | VEEIHNIFA | 0.003 | |
| 8 | 149 | PQVVEEIHN | 0.002 | |
| 9 | 155 | IHNIFAIKS | 0.002 | |

TABLE XVI (E)

VARIANT 3 CDPQVVEEIHNIFAIKSWA
HLA PEPTIDE SCORING RESULTS - 121P1F1 - B7, 10-MERS

| RANK | START POSITION | SUBSEQUENCE RESIDUE LISTING | Score (estimate of half time of disassociation of a molecule containing this subsequence) | |
|---|---|---|---|---|
| 1 | 148 | DPQVVEEIHN | 0.400 | Portion of SEQ ID NO: 11; each |
| 2 | 151 | VVEEIHNIFA | 0.150 | start position is specified, the |
| 3 | 150 | QVVEEIHNIF | 0.100 | length of each peptide is 10 |
| 4 | 156 | HNIFAIKSWA | 0.100 | amino acids, the end position for |
| 5 | 149 | PQVVEEIHNI | 0.040 | each peptide is the start position |
| 6 | 154 | EIHNIFAIKS | 0.020 | plus nine |
| 7 | 152 | VEEIHNIFAI | 0.012 | |
| 8 | 155 | IHNIFAIKSW | 0.002 | |
| 9 | 153 | EEIHNIFAIK | 0.001 | |
| 10 | 147 | CDPQVVEEIH | 0.001 | |

TABLE XVII (E)

VARIANT 3 DPQVVEEIHNIFAIKSW
HLA PEPTIDE SCORING RESULTS - 121P1F1 - B35, 9-MERS

| RANK | START POSITION | SUBSEQUENCE RESIDUE LISTING | Score (estimate of half time of disassociation of a molecule containing this subsequence) | |
|---|---|---|---|---|
| 1 | 150 | QVVEEIHNI | 1.200 | Portion of SEQ ID NO: 11; each |
| 2 | 151 | VVEEIHNIF | 0.600 | start position is specified, the |
| 3 | 156 | HNIFAIKSW | 0.500 | length of each peptide is 9 amino |
| 4 | 148 | DPQVVEEIH | 0.200 | acids, the end position for each |
| 5 | 153 | EEIHNIFAI | 0.040 | peptide is the start position plus |
| 6 | 149 | PQVVEEIHN | 0.015 | eight |

TABLE XVII (E)-continued

VARIANT 3 DPQVVEEIHNIFAIKSW
HLA PEPTIDE SCORING RESULTS - 121P1F1 - B35, 9-MERS

| RANK | START POSITION | SUBSEQUENCE RESIDUE LISTING | Score (estimate of half time of disassociation of a molecule containing this subsequence) |
|---|---|---|---|
| 7 | 154 | EIHNIFAIK | 0.010 |
| 8 | 155 | IHNIFAIKS | 0.010 |
| 9 | 152 | VEEIHNIFA | 0.003 |

TABLE XVIII (E)

VARIANT 3 CDPQVVEEIHNIFAIKSWA
HLA PEPTIDE SCORING RESULTS - 121P1F1 - B35, 10-MERS

| RANK | START POSITION | SUBSEQUENCE RESIDUE LISTING | Score (estimate of half time of disassociation of a molecule containing this subsequence) | |
|---|---|---|---|---|
| 1 | 148 | DPQVVEEIHN | 3.000 | Portion of SEQ ID NO: 11; each |
| 2 | 150 | QVVEEIHNIF | 2.000 | start position is specified, the |
| 3 | 154 | EIHNIFAIKS | 0.100 | length of each peptide is 10 |
| 4 | 156 | HNIFAIKSWA | 0.100 | amino acids, the end position for |
| 5 | 149 | PQVVEEIHNI | 0.060 | each peptide is the start position |
| 6 | 151 | VVEEIHNIFA | 0.060 | plus nine |
| 7 | 155 | IHNIFAIKSW | 0.050 | |
| 8 | 152 | VEEIHNIFAI | 0.012 | |
| 9 | 153 | EEIHNIFAIK | 0.001 | |
| 10 | 147 | CDPQVVEEIH | 0.001 | |

TABLE XIX

Motifs and Post-translational Modifications of 121P1F1

Protein kinase C phosphorylation site
Number of matches: 4

| | |
|---|---|
| 1 | 2-4 SKK |
| 2 | 46-48 SVK |
| 3 | 97-99 SQK |
| 4 | 129-131 SLR |

TABLE XIX-continued

Motifs and Post-translational Modifications of 121P1F1

Casein kinase II phosphorylation site
Number of matches: 4

| | |
|---|---|
| 1 | 8-11 SAEE |
| 2 | 46-49 SVKE |
| 3 | 53-56 SLVD |
| 4 | 129-132 SLRD |

N-myristoylation site

| | |
|---|---|
| | 58-63 GMVDCE |

TABLE XX

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |

TABLE XX-continued

Frequently Occurring Motifs

| Name | avrg. % identity | Description | Potential Function |
|---|---|---|---|
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored_q1 | 32% | NADH-Ubiquinone/plastoquinone (complex I), various chains | membrane associated. Involved in proton translocation across the membrane |
| efhand | 24% | EF hand | calcium-binding domain, consists of a12 residue loop flanked on both sides by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XXI

Properties of 121P1F1

| | Bioinformatic Program | URL located on the World Wide Web at | Outcome |
|---|---|---|---|
| 121P1F1 | | | |
| ORF | ORF finder | | 618 bp |
| Protein length | | | 205 aa |
| Transmembrane region | TM Pred | .ch.embnet.org/ | no TM |
| | HMMTop | .enzim.hu/hmmtop/ | no TM, intracellular |
| | Sosui | .genome.ad.jp/SOSui/ | no TM, soluble protein |
| | TMHMM | .cbs.dtu.dk/services/TMHMM | no TM |
| Signal Peptide | Signal P | .cbs.dtu.dk/services/SignalP/ | none |
| pI | pI/MW tool | .expasy.ch/tools/ | 8.28 |
| Molecular weight | pI/MW tool | .expasy.ch/tools/ | 23.7 kDa |
| Localization | PSORT | /psort.nibb.ac.jp/ | 30% nuclear, 10% mitochondrial |
| | PSORT II | /psort.nibb.ac.jp/ | 65% nuclear, 17% cytoplasmic |
| Motifs | Pfam | .sanger.ac.uk/Pfam/ | Basic Zipper motif, Myc leucine zipper |
| | Prints | .biochem.ucl.ac.uk/ | Steroid hormone receptor signature |
| | Blocks | .blocks.fhcrc.org/ | no significant motif |
| Variant 1A | | | |
| ORF | ORF finder | | 618 bp |
| Protein length | | | 126 aa |
| Transmembrane region | TM Pred | .ch.embnet.org/ | no TM |
| | HMMTop | .enzim.hu/hmmtop/ | no TM, extracellular |
| | Sosui | .genome.ad.jp/SOSui/ | no TM, soluble protein |
| | TMHMM | .cbs.dtu.dk/services/TMHMM | no TM |
| Signal Peptide | Signal P | .cbs.dtu.dk/services/SignalP/ | none |
| pI | pI/MW tool | .expasy.ch/tools/ | 8.65 |
| Molecular weight | pI/MW tool | .expasy.ch/tools/ | 14.3 kDa |
| Localization | PSORT | psort.nibb.ac.jp/ | 30% nuclear, 11% peroxisome |
| | PSORT II | psort.nibb.ac.jp/ | 30% nuclear, 52.2% cytoplasmic |

TABLE XXI-continued

Properties of 121P1F1

| | Bioinformatic Program | URL located on the World Wide Web at | Outcome |
|---|---|---|---|
| Motifs | Pfam | .sanger.ac.uk/Pfam/ | no significant motif |
| | Prints | .biochem.ucl.ac.uk/ | no significant motif |
| | Blocks | .blocks.fhcrc.org/ | no significant motif |
| Variant 4 | | | |
| ORF | ORF finder | | 618 bp |
| Protein length | | | 190 aa |
| Transmembrane region | TM Pred | .ch.embnet.org/ | no TM |
| | HMMTop | .enzim.hu/hmmtop/ | no TM, intracellular |
| | Sosui | .genome.ad.jp/SOSui/ | no TM, soluble protein |
| | TMHMM | .cbs.dtu.dk/services/TMHMM | no TM |
| Signal Peptide | Signal P | .cbs.dtu.dk/services/SignalP/ | none |
| pI | pI/MW tool | .expasy.ch/tools/ | 6.05 |
| Molecular weight | pI/MW tool | .expasy.ch/tools/ | 22.02 kDa |
| Localization | PSORT | psort.nibb.ac.jp/ | 30% nuclear, 10% mitochondrial matrix space, 10% lysosome |
| | PSORT II | psort.nibb.ac.jp/ | 65.2% nuclear, 21.7% mitochondrial, 13% cytoplasmic |
| Motifs | Pfam | .sanger.ac.uk/Pfam/ | bZip transcription factor Myc leucine zipper |
| | Prints | .biochem.ucl.ac.uk/ | steroid hormone receptor signature |
| | Blocks | .blocks.fhcrc.org/ | no significant motif |

TABLE XXIIA

Nucleotide sequence of splice variant 1. (SEQ ID NO 41).

```
ccaaaatcaa acgcgtccgg gcctgtcccg                    60
cccctctccc caagcgcggg cccggccagc ggaagcccct gcgcccgcgc catgtcaaag                   120
aaaaaaggac tgagtgcaga agaaaagaga actcgcatga tggaaatatt ttctgaaaca                   180
aaagatgtat ttcaattaaa agacttggag aagattgctc ccaaagagaa aggcattact                   240
gctatgtcag taaaagaagt ccttcaaagc ttagttgatg atggtatggt tgactgtgag                   300
aggatcggaa cttctaatta ttattgggct tttccaagta aagctcttca tgcaaggaaa                   360
cataagttgg aggttctgga atctcaggac cctggctgct gcttccatga aataattaaa                   420
gtctcctatt atagaaaatt ctggctgggc gcagtggctc acgcctgtaa tcccagcact                   480
ttgggaggct gaggcgggca gatcacgagg tgactttccc ccaccccac atgaagtgca                    540
agatggagtt gtctgaggga agtcaaaagc atgcaagcct acagaaaagc attgagaaag                   600
ctaaaattgg ccgatgtgaa acgaagagc gaaccaggct agcaaaagag ctttcttcac                   660
ttcgagacca aagggaacag ctaaaggcag aagtagaaaa atacaaagac tgtgatccgc                   720
aagttgtgga agaaatacgc caagcaaata aagtagccaa agaagctgct aacagatgga                   780
ctgataacat attcgcaata aaatcttggg ccaaaagaaa atttgggttt gaagaaaata                   840
aaattgatag aacttttgga attccagaag actttgacta catagactaa aatattccat                   900
ggtggtgaag gatgtacaag cttgtgaata tgtaaatttt aaactattat ctaactaagt                   960
gtactgaatt gtcgtttgcc tgtaactgtg tttatcattt tattaatgtt aaataaagtg                  1020
taaaatgcaa aaaaaaaaa aaaaaaaaa aaaaaaaa                                          1028
```

TABLE XXIIIA

Nucleotide sequence alignment of 121P1F1 (SEQ ID NO 42) with splice variant 1. (SEQ ID NO 43).

```
Score = 687 bits (357), Expect = 0.0 Identities = 357/357 (100%) Strand = Plus/Plus 121P1F1   : 1    ccaaaatcaaacgcgtccgggcctgtcccgcccctctccccaagcgcgggcccggccagc    60
                 ||||||||||||||||||||||||||||||||||||||||||||||||||||||||||||
Variant 1: 1    ccaaaatcaaacgcgtccgggcctgtcccgcccctctccccaagcgcgggcccggccagc    60

121P1F1   : 61   ggaagcccctgcgcccgcgccatgtcaaagaaaaaaggactgagtgcagaagaaaagaga   120
                 ||||||||||||||||||||||||||||||||||||||||||||||||||||||||||||
Variant 1: 61   ggaagcccctgcgcccgcgccatgtcaaagaaaaaaggactgagtgcagaagaaaagaga   120
```

TABLE XXIIIA-continued

Nucleotide sequence alignment of 121P1F1 (SEQ ID NO 42) with splice variant 1. (SEQ ID NO 43).

```
121P1F1    : 121  actcgcatgatggaaatattttctgaaacaaaagatgtatttcaattaaaagacttggag  180
                  ||||||||||||||||||||||||||||||||||||||||||||||||||||||||||||
Variant 1: 121   actcgcatgatggaaatattttctgaaacaaaagatgtatttcaattaaaagacttggag  180

121P1F1    : 181  aagattgctcccaaagagaaaggcattactgctatgtcagtaaaagaagtccttcaaagc  240
                  ||||||||||||||||||||||||||||||||||||||||||||||||||||||||||||
Variant 1: 181   aagattgctcccaaagagaaaggcattactgctatgtcagtaaaagaagtccttcaaagc  240

121P1F1    : 241  ttagttgatgatggtatggttgactgtgagaggatcggaacttctaattattattgggct  300
                  ||||||||||||||||||||||||||||||||||||||||||||||||||||||||||||
Variant 1: 241   ttagttgatgatggtatggttgactgtgagaggatcggaacttctaattattattgggct  300

121P1F1    : 301  tttccaagtaaagctcttcatgcaaggaaacataagttggaggttctggaatctcag    357
                  ||||||||||||||||||||||||||||||||||||||||||||||||||||||||
Variant 1: 301   tttccaagtaaagctcttcatgcaaggaaacataagttggaggttctggaatctcag    357

Score = 985 bits (512), Expect = 0.0 Identities = 512/512 (100%) Strand = Plus/Plus 121P1F1    : 356  agttgtctgagggaagtcaaaagcatgcaagcctacagaaaagcattgagaaagctaaaa  415
                  ||||||||||||||||||||||||||||||||||||||||||||||||||||||||||||
Variant 1: 517   agttgtctgagggaagtcaaaagcatgcaagcctacagaaaagcattgagaaagctaaaa  576

121P1F1    : 417  ttgggcgatgtgaaacggaagagcgaaccaggctagcaaaagagctttcttcacttcgag  475
                  ||||||||||||||||||||||||||||||||||||||||||||||||||||||||||||
Variant 1: 577   ttgggcgatgtgaaacggaagagcgaaccaggctagcaaaagagctttcttcacttcgag  636

121P1F1    : 476  accaagggaacagctaaaggcagaagtagaaaaatacaaagactgtgatccgcaagttg   535
                  ||||||||||||||||||||||||||||||||||||||||||||||||||||||||||||
Variant 1: 637   accaagggaacagctaaaggcagaagtagaaaaatacaaagactgtgatccgcaagttg   696

121P1F1    : 536  tggaagaaatacgccaagcaaataaagtagccaaagaagctgctaacagatggactgata  595
                  ||||||||||||||||||||||||||||||||||||||||||||||||||||||||||||
Variant 1: 697   tggaagaaatacgccaagcaaataaagtagccaaagaagctgctaacagatggactgata  756

121P1F1    : 596  acatattcgcaataaaatcttgggccaaaagaaaatttgggtttgaagaaaataaaattg  655
                  ||||||||||||||||||||||||||||||||||||||||||||||||||||||||||||
Variant 1: 757   acatattcgcaataaaatcttgggccaaaagaaaatttgggtttgaagaaaataaaattg  816

121P1F1    : 656  atagaacttttggaattccagaagactttgactacatagactaaaatattccatggtggt  715
                  ||||||||||||||||||||||||||||||||||||||||||||||||||||||||||||
Variant 1: 817   atagaacttttggaattccagaagactttgactacatagactaaaatattccatggtggt  876

121P1F1    : 716  gaaggatgtacaagcttgtgaatatgtaaattttaaactattatctaactaagtgtactg  775
                  ||||||||||||||||||||||||||||||||||||||||||||||||||||||||||||
Variant 1: 877   gaaggatgtacaagcttgtgaatatgtaaattttaaactattatctaactaagtgtactg  936

121P1F1    : 776  aattgtcgtttgcctgtaactgtgtttatcattttattaatgttaaataaagtgtaaaat  835
                  ||||||||||||||||||||||||||||||||||||||||||||||||||||||||||||
Variant 1: 937   aattgtcgtttgcctgtaactgtgtttatcattttattaatgttaaataaagtgtaaaat  996

121P1F1    : 836  gcaaaaaaaaaaaaaaaaaaaaaaaaaaaaaa                              867
                  ||||||||||||||||||||||||||||||||
Variant 1: 997   gcaaaaaaaaaaaaaaaaaaaaaaaaaaaaaa                              1028
```

TABLE XXIVA

Amino acid sequence alignment of 121P1F1 (SEQ ID NO 44) and splice variant 1. (SEQ ID NO 45).

Score = 183 bits (465), Expect = 6e-47 Identities = 92/92 (100%), Positives = 92/92 (100%)

```
121P1F1:    1  MSKKKGLSAEEKRTRMMEIFSETKD-     60
               VFQLKDL
               EKIAPKEKGITAMSVKEVLQSLVDDGMV
               MSKKKGLSAEEKRTRMMEIFSETKD-
               VFQLKDL
               EKIAPKEKGITAMSVKEVLQSLVDDGMV
Variant 1A: 1  MSKKKGLSAEEKRTRMMEIFSETKDVFQ   60
               LKDLEKIAPKEKGITAMSVKEVLQS-
               LVDDGMV 121P1F1:    61 DCERIGTSNYYWAFPSKALHARKHKLEV-   92
               LESQ
               DCERIGTSNYYWAFPSKALHARKHKLEV-
               LESQ
Variant 1A: 61 DCERIGTSNYYWAFPSKALHARKHKLEV-   92
               LESQ
```

TABLE XXIVA-continued

Amino acid sequence alignment of 121P1F1 (SEQ ID NO 44) and splice variant 1. (SEQ ID NO 45).

```
Score = 229 bits (584), Expect = 1e-60 Identities =
113/114 (99%), Positives = 114/114 (99%)

121P1F1:    92 QLSEGSQKHASLQKSIEKAKIGRCET-    151
               EERTRL
               AKELSSLRDQREQLKAEVEKYKDCDPQV
               +LSEGSQKHASLQKSIEKAKIGRCETEERT
               RLAKELSSLRDQREQLKAEVEKYKDCDPQV
Variant 1B:  6 ELSEGSQKHASLQKSIEKAKIGRCET-     65
               EERTRL
               AKELSSLRDQREQLKAEVEKYKDCDPQV 121P1F1:   152 VEEIRQANKVAKEAANRWTDNIFAIK-    205
               SWAKRK
               FGFEENKIDRTFGIPEDFDYID
               VEEIRQANKVAKEAANRWTDNIFAIKSWAKR
               KFGFEENKIDRTFGIPEDFDYID
Variant 1B: 66 VEEIRQANKVAKEAANRWTDNIFAIKSW    119
               AKRKFGFEENKIDRTFGIPEDFDYID
```

TABLE XXVA

Peptide sequences from the translation of the nucleotide sequence of splice variant 1.

```
>splice variant 1A ORF: 82 . . . 462
Frame +1 (SEQ ID NO 46).
MSKKKGLSAE EKRTRMMEIF SETKDVFQLK       60
DLEKIAPKEK GITAMSVKEV LQSLVDDGMV

DCERIGTSNY YWAFPSKALH ARKHKLEVLE      120
SQDPGCCFHE IIKVSYYRKF WLGAVAHACN

PSTLGG                                126

>splice variant 1B ORF: 501 . . . 860
Frame +3 (SEQ ID NO 47).
MKCKMELSEG SQKHASLQKS IEKAKIGRCE       60
TEERTRLAKE LSSLRDQREQ LKAEVEKYKD

CDPQVVEEIR QANKVAKEAA NRWTDNIFAI      119
KSWAKRKFGF EENKIDRTFG IPEDFDYID
```

TABLE XXIIB

Nucleotide sequence of splice variant 2. (SEQ ID NO 48).

```
ccaaaatcaa acgcgtccgg gcctgtcccg       60
cccctctccc caagcgcggg cccggccagc ggaagcccct gcgcccgcgc catgtcaaag      120
aaaaaaggac tgagtgcaga agaaaagaga actcgcatga tggaaatatt ttctgaaaca      180
aaagatgtat ttcaattaaa agacttggag aagattgctc ccaaagagaa aggcattact      240
gctatgtcag taaaagaagt ccttcaaagc ttagttgatg atggtatggt tgactgtgag      300
aggatcggaa cttctaatta ttattgggct tttccaagta aagctcttca tgcaggaaaa      360
cataagttgg aggttctgga atctcagttg tctgagggaa gtcaaaagca tgcaagccta      420
cagaaaagca ttgagaaagc taaaattggc cgatgtgaaa cggccaagca aataaagtag      480
ccaaagaagc tgctaacaga tggactgata acatattcgc aataaaatct tgggccaaaa      540
gaaaatttgg gtttgaagaa aataaaattg atagaacttt tggaattcca gaagactttg      600
actacataga ctaaaatatt ccatggtggt gaaggatgta caagcttgtg aatatgtaaa      660
ttttaaacta ttatctaact aagtgtactg aattgtcgtt tgcctgtaac tgtgtttatc      720
atttattaa tgttaaataa agtgtaaaat gcaaaaaaaa aaaaaaaaa aaaaaaaaa aa      752
```

TABLE XXIIIB

Nucleotide sequence alignment of 121P1F1 (SEQ ID NO 49) with splice variant 2. (SEQ ID NO 50)

```
Score = 833 bits (433), Expect = 0.0 Identities = 433/433 (100%) Strand = Plus/Plus 121P1F1   : 1    ccaaaatcaaacgcgtccgggcctgtcccgcccctctccccaagcgcgggcccggccagc    60
                 ||||||||||||||||||||||||||||||||||||||||||||||||||||||||||||
Variant 2: 1    ccaaaatcaaacgcgtccgggcctgtcccgcccctctccccaagcgcgggcccggccagc    60

121P1F1   : 61   ggaagcccctgcgcccgcgccatgtcaaagaaaaaaggactgagtgcagaagaaaagaga   120
                 ||||||||||||||||||||||||||||||||||||||||||||||||||||||||||||
Variant 2: 61   ggaagcccctgcgcccgcgccatgtcaaagaaaaaaggactgagtgcagaagaaaagaga   120

121P1F1   : 121  actcgcatgatggaaatattttctgaaacaaaagatgtatttcaattaaaagacttggag   180
                 ||||||||||||||||||||||||||||||||||||||||||||||||||||||||||||
Variant 2: 121  actcgcatgatggaaatattttctgaaacaaaagatgtatttcaattaaaagacttggag   180

121P1F1   : 181  aagattgctcccaaagagaaaggcattactgctatgtcagtaaaagaagtccttcaaagc   240
                 ||||||||||||||||||||||||||||||||||||||||||||||||||||||||||||
Variant 2: 181  aagattgctcccaaagagaaaggcattactgctatgtcagtaaaagaagtccttcaaagc   240

121P1F1   : 241  ttagttgatgatggtatggttgactgtgagaggatcggaacttctaattattattgggct   300
                 ||||||||||||||||||||||||||||||||||||||||||||||||||||||||||||
Variant 2: 241  ttagttgatgatggtatggttgactgtgagaggatcggaacttctaattattattgggct   300
```

TABLE XXIIIB-continued

Nucleotide sequence alignment of 121P1F1 (SEQ ID NO 49) with splice variant 2. (SEQ ID NO 50)

```
121P1F1    : 301  tttccaagtaaagctcttcatgcaaggaaacataagttggaggttctggaatctcagttg  360
                  ||||||||||||||||||||||||||||||||||||||||||||||||||||||||||||
Variant 2: 301   tttccaagtaaagctcttcatgcaaggaaacataagttggaggttctggaatctcagttg  360

121P1F1    : 361  tctgagggaagtcaaaagcatgcaagcctacagaaaagcattgagaaagctaaaattggc  420
                  ||||||||||||||||||||||||||||||||||||||||||||||||||||||||||||
Variant 2: 361   tctgagggaagtcaaaagcatgcaagcctacagaaaagcattgagaaagctaaaattggc  420

121P1F1    : 421  cgatgtgaaacgg    433
                  |||||||||||||
Variant 2: 421   cgatgtgaaacgg    433
```

Score = 615 bits (320), Expect = e-173 Identities = 320/320 (100%) Strand = Plus/
Plus 121P1F1 = (SEQ ID NO 51), Variant 2 = (SEQ ID NO 52)

```
121P1F1    : 548  gccaagcaaataaagtagccaaagaagctgctaacagatggactgataacatattcgcaa  607
                  ||||||||||||||||||||||||||||||||||||||||||||||||||||||||||||
Variant 2: 433   gccaagcaaataaagtagccaaagaagctgctaacagatggactgataacatattcgcaa  492

121P1F1    : 608  taaaatcttgggccaaaagaaaatttgggtttgaagaaaataaaattgatagaacttttg  667
                  ||||||||||||||||||||||||||||||||||||||||||||||||||||||||||||
Variant 2: 493   taaaatcttgggccaaaagaaaatttgggtttgaagaaaataaaattgatagaacttttg  552

121P1F1    : 668  gaattccagaagactttgactacatagactaaaatattccatggtggtgaaggatgtaca  727
                  ||||||||||||||||||||||||||||||||||||||||||||||||||||||||||||
Variant 2: 553   gaattccagaagactttgactacatagactaaaatattccatggtggtgaaggatgtaca  612

121P1F1    : 728  agcttgtgaatatgtaaattttaaactattatctaactaagtgtactgaattgtcgtttg  787
                  ||||||||||||||||||||||||||||||||||||||||||||||||||||||||||||
Variant 2: 613   agcttgtgaatatgtaaattttaaactattatctaactaagtgtactgaattgtcgtttg  672

121P1F1    : 788  cctgtaactgtgtttatcattttattaatgttaaataaagtgtaaaatgcaaaaaaaaaa  847
                  ||||||||||||||||||||||||||||||||||||||||||||||||||||||||||||
Variant 2: 673   cctgtaactgtgtttatcattttattaatgttaaataaagtgtaaaatgcaaaaaaaaaa  732

121P1F1    : 848  aaaaaaaaaaaaaaaaaaa    867
                  |||||||||||||||||||
Variant 2: 733   aaaaaaaaaaaaaaaaaaa    752
```

TABLE XXIVB

Amino acid sequence alignment of 121P1F1 (SEQ ID NO 53) and splice variant 2. (SEQ ID NO 54)

Score = 232 bits (591), Expect = 2e-61 Identities = 117/122 (95%),
Positives = 120/122 (97%)

```
121P1F1:      1 MSKKKGLSAEEKRTRMMEIFSETKDVFQLKDLEKIAPKEKGITAMSVKEVLQSLVDDGMV   60
                MSKKKGLSAEEKRTRMMEIFSETKDVFQLKDLEKIAPKEKGITAMSVKEVLQSLVDDGMV
Variant 2:    1 MSKKKGLSAEEKRTRMMEIFSETKDVFQLKDLEKIAPKEKGITAMSVKEVLQSLVDDGMV   60

121P1F1:     61 DCERIGTSNYYWAFPSKALHARKHKLEVLESQLSEGSQKHASLQKSIEKAKIGRCETEER  120
                DCERIGTSNYYWAFPSKALHARKHKLEVLESQLSEGSQKHASLQKSIEKAKIGRCET ++
Variant 2:   61 DCERIGTSNYYWAFPSKALHARKHKLEVLESQLSEGSQKHASLQKSIEKAKIGRCETAKQ  120

121P1F1:    121 TR    122
                 +
Variant 2:  121 IK    122
```

TABLE XXVB

Peptide sequences from the translation of the nucleotide sequence of splice variant 2. (SEQ ID NO 55)

```
MSKKKGLSAE EKRTRMMEIF SETKDVFQLK DLEKIAPKEK GITAMSVKEV LQSLVDDGMV    60

DCERIGTSNY YWAFPSKALH ARKHKLEVLE SQLSEGSQKH ASLQKSIEKA KIGRCEIAKQ   120

IK                                                                 122
```

TABLE XXIIC

Nucleotide sequence of splice variant 3. (SEQ ID NO 56).

```
ccaaaatcaa acgcgtccgg gcctgtcccg cccctctccc caagcgcggg cccggccagc    60
ggaagcccct gcgcccgcgc catgtcaaag aaaaaaggac tgagtgcaga agaaaagaga   120
actcgcatga tggaaatatt ttctgaaaca aagatgtat ttcaattaaa agacttggag    180
aagattgctc ccaaagagaa aggcattact gctatgtcag taaaagaagt ccttcaaagc   240
ttagttgatg atggtatggt tgactgtgag aggatcggaa cttctaatta ttattgggct   300
tttccaagta aagctcttca tgcaaggaaa cataagttgg aggttctgga atctcagttg   360
tctgagggaa gtcaaaagca tgcaagccta cagaaaagca ttgagaaagc taaaattggc   420
cgatgtgaaa cggaagagcg aaccaggcta gcaaaagagc tttcttcact tcgagaccaa   480
agggaacagc taaaggcaga agtagaaaaa tacaaagact gtgatccgca agttgtggaa   540
gaaatacata acatattcgc aataaaatct tgggccaaaa gaaaatttgg gtttgaagaa   600
aataaaattg atagaacttt tggaattcca gaagactttg actacataga ctaaaatatt   660
ccatggtggt gaaggatgta caagcttgtg aatatgtaaa ttttaaacta ttatctaact   720
aagtgtactg aattgtcgtt tgcctgtaac tgtgtttatc attttattaa tgttaaataa   780
agtgtaaaat gcaaaaaaaa aaaaaaaaaa aaaaaaaaa  aa                      822
```

TABLE XXIIIC

Nucleotide sequence alignment of 121P1F1 (SEQ ID NO 57) with splice variant 3. (SEQ ID NO 58).

```
Score = 1052 bits (547), Expect = 0.0 Identities = 547/547 (100%) Strand = Plus/Plus 121P1F1    :   1   ccaaaatcaaacgcgtccgggcctgtcccgcccctctccccaagcgcgggcccggccagc    60
                   ||||||||||||||||||||||||||||||||||||||||||||||||||||||||||||
Variant 3: 1   ccaaaatcaaacgcgtccgggcctgtcccgcccctctccccaagcgcgggcccggccagc    60

121P1F1    :  61   ggaagcccctgcgcccgcgccatgtcaaagaaaaaaggactgagtgcagaagaaaagaga   120
                   ||||||||||||||||||||||||||||||||||||||||||||||||||||||||||||
Variant 3: 61   ggaagcccctgcgcccgcgccatgtcaaagaaaaaaggactgagtgcagaagaaaagaga   120

121P1F1    : 121   actcgcatgatggaaatattttctgaaacaaagatgtatttcaattaaaagacttggag   180
                   ||||||||||||||||||||||||||||||||||||||||||||||||||||||||||||
Variant 3: 121   actcgcatgatggaaatattttctgaaacaaagatgtatttcaattaaaagacttggag   180

121P1F1    : 181   aagattgctcccaaagagaaaggcattactgctatgtcagtaaaagaagtccttcaaagc   240
                   ||||||||||||||||||||||||||||||||||||||||||||||||||||||||||||
Variant 3: 181   aagattgctcccaaagagaaaggcattactgctatgtcagtaaaagaagtccttcaaagc   240

121P1F1    : 241   ttagttgatgatggtatggttgactgtgagaggatcggaacttctaattattattgggct   300
                   ||||||||||||||||||||||||||||||||||||||||||||||||||||||||||||
Variant 3: 241   ttagttgatgatggtatggttgactgtgagaggatcggaacttctaattattattgggct   300

121P1F1    : 301   tttccaagtaaagctcttcatgcaaggaaacataagttggaggttctggaatctcagttg   360
                   ||||||||||||||||||||||||||||||||||||||||||||||||||||||||||||
Variant 3: 301   tttccaagtaaagctcttcatgcaaggaaacataagttggaggttctggaatctcagttg   360

121P1F1    : 361   tctgagggaagtcaaaagcatgcaagcctacagaaaagcattgagaaagctaaaattggc   420
                   ||||||||||||||||||||||||||||||||||||||||||||||||||||||||||||
Variant 3: 361   tctgagggaagtcaaaagcatgcaagcctacagaaaagcattgagaaagctaaaattggc   420

121P1F1    : 421   cgatgtgaaacggaagagcgaaccaggctagcaaaagagctttcttcacttcgagaccaa   480
                   ||||||||||||||||||||||||||||||||||||||||||||||||||||||||||||
Variant 3: 421   cgatgtgaaacggaagagcgaaccaggctagcaaaagagctttcttcacttcgagaccaa   480

121P1F1    : 481   agggaacagctaaaggcagaagtagaaaaatacaaagactgtgatccgcaagttgtggaa   540
                   ||||||||||||||||||||||||||||||||||||||||||||||||||||||||||||
Variant 3: 481   agggaacagctaaaggcagaagtagaaaaatacaaagactgtgatccgcaagttgtggaa   540
```

TABLE XXIIIC-continued

Nucleotide sequence alignment of 121P1F1 (SEQ ID NO 57) with splice variant 3. (SEQ ID NO 58).

```
121P1F1   : 541 gaaatac   547
                |||||||
Variant 3 : 541 gaaatac   547

Score = 529 bits (275), Expect = e-147 Identities = 275/275 (100%) Strand = Plus/
Plus 121P1F1 = (SEQ ID NO 59), Variant 3 = (SEQ ID NO 60).

121P1F1   : 593 ataacatattcgcaataaaatcttgggccaaaagaaaatttgggtttgaagaaaataaaa   652
                ||||||||||||||||||||||||||||||||||||||||||||||||||||||||||||
Variant 3 : 548 ataacatattcgcaataaaatcttgggccaaaagaaaatttgggtttgaagaaaataaaa   607

121P1F1   : 653 ttgatagaacttttggaattccagaagactttgactacatagactaaaatattccatggt   712
                ||||||||||||||||||||||||||||||||||||||||||||||||||||||||||||
Variant 3 : 608 ttgatagaacttttggaattccagaagactttgactacatagactaaaatattccatggt   667

121P1F1   : 713 ggtgaaggatgtacaagcttgtgaatatgtaaattttaaactattatctaactaagtgta   772
                ||||||||||||||||||||||||||||||||||||||||||||||||||||||||||||
Variant 3 : 668 ggtgaaggatgtacaagcttgtgaatatgtaaattttaaactattatctaactaagtgta   727

121P1F1   : 773 ctgaattgtcgtttgcctgtaactgtgtttatcattttattaatgttaaataaagtgtaa   832
                ||||||||||||||||||||||||||||||||||||||||||||||||||||||||||||
Variant 3 : 728 ctgaattgtcgtttgcctgtaactgtgtttatcattttattaatgttaaataaagtgtaa   787

121P1F1   : 833 aatgcaaaaaaaaaaaaaaaaaaaaaaaaaaaaa   867
                |||||||||||||||||||||||||||||||||||
Variant 3 : 788 aatgcaaaaaaaaaaaaaaaaaaaaaaaaaaaaa   822
```

TABLE XXIVC

Amino acid sequence alignment of 121P1F1 (SEQ ID NO 61) and splice variant 3. (SEQ ID NO 62).

```
Score = 365 bits (937), Expect = e-101 Identities = 189/205 (92%),
Positives = 189/205 (92%), Gaps = 15/205 (7%)
121P1F1:    1 MSKKKGLSAEEKRTRMMEIFSETKDVFQLKDLEKIAPKEKGITAMSVKEVLQSLVDDGMV   60
              MSKKKGLSAEEKRTRMMEIFSETKDVFQLKDLEKIAPKEKGITAMSVKEVLQSLVDDGMV
Variant 3:  1 MSKKKGLSAEEKRTRMMEIFSETKDVFQLKDLEKIAPKEKGITAMSVKEVLQSLVDDGMV   60

121P1F1:   61 DCERIGTSNYYWAFPSKALHARKHKLEVLESQLSEGSQKHASLQKSIEKAKIGRCETEER  120
              DCERIGTSNYYWAFPSKALHARKHKLEVLESQLSEGSQKHASLQKSIEKAKIGRCETEER
Variant 3: 61 DCERIGTSNYYWAFPSKALHARKHKLEVLESQLSEGSQKHASLQKSIEKAKIGRCETEER  120

121P1F1:  121 TRLAKELSSLRDQREQLKAEVEKYKDCDPQVVEEIRQANKVAKEAANRWTDNIFAIKSWA  180
              TRLAKELSSLRDQREQLKAEVEKYKDCDPQVVEEI             NIFAIKSWA
Variant 3:121 TRLAKELSSLRDQREQLKAEVEKYKDCDPQVVEEIH---------------NIFAIKSWA  165

121P1F1:  181 KRKFGFEENKIDRTFGIPEDFDYID                                     205
              KRKFGFEENKIDRTFGIPEDFDYID
Variant 3:166 KRKFGFEENKIDRTFGIPEDFDYID                                     190
```

TABLE XXVC

Peptide sequences from the translation of the nucleotide sequence of splice variant 3. (SEQ ID NO 63).

```
MSKKKGLSAE EKRTRMMEIF SETKDVFQLK      60
DLEKIAPKEK GITAMSVKEV LQSLVDDGMV

DCERIGTSNY YWAFPSKALH ARKHKLEVLE     120
SQLSEGSQKH ASLQKSIEKA KIGRCETEER

TRLAKELSSL RDQREQLKAE VEKYKDCDPQ     180
VVEEIHNIFA IKSWAKRKFG FEENKIDRTF

GIPEDFDYID                          190
```

TABLE XXIID

Nucleotide sequence of splice variant 4. (SEQ ID NO 64).

```
gttttctgta ttgtaatatg tagagcacat      60
tccagaactg ctcagtttcg agttacctaa tggatcttca ctgtgtgcca attagtcgat     120
ttctgtgaaa acgccccaggt ttctgccaaa gggcaggagt cgctgctctt gtgccgggtg     180
ctgctggttg tgtagggcgc tgttgctttt ttaaggacgc tctgcactga attaggcttc     240
ctcgtgggtc atgatcagtt aagtcctgtc aaagaaaaaa ggactgagtg cagaagaaaa     300
gagaactcgc atgatggaaa tattttctga
```

TABLE XXIID-continued

Nucleotide sequence of splice variant 4.
(SEQ ID NO 64).

| | | | |
|---|---|---|---|
| aacaaaagat | gtatttcaat | taaaagactt | 360 |
| ggagaagatt | gctcccaaag | agaaaggcat | |
| tactgctatg | tcagtaaaag | aagtccttca | 420 |
| aagcttagtt | gatgatggta | tggttgactg | |
| tgagaggatc | ggaacttcta | attattattg | 480 |
| ggcttttcca | agtaaagctc | ttcatgcaag | |
| gaaacataag | ttggaggttc | tggaatctca | 540 |
| gttgtctgag | ggaagtcaaa | agcatgcaag | |
| cctacagaaa | agcattgaga | aagctaaaat | 600 |
| tggccgatgt | gaaacggaag | agcgaaccag | |
| gctagcaaaa | gagcttcctt | cacttcgaga | 660 |
| ccaaagggaa | cagctaaagg | cagaagtaga | |
| aaaatacaaa | gactgtgatc | cgcaagttgt | 720 |
| ggaagaaata | cgccaagcaa | ataaagtagc | |
| caaagaagct | gctaacagat | ggactgataa | 780 |
| catattcgca | ataaaatctt | gggccaaaag | |

TABLE XXIID-continued

Nucleotide sequence of splice variant 4.
(SEQ ID NO 64).

| | | | |
|---|---|---|---|
| aaaatttggg | tttgaagaaa | ataaaattga | 840 |
| tagaactttt | ggaattccag | aagactttga | |
| ctacatagac | taaatattc | catggtggtg | 900 |
| aaggatgtac | aagcttgtga | atatgtaaat | |
| tttaaactat | tatctaacta | agtgtactga | 960 |
| attgtcgttt | gcctgtaact | gtgtttatca | |
| ttttattaat | gttaaataaa | gtgtaaaatg | 1020 |
| cagatgttct | tcacccctt | tggtagaaca | |
| aaagcaggat | gataaccata | tccccccagt | 1080 |
| gctcatcaaa | gtaggacact | aaaaatccat | |
| ccatctcagt | caaagtcgag | cggccgcgaa | 1140 |
| tttagtagta | gtagcggccg | ctctagagga | |
| tccaagctta | cgtacgcgtg | catgcgacgt | 1200 |
| catagctctt | ctatagtgtc | acctaaattc | |
| aagtt | | | 1205 |

TABLE XXIIID

Nucleotide sequence alignment of 121P1F1 (SEQ ID NO 65) with splice variant 4. (SEQ ID NO 66).

```
Score = 1454 bits (756), Expect = 0.0Identities = 756/756 (100%) Strand = Plus/Plus 121P1F1   :  83 tgtcaaagaaaaaaggactgagtgcagaagaaaagagaactcgcatgatggaaatatttt  142
                ||||||||||||||||||||||||||||||||||||||||||||||||||||||||||||
Variant 4: 237 tgtcaaagaaaaaaggactgagtgcagaagaaaagagaactcgcatgatggaaatatttt  296

121P1F1   : 143 ctgaaacaaaagatgtatttcaattaaaagacttggagaagattgctcccaaagagaaag  202
                ||||||||||||||||||||||||||||||||||||||||||||||||||||||||||||
Variant 4: 297 ctgaaacaaaagatgtatttcaattaaaagacttggagaagattgctcccaaagagaaag  356

121P1F1   : 203 gcattactgctatgtcagtaaaagaagtccttcaaagcttagttgatgatggtatggttg  262
                ||||||||||||||||||||||||||||||||||||||||||||||||||||||||||||
Variant 4: 357 gcattactgctatgtcagtaaaagaagtccttcaaagcttagttgatgatggtatggttg  416

121P1F1   : 263 actgtgagaggatcggaacttctaattattattgggcttttccaagtaaagctcttcatg  322
                ||||||||||||||||||||||||||||||||||||||||||||||||||||||||||||
Variant 4: 417 actgtgagaggatcggaacttctaattattattgggcttttccaagtaaagctcttcatg  476

121P1F1   : 323 caaggaaacataagttggaggttctggaatctcagttgtctgagggaagtcaaaagcatg  382
                ||||||||||||||||||||||||||||||||||||||||||||||||||||||||||||
Variant 4: 477 caaggaaacataagttggaggttctggaatctcagttgtctgagggaagtcaaaagcatg  536

121P1F1   : 383 caagcctacagaaaagcattgagaaagctaaaattggccgatgtgaaacggaagagcgaa  442
                ||||||||||||||||||||||||||||||||||||||||||||||||||||||||||||
Variant 4: 537 caagcctacagaaaagcattgagaaagctaaaattggccgatgtgaaacggaagagcgaa  596

121P1F1   : 443 ccaggctagcaaaagagcttcttcacttcgagaccaaagggaacagctaaaggcagaag  502
                ||||||||||||||||||||||||||||||||||||||||||||||||||||||||||||
Variant 4: 597 ccaggctagcaaaagagcttcttcacttcgagaccaaagggaacagctaaaggcagaag  656

121P1F1   : 503 tagaaaaatacaaagactgtgatccgcaagttgtggaagaaatacgccaagcaaataaag  562
                ||||||||||||||||||||||||||||||||||||||||||||||||||||||||||||
Variant 4: 657 tagaaaaatacaaagactgtgatccgcaagttgtggaagaaatacgccaagcaaataaag  716

121P1F1   : 563 tagccaaagaagctgctaacagatggactgataacatattcgcaataaaatcttgggcca  622
                ||||||||||||||||||||||||||||||||||||||||||||||||||||||||||||
Variant 4: 717 tagccaaagaagctgctaacagatggactgataacatattcgcaataaaatcttgggcca  776

121P1F1   : 623 aaagaaaatttgggtttgaagaaaataaaattgatagaacttttggaattccagaagact  682
                ||||||||||||||||||||||||||||||||||||||||||||||||||||||||||||
Variant 4: 777 aaagaaaatttgggtttgaagaaaataaaattgatagaacttttggaattccagaagact  836
```

TABLE XXIIID-continued

Nucleotide sequence alignment of 121P1F1 (SEQ ID NO 65) with splice variant 4. (SEQ ID NO 66).

```
121P1F1    : 683  ttgactacatagactaaaatattccatggtggtgaaggatgtacaagcttgtgaatatgt  742
                  ||||||||||||||||||||||||||||||||||||||||||||||||||||||||||||
Variant 4: 837   ttgactacatagactaaaatattccatggtggtgaaggatgtacaagcttgtgaatatgt  896

121P1F1    : 743  aaattttaaactattatctaactaagtgtactgaattgtcgtttgcctgtaactgtgttt  802
                  ||||||||||||||||||||||||||||||||||||||||||||||||||||||||||||
Variant 4: 897   aaattttaaactattatctaactaagtgtactgaattgtcgtttgcctgtaactgtgttt  956

121P1F1    : 803  atcattttattaatgttaaataaagtgtaaaatgca  838
                  |||||||||||||||||||||||||||||||||||
Variant 4: 957   atcattttattaatgttaaataaagtgtaaaatgca  992
```

TABLE XXIVD

Amino acid sequence alignment of 121P1F1 (SEQ ID NO 67) and splice variant 4. (SEQ ID NO 68).

```
Score = 380 bits (975), Expect = e-105 Identities = 190/190 (100%),
Positives = 190/190 (100%)
121P1F1:     16 MMEIFSETKDVFQLKDLEKIAPKEKGITAMSVKEVLQSLVDDGMVDCERIGTSNYYWAFP   75
                MMEIFSETKDVFQLKDLEKIAPKEKGITAMSVKEVLQSLVDDGMVDCERIGTSNYYWAFP
Variant 4:    1 MMEIFSETKDVFQLKDLEKIAPKEKGITAMSVKEVLQSLVDDGMVDCERIGTSNYYWAFP   60

121P1F1:     76 SKALHARKHKLEVLESQLSEGSQKHASLQKSIEKAKIGRCETEERTRLAKELSSLRDQRE  135
                SKALHARKHKLEVLESQLSEGSQKHASLQKSIEKAKIGRCETEERTRLAKELSSLRDQRE
Variant 4:   61 SKALHARKHKLEVLESQLSEGSQKHASLQKSIEKAKIGRCETEERTRLAKELSSLRDQRE  120

121P1F1:    136 QLKAEVEKYKDCDPQVVEEIRQANKVAKEAANRWTDNIFAIKSWAKRKFGFEENKIDRTF  195
                QLKAEVEKYKDCDPQVVEEIRQANKVAKEAANRWTDNIFAIKSWAKRKFGFEENKIDRTF
Variant 4:  121 QLKAEVEKYKDCDPQVVEEIRQANKVAKEAANRWTDNIFAIKSWAKRKFGFEENKIDRTF  180

121P1F1:    196 GIPEDFDYID  205
                GIPEDFDYID
Variant 4:  181 GIPEDFDYID  190
```

TABLE XXVD

Peptide sequences from the translation of the nucleotide sequence of splice variant 4. (SEQ ID NO 69).

```
MMEIFSETKD VFQLKDLEKI APKEKGITAM              60
SVKEVLQSLV DDGMVDCERI GTSNYYWAFP

SKALHARKHK LEVLESQLSE GSQKHASLQK             120
SIEKAKIGRC ETEERTRLAK ELSSLRDQRE

QLKAEVEKYK DCDPQVVEEI RQANKVAKEA             180
ANRWTDNIFA IKSWAKRKFG FEENKIDRTF

GIPEDFDYID                                   190
```

TABLE XXVI

MHC Class 1 nonamer and decamer analysis of 121P1F1 for selected alleles. Listed are scores that fall within the top 50% (rounded up) of all scores for the selected allele.

HLA-A*0201 nonamers

```
Pos1 2 3 4 5 6 7 8 9   score

122R L A K E L S S L     28     Portion of SEQ ID NO: 3;
 78A L H A R K H K L     25     each start position is
 42I T A M S V K E V     23     specified, the length of
 46S V K E V L Q S L     23     each peptide is 9 amino
129S L R D Q R E Q L     23     acids, the end position
```

TABLE XXVI-continued

MHC Class 1 nonamer and decamer analysis of 121P1F1 for selected alleles. Listed are scores that fall within the top 50% (rounded up) of all scores for the selected allele.

```
 34K I A P K E K G I     22     for each peptide is the
102S L Q K S I E K A     22     start position plus
 85K L E V L E S Q L     21     eight
196G I P E D F D Y I     19
 15R M M E I F S E T     17
 18E I F S E T K D V     17
 27F Q L K D L E K I     17
 80H A R K H K L E V     17
165A A N R W T D N I     17
 50V L Q S L V D D G     16
 81A R K H K L E V L     16
 88V L E S Q L S E G     16
 92Q L S E G S Q K H     16
 21S E T K D V F Q L     15
 43T A M S V K E V L     15
136Q L K A E V E K Y     15
  6G L S A E E K R T     14
 28Q L K D L E K I A     14
 71Y W A F P S K A L     14
133Q R E Q L K A E V     14
147C D P Q V V E E I     14
150Q V V E E I R Q A     14
189N K I D R T F G I     14
```

TABLE XXVI-continued

MHC Class 1 nonamer and decamer analysis of 121P1F1 for selected alleles. Listed are scores that fall within the top 50% (rounded up) of all scores for the selected allele.

HLA-A1 nonamers

| Pos 1 2 3 4 5 6 7 8 9 | score | |
|---|---|---|
| 195F G I P E D F D Y | 20 | Portion of SEQ ID NO: 3; each start position is specified, the length of each peptide is 9 amino acids, the end position for each peptide is the start position plus eight |
| 136Q L K A E V E K Y | 19 | |
| 169W T D N I F A I K | 19 | |
| 23T K D V F Q L K D | 18 | |
| 116E T E E R T R L A | 18 | |
| 62C E R I G T S N Y | 17 | |
| 117T E E R T R L A K | 17 | |
| 124A K E L S S L R D | 17 | |
| 146D C D P Q V V E E | 17 | |
| 63E R I G T S N Y Y | 16 | |
| 106S I E K A K I G R | 16 | |
| 20F S E T K D V F Q | 15 | |
| 59M V D C E R I G T | 15 | |
| 93L S E G S Q K H A | 15 | |
| 29L K D L E K I A P | 14 | |
| 88V L E S Q L S E G | 14 | |
| 185G F E E N K I D R | 14 | |
| 8S A E E K R T R M | 13 | |
| 22E T K D V F Q L K | 13 | |
| 31D L E K I A P K E | 13 | |
| 47V K E V L Q S L V | 13 | |
| 55V D D G M V D C E | 13 | |
| 144Y K D C D P Q V V | 13 | |
| 190K I D R T F G I P | 13 | |
| 9A E E K R T R M M | 12 | |
| 37P K E K G I T A M | 12 | |
| 54L V D D G M V D C | 12 | |
| 130L R D Q R E Q L K | 12 | |
| 138K A E V E K Y K D | 12 | |
| 151V V E E I R Q A N | 12 | |
| 162A K E A A N R W T | 12 | |
| 1M S K K K G L S A | 11 | |
| 45M S V K E V L Q S | 11 | |
| 61D C E R I G T S N | 11 | |
| 85K L E V L E S Q L | 11 | |
| 140E V E K Y K D C D | 11 | |
| 152V E E I R Q A N K | 11 | |
| 186F E E N K I D R T | 11 | |
| 13R T R M M E I F S | 10 | |
| 16M M E I F S E T K | 10 | |
| 114R C E T E E R T R | 10 | |
| 133Q R E Q L K A E V | 10 | |
| 197I P E D F D Y I D | 10 | |

HLA-A26 nonamers

| Pos 1 2 3 4 5 6 7 8 9 | score | |
|---|---|---|
| 46S V K E V L Q S L | 27 | Portion of SEQ ID NO: 3; each start position is specified, the length of each peptide is 9 amino acids, the end position for each peptide is the start position plus eight |
| 66G T S N Y Y W A F | 25 | |
| 122R L A K E L S S L | 24 | |
| 136Q L K A E V E K Y | 24 | |
| 193R T F G I P E D F | 24 | |
| 22E T K D V F Q L K | 23 | |
| 49E V L Q S L V D D | 23 | |
| 25D V F Q L K D L E | 20 | |
| 63E R I G T S N Y Y | 20 | |
| 87E V L E S Q L S E | 20 | |
| 18E I F S E T K D V | 19 | |
| 85K L E V L E S Q L | 19 | |
| 129S L R D Q R E Q L | 19 | |
| 19I F S E T K D V F | 18 | |
| 95E G S Q K H A S L | 18 | |
| 116E T E E R T R L A | 18 | |
| 31D L E K I A P K E | 17 | |
| 42I T A M S V K E V | 17 | |
| 54L V D D G M V D C | 17 | |
| 78A L H A R K H K L | 17 | |
| 126E L S S L R D Q R | 17 | |
| 140E V E K Y K D C D | 17 | |
| 150Q V V E E I R Q A | 17 | |
| 154E I R Q A N K V A | 17 | |
| 187E E N K I D R T F | 17 | |
| 196G I P E D F D Y I | 17 | |
| 88V L E S Q L S E G | 16 | |
| 119E R T R L A K E L | 16 | |
| 146D C D P Q V V E E | 16 | |
| 169W T D N I F A I K | 16 | |
| 34K I A P K E K G I | 15 | |
| 102S L Q K S I E K A | 15 | |
| 190K I D R T F G I P | 15 | |
| 12K R T R M M E I F | 14 | |
| 21S E T K D V F Q L | 14 | |
| 37P K E K G I T A M | 14 | |
| 50V L Q S L V D D G | 14 | |
| 81A R K H K L E V L | 14 | |
| 132D Q R E Q L K A E | 14 | |
| 151V V E E I R Q A N | 14 | |
| 160K V A K E A A N R | 14 | |
| 195F G I P E D F D Y | 14 | |
| 24K D V F Q L K D L | 13 | |
| 171D N I F A I K S W | 13 | |
| 172N I F A I K S W A | 13 | |
| 175A I K S W A K R K | 13 | |
| 178S W A K R K F G F | 13 | |

HLA-A3 nonamers

| Pos 1 2 3 4 5 6 7 8 9 | score | |
|---|---|---|
| 175A I K S W A K R K | 25 | Portion of SEQ ID NO: 3; each start position is specified, the length of each peptide is 9 amino acids, the end position for each peptide is the start position plus eight |
| 160K V A K E A A N R | 24 | |
| 40K G I T A M S V K | 23 | |
| 91S Q L S E G S Q K | 22 | |
| 136Q L K A E V E K Y | 21 | |
| 30K D L E K I A P K | 20 | |
| 53S L V D D G M V D | 20 | |
| 122R L A K E L S S L | 20 | |
| 85K L E V L E S Q L | 19 | |
| 92Q L S E G S Q K H | 19 | |
| 129S L R D Q R E Q L | 19 | |
| 155I R Q A N K V A K | 19 | |
| 87E V L E S Q L S E | 18 | |
| 97S Q K H A S L Q K | 18 | |
| 117T E E R T R L A K | 18 | |
| 126E L S S L R D Q R | 18 | |
| 4K K G L S A E E K | 17 | |
| 54L V D D G M V D C | 17 | |
| 78A L H A R K H K L | 17 | |
| 34K I A P K E K G I | 16 | |
| 46S V K E V L Q S L | 16 | |
| 49E V L Q S L V D D | 16 | |
| 69N Y Y W A F P S K | 16 | |
| 75P S K A L H A R K | 16 | |
| 77K A L H A R K H K | 16 | |
| 101A S L Q K S I E K | 16 | |
| 135E Q L K A E V E K | 16 | |
| 150Q V V E E I R Q A | 16 | |
| 152V E E I R Q A N K | 16 | |
| 173I F A I K S W A K | 16 | |
| 182R K F G F E E N K | 16 | |
| 16M M E I F S E T K | 15 | |
| 26V F Q L K D L E K | 15 | |
| 62C E R I G T S N Y | 15 | |
| 111K I G R C E T E E | 15 | |
| 154E I R Q A N K V A | 15 | |
| 190K I D R T F G I P | 15 | |
| 28Q L K D L E K I A | 14 | |
| 41G I T A M S V K E | 14 | |
| 110A K I G R C E T E | 14 | |
| 169W T D N I F A I K | 14 | |
| 172N I F A I K S W A | 14 | |
| 22E T K D V F Q L K | 13 | |
| 31D L E K I A P K E | 13 | |
| 32L E K I A P K E K | 13 | |
| 36A P K E K G I T A | 13 | |

TABLE XXVI-continued

MHC Class 1 nonamer and decamer analysis of 121P1F1 for selected alleles. Listed are scores that fall within the top 50% (rounded up) of all scores for the selected allele.

| Pos | 1 2 3 4 5 6 7 8 9 | score | |
|---|---|---|---|
| 88 V | L E S Q L S E G | 13 | |
| 106 S | I E K A K I G R | 13 | |
| 134 R | E Q L K A E V E | 13 | |
| 137 L | K A E V E K Y K | 13 | |
| 151 V | V E E I R Q A N | 13 | |
| 6 G | L S A E E K R T | 12 | |
| 64 R | I G T S N Y Y W | 12 | |
| 103 L | Q K S I E K A K | 12 | |
| 114 R | C E T E E R T R | 12 | |
| 130 L | R D Q R E Q L K | 12 | |
| 145 K | D C D P Q V V E | 12 | |
| 195 F | G I P E D F D Y | 12 | |

HLA-B*0702 nonamers

| Pos | 1 2 3 4 5 6 7 8 9 | score | |
|---|---|---|---|
| 36 A | P K E K G I T A | 19 | Portion of SEQ ID NO: 3; each start position is specified, the length of each peptide is 9 amino acids, the end position for each peptide is the start position plus eight |
| 71 Y | W A F P S K A L | 15 | |
| 74 F | P S K A L H A R | 14 | |
| 95 E | G S Q K H A S L | 14 | |
| 78 A | L H A R K H K L | 13 | |
| 81 A | R K H K L E V L | 13 | |
| 122 R | L A K E L S S L | 13 | |
| 129 S | L R D Q R E Q L | 13 | |
| 21 S | E T K D V F Q L | 12 | |
| 43 T | A M S V K E V L | 12 | |
| 115 C | E T E E R T R L | 12 | |
| 24 K | D V F Q L K D L | 11 | |
| 80 H | A R K H K L E V | 11 | |
| 85 K | L E V L E S Q L | 11 | |
| 119 E | R T R L A K E L | 11 | |
| 197 I | P E D F D Y I D | 11 | |
| 1 M | S K K K G L S A | 10 | |
| 9 A | E E K R T R M M | 10 | |
| 19 I | F S E T K D V F | 10 | |
| 46 S | V K E V L Q S L | 10 | |
| 73 A | F P S K A L H A | 10 | |
| 148 D | P Q V V E E I R | 10 | |
| 154 E | I R Q A N K V A | 10 | |
| 166 A | N R W T D N I F | 10 | |
| 6 G | L S A E E K R T | 9 | |
| 11 E | K R T R M M E I | 9 | |
| 15 R | M M E I F S E T | 9 | |
| 34 K | I A P K E K G I | 9 | |
| 37 P | K E K G I T A M | 9 | |
| 42 I | T A M S V K E V | 9 | |
| 66 G | T S N Y Y W A F | 9 | |
| 104 Q | K S I E K A K I | 9 | |
| 131 R | D Q R E Q L K A | 9 | |
| 158 A | N K V A K E A A | 9 | |
| 162 A | K E A A N R W T | 9 | |
| 165 A | A N R W T D N I | 9 | |
| 176 I | K S W A K R K F | 9 | |
| 193 R | T F G I P E D F | 9 | |

HLA-B*08 nonamers

| Pos | 1 2 3 4 5 6 7 8 9 | score | |
|---|---|---|---|
| 81 A | R K H K L E V L | 30 | Portion of SEQ ID NO: 3; each start position is specified, the length of each peptide is 9 amino acids, the end position for each peptide is the position position plus eight |
| 36 A | P K E K G I T A | 28 | |
| 46 S | V K E V L Q S L | 24 | |
| 78 A | L H A R K H K L | 24 | |
| 129 S | L R D Q R E Q L | 24 | |
| 179 W | A K R K F G F E | 24 | |
| 11 E | K R T R M M E I | 23 | |
| 95 E | G S Q K H A S L | 22 | |
| 107 I | E K A K I G R C | 22 | |
| 141 V | E K Y K D C D P | 22 | |
| 34 K | I A P K E K G I | 21 | |
| 1 M | S K K K G L S A | 20 | |
| 8 S | A E E K R T R M | 18 | |
| 28 Q | L K D L E K I A | 17 | |
| 85 K | L E V L E S Q L | 17 | |

TABLE XXVI-continued

MHC Class 1 nonamer and decamer analysis of 121P1F1 for selected alleles. Listed are scores that fall within the top 50% (rounded up) of all scores for the selected allele.

| Pos | 1 2 3 4 5 6 7 8 9 | score |
|---|---|---|
| 136 Q | L K A E V E K Y | 17 |
| 161 V | A K E A A N R W | 17 |
| 118 E | E R T R L A K E | 16 |
| 122 R | L A K E L S S L | 16 |
| 123 L | A K E L S S L R | 16 |
| 178 S | W A K R K F G F | 16 |
| 109 K | A K I G R C E T | 15 |
| 175 A | I K S W A K R K | 15 |

HLA-B*1510 nonamers

| Pos | 1 2 3 4 5 6 7 8 9 | score | |
|---|---|---|---|
| 43 T | A M S V K E V L | 14 | Portion of SEQ ID NO: 3; each start position is specified, the length of each peptide is 9 amino acids, the end position for each peptide is the start position plus eight |
| 71 Y | W A F P S K A L | 14 | |
| 115 C | E T E E R T R L | 14 | |
| 19 I | F S E T K D V F | 13 | |
| 95 E | G S Q K H A S L | 13 | |
| 21 S | E T K D V F Q L | 12 | |
| 81 A | R K H K L E V L | 12 | |
| 83 K | H K L E V L E S | 12 | |
| 85 K | L E V L E S Q L | 12 | |
| 119 E | R T R L A K E L | 12 | |
| 122 R | L A K E L S S L | 12 | |
| 129 S | L R D Q R E Q L | 12 | |
| 176 I | K S W A K R K F | 12 | |
| 8 S | A E E K R T R M | 11 | |
| 37 P | K E K G I T A M | 11 | |
| 46 S | V K E V L Q S L | 11 | |
| 78 A | L H A R K H K L | 11 | |
| 79 L | H A R K H K L E | 11 | |
| 99 K | H A S L Q K S I | 11 | |
| 187 E | E N K I D R T F | 11 | |
| 9 A | E E K R T R M M | 10 | |
| 24 K | D V F Q L K D L | 10 | |
| 66 G | T S N Y Y W A F | 9 | |
| 178 S | W A K R K F G F | 9 | |
| 193 R | T F G I P E D F | 8 | |
| 12 K | R T R M M E I F | 7 | |
| 51 Q | S L V D D G M | 7 | |
| 155 I | R Q A N K V A K | 7 | |

HLA-B*2705 nonamers

| Pos | 1 2 3 4 5 6 7 8 9 | score | |
|---|---|---|---|
| 63 E | R I G T S N Y Y | 24 | Portion of SEQ ID NO: 3; each start position is specified, the length of each peptide is 9 amino acids, the end position for each peptide is the start position plus eight |
| 81 A | R K H K L E V L | 24 | |
| 119 E | R T R L A K E L | 23 | |
| 155 I | R Q A N K V A K | 23 | |
| 12 K | R T R M M E I F | 22 | |
| 130 L | R D Q R E Q L K | 22 | |
| 182 R | K F G F E E N K | 21 | |
| 30 K | D L E K I A P K | 20 | |
| 122 R | L A K E L S S L | 20 | |
| 193 R | T F G I P E D F | 20 | |
| 101 A | S L Q K S I E K | 19 | |
| 160 K | V A K E A A N R | 19 | |
| 174 F | A I K S W A K R | 18 | |
| 37 P | K E K G I T A M | 17 | |
| 192 D | R T F G I P E D | 17 | |
| 4 K | K G L S A E E K | 16 | |
| 5 K | G L S A E E K R | 16 | |
| 40 K | G I T A M S V K | 16 | |
| 113 G | R C E T E E R T | 16 | |
| 114 R | C E T E E R T R | 16 | |
| 115 C | E T E E R T R L | 16 | |
| 133 Q | R E Q L K A E V | 16 | |
| 135 E | Q L K A E V E K | 16 | |
| 185 G | F E E N K I D R | 16 | |
| 14 T | R M M E I F S E | 15 | |
| 26 V | F Q L K D L E K | 15 | |
| 72 W | A F P S K A L H | 15 | |
| 85 K | L E V L E S Q L | 15 | |
| 91 S | Q L S E G S Q K | 15 | |

TABLE XXVI-continued

MHC Class 1 nonamer and decamer analysis of 121P1F1 for selected alleles. Listed are scores that fall within the top 50% (rounded up) of all scores for the selected allele.

| Pos | 1 2 3 4 5 6 7 8 9 | score |
|---|---|---|
| 95E | G S Q K H A S L | 15 |
| 121T | R L A K E L S S | 15 |
| 152V | E E I R Q A N K | 15 |
| 181K | R K F G F E E N | 15 |
| 187E | E N K I D R T F | 15 |
| 7L | S A E E K R T R | 14 |
| 8S | A E E K R T R M | 14 |
| 19I | F S E T K D V F | 14 |
| 21S | E T K D V F Q L | 14 |
| 24K | D V F Q L K D L | 14 |
| 46S | V K E V L Q S L | 14 |
| 66G | T S N Y Y W A F | 14 |
| 69N | Y Y W A F P S K | 14 |
| 75P | S K A L H A R K | 14 |
| 77K | A L H A R K H K | 14 |
| 78A | L H A R K H K L | 14 |
| 92Q | L S E G S Q K H | 14 |
| 106S | I E K A K I G R | 14 |
| 123L | A K E L S S L R | 14 |
| 173I | F A I K S W A K | 14 |
| 175A | I K S W A K R K | 14 |
| 176I | K S W A K R K F | 14 |
| 27F | Q L K D L E K I | 13 |
| 43T | A M S V K E V L | 13 |
| 56D | D G M V D C E R | 13 |
| 62C | E R I G T S N Y | 13 |
| 74F | P S K A L H A R | 13 |
| 97S | Q K H A S L Q K | 13 |
| 112I | G R C E T E E R | 13 |
| 166A | N R W T D N I F | 13 |
| 168R | W T D N I F A I | 13 |
| 178S | W A K R K F G F | 13 |
| 195F | G I P E D F D Y | 13 |
| 16M | M E I F S E T K | 12 |
| 71Y | W A F P S K A L | 12 |
| 76S | K A L H A R K H | 12 |
| 99K | H A S L Q K S I | 12 |
| 126E | L S S L R D Q R | 12 |
| 136Q | L K A E V E K Y | 12 |
| 137L | K A E V E K Y K | 12 |
| 167N | R W T D N I F A | 12 |
| 169W | T D N I F A I K | 12 |
| 183K | F G F E E N K I | 12 |

HLA-B*2709 nonamers

| Pos | 1 2 3 4 5 6 7 8 9 | score | |
|---|---|---|---|
| 119E | R T R L A K E L | 22 | Portion of SEQ ID NO: 3; |
| 12K | R T R M M E I F | 21 | each start position is |
| 81A | R K H K L E V L | 21 | specified, the length of |
| 133Q | R E Q L K A E V | 18 | each peptide is 9 amino |
| 193R | T F G I P E D F | 15 | acids, the end position |
| 21S | E T K D V F Q L | 14 | for each peptide is the |
| 113G | R C E T E E R T | 14 | start position plus |
| 122R | L A K E L S S L | 14 | eight |
| 24K | D V F Q L K D L | 13 | |
| 85K | L E V L E S Q L | 13 | |
| 121T | R L A K E L S S | 13 | |
| 168R | W T D N I F A I | 13 | |
| 115C | E T E E R T R L | 12 | |
| 143K | Y K D C D P Q V | 12 | |
| 155I | R Q A N K V A K | 12 | |
| 181K | R K F G F E E N | 12 | |
| 192D | R T F G I P E D | 12 | |
| 196G | I P E D F D Y I | 12 | |
| 18E | I F S E T K D V | 11 | |
| 27F | Q L K D L E K I | 11 | |
| 34K | I A P K E K G I | 11 | |
| 43T | A M S V K E V L | 11 | |
| 52Q | S L V D D G M V | 11 | |
| 63E | R I G T S N Y Y | 11 | |
| 66G | T S N Y Y W A F | 11 | |
| 78A | L H A R K H K L | 11 | |
| 99K | H A S L Q K S I | 11 | |

TABLE XXVI-continued

MHC Class 1 nonamer and decamer analysis of 121P1F1 for selected alleles. Listed are scores that fall within the top 50% (rounded up) of all scores for the selected allele.

| Pos | 1 2 3 4 5 6 7 8 9 | score |
|---|---|---|
| 129S | L R D Q R E Q L | 11 |
| 167N | R W T D N I F A | 11 |

HLA-B*4402 nonamers

| Pos | 1 2 3 4 5 6 7 8 9 | score | |
|---|---|---|---|
| 187E | E N K I D R T F | 25 | Portion of SEQ ID NO: 3; |
| 21S | E T K D V F Q L | 23 | each start position is |
| 62C | E R I G T S N Y | 21 | specified, the length of |
| 115C | E T E E R T R L | 21 | each peptide is 9 amino |
| 153E | E I R Q A N K V | 19 | acids, the end position |
| 171D | N I F A I K S W | 18 | for each peptide is the |
| 63E | R I G T S N Y Y | 17 | start position plus |
| 9A | E E K R T R M M | 16 | eight |
| 78A | L H A R K H K L | 16 | |
| 118E | E R T R L A K E | 16 | |
| 119E | R T R L A K E L | 16 | |
| 195F | G I P E D F D Y | 16 | |
| 81A | R K H K L E V L | 15 | |
| 117T | E E R T R L A K | 15 | |
| 139A | E V E K Y K D C | 15 | |
| 168R | W T D N I F A I | 15 | |
| 189N | K I D R T F G I | 15 | |
| 193R | T F G I P E D F | 15 | |
| 10E | E K R T R M M E | 14 | |
| 17M | E I F S E T K D | 14 | |
| 24K | D V F Q L K D L | 14 | |
| 34K | I A P K E K G I | 14 | |
| 38K | E K G I T A M S | 14 | |
| 48K | E V L Q S L V D | 14 | |
| 66G | T S N Y Y W A F | 14 | |
| 71Y | W A F P S K A L | 14 | |
| 94S | E G S Q K H A S | 14 | |
| 125K | E L S S L R D Q | 14 | |
| 129S | L R D Q R E Q L | 14 | |
| 163K | E A A N R W T D | 14 | |
| 166A | N R W T D N I F | 14 | |
| 186F | E E N K I D R T | 14 | |
| 32L | E K I A P K E K | 13 | |
| 95E | G S Q K H A S L | 13 | |
| 107I | E K A K I G R C | 13 | |
| 134R | E Q L K A E V E | 13 | |
| 165A | A N R W T D N I | 13 | |
| 176I | K S W A K R K F | 13 | |
| 11E | K R T R M M E I | 12 | |
| 12K | R T R M M E I F | 12 | |
| 19I | F S E T K D V F | 12 | |
| 43T | A M S V K E V L | 12 | |
| 46S | V K E V L Q S L | 12 | |
| 85K | L E V L E S Q L | 12 | |
| 86L | E V L E S Q L S | 12 | |
| 136Q | L K A E V E K Y | 12 | |
| 161V | A K E A A N R W | 12 | |
| 178S | W A K R K F G F | 12 | |

HLA-B*5101 nonamers

| Pos | 1 2 3 4 5 6 7 8 9 | score | |
|---|---|---|---|
| 43T | A M S V K E V L | 22 | Portion of SEQ ID NO: 3; |
| 57D | G M V D C E R I | 21 | each start position is |
| 80H | A R K H K L E V | 20 | specified, the length of |
| 165A | A N R W T D N I | 20 | each peptide is 9 amino |
| 27F | Q L K D L E K I | 17 | acids, the end position |
| 36A | P K E K G I T A | 16 | for each peptide is the |
| 148D | P Q V V E E I R | 16 | start position plus |
| 161V | A K E A A N R W | 16 | eight |
| 8S | A E E K R T R M | 15 | |
| 147C | D P Q V V E E I | 15 | |
| 157Q | A N K V A K E A | 15 | |
| 174F | A I K S W A K R | 15 | |
| 35I | A P K E K G I T | 14 | |
| 42I | T A M S V K E V | 14 | |
| 77K | A L H A R K H K | 14 | |

TABLE XXVI-continued

MHC Class 1 nonamer and decamer analysis of 121P1F1 for selected alleles. Listed are scores that fall within the top 50% (rounded up) of all scores for the selected allele.

| Pos | 1 2 3 4 5 6 7 8 9 | score | |
|---|---|---|---|
| 123L | A K E L S S L R | 14 | |
| 144Y | K D C D P Q V V | 14 | |
| 196G | I P E D F D Y I | 14 | |
| 74F | P S K A L H A R | 13 | |
| 95E | G S Q K H A S L | 13 | |
| 183K | F G F E E N K I | 13 | |
| 197I | P E D F D Y I D | 13 | |
| 34K | I A P K E K G I | 12 | |
| 72W | A F P S K A L H | 12 | |
| 104Q | K S I E K A K I | 12 | |
| 138K | A E V E K Y K D | 12 | |
| 153E | E I R Q A N K V | 12 | |
| 168R | W T D N I F A I | 12 | |
| 179W | A K R K F G F E | 12 | |
| 184F | G F E E N K I D | 12 | |
| 189N | K I D R T F G I | 12 | |
| 11E | K R T R M M E I | 11 | |
| 46S | V K E V L Q S L | 11 | |
| 81A | R K H K L E V L | 11 | |
| 99K | H A S L Q K S I | 11 | |
| 164E | A A N R W T D N | 11 | |

HLA-A*0201 decamers

Pos1 2 3 4 5 6 7 8 9 0  score

| Pos | 1 2 3 4 5 6 7 8 9 0 | score | |
|---|---|---|---|
| 41G | I T A M S V K E V | 23 | Portion of SEQ ID NO: 3; each start position is specified, the length of each peptide is 10 amino acids, the end position for each peptide is the start position plus nine |
| 77K | A L H A R K H K L | 20 | |
| 42I | T A M S V K E V L | 18 | |
| 80H | A R K H K L E V L | 18 | |
| 121T | R L A K E L S S L | 18 | |
| 34K | I A P K E K G I T | 17 | |
| 46S | V K E V L Q S L V | 17 | |
| 79L | H A R K H K L E V | 17 | |
| 45M | S V K E V L Q S L | 16 | |
| 50V | L Q S L V D D G M | 16 | |
| 94S | E G S Q K H A S L | 16 | |
| 26V | F Q L K D L E K I | 15 | |
| 44A | M S V K E V L Q S | 15 | |
| 53S | L V D D G M V D C | 15 | |
| 58G | M V D C E R I G T | 15 | |
| 92Q | L S E G S Q K H A | 15 | |
| 132D | Q R E Q L K A E V | 15 | |
| 146D | C D P Q V V E E I | 15 | |
| 20F | S E T K D V F Q L | 14 | |
| 38K | E K G I T A M S V | 14 | |
| 84H | K L E V L E S Q L | 14 | |
| 101A | S L Q K S I E K A | 14 | |
| 128S | S L R D Q R E Q L | 14 | |
| 167N | R W T D N I F A I | 14 | |
| 182R | K F G F E E N K I | 14 | |
| 6G | L S A E E K R T R | 13 | |
| 15R | M M E I F S E T K | 13 | |
| 23T | K D V F Q L K D L | 13 | |
| 64R | I G T S N Y Y W A | 13 | |
| 70Y | Y W A F P S K A L | 13 | |
| 103L | Q K S I E K A K I | 13 | |
| 106S | I E K A K I G R C | 13 | |
| 129S | L R D Q R E Q L K | 13 | |
| 152V | E E I R Q A N K V | 13 | |
| 195F | G I P E D F D Y I | 13 | |
| 35I | A P K E K G I T A | 12 | |
| 36A | P K E K G I T A M | 12 | |
| 51L | Q S L V D D G M V | 12 | |
| 72W | A F P S K A L H A | 12 | |
| 102S | L Q K S I E K A K | 12 | |
| 122R | L A K E L S S L R | 12 | |
| 196G | I P E D F D Y I D | 12 | |

HLA-A*0203 decamers

Pos1 2 3 4 5 6 7 8 9 0  score

| Pos | 1 2 3 4 5 6 7 8 9 0 | score | |
|---|---|---|---|
| 157Q | A N K V A K E A A | 19 | Portion of SEQ ID NO: 3; each start position is specified, the length of each peptide is 10 amino acids, the end position for each peptide is the start position plus nine |
| 158A | N K V A K E A A N | 17 | |
| 27F | Q L K D L E K I A | 10 | |
| 35I | A P K E K G I T A | 10 | |
| 64R | I G T S N Y Y W A | 10 | |
| 69N | Y Y W A F P S K A | 10 | |
| 72W | A F P S K A L H A | 10 | |
| 92Q | L S E G S Q K H A | 10 | |
| 101A | S L Q K S I E K A | 10 | |
| 115C | E T E E R T R L A | 10 | |
| 130L | R D Q R E Q L K A | 10 | |
| 149P | Q V V E E I R Q A | 10 | |
| 153E | E I R Q A N K V A | 10 | |
| 156R | Q A N K V A K E A | 10 | |
| 166A | N R W T D N I F A | 10 | |
| 171D | N I F A I K S W A | 10 | |
| 1M | S K K K G L S A E | 9 | |
| 28Q | L K D L E K I A P | 9 | |
| 36A | P K E K G I T A M | 9 | |
| 65I | G T S N Y Y W A F | 9 | |
| 70Y | Y W A F P S K A L | 9 | |
| 73F | P S K A L H A R | 9 | |
| 93L | S E G S Q K H A S | 9 | |
| 102S | L Q K S I E K A K | 9 | |
| 116E | T E E R T R L A K | 9 | |
| 131R | D Q R E Q L K A E | 9 | |
| 150Q | V V E E I R Q A N | 9 | |
| 154E | I R Q A N K V A K | 9 | |
| 167N | R W T D N I F A I | 9 | |
| 172N | I F A I K S W A K | 9 | |

HLA-A1 decamers

Pos1 2 3 4 5 6 7 8 9 0  score

| Pos | 1 2 3 4 5 6 7 8 9 0 | score | |
|---|---|---|---|
| 61D | C E R I G T S N Y | 25 | Portion of SEQ ID NO: 3; each start position is specified, the length of each peptide is 10 amino acids, the end position for each peptide is the start position plus nine |
| 116E | T E E R T R L A K | 23 | |
| 169W | T D N I F A I K S | 22 | |
| 47V | K E V L Q S L V D | 18 | |
| 130L | R D Q R E Q L K A | 18 | |
| 135E | Q L K A E V E K Y | 18 | |
| 20F | S E T K D V F Q L | 16 | |
| 62C | E R I G T S N Y Y | 15 | |
| 93L | S E G S Q K H A S | 15 | |
| 146D | C D P Q V V E E I | 15 | |
| 190K | I D R T F G I P E | 15 | |
| 194T | F G I P E D F D Y | 15 | |
| 22E | T K D V F Q L K D | 14 | |
| 8S | A E E K R T R M M | 13 | |
| 9A | E E K R T R M M E | 13 | |
| 85K | L E V L E S Q L S | 13 | |
| 144Y | K D C D P Q V V E | 13 | |
| 152V | E E I R Q A N K V | 13 | |
| 16M | M E I F S E T K D | 12 | |
| 55V | D D G M V D C E R | 12 | |
| 88V | L E S Q L S E G S | 12 | |
| 106S | I E K A K I G R C | 12 | |
| 117T | E E R T R L A K E | 12 | |
| 120R | T R L A K E L S S | 12 | |
| 162A | K E A A N R W T D | 12 | |

HLA-A26 decamers

Pos1 2 3 4 5 6 7 8 9 0  score

| Pos | 1 2 3 4 5 6 7 8 9 0 | score | |
|---|---|---|---|
| 18E | I F S E T K D V F | 29 | Portion of SEQ ID NO: 3; each start position is specified, the length of each peptide is 10 amino acids, the end position for each peptide is the start position plus nine |
| 87E | V L E S Q L S E G | 24 | |
| 175A | I K S W A K R K F | 23 | |
| 135E | Q L K A E V E K Y | 22 | |
| 49E | V L Q S L V D D G | 21 | |
| 11E | K R T R M M E I F | 20 | |
| 25D | V F Q L K D L E K | 20 | |
| 22E | T K D V F Q L K D | 19 | |
| 42I | T A M S V K E V L | 19 | |
| 116E | T E E R T R L A K | 19 | |
| 154E | I R Q A N K V A K | 19 | |
| 50V | L Q S L V D D G M | 18 | |

TABLE XXVI-continued

MHC Class 1 nonamer and decamer analysis of 121P1F1 for selected alleles. Listed are scores that fall within the top 50% (rounded up) of all scores for the selected allele.

```
 61D C E R I G T S N Y      18
126E L S S L R D Q R E      17
140E V E K Y K D C D P      17
 31D L E K I A P K E K      16
 36A P K E K G I T A M      16
 54L V D D G M V D C E      16
 65I G T S N Y Y W A F      16
106S I E K A K I G R C      16
192D R T F G I P E D F      16
194T F G I P E D F D Y      16
 13R T M M E I F S E        15
 41G I T A M S V K E V      15
 45M S V K E V L Q S L      15
 59M V D C E R I G T S      15
118E E R T R L A K E L      15
 46S V K E V L Q S L V      14
 53S L V D D G M V D C      14
 64R I G T S N Y Y W A      14
121T R L A K E L S S L      14
146D C D P Q V V E E I      14
150Q V V E E I R Q A N      14
151V V E E I R Q A N K      14
193R T F G I P E D F D      14
```

HLA-A3 decamers

Pos1 2 3 4 5 6 7 8 9 0  score

```
154E I R Q A N K V A K      26   Portion of SEQ ID NO: 3;
129S L R D Q R E Q L K      25   each start position is
136Q L K A E V E K Y K      25   specified, the length of
151V V E E I R Q A N K      24   each peptide is 10 amino
 25D V F Q L K D L E K      23   acids, the end position
102S L Q K S I E K A K      22   for each peptide is the
122R L A K E L S S L R      22   start position plus nine
 31D L E K I A P K E K      21
172N I F A I K S W A K      21
  6G L S A E E K R T R      20
 90E S Q L S E G S Q K      20
  3K K K G L S A E E K      19
 15R M M E I F S E T K      19
134R E Q L K A E V E K      19
 39E K G I T A M S V K      18
111K I G R C E T E E R      18
168R W T D N I F A I K      18
 68S N Y Y W A F P S K      17
160K V A K E A A N R W      17
190K I D R T F G I P E      17
 18E I F S E T K D V F      16
 34K I A P K E K G I T      16
 46S V K E V L Q S L V      16
 53S L V D D G M V D C      16
 87E V L E S Q L S E G      16
 96G S Q K H A S L Q K      16
116E T E E R T R L A K      16
174F A I K S W A K R K      16
175A I K S W A K R K F      16
 28Q L K D L E K I A P      15
 59M V D C E R I G T S      15
 78A L H A R K H K L E      15
150Q V V E E I R Q A N      15
 29L K D L E K I A P K      14
 76S K A L H A R K H K      14
181K R K F G F E E N K      14
 64R I G T S N Y Y W A      13
 74F P S K A L H A R K      13
 85K L E V L E S Q L S      13
 92Q L S E G S Q K H A      13
120R T R L A K E L S S      13
125K E L S S L R D Q R      13
```

HLA-B*0702 decamers

Pos1 2 3 4 5 6 7 8 9 0  score

```
 36A P K E K G I T A M      20   Portion of SEQ ID NO: 3;
 74F P S K A L H A R K      14   each start position is
 80H A R K H K L E V L      14   specified, the length of
 42I T A M S V K E V L      13   each peptide is 10 amino
114R C E T E E R T R L      13   acids, the end position
118E E R T R L A K E L      13   for each peptide is the
 70Y Y W A F P S K A L      12   start position plus nine
 94S E G S Q K H A S L      12
 20F S E T K D V F Q L      11
 23T K D V F Q L K D L      11
 45M S V K E V L Q S L      11
 77K A L H A R K H K L      11
121T R L A K E L S S L      11
128S S L R D Q R E Q L      11
166A N R W T D N I F A      11
 84H K L E V L E S Q L      10
108E K A K I G R C E T      10
148D P Q V V E E I R Q      10
```

HLA-B*4402 decamers

Pos1 2 3 4 5 6 7 8 9 0  score

```
118E E R T R L A K E L      26   Portion of SEQ ID NO: 3;
186F E E N K I D R T F      23   each start position is
 10E E K R T R M M E I      21   specified, the length of
 62C E R I G T S N Y Y      21   each peptide is 10 amino
 94S E G S Q K H A S L      21   acids, the end position
153E E I R Q A N K V A      19   for each peptide is the
 17M E I F S E T K D V      16   start position plus nine
 63E R I G T S N Y Y W      16
 18E I F S E T K D V F      15
 33E K I A P K E K G I      15
128S S L R D Q R E Q L      15
135E Q L K A E V E K Y      15
165A A N R W T D N I F      15
167N R W T D N I F A I      15
170T D N I F A I K S W      15
175A I K S W A K R K F      15
195F G I P E D F D Y I      15
  9A E E K R T R M M E      14
 23T K D V F Q L K D L      14
 48K E V L Q S L V D D      14
 70Y Y W A F P S K A L      14
 77K A L H A R K H K L      14
125K E L S S L R D Q R      14
 11E K R T R M M E I F      13
 20F S E T K D V F Q L      13
 21S E T K D V F Q L K      13
 38K E K G I T A M S V      13
115C E T E E R T R L A      13
117T E E R T R L A K E      13
139A E V E K Y K D C D      13
146D C D P Q V V E E I      13
152V E E I R Q A N K V      13
160K V A K E A A N R W      13
182R K F G F E E N K I      13
187E E N K I D R T F G      13
```

TABLE XXVI-continued

MHC Class 1 nonamer and decamer analysis of 121P1F1 for selected alleles. Listed are scores that fall within the top 50% (rounded up) of all scores for the selected allele.

Class I nonamer analysis of amino acids 85-126 (KLEVLESQDPGCCFHEIIKVSYYRKFWLGAVAHACNPSTLGG) of 121P1F1 splice variant 1a. Listed are those alleles and peptides in which the score falls within the top 50% (rounded up) of the scores from the analysis of the full length 121P1F1 base peptide sequence.

HLA-A*0201 nonamers

| Pos | 1 | 2 | 3 | 4 | 5 | 6 | 7 | 8 | 9 | score | |
|---|---|---|---|---|---|---|---|---|---|---|---|
| 96 | C | C | F | H | E | I | I | K | V | 17 | Portion of SEQ ID NO: 5; each start position is specified, the length of each peptide is 9 amino acids, the end position for each peptide is the start position plus eight |
| 116 | A | H | A | C | N | P | S | T | L | 16 | |
| 107 | Y | R | K | F | W | L | G | A | V | 15 | |
| 110 | F | W | L | G | A | V | A | H | A | 15 | |

HLA-A1 nonamers

| Pos | 1 | 2 | 3 | 4 | 5 | 6 | 7 | 8 | 9 | score | |
|---|---|---|---|---|---|---|---|---|---|---|---|
| 98 | F | H | E | I | I | K | V | S | Y | 26 | Portion of SEQ ID NO: 5; each start position is specified, the length of each peptide is 9 amino acids, the end position for each peptide is the start position plus eight |
| 91 | S | Q | D | P | G | C | C | F | H | 18 | |
| 99 | H | E | I | I | K | V | S | Y | Y | 16 | |
| 88 | V | L | E | S | Q | D | P | G | C | 14 | |
| 85 | K | L | E | V | L | E | S | Q | D | 11 | |
| 118 | A | C | N | P | S | T | L | G | G | 11 | |

HLA-A26 nonamers

| Pos | 1 | 2 | 3 | 4 | 5 | 6 | 7 | 8 | 9 | score | |
|---|---|---|---|---|---|---|---|---|---|---|---|
| 87 | E | V | L | E | S | Q | D | P | G | 19 | Portion of SEQ ID NO: 5; each start position is specified, the length of each peptide is 9 amino acids, the end position for each peptide is the start position plus eight |
| 100 | E | I | I | K | V | S | Y | Y | R | 19 | |
| 99 | H | E | I | I | K | V | S | Y | Y | 18 | |
| 90 | E | S | Q | D | P | G | C | C | F | 17 | |
| 101 | I | I | K | V | S | Y | Y | R | K | 17 | |
| 102 | I | K | V | S | Y | Y | R | K | F | 16 | |

HLA-A3 nonamers

| Pos | 1 | 2 | 3 | 4 | 5 | 6 | 7 | 8 | 9 | score | |
|---|---|---|---|---|---|---|---|---|---|---|---|
| 101 | I | K | V | S | Y | Y | R | K | 21 | Portion of SEQ ID NO: 5; each start position is specified, the length of each peptide is 9 amino acids, the end position for each peptide is the start position plus eight |
| 85 | K | L | E | V | L | E | S | Q | D | 19 | |
| 109 | K | F | W | L | G | A | V | A | H | 18 | |
| 111 | W | L | G | A | V | A | H | A | C | 17 | |
| 100 | E | I | I | K | V | S | Y | Y | R | 16 | |
| 99 | H | E | I | I | K | V | S | Y | Y | 14 | |
| 103 | K | V | S | Y | Y | R | K | F | W | 14 | |
| 108 | R | K | F | W | L | G | A | V | A | 14 | |
| 114 | A | V | A | H | A | C | N | P | S | 14 | |
| 87 | E | V | L | E | S | Q | D | P | G | 13 | |
| 98 | F | H | E | I | I | K | V | S | Y | 13 | |
| 116 | A | H | A | C | N | P | S | T | L | 12 | |

HLA-B*0702 nonamers

| Pos | 1 | 2 | 3 | 4 | 5 | 6 | 7 | 8 | 9 | score | |
|---|---|---|---|---|---|---|---|---|---|---|---|
| 93 | D | P | G | C | C | F | H | E | I | 18 | Portion of SEQ ID NO: 5; each start position is specified, the length of each peptide is 9 amino acids, the end position for each peptide is the start position plus eight |
| 116 | A | H | A | C | N | P | S | T | L | 13 | |
| 90 | E | S | Q | D | P | G | C | C | F | 11 | |
| 106 | Y | Y | R | K | F | W | L | G | A | 11 | |
| 104 | V | S | Y | Y | R | K | F | W | L | 10 | |
| 108 | R | K | F | W | L | G | A | V | A | 10 | |
| 110 | F | W | L | G | A | V | A | H | A | 10 | |

HLA-B*08 nonamers

| Pos | 1 | 2 | 3 | 4 | 5 | 6 | 7 | 8 | 9 | score | |
|---|---|---|---|---|---|---|---|---|---|---|---|
| 104 | V | S | Y | Y | R | K | F | W | L | 20 | Portion of SEQ ID NO: 5; each start position is specified, the length of each peptide is 9 amino acids, the end position for each peptide is the start position plus eight |
| 101 | I | I | K | V | S | Y | Y | R | K | 16 | |

HLA-B*1510 nonamers

| Pos | 1 | 2 | 3 | 4 | 5 | 6 | 7 | 8 | 9 | score | |
|---|---|---|---|---|---|---|---|---|---|---|---|
| 116 | A | H | A | C | N | P | S | T | L | 24 | Portion of SEQ ID NO: 5; each start position is specified, the length of each peptide is 9 amino acids, the end position for each peptide is the start position plus eight |
| 98 | F | H | E | I | I | K | V | S | Y | 14 | |
| 104 | V | S | Y | Y | R | K | F | W | L | 11 | |
| 102 | I | K | V | S | Y | Y | R | K | F | 10 | |
| 90 | E | S | Q | D | P | G | C | C | F | 9 | |

HLA-B*2705 nonamers

| Pos | 1 | 2 | 3 | 4 | 5 | 6 | 7 | 8 | 9 | score | |
|---|---|---|---|---|---|---|---|---|---|---|---|
| 100 | E | I | I | K | V | S | Y | Y | R | 17 | Portion of SEQ ID NO: 5; each start position is specified, the length of each peptide is 9 amino acids, the end position for each peptide is the start position plus eight |
| 101 | I | I | K | V | S | Y | Y | R | K | 15 | |
| 109 | K | F | W | L | G | A | V | A | H | 15 | |
| 95 | G | C | C | F | H | E | I | I | K | 14 | |
| 103 | I | K | V | S | Y | Y | R | K | F | 14 | |
| 99 | H | E | I | I | K | V | S | Y | Y | 13 | |
| 104 | V | S | Y | Y | R | K | F | W | L | 13 | |
| 116 | A | H | A | C | N | P | S | T | L | 13 | |
| 98 | F | H | E | I | I | K | V | S | Y | 12 | |

HLA-B*2709 nonamers

| Pos | 1 | 2 | 3 | 4 | 5 | 6 | 7 | 8 | 9 | score | |
|---|---|---|---|---|---|---|---|---|---|---|---|
| 107 | Y | R | K | F | W | L | G | A | V | 18 | Portion of SEQ ID NO: 5; each start position is specified, the length of each peptide is 9 amino acids, the end position for each peptide is the start position plus eight |
| 104 | V | S | Y | Y | R | K | F | W | L | 12 | |
| 102 | I | K | V | S | Y | Y | R | K | F | 11 | |
| 116 | A | H | A | C | N | P | S | T | L | 11 | |

HLA-B*4402 nonamers

| Pos | 1 | 2 | 3 | 4 | 5 | 6 | 7 | 8 | 9 | score | |
|---|---|---|---|---|---|---|---|---|---|---|---|
| 99 | H | E | I | I | K | V | S | Y | Y | 24 | Portion of SEQ ID NO: 5; each start position is specified, the length of each peptide is 9 amino acids, the end position for each peptide is the start position plus eight |
| 116 | A | H | A | C | N | P | S | T | L | 16 | |
| 103 | K | V | S | Y | Y | R | K | F | W | 15 | |
| 90 | E | S | Q | D | P | G | C | C | F | 13 | |
| 89 | L | E | S | Q | D | P | G | C | C | 12 | |
| 98 | F | H | E | I | I | K | V | S | Y | 12 | |
| 102 | I | K | V | S | Y | Y | R | K | F | 12 | |

HLA-B*5101 nonamers

| Pos | 1 | 2 | 3 | 4 | 5 | 6 | 7 | 8 | 9 | score | |
|---|---|---|---|---|---|---|---|---|---|---|---|
| 93 | D | P | G | C | C | F | H | E | I | 25 | Portion of SEQ ID NO: 5; each start position is |
| 94 | P | G | C | C | F | H | E | I | I | 16 | |

TABLE XXVI-continued

MHC Class 1 nonamer and decamer analysis of 121P1F1 for selected alleles. Listed are scores that fall within the top 50% (rounded up) of all scores for the selected allele.

| Pos | Sequence | Score | |
|---|---|---|---|
| 95 | C C F H E I I K V | 13 | specified, the length of each peptide is 9 amino acids, the end position for each peptide is the start position plus eight |
| 115 | V A H A C N P S T | 13 | |
| 113 | G A V A H A C N P | 12 | |
| 104 | V S Y Y R K F W L | 11 | |
| 107 | Y R K F W L G A V | 11 | |
| 117 | H A C N P S T L G | 11 | |
| 116 | A H A C N P S T L | 9 | |

Class I decamer analysis of amino acids 84-126 (HKLEVLESQDPGCCFHEIIKVSYYRKFWLGAVAHACNPSTLGG) of 121P1F1 splice variant 1a. Listed are those alleles and peptides in which the scores fall within the top 50% (rounded up) of the scores from the analysis of the full length 121P1F1 base peptide sequence.

HLA-A*0201 decamers

Pos 1 2 3 4 5 6 7 8 9 0  score

| Pos | Sequence | Score | |
|---|---|---|---|
| 106 | Y R K F W L G A V | 17 | Portion of SEQ ID NO: 5; each start position is specified, the length of each peptide is 10 amino acids, the end position for each peptide is the start position plus nine |
| 115 | V A H A C N P S T L | 17 | |
| 94 | G C C F H E I I K V | 16 | |
| 114 | A V A H A C N P S T | 15 | |
| 103 | K V S Y Y R K F W L | 14 | |
| 92 | Q D P G C C F H E I | 13 | |
| 109 | K F W L G A V A H A | 12 | |
| 111 | W L G A V A H A C N | 12 | |

HLA-A*0203 decamers

Pos 1 2 3 4 5 6 7 8 9 0  score

| Pos | Sequence | Score | |
|---|---|---|---|
| 107 | Y R K F W L G A V A | 18 | Portion of SEQ ID NO: 5; each start position is specified, the length of each peptide is 10 amino acids, the end position for each peptide is the start position plus nine |
| 119 | K F W L G A V A H A | 18 | |
| 105 | S Y Y R K F W L G A | 10 | |
| 106 | Y R K F W L G A V | 9 | |
| 108 | R K F W L G A V A H | 9 | |
| 110 | F W L G A V A H A C | 9 | |

HLA-A1 decamers

Pos 1 2 3 4 5 6 7 8 9 0  score

| Pos | Sequence | Score | |
|---|---|---|---|
| 98 | F H E I I K V S Y Y | 27 | Portion of SEQ ID NO: 5; each start position is specified, the length of each peptide is 10 amino acids, the end position for each peptide is the start position plus nine |
| 91 | S Q D P G C C F H E | 16 | |
| 97 | C F H E I I K V S Y | 15 | |
| 88 | V L E S Q D P G C C | 12 | |

HLA-A26 decamers

Pos 1 2 3 4 5 6 7 8 9 0  score

| Pos | Sequence | Score | |
|---|---|---|---|
| 101 | I I K V S Y Y R K F | 26 | Portion of SEQ ID NO: 5; each start position is specified, the length of each peptide is 10 amino acids, the end position for each peptide is the start position plus nine |
| 100 | E I I K V S Y Y R K | 24 | |
| 87 | E V L E S Q D P G C | 20 | |
| 97 | C F H E I I K V S Y | 20 | |
| 103 | K V S Y Y R K F W L | 18 | |
| 98 | F H E I I K V S Y Y | 15 | |

HLA-A3 decamers

Pos 1 2 3 4 5 6 7 8 9 0  score

| Pos | Sequence | Score | |
|---|---|---|---|
| 100 | E I I K V S Y Y R K | 21 | Portion of SEQ ID NO: 5; each start position is specified, the length of each peptide is 10 amino acids, the end position for each peptide is the start position plus nine |
| 108 | R K F W L G A V A H | 16 | |
| 114 | A V A H A C N P S T | 16 | |
| 101 | I I K V S Y Y R K F | 15 | |
| 111 | W L G A V A H A C N | 15 | |
| 103 | K V S Y Y R K F W L | 14 | |

| Pos | Sequence | Score | |
|---|---|---|---|
| 85 | K L E V L E S Q D P | 13 | start position plus nine |
| 87 | E V L E S Q D P G C | 13 | |
| 97 | C F H E I I K V S Y | 13 | |

HLA-B*0702 decamers

Pos 1 2 3 4 5 6 7 8 9 0  score

| Pos | Sequence | Score | |
|---|---|---|---|
| 93 | D P G C C F H E I I | 17 | Portion of SEQ ID NO: 5; each start position is specified, the length of each peptide is 10 amino acids, the end position for each peptide is the start position plus nine |
| 103 | K V S Y Y R K F W L | 13 | |
| 115 | V A H A C N P S T L | 11 | |
| 106 | Y R K F W L G A V | 10 | |
| 114 | A V A H A C N P S T | 10 | |

HLA-B*4402 decamers

Pos 1 2 3 4 5 6 7 8 9 0  score

| Pos | Sequence | Score | |
|---|---|---|---|
| 89 | L E S Q D P G C C F | 21 | Portion of SEQ ID NO: 5; each start position is specified, the length of each peptide is 10 amino acids, the end position for each peptide is the start position plus nine |
| 99 | H E I I K V S Y Y R | 13 | |
| 102 | I K V S Y Y R K F W | 13 | |

Class I nonamer analysis of amino acids 1-14 (MKCKMELSEGSQKH) of 121P1F1 splice variant 1b. Listed are those alleles and peptides in which the score falls within the top 50% (rounded up) of the scores from the analysis of the full length 121P1F1 base peptide sequence.

HLA-A1 nonamers

Pos 1 2 3 4 5 6 7 8 9  score

| Pos | Sequence | Score | |
|---|---|---|---|
| 4 | K M E L S E G S Q | 10 | Portion of SEQ ID NO: 7; each start position is specified, the length of each peptide is 10 amino acids, the end position for each peptide is the start position plus nine |

HLA-A26 nonamers

Pos 1 2 3 4 5 6 7 8 9  score

| Pos | Sequence | Score | |
|---|---|---|---|
| 6 | E L S E G S Q K H | 18 | Portion of SEQ ID NO: 7; each start position is specified, the length of each peptide is 10 amino acids, the end position for each peptide is the start position plus nine |

HLA-A3 nonamers

Pos 1 2 3 4 5 6 7 8 9  score

| Pos | Sequence | Score | |
|---|---|---|---|
| 5 | M E L S E G S Q K | 21 | Portion of SEQ ID NO: 7; each start position is specified, the length of each peptide is 10 amino acids, the end position for each peptide is the start position plus nine |
| 6 | E L S E G S Q K H | 17 | |

TABLE XXVI-continued

MHC Class 1 nonamer and decamer analysis of 121P1F1 for selected alleles. Listed are scores that fall within the top 50% (rounded up) of all scores for the selected allele.

HLA-B*2705 nonamers

| Pos | 1 2 3 4 5 6 7 8 9 | score | |
|---|---|---|---|
| 5 | M E L S E G S Q K | 15 | Portion of SEQ ID NO: 7; each start position is specified, the length of each peptide is 10 amino acids, the end position for each peptide is the start position plus nine |
| 6 | E L S E G S Q K H | 14 | |

HLA-B*4402 nonamers

| Pos | 1 2 3 4 5 6 7 8 9 | score | |
|---|---|---|---|
| 5 | M E L S E G S Q K | 12 | Portion of SEQ ID NO: 7; each start position is specified, the length of each peptide is 10 amino acids, the end position for each peptide is the start position plus nine |

Class I decamer analysis of amino acids 1-15 (MKCKMELSEGSQKHA) of 121P1F1 splice variant 1b. Listed are those alleles and peptides in which the score falls within the top 50% (rounded up) of the scores from the analysis of the full length 121P1F1 parental peptide sequence.

HLA-A*0201 decamers

| Pos | 1 2 3 4 5 6 7 8 9 0 | score | |
|---|---|---|---|
| 6 | E L S E G S Q K H A | 12 | Portion of SEQ ID NO: 7; each start position is specified, the length of each peptide is 10 amino acids, the end position for each peptide is the start position plus nine |

HLA-A*0203 decamers

| Pos | 1 2 3 4 5 6 7 8 9 0 | score | |
|---|---|---|---|
| 6 | E L S E G S Q K H A | 10 | Portion of SEQ ID NO: 7; each start position is specified, the length of each peptide is 10 amino acids, the end position for each peptide is the start position plus nine |

HLA-A26 decamers

| Pos | 1 2 3 4 5 6 7 8 9 0 | score | |
|---|---|---|---|
| 6 | E L S E G S Q K H A | 17 | Portion of SEQ ID NO: 7; each start position is specified, the length of each peptide is 10 amino acids, the end position for each peptide is the start position plus nine |

HLA-A3 decamers

| Pos | 1 2 3 4 5 6 7 8 9 0 | score | |
|---|---|---|---|
| 4 | K M E L S E G S Q K | 23 | Portion of SEQ ID NO: 7; each start position is specified, the length of each peptide is 10 amino acids, the end position for each peptide is the start position plus nine |

Class I nonamer analysis of amino acids 110-122 (AKIGRCETAKQIK) of 121P1F1 splice variant 2. Listed are those alleles and peptides in which the score falls within the top 50% (rounded up) of the scores from the analysis of the full length 121P1F1 parental peptide sequence.

HLA-A1 nonamers

| Pos | 1 2 3 4 5 6 7 8 9 | score | |
|---|---|---|---|
| 114 | R C E T A K Q I K | 10 | Portion of SEQ ID NO: 9; each start position is specified, the length of each peptide is 9 amino acids, the end position for each peptide is the start position plus eight |

HLA-A3 nonamers

| Pos | 1 2 3 4 5 6 7 8 9 | score | |
|---|---|---|---|
| 111 | K I G R C E T A K | 26 | Portion of SEQ ID NO: 9; each start position is specified, the length of each peptide is 9 amino acids, the end position for each peptide is the start position plus eight |
| 110 | A K I G R C E T A | 14 | |
| 114 | R C E T A K Q I K | 14 | |

HLA-B*0702 nonamers

| Pos | 1 2 3 4 5 6 7 8 9 | score | |
|---|---|---|---|
| 110 | A K I G R C E T A | 10 | Portion of SEQ ID NO: 9; each start position is specified, the length of each peptide is 9 amino acids, the end position for each peptide is the start position plus eight |

HLA-B*2705 nonamers

| Pos | 1 2 3 4 5 6 7 8 9 | score | |
|---|---|---|---|
| 113 | G R C E T A K Q I | 22 | Portion of SEQ ID NO: 9; each start position is specified, the length of each peptide is 9 amino acids, the end position for each peptide is the start position plus eight |
| 114 | R C E T A K Q I K | 15 | |
| 111 | K I G R C E T A K | 14 | |

HLA-B*2709 nonamers

| Pos | 1 2 3 4 5 6 7 8 9 | score | |
|---|---|---|---|
| 113 | G R C E T A K Q I | 23 | Portion of SEQ ID NO: 9; each start position is specified, the length of each peptide is 9 amino acids, the end position |

TABLE XXVI-continued

MHC Class 1 nonamer and decamer analysis of 121P1F1 for selected alleles. Listed are scores that fall within the top 50% (rounded up) of all scores for the selected allele.

for each peptide is the start position plus eight

HLA-B*4402 nonamers

Pos1 2 3 4 5 6 7 8 9   score

113G R C E T A K Q I   12   Portion of SEQ ID NO: 9; each start position is specified, the length of each peptide is 9 amino acids, the end position for each peptide is the start position plus eight

HLA-B*5101 nonamers

Pos1 2 3 4 5 6 7 8 9   score

113G R C E T A K Q I   15   Portion of SEQ ID NO: 9; each start position is specified, the length of each peptide is 9 amino acids, the end position for each peptide is the start position plus eight Class I decamer analysis of amino acids 109-122 (KAKIGRCETAKQIK) of 121P1F1 splice variant 2. Listed are those alleles and peptides in which the score falls within the top 50% (rounded up) of the scores from the analysis of the full length 121P1F1 base peptide sequence.

HLA-A*0201 decamers

Pos1 2 3 4 5 6 7 8 9 0   score

111K I G R C E T A K Q   13   Portion of SEQ ID NO: 9; each start position is specified, the length of each peptide is 10 amino acids, the end position for each peptide is the start position plus nine

HLA-A*0203 decamers

Pos1 2 3 4 5 6 7 8 9 0   score

109K A K I G R C E T A   10   Portion of SEQ ID NO: 9;
110A K I G R C E T A K   9    each start position is specified, the length of each peptide is 10 amino acids, the end position for each peptide is the start position plus nine

HLA-A3 decamers

Pos1 2 3 4 5 6 7 8 9 0   score

110A K I G R C E T A K   20   Portion of SEQ ID NO: 9;
111K I G R C E T A K Q   17   each start position is specified, the length of each peptide is 10 amino acids, the end position for each peptide is the start position plus nine TABLE XXVI-continued MHC Class 1 nonamer and decamer analysis of 121P1F1 for selected alleles. Listed are scores that fall within the top 50% (rounded up) of all scores for the selected allele.

Class I nonamer analysis of amino acids 148-164 (DPQVVEEIHNIFAIKSW) of 121P1F1 splice variant 3. Listed are those alleles and peptides in which the score falls within the top 50% (rounded up) of the scores from the analysis of the full length 121P1F1 base peptide sequence.

HLA-A*0201 nonamers

Pos1 2 3 4 5 6 7 8 9   score

150Q V V E E I H N I   19   Portion of SEQ ID NO: 11; each start position is specified, the length of each peptide is 9 amino acids, the end position for each peptide is the start position plus eight

HLA-A1 nonamers

Pos1 2 3 4 5 6 7 8 9   score

152V E E I H N I F A   16   Portion of SEQ ID NO:
151V V E E I H N I F   11   11; each start position is specified, the length of each peptide is 9 amino acids, the end position for each peptide is the start position plus eight

HLA-A26 nonamers

Pos1 2 3 4 5 6 7 8 9   score

151V V E E I H N I F   22   Portion of SEQ ID NO:
154E I H N I F A I K   21   11; each start position
150Q V V E E I H N I   17   is specified, the length
153E E I H N I F A I   13   of each peptide is 9 amino acids, the end position for each peptide is the start position plus eight

HLA-A3 nonamers

Pos1 2 3 4 5 6 7 8 9   score

154E I H N I F A I K   22   Portion of SEQ ID NO:
151V V E E I H N I F   15   11; each start position
150Q V V E E I H N I   13   is specified, the length of each peptide is 9 amino acids, the end position for each peptide is the start position plus eight

HLA-B*0702 nonamers

Pos1 2 3 4 5 6 7 8 9   score

148D P Q V V E E I H   10   Portion of SEQ ID NO: 11; each start position is specified, the length of each peptide is 9 amino acids, the end position for each peptide is the start position plus eight TABLE XXVI-continued MHC Class 1 nonamer and decamer analysis of 121P1F1 for selected alleles. Listed are scores that fall within the top 50% (rounded up) of all scores for the selected allele.

HLA-B*1510 nonamers

Pos1 2 3 4 5 6 7 8 9  score

| | | |
|---|---|---|
| 155I H N I F A I K S | 12 | Portion of SEQ ID NO: 11; each start position is specified, the length of each peptide is 9 amino acids, the end position for each peptide is the start position plus eight |
| 151V V E E I H N I F | 8 | |

HLA-B*2705 nonamers

Pos1 2 3 4 5 6 7 8 9  score

| | | |
|---|---|---|
| 150Q V V E E I H N I | 14 | Portion of SEQ ID NO: 11; each start position is specified, the length of each peptide is 9 amino acids, the end position for each peptide is the start position plus eight |
| 151V V E E I H N I F | 13 | |
| 154E I H N I F A I K | 12 | |

HLA-B*4402 nonamers

Pos1 2 3 4 5 6 7 8 9  score

| | | |
|---|---|---|
| 153E E I H N I F A I | 29 | Portion of SEQ ID NO: 11; each start position is specified, the length of each peptide is 9 amino acids, the end position for each peptide is the start position plus eight |
| 156H N I F A I K S W | 18 | |
| 150Q V V E E I H N I | 12 | |
| 151V V E E I H N I F | 12 | |

HLA-B*5101 nonamers

Pos1 2 3 4 5 6 7 8 9  score

| | | |
|---|---|---|
| 148D P Q V V E E I H | 16 | Portion of SEQ ID NO: 11; each start position is specified, the length of each peptide is 9 amino acids, the end position for each peptide is the start position plus eight |
| 150Q V V E E I H N I | 13 | |
| 153E E I H N I F A I | 11 | |

Class I decamer analysis of amino acids 147-165 (CDPQVVEEIHNIFAIKSWA) of 121P1F1 splice variant 3. Listed are those alleles and peptides in which the score falls within the top 50% (rounded up) of the scores from the analysis of the full length 121P1F1 base peptide sequence.

HLA-A*0201 decamers

Pos1 2 3 4 5 6 7 8 9 0  score

| | | |
|---|---|---|
| 152V E E I H N̲ I F A I | 13 | Portion of SEQ ID NO: 11; each start position is specified, the length of each peptide is 10 amino acids, the end position for each peptide is the start position plus nine |

HLA-A*0203 decamers

Pos1 2 3 4 5 6 7 8 9 0  score

| | | |
|---|---|---|
| 151V V̲ E E I H N̲ I F A | 10 | Portion of SEQ ID NO: 11; each start position is specified, the length of each peptide is 10 amino acids, the end position for each peptide is the start position plus nine |
| 156H N̲ I F A I K̲ S W A | 10 | |
| 152V E̲ E I H N N̲ I F A I | 9 | |

HLA-A1 decamers

Pos1 2 3 4 5 6 7 8 9 0  score

| | | |
|---|---|---|
| 151V V̲ E E I H N̲ I F A | 16 | Portion of SEQ ID NO: 11; each start position is specified, the length of each peptide is 10 amino acids, the end position for each peptide is the start position plus nine |

HLA-A26 decamers

Pos1 2 3 4 5 6 7 8 9 0  score

| | | |
|---|---|---|
| 150Q V V E E I H N I F | 22 | Portion of SEQ ID NO: 11; each start position is specified, the length of each peptide is 10 amino acids, the end position for each peptide is the start position plus nine |
| 154E I H N I F A I K S | 17 | |

HLA-A3 decamers

Pos1 2 3 4 5 6 7 8 9 0  score

| | | |
|---|---|---|
| 150Q V̲ E E I̲ H N̲ I F F | 17 | Portion of SEQ ID NO: 11; each start position is specified, the length of each peptide is 10 amino acids, the end position for each peptide is the start position plus nine |
| 153E E I̲ H N̲ I̲ F A I K | 16 | |

HLA-B*0702 decamers

Pos1 2 3 4 5 6 7 8 9 0  score

| | | |
|---|---|---|
| 148D P Q V V E E I H N | 10 | Portion of SEQ ID NO: 11; each start position is specified, the length of each peptide is 10 amino acids, the end position for each peptide is the start position plus nine |

HLA-B*4402 decamers

Pos1 2 3 4 5 6 7 8 9 0  score

| | | |
|---|---|---|
| 152V E E I H N I F A I | 23 | Portion of SEQ ID NO: 11; each start position is specified, the length of each peptide is 10 amino acids, the end position for each |
| 153E E I H N I F A I K | 16 | |
| 155I H N I F A I K S W | 15 | |

TABLE XXVI-continued

MHC Class 1 nonamer and decamer analysis of 121P1F1 for selected alleles. Listed are scores that fall within the top 50% (rounded up) of all scores for the selected allele.

peptide is the start
position plus nine

TABLE XXVII

MHC Class II analysis of 121P1F1 for selected alleles. Listed are scores that fall within the top 50% (rounded up) of all scores for the selected allele.

HLA-DRB1*0101 15 - mers

Pos 1 2 3 4 5 6 7 8 9 0 1 2 3 4 5  score

| | |
|---|---|
| 83 K H K L E V L E S Q L S E G S | 31 |
| 86 L E V L E S Q L S E G S Q K H | 30 |
| 26 V F Q L K D L E K I A P K E K | 26 |
| 48 K E V L Q S L V D D G M V D C | 26 |
| 67 T S N Y Y W A F P S K A L H A | 25 |
| 68 S N Y Y W A F P S K A L H A R | 25 |
| 141 V E K Y K D C D P Q V V E E I | 25 |
| 39 E K G I T A M S V K E V L Q S | 24 |
| 29 L K D L E K I A P K E K G I T | 23 |
| 36 A P K E K G I T A M S V K E V | 23 |
| 44 A M S V K E V L Q S L V D D G | 23 |
| 167 N R W T D N I F A I K S W A K | 23 |
| 13 R T R M M E I F S E T K D V F | 20 |
| 24 K D V F Q L K D L E K I A P K | 20 |
| 150 Q V V E E I R Q A N K V A K E | 20 |
| 170 T D N I F A I K S W A K R K F | 20 |
| 186 F E E N K I D R T F G I P E D | 20 |
| 73 A F P S K A L H A R K H K L E | 19 |
| 80 H A R K H K L E V L E S Q L S | 19 |
| 116 E T E E R T R L A K E L S S L | 19 |
| 173 I F A I K S W A K R K F G F E | 19 |
| 33 E K I A P K E K G I T A M S V | 18 |
| 138 K A E V E K Y K D C D P Q V V | 18 |
| 158 A N K V A K E A A N R W T D N | 18 |
| 1 M S K K K G L S A E E K R T R | 17 |
| 15 R M M E I F S E T K D V F Q L | 17 |
| 42 I T A M S V K E V L Q S L V D | 17 |
| 65 I G T S N Y Y W A F P S K A L | 17 |
| 90 E S Q L S E G S Q K H A S L Q | 17 |
| 101 A S L Q K S I E K A K I G R C | 17 |
| 117 T E E R T R L A K E L S S L R | 17 |
| 154 E I R Q A N K V A K E A A N R | 17 |
| 155 I R Q A N K V A K E A A N R W | 17 |
| 16 M M E I F S E T K D V F Q L K | 16 |
| 23 T K D V F Q L K D L E K I A P | 16 |
| 35 I A P K E K G I T A M S V K E | 16 |
| 57 D G M V D C E R I G T S N Y Y | 16 |
| 62 C E R I G T S N Y Y W A F P S | 16 |
| 70 Y Y W A F P S K A L H A R K H | 16 |
| 113 G R C E T E E R T R L A K E L | 16 |
| 120 R T R L A K E L S S L R D Q R | 16 |
| 124 A K E L S S L R D Q R E Q L K | 16 |
| 127 L S S L R D Q R E Q L K A E V | 16 |
| 130 L R D Q R E Q L K A E V E K Y | 16 |
| 131 R D Q R E Q L K A E V E K Y K | 16 |
| 188 E N K I D R T F G I P E D F D | 16 |
| 190 K I D R T F G I P E D F D Y I | 16 |
| 6 G L S A E E K R T R M M E I F | 15 |
| 10 E E K R T R M M E I F S E T K | 15 |
| 49 E V L Q S L V D D G M V D C E | 15 |
| 54 L V D D G M V D C E R I G T S | 15 |
| 109 K A K I G R C E T E E R T R L | 15 |
| 121 T R L A K E L S S L R D Q R E | 15 |
| 151 V V E E I R Q A N K V A K E A | 15 |

Portion of SEQ ID NO: 3 each start position is specified, the length of each peptide is 15 amino acids, the end position for each peptide is the start position plus fourteen

TABLE XXVII-continued

MHC Class II analysis of 121P1F1 for selected alleles. Listed are scores that fall within the top 50% (rounded up) of all scores for the selected allele.

HLA-DRB1*0301 (DR17) 15 - mers

Pos 1 2 3 4 5 6 7 8 9 0 1 2 3 4 5  score

| | |
|---|---|
| 173 I F A I K S W A K R K F G F E | 27 |
| 126 E L S S L R D Q R E Q L K A E | 26 |
| 16 M M E I F S E T K D V F Q L K | 25 |
| 51 L Q S L V D D G M V D C E R I | 23 |
| 44 A M S V K E V L Q S L V D D G | 20 |
| 148 D P Q V V E E I R Q A N K V A | 20 |
| 25 D V F Q L K D L E K I A P K E | 19 |
| 26 V F Q L K D L E K I A P K E K | 19 |
| 127 L S S L R D Q R E Q L K A E V | 19 |
| 149 P Q V V E E I R Q A N K V A K | 19 |
| 152 V E E I R Q A N K V A K E A A | 19 |
| 14 T R M M E I F S E T K D V F Q | 18 |
| 32 L E K I A P K E K G I T A M S | 18 |
| 56 D D G M V D C E R I G T S N Y | 18 |
| 82 R K H K L E V L E S Q L S E G | 18 |
| 90 E S Q L S E G S Q K H A S L Q | 18 |
| 142 E K Y K D C D P Q V V E E I R | 18 |
| 4 K K G L S A E E K R T R M M E | 17 |
| 75 P S K A L H A R K H K L E V L | 17 |
| 100 H A S L Q K S I E K A K I G R | 17 |
| 134 R E Q L K A E V E K Y K D C D | 17 |
| 55 V D D G M V D C E R I G T S N | 16 |
| 40 K G I T A M S V K E V L Q S L | 15 |
| 112 I G R C E T E E R T R L A K E | 15 |
| 181 K R K F G F E E N K I D R T F | 15 |
| 175 A I K S W A K R K F G F E E N | 14 |
| 19 I F S E T K D V F Q L K D L E | 13 |
| 47 V K E V L Q S L V D D G M V D | 13 |
| 83 K H K L E V L E S Q L S E G S | 13 |
| 85 K L E V L E S Q L S E G S Q K | 13 |

Portion of SEQ ID NO: 3; each start position is specified, the length of each peptide is 15 amino acids, the end position for each peptide is the start position plus fourteen

HLA-DRB1*0401 (DR4Dw4) 15 - mers

Pos 1 2 3 4 5 6 7 8 9 0 1 2 3 4 5  score

| | |
|---|---|
| 68 S N Y Y W A F P S K A L H A R | 28 |
| 13 R T R M M E I F S E T K D V F | 26 |
| 44 A M S V K E V L Q S L V D D G | 26 |
| 83 K H K L E V L E S Q L S E G S | 26 |
| 148 D P Q V V E E I R Q A N K V A | 26 |
| 149 P Q V V E E I R Q A N K V A K | 26 |
| 170 T D N I F A I K S W A K R K F | 26 |
| 67 T S N Y Y W A F P S K A L H A | 22 |
| 181 K R K F G F E E N K I D R T F | 22 |
| 23 T K D V F Q L K D L E K I A P | 20 |
| 29 L K D L E K I A P K E K G I T | 20 |
| 48 K E V L Q S L V D D G M V D C | 20 |
| 56 D D G M V D C E R I G T S N Y | 20 |
| 57 D G M V D C E R I G T S N Y Y | 20 |
| 86 L E V L E S Q L S E G S Q K H | 20 |
| 90 E S Q L S E G S Q K H A S L Q | 20 |
| 120 R T R L A K E L S S L R D Q R | 20 |
| 134 R E Q L K A E V E K Y K D C D | 20 |
| 152 V E E I R Q A N K V A K E A A | 20 |
| 5 K G L S A E E K R T R M M E I | 18 |
| 72 W A F P S K A L H A R K H K L | 18 |
| 106 S I E K A K I G R C E T E E R | 18 |
| 112 I G R C E T E E R T R L A K E | 18 |
| 113 G R C E T E E R T R L A K E L | 18 |
| 126 E L S S L R D Q R E Q L K A E | 18 |
| 159 N K V A K E A A N R W T D N I | 18 |
| 186 F E E N K I D R T F G I P E D | 18 |
| 17 M E I F S E T K D V F Q L K D | 16 |
| 141 V E K Y K D C D P Q V V E E I | 16 |
| 166 A N R W T D N I F A I K S W A | 16 |
| 183 R K F G F E E N K I D R T F G I | 16 |
| 4 K K G L S A E E K R T R M M E | 14 |
| 14 T R M M E I F S E T K D V F Q | 14 |
| 16 M M E I F S E T K D V F Q L K | 14 |
| 26 V F Q L K D L E K I A P K E K | 14 |
| 39 E K G I T A M S V K E V L Q S | 14 |

Portion of SEQ ID NO: 3; each start position is specified, the length of each peptide is 15 amino acids, the end position for each peptide is the start position plus fourteen

TABLE XXVII-continued

MHC Class II analysis of 121P1F1 for selected alleles. Listed are scores that fall within the top 50% (rounded up) of all scores for the selected allele.

| Pos | Peptide | Score |
|---|---|---|
| 51 | Q S L V D D G M V D C E R I | 14 |
| 62 | C E R I G T S N Y Y W A F P S | 14 |
| 100 | H A S L Q K S I E K A K I G R | 14 |
| 104 | Q K S I E K A K I G R C E T E | 14 |
| 109 | K A K I G R C E T E E R T R L | 14 |
| 124 | A K E L S S L R D Q R E Q L K | 14 |
| 127 | L S S L R D Q R E Q L K A E V | 14 |
| 158 | A N K V A K E A A N R W T D N | 14 |

HLA-DRB1*1101 15 - mers

Pos 1 2 3 4 5 6 7 8 9 0 1 2 3 4 5  score

| Pos | Peptide | Score | |
|---|---|---|---|
| 26 | V F Q L K D L E K I A P K E K | 26 | Portion of SEQ |
| 117 | T E E R T R L A K E L S S L R | 23 | ID NO: 3; each |
| 83 | K H K L E V L E S Q L S E G S | 20 | start position |
| 155 | I R Q A N K V A K E A A N R W | 20 | is specified, |
| 185 | G F E E N K I D R T F G I P E | 20 | the length of |
| 69 | N Y Y W A F P S K A L H A R K | 19 | each peptide is |
| 67 | T S N Y Y W A F P S K A L H A | 17 | 15 amino acids, |
| 16 | M M E I F S E T K D V F Q L K | 16 | the end position |
| 173 | I F A I K S W A K R K F G F E | 16 | for each peptide |
| 4 | K K G L S A E E K R T R M M E | 15 | is the start |
| 30 | K D L E K I A P K E K G I T A | 15 | position plus |
| 32 | L E K I A P K E K G I T A M S | 15 | fourteen |
| 76 | S K A L H A R K H K L E V L E | 15 | |
| 97 | S Q K H A S L Q K S I E K A K | 15 | |
| 101 | A S L Q K S I E K A K I G R C | 15 | |
| 135 | E Q L K A E V E K Y K D C D P | 15 | |
| 10 | E E K R T R M M E I F S E T K | 14 | |
| 39 | E K G I T A M S V K E V L Q S | 14 | |
| 48 | K E V L Q S L V D D G M V D C | 14 | |
| 56 | D D G M V D C E R I G T S N Y | 14 | |
| 91 | S Q L S E G S Q K H A S L Q K | 14 | |
| 106 | S I E K A K I G R C E T E E R | 14 | |
| 124 | A K E L S S L R D Q R E Q L K | 14 | |
| 148 | D P Q V V E E I R Q A N K V A | 14 | |
| 152 | V E E I R Q A N K V A K E A A | 14 | |
| 169 | W T D N I F A I K S W A K R K | 14 | |
| 174 | F A I K S W A K R K F G F E E | 14 | |
| 23 | T K D V F Q L K D L E K I A P | 13 | |
| 42 | I T A M S V K E V L Q S L V D | 13 | |
| 44 | A M S V K E V L Q S L V D D G | 13 | |
| 166 | A N R W T D N I F A I K S W A | 13 | |
| 167 | N R W T D N I F A I K S W A K | 13 | |
| 170 | T D N I F A I K S W A K R K F | 13 | |

Class II 15-mer analysis of amino acids 80-126 (HARKHKLEVLESQDPGCCFHEIIKVSY YRKFWLGAVAHACNPSTLGG) of 121P1F1 splice variant 1a. Listed are those alleles and peptides in which the score falls within the top 50% (rounded up) of the scores from the analysis of the full length 121P1F1 base peptide sequence.

HLA-DRB1*0101 15 - mers

Pos 1 2 3 4 5 6 7 8 9 0 1 2 3 4 5  score

| Pos | Peptide | Score | |
|---|---|---|---|
| 83 | K H K L E V L E S Q D P G C C | 31 | Portion of SEQ |
| 104 | V S Y Y R K F W L G A V A H A | 22 | ID NO: 5; each |
| 86 | L E V L E S Q D P G C C F H E | 20 | start position |
| 103 | K V S Y Y R K F W L G A V A H | 20 | is specified, |
| 80 | H A R K H K L E V L E S Q D P | 19 | the length of |
| 99 | H E I I K V S Y Y R K F W L G | 19 | each peptide is |
| 107 | Y R K F W L G A V A H A C N P | 19 | 15 amino acids, |
| 105 | S Y Y R K F W L G A V A H A C | 18 | the end position |
| 108 | R K F W L G A V A H A C N P S | 18 | for each peptide |
| 106 | Y Y R K F W L G A V A H A C N | 17 | is the start |
| 87 | E V L E S Q D P G C C F H E I | 16 | position plus |
| 95 | G C C F H E I I K V S Y Y R K | 16 | fourteen |
| 98 | F H E I I K V S Y Y R K F W L | 16 | |

---

TABLE XXVII-continued

MHC Class II analysis of 121P1F1 for selected alleles. Listed are scores that fall within the top 50% (rounded up) of all scores for the selected allele.

| Pos | Peptide | Score |
|---|---|---|
| 101 | I I K V S Y Y R K F W L G A V | 16 |
| 110 | F W L G A V A H A C N P S T L | 16 |

HLA-DRB1*0301 (DR17) 15 - mers

Pos 1 2 3 4 5 6 7 8 9 0 1 2 3 4 5  score

| Pos | Peptide | Score | |
|---|---|---|---|
| 95 | G C C F H E I I K V S Y Y R K | 24 | Portion of SEQ |
| 101 | I I K V S Y Y R K F W L G A V | 24 | ID NO: 5; each |
| 99 | H E I I K V S Y Y R K F W L G | 20 | start position |
| 87 | E V L E S Q D P G C C F H E I | 19 | is specified, |
| 112 | L G A V A H A C N P S T L G G | 16 | the length of |
| 85 | K L E V L E S Q D P G C C F H | 13 | each peptide is 15 amino acids, the end position for each peptide is the start position plus fourteen |

HLA-DRB1*0401 (DR4Dw4) 15 - mers

Pos 1 2 3 4 5 6 7 8 9 0 1 2 3 4 5  score

| Pos | Peptide | Score | |
|---|---|---|---|
| 109 | K F W L G A V A H A C N P S T | 26 | Portion of SEQ |
| 112 | L G A V A H A C N P S T L G G | 26 | ID NO: 5; each |
| 104 | V S Y Y R K F W L G A V A H A | 22 | start position |
| 83 | K H K L E V L E S Q D P G C C | 20 | is specified, |
| 98 | F H E I I K V S Y Y R K F W L | 20 | the length of |
| 95 | G C C F H E I I K V S Y Y R K | 16 | each peptide is |
| 107 | Y R K F W L G A V A H A C N P | 16 | 15 amino acids, |
| 108 | R K F W L G A V A H A C N P S | 16 | the end position |
| 101 | I I K V S Y Y R K F W L G A V | 14 | for each peptide is the start position plus fourteen |

HLA-DRB1*1101 15 - mers

Pos 1 2 3 4 5 6 7 8 9 0 1 2 3 4 5  score

| Pos | Peptide | Score | |
|---|---|---|---|
| 95 | G C C F H E I I K V S Y Y R K | 24 | Portion SEQ |
| 109 | K F W L G A V A H A C N P S T | 20 | ID NO: 5; each |
| 83 | K H K L E V L E S Q D P G C C | 19 | start position |
| 103 | K V S Y Y R K F W L G A V A H | 16 | is specified, |
| 107 | Y R K F W L G A V A H A C N P | 16 | the length of |
| 98 | F H E I I K V S Y Y R K F W L | 14 | each peptide is |
| 101 | I I K V S Y Y R K F W L G A V | 14 | 15 amino acids, the end position for each peptide is the start position plus fourteen |

Class II 15-mer analysis of amino acids 1-20 (MKCKMELSEGSQKHASLQKS) of 121P1F1 splice variant 1b. Listed are those alleles and peptides in which the score falls within the top 50% (rounded up) of the scores from the analysis of the full length 121P1F1 base peptide sequence.

HLA-DRB1*0101 15 - mers

Pos 1 2 3 4 5 6 7 8 9 0 1 2 3 4 5  score

| Pos | Peptide | Score | |
|---|---|---|---|
| 2 | K C K M E L S E G S Q K H A S | 18 | Portion of SEQ |
| 4 | K M E L S E G S Q K H A S L Q | 17 | ID NO: 7; each start position is specified, the length of each peptide is 15 amino acids, the end position for each peptide |

TABLE XXVII-continued

MHC Class II analysis of 121P1F1 for selected alleles. Listed are scores that fall within the top 50% (rounded up) of all scores for the selected allele.

HLA-DRB1*0301 (DR17) 15 - mers

Pos 1 2 3 4 5 6 7 8 9 0 1 2 3 4 5    score

| Position | Sequence | Score | Notes |
|---|---|---|---|
| 4 | K M E L S E G S Q K H A S L Q | 18 | Portion of SEQ ID NO: 7; each start position is specified, the length of each peptide is 15 amino acids, the end position for each peptide is the start position plus fourteen |

HLA-DRB1*0401 (DR4Dw4) 15 - mers

Pos 1 2 3 4 5 6 7 8 9 0 1 2 3 4 5    score

| Position | Sequence | Score | Notes |
|---|---|---|---|
| 4 | K M E L S E G S Q K H A S L Q | 20 | Portion of SEQ ID NO: 7; each start position is specified, the length of each peptide is 15 amino acids, the end position for each peptide is the start position plus fourteen |
| 2 | K C K M E L S E G S Q K H A S | 14 | |

HLA-DRB1*1101 15 - mers

Pos 1 2 3 4 5 6 7 8 9 0 1 2 3 4 5    score

| Position | Sequence | Score | Notes |
|---|---|---|---|
| 5 | M E L S E G S Q K H A S L Q K | 14 | Portion of SEQ ID NO: 7; each start position is specified, the length of each peptide is 15 amino acids, the end position for each peptide is the start position plus fourteen |

Class II 15-mer analysis of amino acids 104-122 (QKSIEKAKIGRCETAKQIK) of 121P1F1 splice variant 2. Listed are those alleles and peptides in which the score falls within the top 50% (rounded up) of the scores from the analysis of the full length 121P1F1 base peptide sequence.

HLA-DRB1*0401 (DR4Dw4) 15 - mers

Pos 1 2 3 4 5 6 7 8 9 0 1 2 3 4 5    score

| Position | Sequence | Score | Notes |
|---|---|---|---|
| 106 | S I E K A K I G R C E T A K Q | 18 | Portion of SEQ ID NO: 9; each start position is specified, the length of each peptide is 15 amino acids, the end position for each peptide is the start position plus fourteen |
| 104 | Q K S I E K A K I G R C E T A | 14 | |

HLA-DRB1*1101 15 - mers

Pos 1 2 3 4 5 6 7 8 9 0 1 2 3 4 5    score

| Position | Sequence | Score | Notes |
|---|---|---|---|
| 106 | S I E K A K I G R C E T A K Q | 14 | Portion of SEQ ID NO: 9; each start position is specified, the length of each peptide is 15 amino acids, the end position for each peptide is the start position plus fourteen |

Class II 15-mer analysis of amino acids 142-170 (EKYKDCDPQVVEEIHNIFA IKSWAKRKFG) of 121P1F1 splice variant 3. Listed are those alleles and peptides in which the score falls within the top 50% (rounded up) of the scores from the analysis of the full length 121P1F1 base peptide sequence.

HLA-DRB1*0101 15 - mers

Pos 1 2 3 4 5 6 7 8 9 0 1 2 3 4 5    score

| Position | Sequence | Score | Notes |
|---|---|---|---|
| 152 | V E E I H N I F A I K S W A K | 31 | Portion of SEQ ID NO: 11; each start position is specified, the length of each peptide is 15 amino acids, the end position for each peptide is the start position plus fourteen |
| 149 | P Q V V E E I H N I F A I K S | 22 | |
| 155 | I H N I F A I K S W A K R K F | 20 | |
| 148 | D P Q V V E E I H N I F A I K | 17 | |

HLA-DRB1*0301 (DR17) 15 - mers

Pos 1 2 3 4 5 6 7 8 9 0 1 2 3 4 5    score

| Position | Sequence | Score | Notes |
|---|---|---|---|
| 148 | D P Q V V E E I H N I F A I K | 21 | Portion of SEQ ID NO: 11; each start position is specified, the length of each peptide is 15 amino acids, the end position for each peptide is the start position plus fourteen |
| 142 | E K Y K D C D P Q V V E E I H | 18 | |
| 149 | P Q V V E E I H N I F A I K S | 17 | |

HLA-DRB1*0401 (DR4Dw4) 15 - mers

Pos 1 2 3 4 5 6 7 8 9 0 1 2 3 4 5    score

| Position | Sequence | Score | Notes |
|---|---|---|---|
| 149 | P Q V V E E I H N I F A I K S | 26 | Portion of SEQ ID NO: 11; each start position is specified, the length of each peptide is |
| 155 | I H N I F A I K S W A K R K F | 26 | |
| 148 | D P Q V V E E I H N I F A I K | 20 | |
| 152 | V E E I H N I F A I K S W A K | 20 | |

TABLE XXVII-continued

MHC Class II analysis of 121P1F1 for selected alleles. Listed are scores that fall within the top 50% (rounded up) of all scores for the selected allele.

| | | | |
|---|---|---|---|
| | | | 15 amino acids, the end position for each peptide is the start position plus fourteen |

HLA-DRB1*1101 15 - mers

Pos 1 2 3 4 5 6 7 8 9 0 1 2 3 4 5   score

| | | | |
|---|---|---|---|
| 152 | V E E I H N I F A I K S W A K | 19 | Portion of SEQ |
| 149 | P Q V V E E I H N I F A I K S | 18 | ID NO: 11; each |
| 7 | D P Q V V E E I H N I F A I K | 15 | start position |
| 13 | E I H N I F A I K S W A K R K | 14 | is specified, |
| 14 | I H N I F A I K S W A K R K F | 13 | the length of each peptide is 15 amino acids, the end position for each peptide is the start position plus fourteen |

---

The invention claimed is:

1. An isolated polynucleotide encoding a 121P1F1 protein, wherein the 121P1F1 protein comprises an amino acid sequence selected from the group consisting of: SEQ ID NO: 7, SEQ ID NO: 9, SEQ ID NO: 11, and SEQ ID NO: 13.

2. The isolated polynucleotide of claim 1, wherein the 121P1F1 protein is immunoreactive with at least one antibody that specifically binds to amino acid residues 93-205 of SEQ ID NO: 3, amino acid residues 1-117 of SEQ ID NO: 3, amino acid residues 1-155 of SEQ ID NO: 3, amino acid residues 172-205 of SEQ ID NO: 3, or amino acid residues 16-205 of SEQ ID NO: 3.

3. The isolated polynucleotide acid of claim 1, wherein the polynucleotide comprises the nucleic acid sequence of SEQ ID NO: 6, SEQ ID NO: 8, SEQ ID NO: 10, or SEQ ID NO: 12.

4. The isolated polynucleotide of claim 1, wherein the polynucleotide is labeled with a detectable marker.

5. The isolated polynucleotide of claim 3, wherein the detectable marker is a radioisotope, a fluorescent compound, a bioluminescent compound, a chemiluminescent compound, a metal chelator, or an enzyme.

6. A pharmaceutical composition, comprising the isolated polynucleotide of claim 1 and a pharmaceutically acceptable carrier.

7. An isolated expression vector that comprises a polynucleotide of claim 1.

8. The isolated expression vector of claim 7, wherein the expression vector is a viral vector.

9. The isolated expression vector of claim 8, wherein the viral vector is a vaccinia vector, a fowlpox vector, a canarypox vector, an adenovirus vector, an influenza vector, a poliovirus vector, an adeno-associated virus vector, a lentivirus vector, or a Sindbis virus vector.

10. An isolated host cell containing the isolated expression vector of claim 7.

11. An isolated host cell containing the isolated expression vector of claim 8.

12. A process for producing a protein having the sequence of SEQ ID NO: 7, SEQ ID NO: 9, SEQ ID NO: 11, or SEQ ID NO: 13, comprising culturing a host cell of claim 11, under conditions sufficient for the production of the protein, and recovering the protein from the culture.

13. An isolated polynucleotide consisting of the nucleic acid sequence of SEQ ID NO: 6, SEQ ID NO: 8, SEQ ID NO: 10, or SEQ ID NO: 12.

14. The isolated polynucleotide of claim 13, wherein the polynucleotide is labeled with a detectable marker.

15. The isolated polynucleotide of claim 14, wherein the detectable marker is a radioisotope, a fluorescent compound, a bioluminescent compound, a chemiluminescent compound, a metal chelator, or an enzyme.

16. A pharmaceutical composition, comprising the polynucleotide of claim 13 and a pharmaceutically acceptable carrier.

17. An isolated expression vector that comprises a polynucleotide of claim 13.

18. The isolated expression vector of claim 17, wherein the expression vector is a viral vector.

19. The isolated expression vector of claim 18, wherein the viral vector is a vaccinia vector, a fowlpox vector, a canarypox vector, an adenovirus vector, an influenza vector, a poliovirus vector, an adeno-associated virus vector, a lentivirus vector, or a Sindbis virus vector.

20. An isolated host cell containing the isolated expression vector of claim 17.

* * * * *

SEQUENCE LISTING

<160> NUMBER OF SEQ ID NOS: 69

<210> SEQ ID NO 1
<211> LENGTH: 254
<212> TYPE: DNA
<213> ORGANISM: Homo sapiens

<400> SEQUENCE: 1

```
gatcacagtc tttgtatttt tctacttctg cctttagctg ttcccttggg tctcgaagtg      60
aagaaagctc ttttgctagc ctggttcgct cttccgtttc acatcggcca attttagctt     120
tctcaatgct tttctgtagg cttgcatgct tttgacttcc ctcagacaac tgagattcca     180
gaacctccaa cttatgtttc cttgcatgaa gagctttact tggaaaagcc caataataat     240
tagaagttcc gatc                                                       254
```

<210> SEQ ID NO 2
<211> LENGTH: 867
<212> TYPE: DNA
<213> ORGANISM: Homo sapiens
<220> FEATURE:
<221> NAME/KEY: CDS
<222> LOCATION: (82)...(696)

<400> SEQUENCE: 2

```
ccaaaatcaa acgcgtccgg gcctgtcccg cccctctccc caagcgcggg cccggccagc      60
ggaagcccct gcgcccgcgc c atg tca aag aaa aaa gga ctg agt gca gaa      111
                         Met Ser Lys Lys Lys Gly Leu Ser Ala Glu
                           1               5                  10 gaa aag aga act cgc atg atg gaa ata ttt tct gaa aca aaa gat gta      159
Glu Lys Arg Thr Arg Met Met Glu Ile Phe Ser Glu Thr Lys Asp Val
             15                  20                  25 ttt caa tta aaa gac ttg gag aag att gct ccc aaa gag aaa ggc att      207
Phe Gln Leu Lys Asp Leu Glu Lys Ile Ala Pro Lys Glu Lys Gly Ile
         30                  35                  40 act gct atg tca gta aaa gaa gtc ctt caa agc tta gtt gat gat ggt      255
Thr Ala Met Ser Val Lys Glu Val Leu Gln Ser Leu Val Asp Asp Gly
     45                  50                  55 atg gtt gac tgt gag agg atc gga act tct aat tat tat tgg gct ttt      303
Met Val Asp Cys Glu Arg Ile Gly Thr Ser Asn Tyr Tyr Trp Ala Phe
 60                  65                  70 cca agt aaa gct ctt cat gca agg aaa cat aag ttg gag gtt ctg gaa      351
Pro Ser Lys Ala Leu His Ala Arg Lys His Lys Leu Glu Val Leu Glu
```

```
                 75                  80                  85                  90
tct cag ttg tct gag gga agt caa aag cat gca agc cta cag aaa agc            399
Ser Gln Leu Ser Glu Gly Ser Gln Lys His Ala Ser Leu Gln Lys Ser
                     95                  100                 105 att gag aaa gct aaa att ggc cga tgt gaa acg gaa gag cga acc agg            447
Ile Glu Lys Ala Lys Ile Gly Arg Cys Glu Thr Glu Glu Arg Thr Arg
            110                 115                 120 cta gca aaa gag ctt tct tca ctt cga gac caa agg gaa cag cta aag            495
Leu Ala Lys Glu Leu Ser Ser Leu Arg Asp Gln Arg Glu Gln Leu Lys
        125                 130                 135 gca gaa gta gaa aaa tac aaa gac tgt gat ccg caa gtt gtg gaa gaa            543
Ala Glu Val Glu Lys Tyr Lys Asp Cys Asp Pro Gln Val Val Glu Glu
    140                 145                 150 ata cgc caa gca aat aaa gta gcc aaa gaa gct gct aac aga tgg act            591
Ile Arg Gln Ala Asn Lys Val Ala Lys Glu Ala Ala Asn Arg Trp Thr
155                 160                 165                 170 gat aac ata ttc gca ata aaa tct tgg gcc aaa aga aaa ttt ggg ttt            639
Asp Asn Ile Phe Ala Ile Lys Ser Trp Ala Lys Arg Lys Phe Gly Phe
                175                 180                 185 gaa gaa aat aaa att gat aga act ttt gga att cca gaa gac ttt gac            687
Glu Glu Asn Lys Ile Asp Arg Thr Phe Gly Ile Pro Glu Asp Phe Asp
            190                 195                 200 tac ata gac taaaatattc catggtggtg aaggatgtac aagcttgtga                    736
Tyr Ile Asp
        205 atatgtaaat tttaaactat tatctaacta agtgtactga attgtcgttt gcctgtaact          796 gtgtttatca ttttattaat gttaaataaa gtgtaaaatg caaaaaaaaa aaaaaaaaaa          856 aaaaaaaaaa a                                                              867

<210> SEQ ID NO 3
<211> LENGTH: 205
<212> TYPE: PRT
<213> ORGANISM: Homo sapiens

<400> SEQUENCE: 3

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140

Lys Asp Cys Asp Pro Gln Val Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175
```

```
Lys Ser Trp Ala Lys Arg Lys Phe Gly Phe Glu Glu Asn Lys Ile Asp
        180                 185                 190

Arg Thr Phe Gly Ile Pro Glu Asp Phe Asp Tyr Ile Asp
        195                 200                 205

<210> SEQ ID NO 4
<211> LENGTH: 1028
<212> TYPE: DNA
<213> ORGANISM: Homo sapiens
<220> FEATURE:
<221> NAME/KEY: CDS
<222> LOCATION: (82)...(459)

<400> SEQUENCE: 4
ccaaaatcaa acgcgtccgg gcctgtcccg ccctctccc caagcgcggg cccggccagc      60
ggaagcccct gcgccgcgc c atg tca aag aaa aaa gga ctg agt gca gaa     111
                        Met Ser Lys Lys Lys Gly Leu Ser Ala Glu
                          1               5                  10 gaa aag aga act cgc atg atg gaa ata ttt tct gaa aca aaa gat gta    159
Glu Lys Arg Thr Arg Met Met Glu Ile Phe Ser Glu Thr Lys Asp Val
            15                  20                  25 ttt caa tta aaa gac ttg gag aag att gct ccc aaa gag aaa ggc att    207
Phe Gln Leu Lys Asp Leu Glu Lys Ile Ala Pro Lys Glu Lys Gly Ile
            30                  35                  40 act gct atg tca gta aaa gaa gtc ctt caa agc tta gtt gat gat ggt    255
Thr Ala Met Ser Val Lys Glu Val Leu Gln Ser Leu Val Asp Asp Gly
        45                  50                  55 atg gtt gac tgt gag agg atc gga act tct aat tat tat tgg gct ttt    303
Met Val Asp Cys Glu Arg Ile Gly Thr Ser Asn Tyr Tyr Trp Ala Phe
    60                  65                  70 cca agt aaa gct ctt cat gca agg aaa cat aag ttg gag gtt ctg gaa    351
Pro Ser Lys Ala Leu His Ala Arg Lys His Lys Leu Glu Val Leu Glu
75                  80                  85                  90 tct cag gac cct ggc tgc tgc ttc cat gaa ata att aaa gtc tcc tat    399
Ser Gln Asp Pro Gly Cys Cys Phe His Glu Ile Ile Lys Val Ser Tyr
                95                  100                 105 tat aga aaa ttc tgg ctg ggc gca gtg gct cac gcc tgt aat ccc agc    447
Tyr Arg Lys Phe Trp Leu Gly Ala Val Ala His Ala Cys Asn Pro Ser
            110                 115                 120 act ttg gga ggc tgaggcgggc agatcacgag gtgactttcc cccaccccca        499
Thr Leu Gly Gly
            125 catgaagtgc aagatggagt tgtctgaggg aagtcaaaag catgcaagcc tacagaaaag   559 cattgagaaa gctaaaattg gccgatgtga acggaagag cgaaccaggc tagcaaaaga   619 gctttcttca cttcgagacc aaagggaaca gctaaaggca gaagtagaaa aatacaaaga   679 ctgtgatccg caagttgtgg aagaaatacg ccaagcaaat aaagtagcca agaagctgc    739 taacagatgg actgataaca tattcgcaat aaaatcttgg gccaaaagaa aattgggtt    799 tgaagaaaat aaaattgata gaacttttgg aattccagaa gactttgact acatagacta   859 aaatattcca tggtggtgaa ggatgtacaa gcttgtgaat atgtaaattt taaactatta   919 tctaactaag tgtactgaat tgtcgtttgc ctgtaactgt gtttatcatt ttattaatgt   979 taaataaagt gtaaaatgca aaaaaaaaa aaaaaaaaa aaaaaaaa                  1028

<210> SEQ ID NO 5
<211> LENGTH: 126
<212> TYPE: PRT
<213> ORGANISM: Homo sapiens
```

-continued

```
<400> SEQUENCE: 5

Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Asp Pro Gly Cys
                85                  90                  95

Cys Phe His Glu Ile Ile Lys Val Ser Tyr Tyr Arg Lys Phe Trp Leu
            100                 105                 110

Gly Ala Val Ala His Ala Cys Asn Pro Ser Thr Leu Gly Gly
        115                 120                 125

<210> SEQ ID NO 6
<211> LENGTH: 1028
<212> TYPE: DNA
<213> ORGANISM: Homo sapiens
<220> FEATURE:
<221> NAME/KEY: CDS
<222> LOCATION: (501)...(857)

<400> SEQUENCE: 6
ccaaaatcaa acgcgtccgg gcctgtcccg cccctctccc caagcgcggg cccggccagc      60
ggaagcccct gcgcccgcgc catgtcaaag aaaaaaggac tgagtgcaga agaaaagaga     120
actcgcatga tggaaatatt ttctgaaaca aaagatgtat tcaattaaa agacttggag      180 aagattgctc ccaaagagaa aggcattact gctatgtcag taaaagaagt ccttcaaagc     240
ttagttgatg atggtatggt tgactgtgag aggatcggaa cttctaatta ttattgggct     300
tttccaagta agctcttca tgcaaggaaa cataagttgg aggttctgga atctcaggac      360
cctggctgct gcttccatga ataattaaa gtctcctatt atagaaaatt ctggctgggc      420
gcagtggctc acgcctgtaa tcccagcact ttgggaggct gaggcgggca gatcacgagg     480
tgactttccc ccaccccac atg aag tgc aag atg gag ttg tct gag gga agt      533
                       Met Lys Cys Lys Met Glu Leu Ser Glu Gly Ser
                        1               5                  10 caa aag cat gca agc cta cag aaa agc att gag aaa gct aaa att ggc      581
Gln Lys His Ala Ser Leu Gln Lys Ser Ile Glu Lys Ala Lys Ile Gly
            15                  20                  25 cga tgt gaa acg gaa gag cga acc agg cta gca aaa gag ctt tct tca      629
Arg Cys Glu Thr Glu Glu Arg Thr Arg Leu Ala Lys Glu Leu Ser Ser
        30                  35                  40 ctt cga gac caa agg gaa cag cta aag gca gaa gta gaa aaa tac aaa      677
Leu Arg Asp Gln Arg Glu Gln Leu Lys Ala Glu Val Glu Lys Tyr Lys
    45                  50                  55 gac tgt gat ccg caa gtt gtg gaa gaa ata cgc caa gca aat aaa gta      725
Asp Cys Asp Pro Gln Val Val Glu Glu Ile Arg Gln Ala Asn Lys Val
60                  65                  70                  75 gcc aaa gaa gct gct aac aga tgg act gat aac ata ttc gca ata aaa      773
Ala Lys Glu Ala Ala Asn Arg Trp Thr Asp Asn Ile Phe Ala Ile Lys
                80                  85                  90 tct tgg gcc aaa aga aaa ttt ggg ttt gaa gaa aat aaa att gat aga      821
Ser Trp Ala Lys Arg Lys Phe Gly Phe Glu Glu Asn Lys Ile Asp Arg
            95                 100                 105
```

```
act ttt gga att cca gaa gac ttt gac tac ata gac taaaatattc         867
Thr Phe Gly Ile Pro Glu Asp Phe Asp Tyr Ile Asp
        110                 115 catggtggtg aaggatgtac aagcttgtga atatgtaaat tttaaactat tatctaacta   927
agtgtactga attgtcgttt gcctgtaact gtgtttatca ttttattaat gttaaataaa   987
gtgtaaaatg caaaaaaaaa aaaaaaaaaa aaaaaaaaaa a                      1028

<210> SEQ ID NO 7
<211> LENGTH: 119
<212> TYPE: PRT
<213> ORGANISM: Homo sapiens

<400> SEQUENCE: 7

Met Lys Cys Lys Met Glu Leu Ser Glu Gly Ser Gln Lys His Ala Ser
 1               5                  10                  15

Leu Gln Lys Ser Ile Glu Lys Ala Lys Ile Gly Arg Cys Glu Thr Glu
            20                  25                  30

Glu Arg Thr Arg Leu Ala Lys Glu Leu Ser Ser Leu Arg Asp Gln Arg
        35                  40                  45

Glu Gln Leu Lys Ala Glu Val Glu Lys Tyr Lys Asp Cys Asp Pro Gln
    50                  55                  60

Val Val Glu Glu Ile Arg Gln Ala Asn Lys Val Ala Lys Glu Ala Ala
65                  70                  75                  80

Asn Arg Trp Thr Asp Asn Ile Phe Ala Ile Lys Ser Trp Ala Lys Arg
                85                  90                  95

Lys Phe Gly Phe Glu Glu Asn Lys Ile Asp Arg Thr Phe Gly Ile Pro
            100                 105                 110

Glu Asp Phe Asp Tyr Ile Asp
        115

<210> SEQ ID NO 8
<211> LENGTH: 752
<212> TYPE: DNA
<213> ORGANISM: Homo sapiens
<220> FEATURE:
<221> NAME/KEY: CDS
<222> LOCATION: (82)...(447)

<400> SEQUENCE: 8
ccaaaatcaa acgcgtccgg gcctgtcccg cccctctccc caagcgcggg cccggccagc    60
ggaagcccct gcgcccgcgc c atg tca aag aaa aaa gga ctg agt gca gaa    111
                        Met Ser Lys Lys Lys Gly Leu Ser Ala Glu
                         1               5                  10 gaa aag aga act cgc atg atg gaa ata ttt tct gaa aca aaa gat gta    159
Glu Lys Arg Thr Arg Met Met Glu Ile Phe Ser Glu Thr Lys Asp Val
            15                  20                  25 ttt caa tta aaa gac ttg gag aag att gct ccc aaa gag aaa ggc att    207
Phe Gln Leu Lys Asp Leu Glu Lys Ile Ala Pro Lys Glu Lys Gly Ile
        30                  35                  40 act gct atg tca gta aaa gaa gtc ctt caa agc tta gtt gat gat ggt    255
Thr Ala Met Ser Val Lys Glu Val Leu Gln Ser Leu Val Asp Asp Gly
    45                  50                  55 atg gtt gac tgt gag agg atc gga act tct aat tat tat tgg gct ttt    303
Met Val Asp Cys Glu Arg Ile Gly Thr Ser Asn Tyr Tyr Trp Ala Phe
60                  65                  70 cca agt aaa gct ctt cat gca agg aaa cat aag ttg gag gtt ctg gaa    351
Pro Ser Lys Ala Leu His Ala Arg Lys His Lys Leu Glu Val Leu Glu
                75                  80                  85                  90
```

| | |
|---|---|
| tct cag ttg tct gag gga agt caa aag cat gca agc cta cag aaa agc<br>Ser Gln Leu Ser Glu Gly Ser Gln Lys His Ala Ser Leu Gln Lys Ser<br>         95                     100                     105 | 399 |
| att gag aaa gct aaa att ggc cga tgt gaa acg gcc aag caa ata aag<br>Ile Glu Lys Ala Lys Ile Gly Arg Cys Glu Thr Ala Lys Gln Ile Lys<br>110                     115                     120 | 447 |
| tagccaaaga agctgctaac agatggactg ataacatatt cgcaataaaa tcttgggcca | 507 |
| aaagaaaatt tgggtttgaa gaaaataaaa ttgatagaac ttttggaatt ccagaagact | 567 |
| ttgactacat agactaaaat attccatggt ggtgaaggat gtacaagctt gtgaatatgt | 627 |
| aaattttaaa ctattatcta actaagtgta ctgaattgtc gtttgcctgt aactgtgttt | 687 |
| atcattttat taatgttaaa taaagtgtaa aatgcaaaaa aaaaaaaaaa aaaaaaaaaa | 747 |
| aaaaa | 752 |

<210> SEQ ID NO 9
<211> LENGTH: 122
<212> TYPE: PRT
<213> ORGANISM: Homo sapiens

<400> SEQUENCE: 9

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Ala Lys Gln Ile Lys
        115                 120

<210> SEQ ID NO 10
<211> LENGTH: 822
<212> TYPE: DNA
<213> ORGANISM: Homo sapiens
<220> FEATURE:
<221> NAME/KEY: CDS
<222> LOCATION: (82)...(651)

<400> SEQUENCE: 10

| | |
|---|---|
| ccaaaatcaa acgcgtccgg gcctgtcccg cccctctccc caagcgcggg cccggccagc | 60 |
| ggaagcccct gcgcccgcgc c atg tca aag aaa aaa gga ctg agt gca gaa<br>                              Met Ser Lys Lys Lys Gly Leu Ser Ala Glu<br>                              1               5                   10 | 111 |
| gaa aag aga act cgc atg atg gaa ata ttt tct gaa aca aaa gat gta<br>Glu Lys Arg Thr Arg Met Met Glu Ile Phe Ser Glu Thr Lys Asp Val<br>                15                  20                  25 | 159 |
| ttt caa tta aaa gac ttg gag aag att gct ccc aaa gag aaa ggc att<br>Phe Gln Leu Lys Asp Leu Glu Lys Ile Ala Pro Lys Glu Lys Gly Ile<br>        30                  35                  40 | 207 |
| act gct atg tca gta aaa gaa gtc ctt caa agc tta gtt gat gat ggt<br>Thr Ala Met Ser Val Lys Glu Val Leu Gln Ser Leu Val Asp Asp Gly<br>   45                  50                  55 | 255 |

```
atg gtt gac tgt gag agg atc gga act tct aat tat tat tgg gct ttt        303
Met Val Asp Cys Glu Arg Ile Gly Thr Ser Asn Tyr Tyr Trp Ala Phe
    60                  65                  70 cca agt aaa gct ctt cat gca agg aaa cat aag ttg gag gtt ctg gaa        351
Pro Ser Lys Ala Leu His Ala Arg Lys His Lys Leu Glu Val Leu Glu
75                  80                  85                  90 tct cag ttg tct gag gga agt caa aag cat gca agc cta cag aaa agc        399
Ser Gln Leu Ser Glu Gly Ser Gln Lys His Ala Ser Leu Gln Lys Ser
                95                  100                 105 att gag aaa gct aaa att ggc cga tgt gaa acg gaa gag cga acc agg        447
Ile Glu Lys Ala Lys Ile Gly Arg Cys Glu Thr Glu Glu Arg Thr Arg
        110                 115                 120 cta gca aaa gag ctt tct tca ctt cga gac caa agg gaa cag cta aag        495
Leu Ala Lys Glu Leu Ser Ser Leu Arg Asp Gln Arg Glu Gln Leu Lys
            125                 130                 135 gca gaa gta gaa aaa tac aaa gac tgt gat ccg caa gtt gtg gaa gaa        543
Ala Glu Val Glu Lys Tyr Lys Asp Cys Asp Pro Gln Val Val Glu Glu
140                 145                 150 ata cat aac ata ttc gca ata aaa tct tgg gcc aaa aga aaa ttt ggg        591
Ile His Asn Ile Phe Ala Ile Lys Ser Trp Ala Lys Arg Lys Phe Gly
155                 160                 165                 170 ttt gaa gaa aat aaa att gat aga act ttt gga att cca gaa gac ttt        639
Phe Glu Glu Asn Lys Ile Asp Arg Thr Phe Gly Ile Pro Glu Asp Phe
                175                 180                 185 gac tac ata gac taaaatattc catggtggtg aaggatgtac aagcttgtga            691
Asp Tyr Ile Asp
                190 atatgtaaat tttaaactat tatctaacta agtgtactga attgtcgttt gcctgtaact      751 gtgtttatca ttttattaat gttaaataaa gtgtaaaatg caaaaaaaaa aaaaaaaaaa      811 aaaaaaaaaa a                                                          822

<210> SEQ ID NO 11
<211> LENGTH: 190
<212> TYPE: PRT
<213> ORGANISM: Homo sapiens

<400> SEQUENCE: 11

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140

Lys Asp Cys Asp Pro Gln Val Val Glu Glu Ile His Asn Ile Phe Ala
145                 150                 155                 160
```

```
Ile Lys Ser Trp Ala Lys Arg Lys Phe Gly Phe Glu Glu Asn Lys Ile
            165                 170                 175
Asp Arg Thr Phe Gly Ile Pro Glu Asp Phe Asp Tyr Ile Asp
            180                 185                 190

<210> SEQ ID NO 12
<211> LENGTH: 1205
<212> TYPE: DNA
<213> ORGANISM: Homo sapiens
<220> FEATURE:
<221> NAME/KEY: CDS
<222> LOCATION: (281)...(850)

<400> SEQUENCE: 12
gttttctgta ttgtaatatg tagagcacat tccagaactg ctcagtttcg agttacctaa      60
tggatcttca ctgtgtgcca attagtcgat ttctgtgaaa acgccccggt ttctgccaaa     120
gggcaggagt cgctgctctt gtgccgggtg ctgctggttg tgtagggcgc tgttgctttt     180
ttaaggacgc tctgcactga attaggcttc ctcgtgggtc atgatcagtt aagtcctgtc     240
aaagaaaaaa ggactgagtg cagaagaaaa gagaactcgc atg atg gaa ata ttt       295
                                              Met Met Glu Ile Phe
                                                1               5 tct gaa aca aaa gat gta ttt caa tta aaa gac ttg gag aag att gct       343
Ser Glu Thr Lys Asp Val Phe Gln Leu Lys Asp Leu Glu Lys Ile Ala
            10                  15                  20 ccc aaa gag aaa ggc att act gct atg tca gta aaa gaa gtc ctt caa       391
Pro Lys Glu Lys Gly Ile Thr Ala Met Ser Val Lys Glu Val Leu Gln
        25                  30                  35 agc tta gtt gat gat ggt atg gtt gac tgt gag agg atc gga act tct       439
Ser Leu Val Asp Asp Gly Met Val Asp Cys Glu Arg Ile Gly Thr Ser
    40                  45                  50 aat tat tat tgg gct ttt cca agt aaa gct ctt cat gca agg aaa cat       487
Asn Tyr Tyr Trp Ala Phe Pro Ser Lys Ala Leu His Ala Arg Lys His
 55                  60                  65 aag ttg gag gtt ctg gaa tct cag ttg tct gag gga agt caa aag cat       535
Lys Leu Glu Val Leu Glu Ser Gln Leu Ser Glu Gly Ser Gln Lys His
 70                  75                  80                  85 gca agc cta cag aaa agc att gag aaa gct aaa att ggc cga tgt gaa       583
Ala Ser Leu Gln Lys Ser Ile Glu Lys Ala Lys Ile Gly Arg Cys Glu
            90                  95                 100 acg gaa gag cga acc agg cta gca aaa gag ctt tct tca ctt cga gac       631
Thr Glu Glu Arg Thr Arg Leu Ala Lys Glu Leu Ser Ser Leu Arg Asp
        105                 110                 115 caa agg gaa cag cta aag gca gaa gta gaa aaa tac aaa gac tgt gat       679
Gln Arg Glu Gln Leu Lys Ala Glu Val Glu Lys Tyr Lys Asp Cys Asp
    120                 125                 130 ccg caa gtt gtg gaa gaa ata cgc caa gca aat aaa gta gcc aaa gaa       727
Pro Gln Val Val Glu Glu Ile Arg Gln Ala Asn Lys Val Ala Lys Glu
135                 140                 145 gct gct aac aga tgg act gat aac ata ttc gca ata aaa tct tgg gcc       775
Ala Ala Asn Arg Trp Thr Asp Asn Ile Phe Ala Ile Lys Ser Trp Ala
150                 155                 160                 165 aaa aga aaa ttt ggg ttt gaa gaa aat aaa att gat aga act ttt gga       823
Lys Arg Lys Phe Gly Phe Glu Glu Asn Lys Ile Asp Arg Thr Phe Gly
            170                 175                 180 att cca gaa gac ttt gac tac ata gac taaaatattc catggtggtg             870
Ile Pro Glu Asp Phe Asp Tyr Ile Asp
        185                 190 aaggatgtac aagcttgtga atatgtaaat tttaaactat tatctaacta agtgtactga     930
```

```
attgtcgttt gcctgtaact gtgtttatca ttttattaat gttaaataaa gtgtaaaatg      990
cagatgttct tcacccattt tggtagaaca aaagcaggat gataaccata tcccccagt     1050 gctcatcaaa gtaggacact aaaaatccat ccatctcagt caaagtcgag cggccgcgaa    1110
tttagtagta gtagcggccg ctctagagga tccaagctta cgtacgcgtg catgcgacgt    1170
catagctctt ctatagtgtc acctaaattc aagtt                               1205
```

<210> SEQ ID NO 13
<211> LENGTH: 190
<212> TYPE: PRT
<213> ORGANISM: Homo sapiens

<400> SEQUENCE: 13

```
Met Met Glu Ile Phe Ser Glu Thr Lys Asp Val Phe Gln Leu Lys Asp
 1               5                  10                  15

Leu Glu Lys Ile Ala Pro Lys Glu Lys Gly Ile Thr Ala Met Ser Val
                20                  25                  30

Lys Glu Val Leu Gln Ser Leu Val Asp Asp Gly Met Val Asp Cys Glu
            35                  40                  45

Arg Ile Gly Thr Ser Asn Tyr Tyr Trp Ala Phe Pro Ser Lys Ala Leu
        50                  55                  60

His Ala Arg Lys His Lys Leu Glu Val Leu Glu Ser Gln Leu Ser Glu
 65                 70                  75                  80

Gly Ser Gln Lys His Ala Ser Leu Gln Lys Ser Ile Glu Lys Ala Lys
                85                  90                  95

Ile Gly Arg Cys Glu Thr Glu Glu Arg Thr Arg Leu Ala Lys Glu Leu
            100                 105                 110

Ser Ser Leu Arg Asp Gln Arg Glu Gln Leu Lys Ala Glu Val Glu Lys
        115                 120                 125

Tyr Lys Asp Cys Asp Pro Gln Val Val Glu Glu Ile Arg Gln Ala Asn
    130                 135                 140

Lys Val Ala Lys Glu Ala Ala Asn Arg Trp Thr Asp Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
            180                 185                 190
```

<210> SEQ ID NO 14
<211> LENGTH: 205
<212> TYPE: PRT
<213> ORGANISM: Homo sapiens

<400> SEQUENCE: 14

```
Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
 65                 70                  75                  80

Ala Arg Lys His Lys Leu Glu Val Leu Glu Ser Gln Leu Ser Glu Gly
                85                  90                  95
```

```
Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140

Lys Asp Cys Asp Pro Gln Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Glu Asn Lys Ile Asp
            180                 185                 190

Arg Thr Phe Gly Ile Pro Glu Asp Phe Asp Tyr Ile Asp
        195                 200                 205

<210> SEQ ID NO 15
<211> LENGTH: 126
<212> TYPE: PRT
<213> ORGANISM: Homo sapiens

<400> SEQUENCE: 15

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Asp Pro Gly Cys
                85                  90                  95

Cys Phe His Glu Ile Ile Lys Val Ser Tyr Tyr Arg Lys Phe Trp Leu
            100                 105                 110

Gly Ala Val Ala His Ala Cys Asn Pro Ser Thr Leu Gly Gly
        115                 120                 125

<210> SEQ ID NO 16
<211> LENGTH: 119
<212> TYPE: PRT
<213> ORGANISM: Homo sapiens

<400> SEQUENCE: 16

Met Lys Cys Lys Met Glu Leu Ser Glu Gly Ser Gln Lys His Ala Ser
1               5                   10                  15

Leu Gln Lys Ser Ile Glu Lys Ala Lys Ile Gly Arg Cys Glu Thr Glu
            20                  25                  30

Glu Arg Thr Arg Leu Ala Lys Glu Leu Ser Ser Leu Arg Asp Gln Arg
        35                  40                  45

Glu Gln Leu Lys Ala Glu Val Glu Lys Tyr Lys Asp Cys Asp Pro Gln
    50                  55                  60

Val Val Glu Glu Ile Arg Gln Ala Asn Lys Val Ala Lys Glu Ala Ala
65                  70                  75                  80

Asn Arg Trp Thr Asp Asn Ile Phe Ala Ile Lys Ser Trp Ala Lys Arg
                85                  90                  95

Lys Phe Gly Phe Glu Glu Asn Lys Ile Asp Arg Thr Phe Gly Ile Pro
```

```
                        100                 105                 110

Glu Asp Phe Asp Tyr Ile Asp
        115

<210> SEQ ID NO 17
<211> LENGTH: 122
<212> TYPE: PRT
<213> ORGANISM: Homo sapiens

<400> SEQUENCE: 17

Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
 65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Ala Lys Gln Ile Lys
        115                 120

<210> SEQ ID NO 18
<211> LENGTH: 190
<212> TYPE: PRT
<213> ORGANISM: Homo sapiens

<400> SEQUENCE: 18

Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
 65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
        130                 135                 140

Lys Asp Cys Asp Pro Gln Val Val Glu Glu Ile His Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
            180                 185                 190
```

```
<210> SEQ ID NO 19
<211> LENGTH: 190
<212> TYPE: PRT
<213> ORGANISM: Homo sapiens

<400> SEQUENCE: 19
```

Met Met Glu Ile Phe Ser Glu Thr Lys Asp Val Phe Gln Leu Lys Asp
 1               5                   10                  15

Leu Glu Lys Ile Ala Pro Lys Glu Lys Gly Ile Thr Ala Met Ser Val
                 20                  25                  30

Lys Glu Val Leu Gln Ser Leu Val Asp Asp Gly Met Val Asp Cys Glu
             35                  40                  45

Arg Ile Gly Thr Ser Asn Tyr Tyr Trp Ala Phe Pro Ser Lys Ala Leu
 50                  55                  60

His Ala Arg Lys His Lys Leu Glu Val Leu Glu Ser Gln Leu Ser Glu
 65                  70                  75                  80

Gly Ser Gln Lys His Ala Ser Leu Gln Lys Ser Ile Glu Lys Ala Lys
                 85                  90                  95

Ile Gly Arg Cys Glu Thr Glu Glu Arg Thr Arg Leu Ala Lys Glu Leu
            100                 105                 110

Ser Ser Leu Arg Asp Gln Arg Glu Gln Leu Lys Ala Glu Val Glu Lys
            115                 120                 125

Tyr Lys Asp Cys Asp Pro Gln Val Val Glu Glu Ile Arg Gln Ala Asn
130                 135                 140

Lys Val Ala Lys Glu Ala Ala Asn Arg Trp Thr Asp Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
                180                 185                 190

```
<210> SEQ ID NO 20
<211> LENGTH: 205
<212> TYPE: PRT
<213> ORGANISM: Homo sapiens

<400> SEQUENCE: 20
```

Met Ser Lys Lys Lys Gly Leu Ser Ala Glu Glu Lys Arg Thr Arg Met
 1               5                   10                  15

Met Glu Ile Phe Ser Glu Thr Lys Asp Val Phe Gln Leu Lys Asp Leu
                 20                  25                  30

Glu Lys Ile Ala Pro Lys Glu Lys Gly Ile Thr Ala Met Ser Val Lys
             35                  40                  45

Glu Val Leu Gln Ser Leu Val Asp Asp Gly Met Val Asp Cys Glu Arg
 50                  55                  60

Ile Gly Thr Ser Asn Tyr Tyr Trp Ala Phe Pro Ser Lys Ala Leu His
 65                  70                  75                  80

Ala Arg Lys His Lys Leu Glu Val Leu Glu Ser Gln Leu Ser Glu Gly
                 85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
            115                 120                 125

Ser Leu Arg Asp Gln Arg Glu Gln Leu Lys Ala Glu Val Glu Lys Tyr
130                 135                 140

```
Lys Asp Cys Asp Pro Gln Val Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Glu Asn Lys Ile Asp
                180                 185                 190

Arg Thr Phe Gly Ile Pro Glu Asp Phe Asp Tyr Ile Asp
                195                 200                 205
```

<210> SEQ ID NO 21
<211> LENGTH: 205
<212> TYPE: PRT
<213> ORGANISM: Homo sapiens

<400> SEQUENCE: 21

```
Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
                35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
                100                 105                 110

Gly Arg Cys Glu Thr Glu Glu Arg Thr Arg Leu Ala Lys Glu Leu Ser
            115                 120                 125

Ser Leu Arg Asp Gln Arg Glu Gln Leu Lys Ala Glu Val Glu Lys Tyr
    130                 135                 140

Lys Asp Cys Asp Pro Gln Val Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Glu Asn Lys Ile Asp
                180                 185                 190

Arg Thr Phe Gly Ile Pro Glu Asp Phe Asp Tyr Ile Asp
                195                 200                 205
```

<210> SEQ ID NO 22
<211> LENGTH: 205
<212> TYPE: PRT
<213> ORGANISM: Homo sapiens

<400> SEQUENCE: 22

```
Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
                35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
```

```
            65                  70                  75                  80
Ala Arg Lys His Lys Leu Glu Val Leu Glu Ser Gln Leu Ser Glu Gly
                    85                  90                  95

Ser Gln Lys His Ala Ser Leu Gln Lys Ser Ile Glu Lys Ala Lys Ile
                100                 105                 110

Gly Arg Cys Glu Thr Glu Arg Thr Arg Leu Ala Lys Glu Leu Ser
                115                 120                 125

Ser Leu Arg Asp Gln Arg Glu Gln Leu Lys Ala Glu Val Glu Lys Tyr
        130                 135                 140

Lys Asp Cys Asp Pro Gln Val Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Asn Lys Ile Asp
                180                 185                 190

Arg Thr Phe Gly Ile Pro Glu Asp Phe Asp Tyr Ile Asp
                195                 200                 205
```

<210> SEQ ID NO 23
<211> LENGTH: 205
<212> TYPE: PRT
<213> ORGANISM: Mus musculus

<400> SEQUENCE: 23

```
Met Ser Lys Lys Arg Gly Leu Ser Gly Glu Glu Lys Arg Thr Arg Met
  1               5                  10                  15

Met Glu Ile Phe Phe Glu Thr Lys Asp Val Phe Gln Leu Lys Asp Leu
                20                  25                  30

Glu Lys Leu Ala Pro Lys Glu Lys Gly Ile Thr Ala Met Ser Val Lys
                35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
65                  70                  75                  80

Ala Arg Lys Arg Lys Leu Glu Ala Leu Asn Ser Gln Leu Ser Glu Gly
                85                  90                  95

Ser Gln Lys His Ala Asp Leu Gln Lys Ser Ile Glu Lys Ala Arg Val
                100                 105                 110

Gly Arg Gln Glu Thr Glu Glu Arg Ala Met Leu Ala Lys Glu Leu Phe
                115                 120                 125

Ser Phe Arg Asp Gln Arg Gln Gln Leu Lys Ala Glu Val Glu Lys Tyr
        130                 135                 140

Arg Glu Cys Asp Pro Gln Val Val Glu Glu Ile Arg Glu Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Glu Ser Lys Ile Asp
                180                 185                 190

Lys Asn Phe Gly Ile Pro Glu Asp Phe Asp Tyr Ile Asp
                195                 200                 205
```

<210> SEQ ID NO 24
<211> LENGTH: 198
<212> TYPE: PRT
<213> ORGANISM: Homo sapiens

<400> SEQUENCE: 24

Lys Gly Leu Ser Ala Glu Glu Lys Arg Thr Arg Met Met Glu Ile Phe
1               5                   10                  15

Ser Glu Thr Lys Asp Val Phe Gln Leu Lys Asp Leu Glu Lys Ile Ala
            20                  25                  30

Pro Lys Glu Lys Gly Ile Thr Ala Met Ser Val Lys Glu Val Leu Gln
            35                  40                  45

Ser Leu Val Asp Asp Gly Met Val Asp Cys Glu Arg Ile Gly Thr Ser
50                      55                  60

Asn Tyr Tyr Trp Ala Phe Pro Ser Lys Ala Leu His Ala Arg Lys His
65                      70                  75                  80

Lys Leu Glu Val Leu Glu Ser Gln Leu Ser Glu Gly Ser Gln Lys His
                85                  90                  95

Ala Ser Leu Gln Lys Ser Ile Glu Lys Ala Lys Ile Gly Arg Cys Glu
                100                 105                 110

Thr Glu Glu Arg Thr Arg Leu Ala Lys Glu Leu Ser Ser Leu Arg Asp
            115                 120                 125

Gln Arg Glu Gln Leu Lys Ala Glu Val Glu Lys Tyr Lys Asp Cys Asp
130                 135                 140

Pro Gln Val Val Glu Glu Ile Arg Gln Ala Asn Lys Val Ala Lys Glu
145                 150                 155                 160

Ala Ala Asn Arg Trp Thr Asp Asn Ile Phe Ala Ile Lys Ser Trp Ala
                165                 170                 175

Lys Arg Lys Phe Gly Phe Glu Glu Asn Lys Ile Asp Arg Thr Phe Gly
                180                 185                 190

Ile Pro Glu Asp Phe Asp
                195

<210> SEQ ID NO 25
<211> LENGTH: 200
<212> TYPE: PRT
<213> ORGANISM: Schizosaccharomyces pombe

<400> SEQUENCE: 25

Lys Gly Leu Ser Leu Ala Glu Lys Arg Arg Leu Glu Ala Ile Phe
1               5                   10                  15

His Asp Ser Lys Asp Phe Phe Gln Leu Lys Glu Val Glu Lys Leu Gly
            20                  25                  30

Ser Lys Lys Gln Ile Val Leu Gln Thr Val Lys Asp Val Leu Gln Ser
            35                  40                  45

Leu Val Asp Asp Asn Ile Val Lys Thr Glu Lys Ile Gly Thr Ser Asn
50                      55                  60

Tyr Tyr Trp Ser Phe Pro Ser Asp Ala Lys Arg Ser Arg Glu Ser Val
65                      70                  75                  80

Leu Gly Ser Leu Gln Ala Gln Leu Asp Leu Lys Gln Lys Ser Lys
                85                  90                  95

Thr Leu Asp Glu Asn Ile Ser Phe Glu Lys Ser Lys Arg Asp Asn Glu
            100                 105                 110

Gly Thr Glu Asn Asp Ala Asn Gln Tyr Thr Leu Glu Leu Leu His Ala
            115                 120                 125

Lys Glu Ser Glu Leu Lys Leu Leu Lys Thr Gln Leu Ser Asn Leu Asn
130                 135                 140

His Cys Asn Pro Glu Thr Phe Glu Leu Lys Asn Glu Asn Thr Lys Lys
145                 150                 155                 160

Tyr Met Glu Ala Ala Asn Leu Trp Thr Asp Gln Ile His Thr Leu Ile
                165                 170                 175

```
Ala Phe Cys Arg Asp Met Gly Ala Asp Thr Asn Gln Ile Arg Glu Tyr
            180                 185                 190
Cys Ser Ile Pro Glu Asp Leu Asp
        195                 200

<210> SEQ ID NO 26
<211> LENGTH: 14
<212> TYPE: PRT
<213> ORGANISM: Clostridium toxin

<400> SEQUENCE: 26

Gln Tyr Ile Lys Ala Asn Ser Lys Phe Ile Gly Ile Thr Glu
1               5                   10

<210> SEQ ID NO 27
<211> LENGTH: 21
<212> TYPE: PRT
<213> ORGANISM: Plasmodium falciparum

<400> SEQUENCE: 27

Asp Ile Glu Lys Lys Ile Ala Lys Met Glu Lys Ala Ser Ser Val Phe
1               5                   10                  15
Asn Val Val Asn Ser
            20

<210> SEQ ID NO 28
<211> LENGTH: 16
<212> TYPE: PRT
<213> ORGANISM: Streptococcus aureus

<400> SEQUENCE: 28

Gly Ala Val Asp Ser Ile Leu Gly Gly Val Ala Thr Tyr Gly Ala Ala
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: VARIANT
<222> LOCATION: 3
<223> OTHER INFORMATION: Xaa = cyclohexylalanine, phenylalanine, or
      tyrosine
<220> FEATURE:
<221> NAME/KEY: VARIANT
<222> LOCATION: 1, 13
<223> OTHER INFORMATION: Xaa = D-alanine or L-alanine

<400> SEQUENCE: 29

Xaa Lys Xaa Val Ala Ala Trp Thr Leu Lys Ala Ala Xaa
1               5                   10

<210> SEQ ID NO 30
<211> LENGTH: 43
<212> TYPE: DNA
<213> ORGANISM: Homo sapiens

<400> SEQUENCE: 30
ttttgatcaa gcttttttttt tttttttttt tttttttttt ttt            43

<210> SEQ ID NO 31
<211> LENGTH: 42
<212> TYPE: DNA
<213> ORGANISM: Homo sapiens
```

```
<400> SEQUENCE: 31
ctaatacgac tcactatagg gctcgagcgg ccgcccgggc ag          42

<210> SEQ ID NO 32
<211> LENGTH: 12
<212> TYPE: DNA
<213> ORGANISM: Homo sapiens

<400> SEQUENCE: 32
gatcctgccc gg                                            12

<210> SEQ ID NO 33
<211> LENGTH: 40
<212> TYPE: DNA
<213> ORGANISM: Homo sapiens

<400> SEQUENCE: 33
gtaatacgac tcactatagg gcagcgtggt cgcggccgag              40

<210> SEQ ID NO 34
<211> LENGTH: 10
<212> TYPE: DNA
<213> ORGANISM: Homo sapiens

<400> SEQUENCE: 34
gatcctcggc                                               10

<210> SEQ ID NO 35
<211> LENGTH: 22
<212> TYPE: DNA
<213> ORGANISM: Homo sapiens

<400> SEQUENCE: 35
ctaatacgac tcactatagg gc                                 22

<210> SEQ ID NO 36
<211> LENGTH: 22
<212> TYPE: DNA
<213> ORGANISM: Homo sapiens

<400> SEQUENCE: 36
tcgagcggcc gcccgggcag ga                                 22

<210> SEQ ID NO 37
<211> LENGTH: 20
<212> TYPE: DNA
<213> ORGANISM: Homo sapiens

<400> SEQUENCE: 37
agcgtggtcg cggccgagga                                    20

<210> SEQ ID NO 38
<211> LENGTH: 25
<212> TYPE: DNA
<213> ORGANISM: Homo sapiens

<400> SEQUENCE: 38
atatcgccgc gctcgtcgtc gacaa                              25

<210> SEQ ID NO 39
<211> LENGTH: 26
<212> TYPE: DNA
<213> ORGANISM: Homo sapiens
```

```
<400> SEQUENCE: 39
agccacacgc agctcattgt agaagg                                           26

<210> SEQ ID NO 40
<211> LENGTH: 24
<212> TYPE: DNA
<213> ORGANISM: Homo sapiens

<400> SEQUENCE: 40
gattacaagg atgacgacga taag                                             24

<210> SEQ ID NO 41
<211> LENGTH: 1028
<212> TYPE: DNA
<213> ORGANISM: Homo sapiens

<400> SEQUENCE: 41
ccaaaatcaa acgcgtccgg gcctgtcccg ccctctccc caagcgcggg cccggccagc       60
ggaagcccct gcgcccgcgc catgtcaaag aaaaaggac tgagtgcaga agaaaagaga      120
actcgcatga tggaaatatt ttctgaaaca aagatgtat ttcaattaaa agacttggag      180
aagattgctc ccaaagagaa aggcattact gctatgtcag taaaagaagt ccttcaaagc    240
ttagttgatg atggtatggt tgactgtgag aggatcggaa cttctaatta ttattgggct    300
tttccaagta aagctcttca tgcaaggaaa cataagttgg aggttctgga atctcaggac    360
cctggctgct gcttccatga ataattaaa gtctcctatt atagaaaatt ctggctgggc    420
gcagtggctc acgcctgtaa tcccagcact ttgggaggct gaggcgggca gatcacgagg    480
tgactttccc ccaccccac atgaagtgca agatggagtt gtctgaggga agtcaaaagc     540
atgcaagcct acagaaaagc attgagaaag ctaaaattgg ccgatgtgaa acggaagagc    600
gaaccaggct agcaaaagag cttttcttcac ttcgagacca aagggaacag ctaaaggcag   660
aagtagaaaa atacaaagac tgtgatccgc aagttgtgga agaaatacgc caagcaaata    720
aagtagccaa agaagctgct aacagatgga ctgataacat attcgcaata aaatcttggg    780
ccaaaagaaa atttgggttt gaagaaaata aaattgatag aacttttgga attccagaag    840
actttgacta catagactaa aatattccat ggtggtgaag gatgtacaag cttgtgaata    900
tgtaaatttt aaactattat ctaactaagt gtactgaatt gtcgtttgcc tgtaactgtg    960
tttatcattt tattaatgtt aaataaagtg taaaatgcaa aaaaaaaaa aaaaaaaaa     1020 aaaaaaaa                                                            1028

<210> SEQ ID NO 42
<211> LENGTH: 869
<212> TYPE: DNA
<213> ORGANISM: Homo sapiens

<400> SEQUENCE: 42
ccaaaatcaa acgcgtccgg gcctgtcccg ccctctccc caagcgcggg cccggccagc       60
ggaagcccct gcgcccgcgc catgtcaaag aaaaaggac tgagtgcaga agaaaagaga      120
actcgcatga tggaaatatt ttctgaaaca aagatgtat ttcaattaaa agacttggag      180
aagattgctc ccaaagagaa aggcattact gctatgtcag taaaagaagt ccttcaaagc    240
ttagttgatg atggtatggt tgactgtgag aggatcggaa cttctaatta ttattgggct    300
tttccaagta aagctcttca tgcaaggaaa cataagttgg aggttctgga atctcagagt    360
tgtctgaggg aagtcaaaag catgcaagcc tacagaaaag cattgagaaa gctaaaattg    420
```

```
gccgatgtga acggaagag cgaaccaggc tagcaaaaga gctttcttca cttcgagacc    480
aaagggaaca gctaaaggca gaagtagaaa aatacaaaga ctgtgatccg caagttgtgg    540
aagaaatacg ccaagcaaat aaagtagcca agaagctgc taacagatgg actgataaca     600
tattcgcaat aaaatcttgg gccaaaagaa aatttgggtt tgaagaaaat aaaattgata    660
gaacttttgg aattccagaa gactttgact acatagacta aaatattcca tggtggtgaa    720
ggatgtacaa gcttgtgaat atgtaaattt taaactatta tctaactaag tgtactgaat    780 tgtcgttttgc ctgtaactgt gtttatcatt ttattaatgt taaataaagt gtaaaatgca    840
aaaaaaaaaa aaaaaaaaaa aaaaaaaaa                                      869
```

<210> SEQ ID NO 43
<211> LENGTH: 869
<212> TYPE: DNA
<213> ORGANISM: Homo sapiens

<400> SEQUENCE: 43

```
ccaaaatcaa acgcgtccgg gcctgtcccg cccctctccc caagcgcggg cccggccagc    60
ggaagcccct gcgcccgcgc catgtcaaag aaaaaggac tgagtgcaga agaaaagaga     120
actcgcatga tggaaatatt ttctgaaaca aagatgtat ttcaattaaa agacttggag      180
aagattgctc ccaaagagaa aggcattact gctatgtcag taaagaagt ccttcaaagc     240 ttagttgatg atggtatggt tgactgtgag aggatcggaa cttctaatta ttattgggct    300
tttccaagta aagctcttca tgcaaggaaa cataagttgg aggttctgga atctcagagt    360
tgtctgaggg aagtcaaaag catgcaagcc tacagaaaag cattgagaaa gctaaaattg    420
gccgatgtga acggaagag cgaaccaggc tagcaaaaga gctttcttca cttcgagacc    480
aaagggaaca gctaaaggca gaagtagaaa aatacaaaga ctgtgatccg caagttgtgg    540
aagaaatacg ccaagcaaat aaagtagcca agaagctgc taacagatgg actgataaca     600
tattcgcaat aaaatcttgg gccaaaagaa aatttgggtt tgaagaaaat aaaattgata    660
gaacttttgg aattccagaa gactttgact acatagacta aaatattcca tggtggtgaa    720
ggatgtacaa gcttgtgaat atgtaaattt taaactatta tctaactaag tgtactgaat    780 tgtcgttttgc ctgtaactgt gtttatcatt ttattaatgt taaataaagt gtaaaatgca    840
aaaaaaaaaa aaaaaaaaaa aaaaaaaaa                                      869
```

<210> SEQ ID NO 44
<211> LENGTH: 206
<212> TYPE: PRT
<213> ORGANISM: Homo sapiens

<400> SEQUENCE: 44

```
Met Ser Lys Lys Lys Gly Leu Ser Ala Glu Glu Lys Arg Thr Arg Met
  1               5                  10                  15

Met Glu Ile Phe Ser Glu Thr Lys Asp Val Phe Gln Leu Lys Asp Leu
             20                  25                  30

Glu Lys Ile Ala Pro Lys Glu Lys Gly Ile Thr Ala Met Ser Val Lys
         35                  40                  45

Glu Val Leu Gln Ser Leu Val Asp Asp Gly Met Val Asp Cys Glu Arg
     50                  55                  60

Ile Gly Thr Ser Asn Tyr Tyr Trp Ala Phe Pro Ser Lys Ala Leu His
 65                  70                  75                  80

Ala Arg Lys His Lys Leu Glu Val Leu Glu Ser Gln Gln Leu Ser Glu
                 85                  90                  95
```

```
Gly Ser Gln Lys His Ala Ser Leu Gln Lys Ser Ile Glu Lys Ala Lys
            100                 105                 110

Ile Gly Arg Cys Glu Thr Glu Arg Thr Arg Leu Ala Lys Glu Leu
        115                 120                 125

Ser Ser Leu Arg Asp Gln Arg Glu Gln Leu Lys Ala Glu Val Glu Lys
130                 135                 140

Tyr Lys Asp Cys Asp Pro Gln Val Val Glu Glu Ile Arg Gln Ala Asn
145                 150                 155                 160

Lys Val Ala Lys Glu Ala Ala Asn Arg Trp Thr Asp Asn Ile Phe Ala
                165                 170                 175

Ile Lys Ser Trp Ala Lys Arg Lys Phe Gly Phe Glu Glu Asn Lys Ile
                180                 185                 190

Asp Arg Thr Phe Gly Ile Pro Glu Asp Phe Asp Tyr Ile Asp
                195                 200                 205

<210> SEQ ID NO 45
<211> LENGTH: 206
<212> TYPE: PRT
<213> ORGANISM: Homo sapiens

<400> SEQUENCE: 45

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
                20                  25                  30

Glu Lys Ile Ala Pro Lys Glu Lys Gly Ile Thr Ala Met Ser Val Lys
            35                  40                  45

Glu Val Leu Gln Ser Leu Val Asp Asp Gly Met Val Asp Cys Glu Arg
        50                  55                  60

Ile Gly Thr Ser Asn Tyr Tyr Trp Ala Phe Pro Ser Lys Ala Leu His
65              70                  75                  80

Ala Arg Lys His Lys Leu Glu Val Leu Glu Ser Gln Glu Leu Ser Glu
                85                  90                  95

Gly Ser Gln Lys His Ala Ser Leu Gln Lys Ser Ile Glu Lys Ala Lys
            100                 105                 110

Ile Gly Arg Cys Glu Thr Glu Arg Thr Arg Leu Ala Lys Glu Leu
        115                 120                 125

Ser Ser Leu Arg Asp Gln Arg Glu Gln Leu Lys Ala Glu Val Glu Lys
130                 135                 140

Tyr Lys Asp Cys Asp Pro Gln Val Val Glu Glu Ile Arg Gln Ala Asn
145                 150                 155                 160

Lys Val Ala Lys Glu Ala Ala Asn Arg Trp Thr Asp Asn Ile Phe Ala
                165                 170                 175

Ile Lys Ser Trp Ala Lys Arg Lys Phe Gly Phe Glu Glu Asn Lys Ile
                180                 185                 190

Asp Arg Thr Phe Gly Ile Pro Glu Asp Phe Asp Tyr Ile Asp
                195                 200                 205

<210> SEQ ID NO 46
<211> LENGTH: 126
<212> TYPE: PRT
<213> ORGANISM: Homo sapiens

<400> SEQUENCE: 46

Met Ser Lys Lys Lys Gly Leu Ser Ala Glu Glu Lys Arg Thr Arg Met
1               5                   10                  15
```

```
Met Glu Ile Phe Ser Glu Thr Lys Asp Val Phe Gln Leu Lys Asp Leu
         20                  25                  30

Glu Lys Ile Ala Pro Lys Glu Gly Ile Thr Ala Met Ser Val Lys
     35                  40                  45

Glu Val Leu Gln Ser Leu Val Asp Asp Gly Met Val Asp Cys Glu Arg
 50                  55                  60

Ile Gly Thr Ser Asn Tyr Tyr Trp Ala Phe Pro Ser Lys Ala Leu His
 65                  70                  75                  80

Ala Arg Lys His Lys Leu Glu Val Leu Glu Ser Gln Asp Pro Gly Cys
             85                  90                  95

Cys Phe His Glu Ile Ile Lys Val Ser Tyr Tyr Arg Lys Phe Trp Leu
            100                 105                 110

Gly Ala Val Ala His Ala Cys Asn Pro Ser Thr Leu Gly Gly
        115                 120                 125

<210> SEQ ID NO 47
<211> LENGTH: 119
<212> TYPE: PRT
<213> ORGANISM: Homo sapiens

<400> SEQUENCE: 47

Met Lys Cys Lys Met Glu Leu Ser Glu Gly Ser Gln Lys His Ala Ser
 1               5                  10                  15

Leu Gln Lys Ser Ile Glu Lys Ala Lys Ile Gly Arg Cys Glu Thr Glu
             20                  25                  30

Glu Arg Thr Arg Leu Ala Lys Glu Leu Ser Ser Leu Arg Asp Gln Arg
         35                  40                  45

Glu Gln Leu Lys Ala Glu Val Glu Lys Tyr Lys Asp Cys Asp Pro Gln
 50                  55                  60

Val Val Glu Glu Ile Arg Gln Ala Asn Lys Val Ala Lys Glu Ala Ala
 65                  70                  75                  80

Asn Arg Trp Thr Asp Asn Ile Phe Ala Ile Lys Ser Trp Ala Lys Arg
             85                  90                  95

Lys Phe Gly Phe Glu Glu Asn Lys Ile Asp Arg Thr Phe Gly Ile Pro
            100                 105                 110

Glu Asp Phe Asp Tyr Ile Asp
            115

<210> SEQ ID NO 48
<211> LENGTH: 752
<212> TYPE: DNA
<213> ORGANISM: Homo sapiens

<400> SEQUENCE: 48
ccaaaatcaa acgcgtccgg gcctgtcccg cccctctccc caagcgcggg cccggccagc      60
ggaagcccct gcgcccgcgc catgtcaaag aaaaaaggac tgagtgcaga agaaaagaga     120
actcgcatga tggaaatatt ttctgaaaca aagatgtat tcaattaaa agacttggag      180 aagattgctc ccaaagagaa aggcattact gctatgtcag taaagaagt ccttcaaagc     240 ttagttgatg atggtatggt tgactgtgag aggatcggaa cttctaatta ttattgggct    300
tttccaagta agctcttca tgcaaggaaa cataagttgg aggttctgga atctcagttg     360
tctgagggaa gtcaaaagca tgcaagccta cagaaaagca ttgagaaagc taaaattggc    420
cgatgtgaaa cggccaagca aataaagtag ccaagaagc tgctaacaga tggactgata    480
acatattcgc aataaaatct tgggccaaaa gaaaatttgg gttgaagaa aataaaattg     540 atagaacttt tggaattcca gaagactttg actacataga ctaaaatatt ccatggtggt    600
```

```
gaaggatgta caagcttgtg aatatgtaaa ttttaaacta ttatctaact aagtgtactg      660
aattgtcgtt tgcctgtaac tgtgtttatc attttattaa tgttaaataa agtgtaaaat      720
gcaaaaaaaa aaaaaaaaaa aaaaaaaaaa aa                                    752

<210> SEQ ID NO 49
<211> LENGTH: 433
<212> TYPE: DNA
<213> ORGANISM: Homo sapiens

<400> SEQUENCE: 49
ccaaaatcaa acgcgtccgg gcctgtcccg cccctctccc caagcgcggg cccggccagc       60
ggaagcccct gcgcccgcgc catgtcaaag aaaaaaggac tgagtgcaga agaaaagaga      120
actcgcatga tggaaatatt ttctgaaaca aaagatgtat ttcaattaaa agacttggag      180
aagattgctc ccaaagagaa aggcattact gctatgtcag taaaagaagt ccttcaaagc      240
ttagttgatg atggtatggt tgactgtgag aggatcggaa cttctaatta ttattgggct      300
tttccaagta aagctcttca tgcaaggaaa cataagttgg aggttctgga atctcagttg      360
tctgagggaa gtcaaaagca tgcaagccta cagaaaagca ttgagaaagc taaaattggc      420
cgatgtgaaa cgg                                                         433

<210> SEQ ID NO 50
<211> LENGTH: 433
<212> TYPE: DNA
<213> ORGANISM: Homo sapiens

<400> SEQUENCE: 50
ccaaaatcaa acgcgtccgg gcctgtcccg cccctctccc caagcgcggg cccggccagc       60
ggaagcccct gcgcccgcgc catgtcaaag aaaaaaggac tgagtgcaga agaaaagaga      120
actcgcatga tggaaatatt ttctgaaaca aaagatgtat ttcaattaaa agacttggag      180
aagattgctc ccaaagagaa aggcattact gctatgtcag taaaagaagt ccttcaaagc      240
ttagttgatg atggtatggt tgactgtgag aggatcggaa cttctaatta ttattgggct      300
tttccaagta aagctcttca tgcaaggaaa cataagttgg aggttctgga atctcagttg      360
tctgagggaa gtcaaaagca tgcaagccta cagaaaagca ttgagaaagc taaaattggc      420
cgatgtgaaa cgg                                                         433

<210> SEQ ID NO 51
<211> LENGTH: 320
<212> TYPE: DNA
<213> ORGANISM: Homo sapiens

<400> SEQUENCE: 51
gccaagcaaa taaagtagcc aaagaagctg ctaacagatg gactgataac atattcgcaa       60
taaaatcttg ggccaaaaga aaatttgggt ttgaagaaaa taaaattgat agaacttttg      120
gaattccaga agactttgac tacatagact aaaaatattcc atggtggtga aggatgtaca      180
agcttgtgaa tatgtaaatt ttaaactatt atctaactaa gtgtactgaa ttgtcgtttg      240
cctgtaactg tgtttatcat tttattaatg ttaaataaag tgtaaatgc aaaaaaaaa       300 aaaaaaaaaa aaaaaaaaa                                                   320

<210> SEQ ID NO 52
<211> LENGTH: 320
<212> TYPE: DNA
<213> ORGANISM: Homo sapiens
```

-continued

<400> SEQUENCE: 52

```
gccaagcaaa taaagtagcc aaagaagctg ctaacagatg gactgataac atattcgcaa      60
taaaatcttg ggccaaaaga aaatttgggt ttgaagaaaa taaaattgat agaactttg      120
gaattccaga agactttgac tacatagact aaaatattcc atggtggtga aggatgtaca    180
agcttgtgaa tatgtaaatt ttaaactatt atctaactaa gtgtactgaa ttgtcgtttg    240
cctgtaactg tgtttatcat tttattaatg ttaaataaag tgtaaaatgc aaaaaaaaaa    300
aaaaaaaaaa aaaaaaaaaa                                                 320
```

<210> SEQ ID NO 53
<211> LENGTH: 122
<212> TYPE: PRT
<213> ORGANISM: Homo sapiens

<400> SEQUENCE: 53

```
Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg
        115                 120
```

<210> SEQ ID NO 54
<211> LENGTH: 122
<212> TYPE: PRT
<213> ORGANISM: Homo sapiens

<400> SEQUENCE: 54

```
Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Ala Lys Gln Ile Lys
        115                 120
```

<210> SEQ ID NO 55
<211> LENGTH: 122
<212> TYPE: PRT
<213> ORGANISM: Homo sapiens

<400> SEQUENCE: 55

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Ala Lys Gln Ile Lys
        115                 120

<210> SEQ ID NO 56
<211> LENGTH: 822
<212> TYPE: DNA
<213> ORGANISM: Homo sapiens

<400> SEQUENCE: 56
ccaaaatcaa acgcgtccgg gcctgtcccg cccctctccc caagcgcggg cccggccagc      60
ggaagcccct gcgcccgcgc catgtcaaag aaaaaaggac tgagtgcaga agaaaagaga     120
actcgcatga tggaaatatt ttctgaaaca aagatgtat ttcaattaaa agacttggag     180
aagattgctc ccaaagagaa aggcattact gctatgtcag taaaagaagt ccttcaaagc     240
ttagttgatg atggtatggt tgactgtgag aggatcggaa cttctaatta ttattgggct     300
tttccaagta aagctcttca tgcaaggaaa cataagttgg aggttctgga atctcagttg     360
tctgagggaa gtcaaaagca tgcaagccta cagaaaagca ttgagaaagc taaaattggc     420
cgatgtgaaa cggaagagcg aaccaggcta gcaaagagc tttcttcact tcgagaccaa     480
agggaacagc taaaggcaga agtagaaaaa tacaaagact gtgatccgca agttgtggaa     540
gaaatacata acatattcgc aataaaatct tgggccaaaa gaaaatttgg gtttgaagaa     600
aataaaattg atagaacttt tggaattcca gaagactttg actacataga ctaaaatatt     660
ccatggtggt gaaggatgta caagcttgtg aatatgtaaa ttttaaacta ttatctaact     720
aagtgtactg aattgtcgtt tgcctgtaac tgtgtttatc attttattaa tgttaaataa     780
agtgtaaaat gcaaaaaaaa aaaaaaaaa aaaaaaaaaa aa     822

<210> SEQ ID NO 57
<211> LENGTH: 547
<212> TYPE: DNA
<213> ORGANISM: Homo sapiens

<400> SEQUENCE: 57
ccaaaatcaa acgcgtccgg gcctgtcccg cccctctccc caagcgcggg cccggccagc      60
ggaagcccct gcgcccgcgc catgtcaaag aaaaaaggac tgagtgcaga agaaaagaga     120
actcgcatga tggaaatatt ttctgaaaca aagatgtat ttcaattaaa agacttggag     180

```
aagattgctc ccaaagagaa aggcattact gctatgtcag taaaagaagt ccttcaaagc      240
ttagttgatg atggtatggt tgactgtgag aggatcggaa cttctaatta ttattgggct      300
tttccaagta aagctcttca tgcaaggaaa cataagttgg aggttctgga atctcagttg      360
tctgagggaa gtcaaaagca tgcaagccta cagaaaagca ttgagaaagc taaaattggc      420
cgatgtgaaa cggaagagcg aaccaggcta gcaaaagagc tttcttcact tcgagaccaa      480
agggaacagc taaaggcaga agtagaaaaa tacaaagact gtgatccgca agttgtggaa      540
gaaatac                                                                547

<210> SEQ ID NO 58
<211> LENGTH: 547
<212> TYPE: DNA
<213> ORGANISM: Homo sapiens

<400> SEQUENCE: 58
ccaaaatcaa acgcgtccgg gcctgtcccg cccctctccc caagcgcggg cccggccagc       60
ggaagcccct gcgcccgcgc catgtcaaag aaaaaggac tgagtgcaga agaaaagaga      120
actcgcatga tggaaatatt ttctgaaaca aagatgtat ttcaattaaa agacttggag      180
aagattgctc ccaaagagaa aggcattact gctatgtcag taaaagaagt ccttcaaagc      240
ttagttgatg atggtatggt tgactgtgag aggatcggaa cttctaatta ttattgggct      300
tttccaagta aagctcttca tgcaaggaaa cataagttgg aggttctgga atctcagttg      360
tctgagggaa gtcaaaagca tgcaagccta cagaaaagca ttgagaaagc taaaattggc      420
cgatgtgaaa cggaagagcg aaccaggcta gcaaaagagc tttcttcact tcgagaccaa      480
agggaacagc taaaggcaga agtagaaaaa tacaaagact gtgatccgca agttgtggaa      540
gaaatac                                                                547

<210> SEQ ID NO 59
<211> LENGTH: 275
<212> TYPE: DNA
<213> ORGANISM: Homo sapiens

<400> SEQUENCE: 59
ataacatatt cgcaataaaa tcttgggcca aagaaaatt tgggtttgaa gaaaataaaa       60
ttgatagaac ttttggaatt ccagaagact ttgactacat agactaaaat attccatggt      120
ggtgaaggat gtacaagctt gtgaatatgt aaattttaaa ctattatcta actaagtgta      180
ctgaattgtc gttttgcctgt aactgtgttt atcattttat taatgttaaa taaagtgtaa      240
aatgcaaaaa aaaaaaaaa aaaaaaaaaa aaaaa                                  275

<210> SEQ ID NO 60
<211> LENGTH: 275
<212> TYPE: DNA
<213> ORGANISM: Homo sapiens

<400> SEQUENCE: 60
ataacatatt cgcaataaaa tcttgggcca aagaaaatt tgggtttgaa gaaaataaaa       60
ttgatagaac ttttggaatt ccagaagact ttgactacat agactaaaat attccatggt      120
ggtgaaggat gtacaagctt gtgaatatgt aaattttaaa ctattatcta actaagtgta      180
ctgaattgtc gttttgcctgt aactgtgttt atcattttat taatgttaaa taaagtgtaa      240
aatgcaaaaa aaaaaaaaa aaaaaaaaaa aaaaa                                  275
```

-continued

```
<210> SEQ ID NO 61
<211> LENGTH: 205
<212> TYPE: PRT
<213> ORGANISM: Homo sapiens

<400> SEQUENCE: 61

Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140

Lys Asp Cys Asp Pro Gln Val Val Glu Glu Ile Arg Gln Ala Asn Lys
145                 150                 155                 160

Val Ala Lys Glu Ala Ala Asn Arg Trp Thr Asp Asn Ile Phe Ala Ile
                165                 170                 175

Lys Ser Trp Ala Lys Arg Lys Phe Gly Phe Glu Glu Asn Lys Ile Asp
            180                 185                 190

Arg Thr Phe Gly Ile Pro Glu Asp Phe Asp Tyr Ile Asp
        195                 200                 205

<210> SEQ ID NO 62
<211> LENGTH: 190
<212> TYPE: PRT
<213> ORGANISM: Homo sapiens

<400> SEQUENCE: 62

Met Ser Lys Lys Lys Gly Leu Ser Ala Glu Glu Lys Arg Thr Arg Met
 1               5                  10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140
```

```
Lys Asp Cys Asp Pro Gln Val Val Glu Glu Ile His Asn Ile Phe Ala
145                 150                 155                 160

Ile Lys Ser Trp Ala Lys Arg Lys Phe Gly Phe Glu Glu Asn Lys Ile
            165                 170                 175

Asp Arg Thr Phe Gly Ile Pro Glu Asp Phe Asp Tyr Ile Asp
        180                 185                 190

<210> SEQ ID NO 63
<211> LENGTH: 190
<212> TYPE: PRT
<213> ORGANISM: Homo sapiens

<400> SEQUENCE: 63

Met Ser Lys Lys Lys Gly Leu Ser Ala Glu Glu Lys Arg Thr Arg Met
1               5                   10                  15

Met Glu Ile Phe Ser Glu Thr Lys Asp Val Phe Gln Leu Lys Asp Leu
            20                  25                  30

Glu Lys Ile Ala Pro Lys Glu Lys Gly Ile Thr Ala Met Ser Val Lys
        35                  40                  45

Glu Val Leu Gln Ser Leu Val Asp Asp Gly Met Val Asp Cys Glu Arg
    50                  55                  60

Ile Gly Thr Ser Asn Tyr Tyr Trp Ala Phe Pro Ser Lys Ala Leu His
65                  70                  75                  80

Ala Arg Lys His Lys Leu Glu Val Leu Glu Ser Gln Leu Ser Glu Gly
                85                  90                  95

Ser Gln Lys His Ala Ser Leu Gln Lys Ser Ile Glu Lys Ala Lys Ile
            100                 105                 110

Gly Arg Cys Glu Thr Glu Glu Arg Thr Arg Leu Ala Lys Glu Leu Ser
        115                 120                 125

Ser Leu Arg Asp Gln Arg Glu Gln Leu Lys Ala Glu Val Glu Lys Tyr
    130                 135                 140

Lys Asp Cys Asp Pro Gln Val Val Glu Glu Ile His Asn Ile Phe Ala
145                 150                 155                 160

Ile Lys Ser Trp Ala Lys Arg Lys Phe Gly Phe Glu Glu Asn Lys Ile
            165                 170                 175

Asp Arg Thr Phe Gly Ile Pro Glu Asp Phe Asp Tyr Ile Asp
        180                 185                 190

<210> SEQ ID NO 64
<211> LENGTH: 1205
<212> TYPE: DNA
<213> ORGANISM: Homo sapiens

<400> SEQUENCE: 64
gttttctgta ttgtaatatg tagagcacat tccagaactg ctcagtttcg agttacctaa      60
tggatcttca ctgtgtgcca attagtcgat ttctgtgaaa acgccccggt ttctgccaaa     120
gggcaggagt cgctgctctt gtgccgggtg ctgctggttg tgtagggcgc tgttgctttt     180
ttaaggacgc tctgcactga attaggcttc ctcgtgggtc atgatcagtt aagtcctgtc     240
aaagaaaaaa ggactgagtg cagaagaaaa gagaactcgc atgatggaaa tattttctga     300
aacaaaagat gtatttcaat taaaagactt ggagaagatt gctcccaaag agaaaggcat     360
tactgctatg tcagtaaaag aagtccttca aagcttagtt gatgatggta tggttgactg     420
tgagaggatc ggaacttcta attattattg gcttttccca agtaaagctc ttcatgcaag     480
gaaacataag ttggaggttc tggaatctca gttgtctgag gaagtcaaa agcatgcaag      540
```

| cctacagaaa agcattgaga aagctaaaat tggccgatgt gaaacggaag agcgaaccag | 600 |
| gctagcaaaa gagctttctt cacttcgaga ccaaagggaa cagctaaagg cagaagtaga | 660 |
| aaaatacaaa gactgtgatc cgcaagttgt ggaagaaata cgccaagcaa ataaagtagc | 720 |
| caaagaagct gctaacagat ggactgataa catattcgca ataaaatctt gggccaaaag | 780 |
| aaaatttggg tttgaagaaa ataaaattga tagaacttt ggaattccag aagactttga | 840 |
| ctacatagac taaaatattc catggtggtg aaggatgtac aagcttgtga atatgtaaat | 900 |
| tttaaactat tatctaacta agtgtactga attgtcgttt gcctgtaact gtgtttatca | 960 |
| ttttattaat gttaaataaa gtgtaaaatg cagatgttct tcaccccttt tggtagaaca | 1020 |
| aaagcaggat gataaccata tcccccagt gctcatcaaa gtaggacact aaaaatccat | 1080 |
| ccatctcagt caaagtcgag cggccgcgaa tttagtagta gtagcggccg ctctagagga | 1140 |
| tccaagctta cgtacgcgtg catgcgacgt catagctctt ctatagtgtc acctaaattc | 1200 |
| aagtt | 1205 |

<210> SEQ ID NO 65
<211> LENGTH: 756
<212> TYPE: DNA
<213> ORGANISM: Homo sapiens

<400> SEQUENCE: 65

| tgtcaaagaa aaaggactg agtgcagaag aaaagagaac tcgcatgatg gaaatatttt | 60 |
| ctgaaacaaa agatgtattt caattaaaag acttggagaa gattgctccc aaagagaaag | 120 |
| gcattactgc tatgtcagta aaagaagtcc ttcaaagctt agttgatgat ggtatggttg | 180 |
| actgtgagag gatcggaact tctaattatt attgggcttt tccaagtaaa gctcttcatg | 240 |
| caaggaaaca taagttggag gttctggaat ctcagttgtc tgagggaagt caaaagcatg | 300 |
| caagcctaca gaaaagcatt gagaaagcta aaattggccg atgtgaaacg gaagagcgaa | 360 |
| ccaggctagc aaaagagctt tcttcacttc gagaccaaag ggaacagcta aaggcagaag | 420 |
| tagaaaaata caaagactgt gatccgcaag ttgtggaaga atacgccaa gcaaataaag | 480 |
| tagccaaaga agctgctaac agatggactg ataacatatt cgcaataaaa tcttgggcca | 540 |
| aaagaaaatt tgggtttgaa gaaataaaa ttgatagaac ttttggaatt ccagaagact | 600 |
| ttgactacat agactaaaat attccatggt ggtgaaggat gtacaagctt gtgaatatgt | 660 |
| aaatttaaa ctattatcta actaagtgta ctgaattgtc gtttgcctgt aactgtgttt | 720 |
| atcattttat taatgttaaa taaagtgtaa aatgca | 756 |

<210> SEQ ID NO 66
<211> LENGTH: 756
<212> TYPE: DNA
<213> ORGANISM: Homo sapiens

<400> SEQUENCE: 66

| tgtcaaagaa aaaggactg agtgcagaag aaaagagaac tcgcatgatg gaaatatttt | 60 |
| ctgaaacaaa agatgtattt caattaaaag acttggagaa gattgctccc aaagagaaag | 120 |
| gcattactgc tatgtcagta aaagaagtcc ttcaaagctt agttgatgat ggtatggttg | 180 |
| actgtgagag gatcggaact tctaattatt attgggcttt tccaagtaaa gctcttcatg | 240 |
| caaggaaaca taagttggag gttctggaat ctcagttgtc tgagggaagt caaaagcatg | 300 |
| caagcctaca gaaaagcatt gagaaagcta aaattggccg atgtgaaacg gaagagcgaa | 360 |
| ccaggctagc aaaagagctt tcttcacttc gagaccaaag ggaacagcta aaggcagaag | 420 |

```
tagaaaaata caaagactgt gatccgcaag ttgtggaaga aatacgccaa gcaaataaag      480
tagccaaaga agctgctaac agatggactg ataacatatt cgcaataaaa tcttgggcca      540
aaagaaaatt tgggtttgaa gaaaataaaa ttgatagaac ttttggaatt ccagaagact      600
ttgactacat agactaaaat attccatggt ggtgaaggat gtacaagctt gtgaatatgt      660 aaatttttaaa ctattatcta actaagtgta ctgaattgtc gtttgcctgt aactgtgttt      720
atcattttat taatgttaaa taaagtgtaa aatgca                               756
```

```
<210> SEQ ID NO 67
<211> LENGTH: 190
<212> TYPE: PRT
<213> ORGANISM: Homo sapiens

<400> SEQUENCE: 67

Met Met Glu Ile Phe Ser Glu Thr Lys Asp Val Phe Gln Leu Lys Asp
1               5                   10                  15

Leu Glu Lys Ile Ala Pro Lys Glu Lys Gly Ile Thr Ala Met Ser Val
            20                  25                  30

Lys Glu Val Leu Gln Ser Leu Val Asp Asp Gly Met Val Asp Cys Glu
        35                  40                  45

Arg Ile Gly Thr Ser Asn Tyr Tyr Trp Ala Phe Pro Ser Lys Ala Leu
    50                  55                  60

His Ala Arg Lys His Lys Leu Glu Val Leu Ser Gln Leu Ser Glu
65                  70                  75                  80

Gly Ser Gln Lys His Ala Ser Leu Gln Lys Ser Ile Glu Lys Ala Lys
                85                  90                  95

Ile Gly Arg Cys Glu Thr Glu Arg Thr Arg Leu Ala Lys Glu Leu
            100                 105                 110

Ser Ser Leu Arg Asp Gln Arg Glu Gln Leu Lys Ala Glu Val Glu Lys
        115                 120                 125

Tyr Lys Asp Cys Asp Pro Gln Val Val Glu Ile Arg Gln Ala Asn
    130                 135                 140

Lys Val Ala Lys Glu Ala Ala Asn Arg Trp Thr Asp Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
            180                 185                 190

<210> SEQ ID NO 68
<211> LENGTH: 190
<212> TYPE: PRT
<213> ORGANISM: Homo sapiens

<400> SEQUENCE: 68

Met Met Glu Ile Phe Ser Glu Thr Lys Asp Val Phe Gln Leu Lys Asp
1               5                   10                  15

Leu Glu Lys Ile Ala Pro Lys Glu Lys Gly Ile Thr Ala Met Ser Val
            20                  25                  30

Lys Glu Val Leu Gln Ser Leu Val Asp Asp Gly Met Val Asp Cys Glu
        35                  40                  45

Arg Ile Gly Thr Ser Asn Tyr Tyr Trp Ala Phe Pro Ser Lys Ala Leu
    50                  55                  60

His Ala Arg Lys His Lys Leu Glu Val Leu Ser Gln Leu Ser Glu
65                  70                  75                  80

Gly Ser Gln Lys His Ala Ser Leu Gln Lys Ser Ile Glu Lys Ala Lys
```

-continued

```
                    85                  90                  95
Ile Gly Arg Cys Glu Thr Glu Glu Arg Thr Arg Leu Ala Lys Glu Leu
                100                 105                 110

Ser Ser Leu Arg Asp Gln Arg Glu Gln Leu Lys Ala Glu Val Glu Lys
                115                 120                 125

Tyr Lys Asp Cys Asp Pro Gln Val Val Glu Glu Ile Arg Gln Ala Asn
                130                 135                 140

Lys Val Ala Lys Glu Ala Ala Asn Arg Trp Thr Asp Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
                180                 185                 190

<210> SEQ ID NO 69
<211> LENGTH: 190
<212> TYPE: PRT
<213> ORGANISM: Homo sapiens

<400> SEQUENCE: 69

Met Met Glu Ile Phe Ser Glu Thr Lys Asp Val Phe Gln Leu Lys Asp
 1               5                  10                  15

Leu Glu Lys Ile Ala Pro Lys Lys Gly Ile Thr Ala Met Ser Val
                20                  25                  30

Lys Glu Val Leu Gln Ser Leu Val Asp Asp Gly Met Val Asp Cys Glu
                35                  40                  45

Arg Ile Gly Thr Ser Asn Tyr Tyr Trp Ala Phe Pro Ser Lys Ala Leu
                50                  55                  60

His Ala Arg Lys His Lys Leu Glu Val Leu Glu Ser Gln Leu Ser Glu
65                  70                  75                  80

Gly Ser Gln Lys His Ala Ser Leu Gln Lys Ser Ile Glu Lys Ala Lys
                85                  90                  95

Ile Gly Arg Cys Glu Thr Glu Glu Arg Thr Arg Leu Ala Lys Glu Leu
                100                 105                 110

Ser Ser Leu Arg Asp Gln Arg Glu Gln Leu Lys Ala Glu Val Glu Lys
                115                 120                 125

Tyr Lys Asp Cys Asp Pro Gln Val Val Glu Glu Ile Arg Gln Ala Asn
                130                 135                 140

Lys Val Ala Lys Glu Ala Ala Asn Arg Trp Thr Asp Asn Ile Phe Ala
145                 150                 155                 160

Ile Lys Ser Trp Ala Lys Arg Lys Phe Gly Phe Glu Glu Asn Lys Ile
                165                 170                 175

Asp Arg Thr Phe Gly Ile Pro Glu Asp Phe Asp Tyr Ile Asp
                180                 185                 190
```